(12) United States Patent
Treu

(10) Patent No.: US 8,735,386 B2
(45) Date of Patent: May 27, 2014

(54) AMINOPYRAZOLOQUINAZOLINES

(75) Inventor: Matthias Treu, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/187,100

(22) Filed: Jul. 20, 2011

(65) Prior Publication Data

US 2012/0238542 A1 Sep. 20, 2012

(30) Foreign Application Priority Data

Jul. 23, 2010 (EP) ..................................... 10170683

(51) Int. Cl.
*A01N 43/00* (2006.01)

(52) U.S. Cl.
USPC .............. 514/210.21; 514/232.8; 514/252.16; 514/267; 544/115; 544/251

(58) Field of Classification Search
USPC ........ 514/210.2, 232.8, 252.16, 260.1, 266.4, 514/265.1, 210.21, 267; 544/115, 251, 278, 544/280, 284, 292
See application file for complete search history.

(56) References Cited

U.S. PATENT DOCUMENTS

2005/0148603 A1* 7/2005 Jimenez et al. ............ 514/260.1

FOREIGN PATENT DOCUMENTS

WO 2004104007 A1 12/2004
WO 2005037843 A1 4/2005

OTHER PUBLICATIONS

International Search Report, form PCT/ISA/210, and Written Opinion, PCT/ISA/237, for corresponding application PCT/EP2011/062683, date of mailing Sep. 21, 2011.

* cited by examiner

*Primary Examiner* — Jason Sims
*Assistant Examiner* — Ibrahim D Bori
(74) *Attorney, Agent, or Firm* — Michael P. Morris; Alan R. Stempel

(57) ABSTRACT

Compounds of general formula (I)

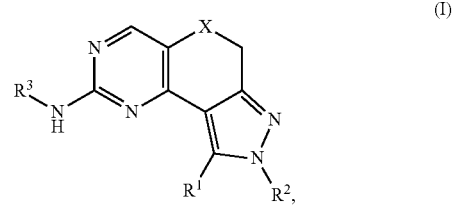

wherein the groups $R^1$ to $R^3$ and X are defined as in claim 1, which are suitable for the treatment of diseases characterised by excessive or abnormal cell proliferation, pharmaceutical preparations which contain such compounds and their use as medicaments.

42 Claims, No Drawings

AMINOPYRAZOLOQUINAZOLINES

The present invention relates to new aminopyrazoloquinazolines of general formula (I)

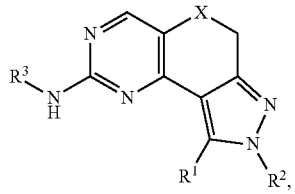

wherein the groups $R^1$ to $R^3$ and X have the meanings given in the specification, which are suitable for the treatment of diseases characterised by excessive or abnormal cell proliferation, pharmaceutical preparations which contain such compounds and their use as medicaments. The compounds according to the invention display an inhibitory effect on the phosphorylation activity of the IGF-1 receptor located in cell membranes.

BACKGROUND TO THE INVENTION

WO 2005/037843 describes partially saturated quinazolines anellated with heteroaryls as kinase inhibitors.

The aim of the present invention is to indicate new compounds which can be used for the prevention and/or treatment of diseases characterised by excessive or abnormal cell proliferation. The compounds according to the invention are characterised by a powerful inhibitory effect on the phosphorylation activity of the IGF-1 receptor located in cell membranes and a potent efficacy against tumour cells, e.g. glioblastoma cells, which is mediated through the inhibition of phosphorylation of the receptor. In addition to the inhibitory effect and cell activity the compounds have good solubility and good PK properties.

The insulin-like growth factor (IGF) and insulin signalling network is a highly conserved and essential pathway involved in biological processes including growth, metabolism and homeostasis. In addition, deregulated signalling via this network can enhance tumorigenesis and metastasis of certain cancers.

The ligands IGF-1, IGF-2 and insulin are highly homologous and activate specific hetero or homodimers of the IGF-1R and IR. Following ligand binding, the IGF-1R and IR undergo autophosphorylation mediated via the receptor tyrosine kinase domains. The phosphorylated receptors activate the canonical Ras-Raf-MEK-ERK1/2 and PI3K-PDK1-Akt intracellular signaling cascades, which leads to cell proliferation and survival. In addition, activation of the IR by insulin stimulates the uptake of glucose and storage of glycogen in metabolic tissues such as the liver, adipose and muscle.

Published research articles as well as medical and epidemiological investigations have identified a strong correlation between expression of the IGF-1R and IR and ligands for these receptors in tumor development and progression. Developing a small molecule competitive inhibitor of the ATP-binding pocket of the IGF-1R and IR as a means of blocking growth and survival signaling cascades in cancer is therefore desirable. The anticipated clinical benefit of blocking such an interaction would be to reduced tumor growth rate and potentially sensitize tumors to cytotoxic agents or targeted therapies.

DETAILED DESCRIPTION OF THE INVENTION

Surprisingly it has been found that compounds of general formula (I), wherein the groups $R^1$ to $R^3$ and X have the meanings stated hereinafter act as inhibitors of receptors that are involved in controlling cell proliferation. Thus, the compounds according to the invention may be used for example for the treatment of diseases associated with the activity of these receptors and characterised by excessive or abnormal cell proliferation.

The present invention therefore relates to compounds of general formula (I)

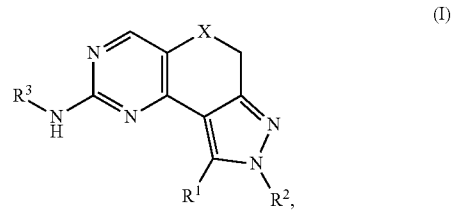

(A0)
wherein
$R^1$ denotes hydrogen or a group optionally substituted by one or more identical or different $R^a$ and/or $R^b$, selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

(B0)
$R^2$ denotes hydrogen or a group optionally substituted by one or more identical or different $R^a$ and/or $R^b$, selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

$R^3$ denotes a group

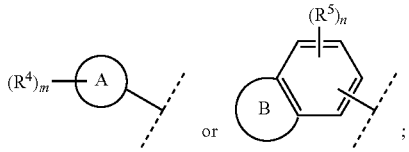

(C0)
A is selected from among $C_{6-10}$aryl and 5-12 membered heteroaryl;
B denotes a 5- to 7-membered, non-aromatic hetero ring with at least one heteroatom, selected from among nitrogen, sulphur and oxygen, which optionally carries one or more substituents selected from among $C_{1-6}$alkyl and =O;

(D0)
each $R^4$ is independently selected from among $R^a$ and $R^b$;
m denotes 0, 1, 2 or 3;
$R^5$ is selected from among $R^a$ and $R^b$;
n denotes 0 or 1;

(E0)
X denotes a bond or is selected from among —$CH_2$— and —$CH_2$—$CH_2$— and in the above-mentioned —$CH_2$— and —$CH_2$—$CH_2$— one or two hydrogen atoms are optionally substituted independently of one another by $C_{1-4}$alkyl, $C_{1-4}$haloalkyl, —O—$C_{1-4}$alkyl or halogen;

each $R^a$ independently denotes a group optionally substituted by one or more identical or different $R^b$ and/or $R^c$, selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^b$ is independently selected from among —$OR^c$, —$SR^c$, —$NR^cR^c$, halogen, —CN, —$NO_2$, —$C(O)R^c$, —$C(O)OR^c$, —$C(O)NR^cR^c$, —$C(NR^h)NR^cR^c$, —$OC(O)R^c$, —$OC(O)OR^c$, —$S(O)_2R^c$, —$S(O)_2NR^cR^c$, —$NR^hC(O)R^c$, —$NR^hC(O)OR^c$, —$NR^hC(O)NR^cR^c$, —$NR^hC(NR^h)NR^cR^c$ and —$NR^hS(O)_2R^c$, as well as the bivalent substituent ═O, while the latter may only be a substituent in non-aromatic ring systems;

each $R^c$ independently denotes hydrogen or a group optionally substituted by one or more identical or different $R^d$ and/or $R^e$, selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^d$ is independently selected from among —$OR^e$, —$SR^e$, —$NR^eR^e$, halogen, —CN, —$NO_2$, —$C(O)R^e$, —$C(O)OR^e$, —$C(O)NR^eR^e$, —$C(NR^h)NR^eR^e$, —$OC(O)R^e$, —$OC(O)OR^e$, —$S(O)_2R^e$, —$S(O)_2NR^eR^e$, —$NR^hC(O)R^e$, —$NR^hC(O)OR^e$, —$NR^hC(O)NR^eR^e$, —$NR^hC(NR^h)NR^eR^e$ and —$NR^hS(O)_2R^e$, as well as the bivalent substituent ═O, while the latter may only be a substituent in non-aromatic ring systems;

each $R^e$ independently denotes hydrogen or a group optionally substituted by one or more identical or different $R^f$ and/or $R^g$, selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^f$ is independently selected from among —$OR^g$, —$SR^g$, —$NR^gR^g$, halogen, —CN, —$NO_2$, —$C(O)R^g$, —$C(O)OR^g$, —$C(O)NR^gR^g$, —$C(NR^h)NR^gR^g$, —$OC(O)R^g$, —$OC(O)OR^g$, —$S(O)_2R^g$, —$S(O)_2NR^gR^g$, —$NR^hC(O)R^g$, —$NR^hC(O)OR^g$, —$NR^hC(O)NR^gR^g$, —$NR^hC(NR^h)NR^gR^g$ and —$NR^hS(O)_2R^g$, as well as the bivalent substituent ═O, while the latter may only be a substituent in non-aromatic ring systems;

each $R^g$ is independently selected from among hydrogen, $C_{1-6}$alkyl, $C_{2-6}$alkenyl, $C_{2-6}$alkynyl, $C_{1-6}$haloalkyl, $C_{3-10}$cycloalkyl, $C_{4-10}$cycloalkylalkyl, $C_{4-10}$cycloalkenyl, $C_{6-10}$aryl, 5-12 membered heteroaryl and 3- to 14-membered heterocyclyl, and each $R^h$ is independently selected from among hydrogen and $C_{1-6}$alkyl, while the compounds (I) may optionally also be present in the form of their tautomers, their racemates, their enantiomers, their diastereomers or their mixtures or as the respective salts of all the above-mentioned forms.

In one aspect (A1) the invention relates to compounds (I), wherein $R^1$ is a group optionally substituted by one or more identical or different $R^{a1}$ and/or $R^{b1}$, selected from among $C_{1-6}$alkyl, $C_{3-10}$cycloalkyl, $C_{6-10}$aryl, 5-12 membered heteroaryl and 3- to 14-membered heterocyclyl;

each $R^{a1}$ independently denotes a group optionally substituted by one or more identical or different $R^{b1}$ and/or $C_{1-6}$alkyl, selected from among $C_{1-6}$alkyl, $C_{3-10}$cycloalkyl and $C_{6-10}$aryl, and each $R^{b1}$ is independently selected from among —OH, —O—$C_{1-6}$alkyl, halogen and —CN.

In another aspect (A2) the invention relates to compounds (I), wherein $R^1$ is a group optionally substituted by one or more identical or different $R^{a1}$ and/or $R^{b1}$, selected from among $C_{1-4}$alkyl, $C_{3-6}$cycloalkyl, phenyl, 5- to 6-membered heteroaryl and 3-7 membered heterocyclyl;

each $R^{a1}$ independently denotes a group optionally substituted by one or more identical or different $R^{b1}$ and/or $C_{1-4}$alkyl, selected from among $C_{1-4}$alkyl, $C_{3-6}$cycloalkyl and phenyl, and each $R^{b1}$ is independently selected from among —O—$C_{1-4}$alkyl, halogen and —CN.

In another aspect (A3) the invention relates to compounds (I), wherein $R^1$ denotes $C_{3-6}$alkyl.

In another aspect (A4) the invention relates to compounds (I), wherein $R^1$ denotes phenyl or benzyl, while the above-mentioned phenyl and benzyl optionally carry one or more substituents selected from among $C_{1-6}$alkyl, halogen, —O—$C_{1-6}$alkyl and —CN.

In another aspect (A5) the invention relates to compounds (I), wherein $R^1$ denotes phenyl or benzyl, while the above-mentioned phenyl and benzyl optionally carry one or more substituents selected from among $C_{1-4}$alkyl, $C_{1-4}$haloalkyl, halogen, —O—$C_{1-4}$alkyl, —O—$C_{1-4}$haloalkyl and —CN.

In another aspect (A6) the invention relates to compounds (I), wherein $R^1$ denotes thienyl, this thienyl optionally carrying one or more substituents selected from among $C_{1-4}$alkyl and halogen.

In another aspect (B1) the invention relates to compounds (I), wherein $R^2$ is hydrogen or a group optionally substituted by one or more identical or different $R^{b2}$ and/or $C_{6-10}$aryl selected from among $C_{1-6}$alkyl, $C_{2-6}$alkenyl and 5-12 membered heteroaryl;

each $R^{b2}$ is independently selected from among —OH, —O—$C_{1-6}$alkyl, —$NH_2$, —NH($C_{1-6}$alkyl) and —N($C_{1-6}$alkyl)$_2$.

In another aspect (B2) the invention relates to compounds (I), wherein $R^2$ is a group optionally substituted by one or more identical or different $R^{b2}$ and/or phenyl selected from among $C_{1-4}$alkyl, and 5- to 6-membered heteroaryl;

each $R^{b2}$ is independently selected from among —O—$C_{1-4}$alkyl and —N($C_{1-4}$alkyl)$_2$.

In another aspect (B3) the invention relates to compounds (I), wherein $R^2$ denotes methyl or ethyl.

In another aspect (E1) the invention relates to compounds (I), wherein

X denotes a bond or is selected from among —$CH_2$— and —$CH_2$—$CH_2$— and in the above-mentioned —$CH_2$— and —$CH_2$—$CH_2$— optionally one or two hydrogen atoms are substituted by $C_{1-4}$alkyl.

In another aspect (E2) the invention relates to compounds (I), wherein

X is selected from among —$CH_2$— and —$CH_2$—$CH_2$— and in the above-mentioned —$CH_2$— and —$CH_2$—$CH_2$— optionally one or two hydrogen atoms are substituted by $C_{1-4}$alkyl.

In another aspect (E3) the invention relates to compounds (I), wherein

X is selected from among —$CH_2$, —$CH(CH_3)$, —$C(CH_3)_2$— and —$CH_2$—$CH_2$—.

In another aspect (E4) the invention relates to compounds (I), wherein
X denotes —CH$_2$ or —CH(CH$_3$)—.

In another aspect (C1) the invention relates to compounds (I), wherein
A is selected from among phenyl, naphthyl, 5- to 6-membered, monocyclic heteroaryl and 9- to 10-membered bicyclic heteroaryl.

In another aspect (C2) the invention relates to compounds (I), wherein
A is selected from among phenyl, benzofuryl, benzothienyl, naphthyl, isoquinolinyl, pyrazolyl, indazolyl, isoxazolyl and imidazo[1,2-a]pyridyl.

In another aspect (C3) the invention relates to compounds (I), wherein
A denotes phenyl.

In another aspect (C4) the invention relates to compounds (I), wherein
A denotes pyrazolyl.

In another aspect (D1) the invention relates to compounds (I), wherein
each R$^4$ is independently selected from among R$^{a3}$ and R$^{b3}$;
m denotes 0, 1, 2 or 3;
  each R$^{a3}$ independently denotes a group optionally substituted by one or more identical or different R$^{b3}$ and/or R$^{c3}$ selected from among C$_{1-6}$alkyl, C$_{3-10}$cycloalkyl and 3- to 14-membered heterocyclyl;
  each R$^{b3}$ is independently selected from among —OR$^{c3}$, —NR$^{c3}$R$^{c3}$, halogen, —C(O)R$^{c3}$, —C(O)OR$^{c3}$, —C(O)NR$^{c3}$R$^{c3}$ and —S(O)$_2$R$^{c3}$;
  each R$^{c3}$ independently denotes hydrogen or a group optionally substituted by one or more identical or different R$^{d3}$ and/or R$^{e3}$ selected from among C$_{1-6}$alkyl, C$_{2-6}$alkenyl, C$_{3-10}$cycloalkyl and 3- to 14-membered heterocyclyl;
  each R$^{d3}$ is independently selected from among —OR$^{e3}$, —NR$^{e3}$R$^{e3}$, halogen, —C(O)R$^{e3}$, —C(O)OR$^{e3}$ and —C(O)NR$^{e3}$R$^{e3}$;
  each R$^{e3}$ independently denotes hydrogen or a group optionally substituted by one or more identical or different R$^{f3}$ and/or R$^{g3}$ selected from among C$_{1-6}$alkyl, C$_{3-10}$cycloalkyl and 3- to 14-membered heterocyclyl;
  each R$^{f3}$ is independently selected from among —OR$^{g3}$, —NR$^{g3}$R$^{g3}$, halogen, —C(O)R$^{g3}$, —C(O)OR$^{g3}$ and —C(O)NR$^{g3}$R$^{g3}$ and
  each R$^{g3}$ is independently selected from among hydrogen, C$_{1-6}$alkyl, C$_{1-6}$haloalkyl, C$_{3-10}$cycloalkyl, C$_{4-10}$cycloalkylalkyl, C$_{6-10}$aryl, and 5-12 membered heteroaryl.

In another aspect (D2) the invention relates to compounds with the structural aspect (D1), wherein m denotes 1, 2 or 3.

In another aspect (D3) the invention relates to compounds with the structural aspect (D1), wherein m denotes 2.

In another aspect (CD1) the invention relates to compounds (I), wherein R$^3$ denotes a group

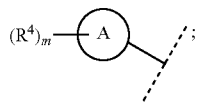

A is selected from among C$_{6-10}$aryl and 5-12 membered heteroaryl;
each R$^4$ is independently selected from among R$^a$ and R$^b$;
m denotes 0, 1, 2 or 3 and
R$^a$ and R$^b$ are as hereinbefore defined.

In another aspect (CD2) the invention relates to compounds (I), wherein
R$^3$ denotes a group

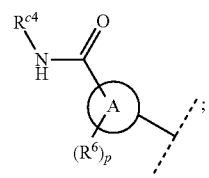

A is selected from among C$_{6-10}$aryl and 5-12 membered heteroaryl;
each R$^6$ is independently selected from among C$_{1-4}$alkyl, —O—C$_{1-4}$alkyl and halogen;
p denotes 0, 1 or 2;
R$^{c4}$ denotes hydrogen or a group optionally substituted by one or more identical or different R$^{d4}$ and/or R$^{e4}$ selected from among C$_{1-6}$alkyl, C$_{2-6}$alkenyl, C$_{2-6}$alkynyl, C$_{3-10}$cycloalkyl, C$_{4-10}$cycloalkenyl, C$_{6-10}$aryl, 5-12 membered heteroaryl and 3- to 14-membered heterocyclyl;
each R$^{d4}$ is independently selected from among —OR$^{e4}$, SR$^{e4}$—NR$^{e4}$R$^{e4}$, halogen, —CN, —NO$_2$, C(O)R$^{e4}$, —C(O)OR$^{e4}$, —C(O)NR$^{e4}$, —C(O)CR$^{e4}$R$^{e4}$, —C(NR$^{h4}$)NR$^{e4}$R$^{e4}$, —OC(O)R$^{e4}$, —OC(O)OR$^{e4}$, —S(O)$_2$R$^{e4}$, —S(O)$_2$NR$^{e4}$R$^{e4}$, NR$^{h4}$C(O)R$^{e4}$, —NR$^{h4}$C(O)OR$^{e4}$, —NR$^{h4}$C(O)NR$^{e4}$R$^{e4}$, —NR$^{h4}$C(NR$^{h4}$)NR$^{e4}$R$^{e4}$ and —NR$^{h4}$S(O)$_2$R$^{e4}$, as well as the bivalent substituent =O, while the latter may only be a substituent in non-aromatic ring systems;
each R$^{e4}$ independently denotes hydrogen or a group optionally substituted by one or more identical or different R$^{f4}$ and/or R$^{g4}$ selected from among C$_{1-6}$alkyl, C$_{2-6}$alkenyl, C$_{2-6}$alkynyl, C$_{3-10}$cycloalkyl, C$_{4-10}$cycloalkenyl, C$_{6-10}$aryl, 5-12 membered heteroaryl and 3- to 14-membered heterocyclyl;
each R$^{g4}$ is independently selected from among —OR$^{g4}$, —SR$^{g4}$, —NR$^{g4}$R$^{g4}$, halogen, —CN, —NO$_2$, —C(O)R$^{g4}$, —C(O)OR$^{g4}$, —C(O)NR$^{g4}$R$^{g4}$, —C(NR$^{h4}$)NR$^{g4}$R$^{g4}$, —OC(O)R$^{g4}$, —OC(O)OR$^{g4}$, —S(O)$_2$R$^{g4}$, —S(O)$_2$NR$^{g4}$R$^{g4}$, —NR$^{h4}$C(O)R$^{g4}$, —NR$^{h4}$C(O)OR$^{g4}$, —NR$^{h4}$C(O)NR$^{g4}$R$^{g4}$, —NR$^{h4}$C(NR$^{h4}$)NR$^{g4}$R$^{g4}$ and —NR$^{h4}$S(O)$_2$R$^{g4}$, as well as the bivalent substituent =O, while the latter may only be a substituent in non-aromatic ring systems;
each R$^{g4}$ is independently selected from among hydrogen, C$_{1-6}$alkyl, C$_{2-6}$alkenyl, C$_{2-6}$alkynyl, C$_{1-6}$haloalkyl, C$_{3-10}$cycloalkyl, C$_{4-10}$cycloalkylalkyl, C$_{4-10}$cycloalkenyl, C$_{6-10}$aryl, 5-12 membered heteroaryl and 3- to 14-membered heterocyclyl and
each R$^{h4}$ is independently selected from among hydrogen and C$_{1-4}$alkyl.

In another aspect (CD3) the invention relates to compounds (I), wherein

R³ denotes a group

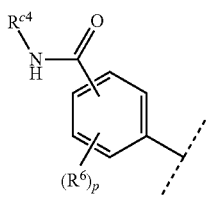

R^{c4}, R^6 and p are as hereinbefore defined.

In another aspect (CD4) the invention relates to compounds (I), wherein
R³ denotes a group

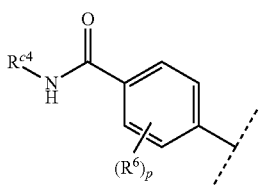

and
R^{c4}, R^6 and p are as hereinbefore defined.

In another aspect (CD5) the invention relates to compounds (I), wherein
R³ denotes a group

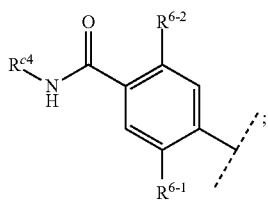

R^{6-1} and R^{6-2} is independently selected from among hydrogen, $C_{1-4}$alkyl, —O—$C_{1-4}$alkyl and halogen and
R^{c4} is as hereinbefore defined.

In further aspects (CD6), (CD7), (CD8) and (CD9) the invention relates to compounds with the structural aspect (CD2), (CD3), (CD4) and (CD5), wherein
R^{c4} denotes hydrogen or a group optionally substituted by one or more identical or different R^{d4} and/or R^{e4} selected from among $C_{1-6}$alkyl, $C_{3-10}$cycloalkyl and 3- to 14-membered heterocyclyl;
each R^{d4} is independently selected from among —OR^{e4}, —NR^{e4}R^{e4}, halogen, —C(O)R^{e4} and —C(O)NR^{e4}R^{e4};
each R^{e4} independently denotes hydrogen or a group optionally substituted by one or more identical or different R^{f4} and/or R^{g4} selected from among $C_{1-6}$alkyl, $C_{3-10}$cycloalkyl and 3- to 14-membered heterocyclyl;
each R^{f4} is independently selected from among —OR^{g4}, —NR^{g4}R^{g4}, halogen, —C(O)R^{g4}, —C(O)NR^{g4}R^{g4} and
each R^{g4} is independently selected from among hydrogen, $C_{1-6}$alkyl, $C_{1-6}$haloalkyl, $C_{3-10}$cycloalkyl, $C_{4-10}$cycloalkylalkyl, $C_{6-10}$aryl and 5-12 membered heteroaryl.

In further aspects (CD10), (CD11), (CD12) and (CD13) the invention relates to compounds with the structural aspect (CD2), (CD3), (CD4) and (CD5), wherein
R^{c4} denotes a group optionally substituted by one or more identical or different R^{d4} and/or R^{e4} selected from among $C_{1-6}$alkyl, cyclopropyl, cyclobutyl, cyclopentyl, cyclohexyl, azetidinyl, pyrrolidinyl, tetrahydropyranyl, 1-aza-bicyclo[2.2.2]octyl, 8-methyl-8-aza-bicyclo[3.2.1]octyl, morpholinyl, piperidinyl and piperazinyl;
each R^{d4} is independently selected from among —OR^{e4}, —NR^{e4}R^{e4}, halogen, —C(O)R^{e4} and —C(O)NR^{e4}R^{e4};
each R^{e4} independently denotes a group optionally substituted by one or more identical or different R^{f4} and/or R^{g4} selected from among $C_{1-6}$alkyl, cyclopropyl, cyclobutyl, cyclopentyl, cyclohexyl, azetidinyl, pyrrolidinyl, tetrahydropyranyl, 1-aza-bicyclo[2.2.2]octyl, 8-methyl-8-aza-bicyclo[3.2.1]octyl, morpholinyl, piperidinyl and piperazinyl;
each R^{f4} is independently selected from among —OR^{g4}, —NR^{g4}R^{g4}, halogen, —C(O)R^{g4}, —C(O)NR^{g4}R^{g4} and
each R^{g4} is independently selected from among hydrogen, $C_{1-6}$alkyl, $C_{1-6}$haloalkyl, cyclopropyl, cyclobutyl, cyclopentyl, cyclohexyl, cyclopropylmethyl, phenyl and 5- to 6-membered heteroaryl.

In further aspects (CD14), (CD15), (CD16) and (CD17) the invention relates to compounds with the structural aspect (CD2), (CD3), (CD4) and (CD5), wherein
R^{c4} is selected from among methyl, methoxyethyl, N,N-dimethyl-ethyl, N,N-dimethyl-propyl,

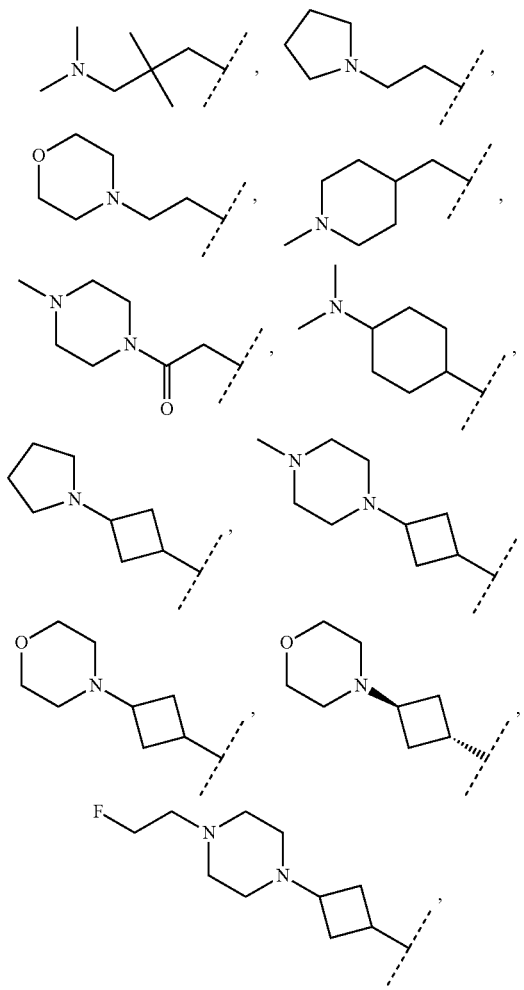

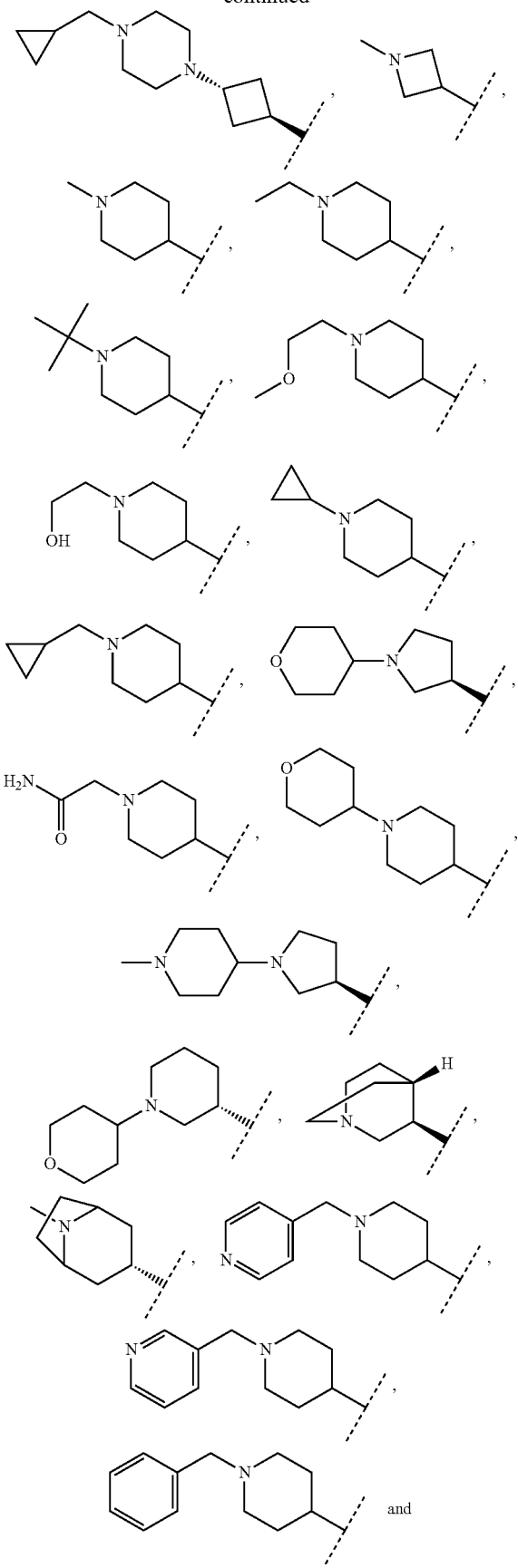

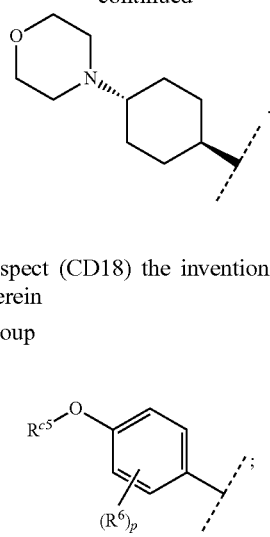

In another aspect (CD18) the invention relates to compounds (I), wherein
$R^3$ denotes a group each $R^6$ is independently selected from among $C_{1-4}$alkyl, —O—$C_{1-4}$alkyl and halogen;

p denotes 0, 1 or 2;

$R^{e5}$ denotes hydrogen or a group optionally substituted by one or more identical or different $R^{d5}$ and/or $R^{e5}$ selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^{d5}$ is independently selected from among —$OR^{e5}$, —$SR^{e5}$, —$NR^{e5}R^{e5}$, halogen, —CN, —$NO_2$, —$C(O)R^{e5}$, —$C(O)OR^{e5}$, —$C(O)NR^{e5}R^{e5}$, —$C(NR^{h5})NR^{e5}R^{e5}$, —$OC(O)R^{e5}$, —$OC(O)OR^{e5}$, —$S(O)_2R^{e5}$, —$S(O)_2NR^{e5}R^{e5}$, —$NR^{h5}C(O)R^{e5}$, —$NR^{h5}C(O)OR^{e5}$, —$NR^{h5}C(O)NR^{e5}R^{e5}$, —$NR^{h5}C(NR^{h5})NR^{e5}R^{e5}$ and —$NR^{h5}S(O)_2R^{e5}$, as well as the bivalent substituent =O, while the latter may only be a substituent in non-aromatic ring systems;

each $R^{e5}$ independently denotes hydrogen or a group optionally substituted by one or more identical or different $R^{f5}$ and/or $R^{g5}$ selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^{f5}$ is independently selected from among —$OR^{g5}$, —$SR^{g5}$, —$NR^{g5}R^{g5}$, halogen, —CN, —$NO_2$, —$C(O)R^{g5}$, —$C(O)OR^{g5}$, —$C(O)NR^{g5}R^{g5}$, —$C(NR^{h5})NR^{g5}R^{g5}$, —$OC(O)R^{g5}$, —$OC(O)OR^{g5}$, —$S(O)_2R^{g5}$, —$S(O)_2NR^{g5}R^{g5}$, —$NR^{h5}C(O)R^{g5}$, —$NR^{h5}C(O)OR^{g5}$, —$NR^{h5}C(O)NR^{g5}R^{g5}$, —$NR^{h5}C(NR^{h5})NR^{g5}R^{g5}$ and —$NR^{h5}S(O)_2R^{g5}$, as well as the bivalent substituent =O, while the latter may only be a substituent in non-aromatic ring systems;

each $R^{g5}$ is independently selected from among hydrogen, $C_{1-6}$alkyl, $C_{2-6}$alkenyl, $C_{2-6}$alkynyl, $C_{1-6}$haloalkyl, $C_{3-10}$cycloalkyl, $C_{4-10}$cycloalkylalkyl, $C_{4-10}$cycloalkenyl, $C_{6-10}$aryl, 5-12 membered heteroaryl and 3- to 14-membered heterocyclyl and each $R^{h5}$ is independently selected from among hydrogen and $C_{1-4}$alkyl.

In another aspect (CD19) the invention relates to compounds (I), wherein $R^3$ denotes a group

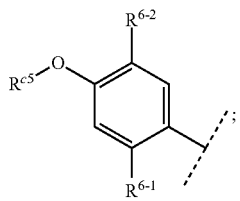

$R^{6-1}$ and $R^{6-2}$ is independently selected from among hydrogen, $C_{1-4}$alkyl, —O—$C_{1-4}$alkyl and halogen and $R^{c5}$ are as hereinbefore defined.

In further aspects (CD20) and (CD21) the invention relates to compounds with the structural aspect (CD18) and (CD19), wherein $R^{c5}$ denotes hydrogen or a group optionally substituted by one or more identical or different $R^{d5}$ and/or $R^{e5}$, selected from among $C_{1-6}$alkyl, $C_{3-10}$cycloalkyl and 3- to 14-membered heterocyclyl;

each $R^{d5}$ is independently selected from among —OR$^{e5}$, —NR$^{e5}$R$^{e5}$, halogen, —C(O)R$^{e5}$ and —C(O)NR$^{e5}$R$^{e5}$ and each $R^{e5}$ is independently selected from among hydrogen, $C_{1-6}$alkyl, $C_{3-10}$cycloalkyl and 3- to 14-membered heterocyclyl.

In further aspects (CD22) and (CD23) the invention relates to compounds with the structural aspect (CD18) and (CD19), wherein $R^{c5}$ denotes a group optionally substituted by one or more identical or different $R^{d5}$ and/or $R^{e5}$ selected from among $C_{1-6}$alkyl and 5- to 6-membered, nitrogen-containing heterocyclyl;

each $R^{d5}$ is independently selected from among —OR$^{e5}$, —NR$^{e5}$R$^{e5}$, halogen, —C(O)R$^{e5}$ and —C(O)NR$^{e5}$R$^{e5}$ and each $R^{e5}$ is independently selected from among $C_{1-6}$alkyl and 5- to 6-membered, nitrogen-containing heterocyclyl.

In further aspects (CD24) and (CD25) the invention relates to compounds with the structural aspect (CD18) and (CD19), wherein $R^{c5}$ is selected from among N,N-dimethylethyl, N,N-dimethyl-propyl,

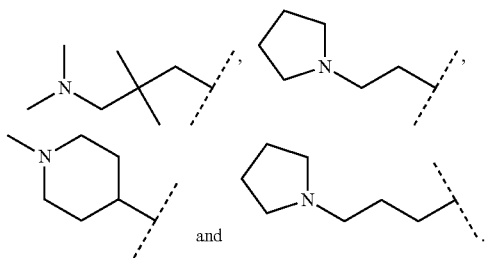

In another aspect (CD26) the invention relates to compounds (I), wherein $R^3$ denotes a group

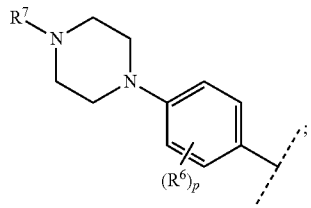

each $R^6$ is independently selected from among $C_{1-4}$alkyl, —O—$C_{1-4}$alkyl and halogen;

$R^7$ is selected from among $R^{b6}$ and $R^{c6}$;

p denotes 0, 1 or 2;

$R^{b6}$ is selected from among —C(O)R$^{c6}$, —C(O)OR$^{c6}$, —C(O)NR$^{c6}$R$^{c6}$, —S(O)$_2$R$^{c6}$ and —S(O)$_2$NR$^{c6}$R$^{c6}$;

each $R^{c6}$ independently denotes hydrogen or a group optionally substituted by one or more identical or different $R^{d6}$ and/or $R^{e6}$ selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^{d6}$ is independently selected from among —OR$^{e6}$, —SR$^{e6}$, —NR$^{e6}$R$^{e6}$, halogen, —CN, —NO$_2$, —C(O)R$^{e6}$, —C(O)OR$^{e6}$, —C(O)NR$^{e6}$R$^{e6}$, —C(NR$^{h6}$)NR$^{e6}$R$^{e6}$, —OC(O)R$^{e6}$, —OC(O)OR$^{e6}$, —S(O)$_2$R$^{e6}$, —S(O)$_2$NR$^{e6}$R$^{e6}$, —NR$^{h6}$C(O)R$^{e6}$, —NR$^{h6}$C(O)OR$^{e6}$, —NR$^{h6}$C(O)NR$^{e6}$R$^{e6}$, —NR$^{h6}$C(NR$^{h6}$)NR$^{e6}$R$^{e6}$ and —NR$^{h6}$S(O)$_2$R$^{e6}$, as well as the bivalent substituent =O, while the latter may only be a substituent in non-aromatic ring systems;

each $R^{e6}$ is independently selected from among hydrogen, $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl, and each $R^{e6}$ is independently selected from among hydrogen and $C_{1-4}$alkyl.

In another aspect (CD27) the invention relates to compounds (I), wherein $R^3$ denotes a group

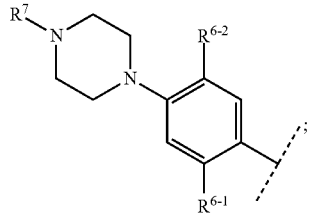

$R^{6-1}$ and $R^{6-2}$ is independently selected from among hydrogen, $C_{1-4}$alkyl, —O—$C_{1-4}$alkyl and halogen and $R^7$ are as hereinbefore defined.

In further aspects (CD28) and (CD29) the invention relates to compounds with the structural aspect (CD26) and (CD27), wherein $R^7$ is selected from among $R^{b6}$ and $R^{c6}$;

$R^{b6}$ is selected from among —C(O)R$^{c6}$, —C(O)NR$^{c6}$R$^{c6}$ and —S(O)$_2$R$^{c6}$;

each $R^{c6}$ independently denotes hydrogen or a group optionally substituted by one or more identical or different $R^{d6}$ and/or $R^{e6}$ selected from among $C_{1-6}$alkyl, $C_{3-6}$cycloalkyl and 5- to 6-membered heterocyclyl;

each $R^{d6}$ is independently selected from among —OR$^{e6}$, —NR$^{e6}$R$^{e6}$, halogen, —C(O)R$^{e6}$ and —C(O)NR$^{e6}$R$^{e6}$ and each $R^{e6}$ is independently selected from among hydrogen, $C_{1-6}$alkyl, $C_{3-6}$cycloalkyl and 5- to 6-membered heterocyclyl.

In another aspect (CD30) the invention relates to compounds (I), wherein
$R^3$ denotes pyrazolyl, which is optionally mono- or disubstituted by $C_{1-4}$alkyl or $C_{3-5}$cycloalkyl.

In another aspect (CD31) the invention relates to compounds (I), wherein
$R^3$ denotes a group

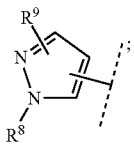

$R^8$ denotes a group optionally substituted by one or more identical or different $R^{b7}$ and/or $R^{c7}$ selected from among $C_{1-6}$alkyl, $C_{3-6}$cycloalkyl and 5- to 7-membered heterocyclyl;
each $R^{b7}$ is independently selected from among —$OR^{c7}$, —$NR^{c7}R^{c7}$, halogen, —$C(O)R^{c7}$ and —$C(O)NR^{c7}R^{c7}$;
each $R^{c7}$ independently denotes hydrogen or a group optionally substituted by one or more identical or different $R^{d7}$ and/or $R^{e7}$ selected from among $C_{1-6}$alkyl, $C_{3-6}$cycloalkyl, 5- to 6-membered heteroaryl and 5- to 7-membered heterocyclyl;
each $R^{d7}$ is independently selected from among —$OR^{e7}$, —$NR^{e7}R^{e7}$, halogen, —$C(O)R^{e7}$ and —$C(O)NR^{e7}R^{e7}$;
each $R^{e7}$ independently denotes hydrogen or a group optionally substituted by one or more identical or different $R^{f7}$ and/or $R^{g7}$ selected from among $C_{1-6}$alkyl, $C_{3-6}$cycloalkyl, 5- to 6-membered heteroaryl and 5- to 7-membered heterocyclyl;
each $R^{f7}$ is independently selected from among —$OR^{g7}$, —$NR^{g7}$—$NR^{g7}R^{g7}$, halogen, —$C(O)R^{g7}$ and —$C(O)NR^{g7}R^{g7}$;
each $R^{g7}$ independently denotes hydrogen or $C_{1-6}$alkyl;
$R^g$ is selected from among hydrogen, $C_{1-4}$alkyl and $C_{3-5}$cycloalkyl.

In another aspect (CD32) the invention relates to compounds (I), wherein
$R^3$ denotes a group

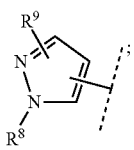

$R^8$ is selected from among $C_{1-4}$alkyl, $C_{3-5}$cycloalkyl, $C_{1-4}$alkoxy-$C_{1-4}$alkyl, ($C_{1-4}$alkyl)NH—$C_{1-4}$alkyl and ($C_{1-4}$alkyl)$_2$N—$C_{1-4}$alkyl;
$R^9$ is selected from among hydrogen, $C_{1-4}$alkyl and $C_{3-5}$cycloalkyl.

All the structural aspects A1 to A6, B1 to B3, C1 to C4, D1 to D3, E1 to E4 and CD1 to CD32 mentioned hereinbefore are preferred embodiments of the respective aspects A0, B0, C0, D0, E0 and CD0, while CD0 is a combination of C0 and D0. The structural aspects A0 to A6, B0 to B3, C0 to C4, D0 to D3, E0 to E4 and CD0 to CD32 with respect to different molecular parts of the compounds (I) according to the invention may be permutated with one another as desired to form ABCDE combinations, thus obtaining preferred compounds (I). Each ABCDE combination represents and defines individual embodiments or generic partial amounts of compounds A0B0C0D0E0 according to the invention. Every individual embodiment or partial quantity defined by this combination is expressly included in and a subject of the invention.

Preferred compounds (I) are:

I-168 (5S)-N-[1-(2-methoxyethyl)pyrazol-3-yl]-5,8-dimethyl-9-phenyl-5,6-dihydropyrazolo[3,4-h]quinazolin-2-amine;

I-194 N-[1-(2-dimethylaminoethyl)pyrazol-3-yl]-5,8-dimethyl-9-phenyl-5,6-dihydropyrazolo[3,4-h]quinazolin-2-amine;

I-201 N-[1-(2-dimethylaminoethyl)pyrazol-3-yl]-8-methyl-9-phenyl-5,6-dihydropyrazolo[3,4-h]quinazolin-2-amine;

I-204 N-[1-(2-methoxyethyl)pyrazol-3-yl]-5,8-dimethyl-9-phenyl-5,6-dihydropyrazolo[3,4-h]quinazolin-2-amine;

I-222 9-[4-(difluoromethoxy)phenyl]-N-[1-(2-dimethylaminoethyl)pyrazol-3-yl]-8-methyl-5,6-dihydropyrazolo[3,4-h]quinazolin-2-amine;

I-271 (5S)-N-[1-(2-methoxyethyl)pyrazol-3-yl]-5,8-dimethyl-9-phenyl-5,6-dihydropyrazolo[3,4-h]quinazolin-2-amine;

I-225 N-[1-(2-methoxyethyl)pyrazol-3-yl]-8-methyl-9-[(3-methylphenyl)methyl]-5,6-dihydropyrazolo[3,4-h]quinazolin-2-amine I-205 1-[4-[4-[[9-[4-(difluoromethoxy)phenyl]-8-methyl-5,6-dihydropyrazolo[3,4-h]quinazolin-2-yl]amino]pyrazol-1-yl]piperidin-1-yl]ethanone;

I-198 N-[1-[2-[2-methoxyethyl(methyl)amino]ethyl]pyrazol-3-yl]-8-methyl-9-phenyl-5,6-dihydropyrazolo[3,4-h]quinazolin-2-amine;

I-197 8-methyl-9-phenyl-N-[1-(2-pyrrolidin-1-ylethyl)pyrazol-3-yl]-5,6-dihydropyrazolo[3,4-h]quinazolin-2-amine;

I-195 N-[1-(2-dimethylaminoethyl)pyrazol-3-yl]-8-methyl-9-(naphthalen-1-ylmethyl)-5,6-dihydropyrazolo[3,4-h]quinazolin-2-amine;

I-193 9-[(2-chlorophenyl)methyl]-N-[1-(2-dimethylaminoethyl)pyrazol-3-yl]-8-methyl-5,6-dihydropyrazolo[3,4-h]quinazolin-2-amine;

I-189 N-[1-(2-dimethylaminoethyl)pyrazol-3-yl]-8-methyl-9-(3-methylthiophen-2-yl)-5,6-dihydropyrazolo[3,4-h]quinazolin-2-amine;

I-187 N-[1-(2-methoxyethyl)pyrazol-3-yl]-8-methyl-9-[(2-methylphenyl)methyl]-5,6-dihydropyrazolo[3,4-h]quinazolin-2-amine;

I-186 1-[4-[4-[(5,8-dimethyl-9-phenyl-5,6-dihydropyrazolo[3,4-h]quinazolin-2-yl)amino]pyrazol-1-yl]piperidin-1-yl]ethanone;

I-185 8-methyl-N-[1-[2-(4-methylpiperazin-1-yl)ethyl]pyrazol-3-yl]-9-phenyl-5,6-dihydropyrazolo[3,4-h]quinazolin-2-amine;

I-171 9-(4-chlorophenyl)-N-[1-(2-methoxyethyl)pyrazol-3-yl]-8-methyl-5,6-dihydropyrazolo[3,4-h]quinazolin-2-amine;

I-166 2-[4-[2-[3-[(8-methyl-9-phenyl-5,6-dihydropyrazolo[3,4-h]quinazolin-2-yl)amino]pyrazol-1-yl]ethyl]piperazin-1-yl]ethanol;

I-167 N-[1-[2-[4-(2-methoxyethyl)piperazin-1-yl]ethyl]pyrazol-3-yl]-8-methyl-9-phenyl-5,6-dihydropyrazolo[3,4-h]quinazolin-2-amine;

I-217 9-[(3-methoxyphenyl)methyl]-8-methyl-N-(1-methylpyrazol-3-yl)-5,6-dihydropyrazolo[3,4-h]quinazolin-2-amine;

I-210 9-[4-(difluoromethoxy)phenyl]-N-[1-(2-methoxyethyl)pyrazol-3-yl]-8-methyl-5,6-dihydropyrazolo[3,4-h]quinazolin-2-amine;

I-208 9-benzyl-N-[1-(2-dimethylaminoethyl)pyrazol-3-yl]-8-methyl-5,6-dihydropyrazolo[3,4-h]quinazolin-2-amine;

I-192 9-[(2-chlorophenyl)methyl]-N-[1-(2-methoxyethyl)pyrazol-3-yl]-8-methyl-5,6-dihydropyrazolo[3,4-h]quinazolin-2-amine;

I-182 8-methyl-9-phenyl-N-[1-(2-piperazin-1-ylethyl)pyrazol-3-yl]-5,6-dihydropyrazolo[3,4-h]quinazolin-2-amine;

I-180 9-(3-chlorothiophen-2-yl)-N-[1-(2-methoxyethyl)pyrazol-3-yl]-8-methyl-5,6-dihydropyrazolo[3,4-h]quinazolin-2-amine;

I-176 1-[4-[4-[[9-(4-methoxyphenyl)-8-methyl-5,6-dihydropyrazolo[3,4-h]quinazolin-2-yl]amino]pyrazol-1-yl]piperidin-1-yl]ethanone;

I-175 N-[1-[2-[4-(dimethylamino)piperidin-1-yl]ethyl]pyrazol-3-yl]-8-methyl-9-phenyl-5,6-dihydropyrazolo[3,4-h]quinazolin-2-amine;

I-181 9-(3-chlorothiophen-2-yl)-N-(1-ethylpyrazol-3-yl)-8-methyl-5,6-dihydropyrazolo[3,4-h]quinazolin-2-amine;

I-202 9-[(2-chlorophenyl)methyl]-N-(1-ethylpyrazol-3-yl)-8-methyl-5,6-dihydropyrazolo[3,4-h]quinazolin-2-amine;

I-224 N-(1-ethylpyrazol-3-yl)-8-methyl-9-[(3-methylphenyl)methyl]-5,6-dihydropyrazolo[3,4-h]quinazolin-2-amine;

I-237 9-[4-(difluoromethoxy)phenyl]-N-(1-ethylpyrazol-3-yl)-8-methyl-5,6-dihydropyrazolo[3,4-h]quinazolin-2-amine;

I-236 9-[4-(difluoromethoxy)phenyl]-N-[1-(2-dimethylaminoethyl)pyrazol-4-yl]-8-methyl-5,6-dihydropyrazolo[3,4-h]quinazolin-2-amine;

I-30 9-(2-chlorophenyl)-N-(1-ethylpyrazol-3-yl)-8-methyl-5,6-dihydropyrazolo[3,4-h]quinazolin-2-amine;

I-112 4-[[9-(2-chlorophenyl)-8-methyl-5,6-dihydropyrazolo[3,4-h]quinazolin-2-yl]amino]-3-methoxy-N-(1-methylpiperidin-4-yl)benzamide;

I-40 9-(2-chlorophenyl)-5,8-dimethyl-N-(1-propane-2-ylpyrazol-3-yl)-5,6-dihydropyrazolo[3,4-h]quinazolin-2-amine;

I-42 9-(2-chlorophenyl)-5,8-dimethyl-N-(1-methylpyrazol-3-yl)-5,6-dihydropyrazolo[3,4-h]quinazolin-2-amine;

I-97 9-(2-chlorophenyl)-N-[2-methoxy-4-(4-methylpiperazin-1-yl)phenyl]-5,8-dimethyl-5,6-dihydropyrazolo[3,4-h]quinazolin-2-amine;

I-157 4-[[9-(2-chlorophenyl)-5,8-dimethyl-5,6-dihydropyrazolo[3,4-h]quinazolin-2-yl]amino]-3-methoxy-N-(1-methylpiperidin-4-yl)benzamide;

II-8 4-[[9-(2-chlorophenyl)-5,8-dimethyl-5,6-dihydropyrazolo[3,4-h]quinazolin-2-yl]amino]-3-methoxybenzoic acid;

The present invention further relates to hydrates, solvates, polymorphs, metabolites, derivatives and prodrugs of compounds of general formula (I).

In another aspect the invention relates to compounds of general formula (I)—or the pharmaceutically acceptable salts thereof—as medicaments.

In another aspect the invention relates to compounds of general formula (I)—or the pharmaceutically acceptable salts thereof—for use in the treatment and/or prevention of cancer, infections, inflammations and autoimmune diseases.

In another aspect the invention relates to compounds of general formula (I)—or the pharmaceutically acceptable salts thereof—for use in the treatment and/or prevention of cancer.

In another aspect the invention relates to compounds of general formula (I)—or the pharmaceutically acceptable salts thereof—for use in the treatment and/or prevention of non-small-cell lung cancers (NSCLC) and hepatocellular carcinomas (HCC).

In another aspect the invention relates to a method for the treatment and/or prevention of cancer comprising administering a therapeutically effective amount of a compound of general formula (I)—or one of the pharmaceutically acceptable salts thereof—to a human.

In another aspect the invention relates to a pharmaceutical preparation containing as active substance one or more compounds of general formula (I)—or the pharmaceutically acceptable salts thereof—optionally in combination with conventional excipients and/or carriers.

In another aspect the invention relates to a pharmaceutical preparation comprising a compound of general formula (I)—or one of the pharmaceutically acceptable salts thereof—and at least one further cytostatic or cytotoxic active substance, different from formula (I).

Definitions

Terms that are not specifically defined here have the meanings that are apparent to the skilled man in the light of the overall disclosure and the context as a whole.

As used herein, the following definitions apply, unless stated otherwise:

The use of the prefix $C_{x-y}$, wherein x and y each represent a natural number (x<y), indicates that the chains or ring structure or combination of chains and ring structure as a whole, specified and mentioned in direct association, may consist of a maximum of y and a minimum of x carbon atoms.

The indication of the number of members in groups that contain one or more heteroatom(s) (heteroalkyl, heteroaryl, heteroarylalkyl, heterocyclyl, heterocyclylalkyl) relates to the total atomic number of all the ring members or chain members or the total of all the ring and chain members.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$-alkyl" includes for example $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

Further examples of alkyl are methyl (Me; $-CH_3$), ethyl (Et; $-CH_2CH_3$), 1-propyl (n-propyl; n-Pr; $-CH_2CH_2CH_3$), 2-propyl (i-Pr; iso-propyl; $-CH(CH_3)_2$), 1-butyl (n-butyl; n-Bu; $-CH_2CH_2CH_2CH_3$), 2-methyl-1-propyl (iso-butyl; i-Bu; $-CH_2CH(CH_3)_2$), 2-butyl (sec-butyl; sec-Bu; $-CH(CH_3)CH_2CH_3$), 2-methyl-2-propyl (tert-butyl; t-Bu; $-C(CH_3)_3$), 1-pentyl (n-pentyl; $-CH_2CH_2CH_2CH_2CH_3$), 2-pentyl ($-CH(CH_3)CH_2CH_2CH_3$), 3-pentyl ($-CH(CH_2CH_3)_2$), 3-methyl-1-butyl (iso-pentyl; $-CH_2CH_2CH(CH_3)_2$), 2-methyl-2-butyl ($-C(CH_3)_2CH_2CH_3$), 3-methyl-2-butyl ($-CH(CH_3)CH(CH_3)_2$), 2,2-dimethyl-1-propyl (neo-pentyl; $-CH_2C(CH_3)_3$), 2-methyl-1-butyl ($-CH_2CH(CH_3)CH_2CH_3$), 1-hexyl (n-hexyl; $-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 2,3-dimethyl-1-butyl (—CH$_2$CH(CH$_3$)CH(CH$_3$)CH$_3$), 2,2-dimethyl-1-butyl (—CH$_2$C(CH$_3$)$_2$CH$_2$CH$_3$), 3,3-dimethyl-1-butyl (—CH$_2$CH$_2$C(CH$_3$)$_3$), 2-methyl-1-pentyl (—CH$_2$CH(CH$_3$)CH$_2$CH$_2$CH$_3$), 3-methyl-1-pentyl (—CH$_2$CH$_2$CH(CH$_3$)CH$_2$CH$_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another group such as for example C$_{x-y}$-alkylamino or C$_{x-y}$-alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —CH$_3$ and —CH$_2$—, —CH$_2$CH$_3$ and —CH$_2$CH$_2$— or >CHCH$_3$ etc.

The term "C$_{1-4}$-alkylene" includes for example —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)- and —C(CH$_3$)(CH$_2$CH$_3$)—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene. The above definition for alkylene also applies if alkylene is part of another group such as for example in HO—C$_{x-y}$-alkylenamino or H$_2$N—C$_{x-y}$-alkylenoxy.

Unlike alkyl, alkenyl consists of at least two carbon atoms, wherein at least two adjacent carbon atoms are joined together by a C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexa-dienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another group such as for example in C$_{x-y}$-alkenylamino or C$_{x-y}$-alkenyloxy.

Unlike alkylene, alkenylene consists of at least two carbon atoms, wherein at least two adjacent carbon atoms are joined together by a C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another group as in for example HO—C$_{x-y}$-alkenylenamino or H$_2$N—C$_{x-y}$-alkenylenoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another group, as in C$_{x-y}$-alkynylamino or C$_{x-y}$-alkynyloxy, for example.

Unlike alkylene, alkenylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another group, as in HO—$C_{x-y}$-alkynyleneamino or $H_2N$—$C_{x-y}$-alkynyleneoxy, for example.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —Cl=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenyl, haloalkynyl), unlike haloalkyl, is bivalent and requires two binding partners. Formally, the second valency is formed by removing a hydrogen atom from a haloalkyl.

Corresponding groups are for example —$CH_2F$ and —CHF—, —$CHFCH_2F$ and —CHFCHF— or >$CFCH_2F$ etc.

The above definitions also apply if the corresponding halogen groups are part of another group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings a carbon atom (spiroatom) belongs to two rings together. If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthalene), bicyclo[2.2.1]heptyl (norbornyl), bicyclo[4.1.0]heptyl (norcaranyl), bicyclo-[3.1.1]heptyl (pinanyl), spiro[2.5]octyl, spiro[3.3]heptyl etc.

The above definition for cycloalkyl also applies if cycloalkyl is part of another group as in $C_{x-y}$-cycloalkylamino or $C_{x-y}$-cycloalkyloxy, for example.

If the free valency of a cycloalkyl is saturated, then an alicyclic group is obtained. The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl.

Corresponding groups are for example

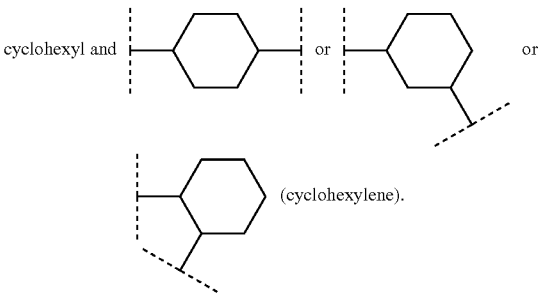

cyclohexyl and    or    or (cyclohexylene).

The above definition for cycloalkylene also applies if cycloalkylene is part of another group as in HO—$C_{x-y}$-cycloalkyleneamino or $H_2N$—$C_{x-y}$-cycloalkyleneoxy, for example.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained. If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4.5]dec-2-ene etc.

The above definition for cycloalkenyl also applies when cycloalkenyl is part of another group as in $C_{x-y}$-cycloalkenylamino or $C_{x-y}$-cycloalkenyloxy, for example.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally the second valency is obtained by removing a hydrogen atom from a cycloalkenyl. Corresponding groups are for example

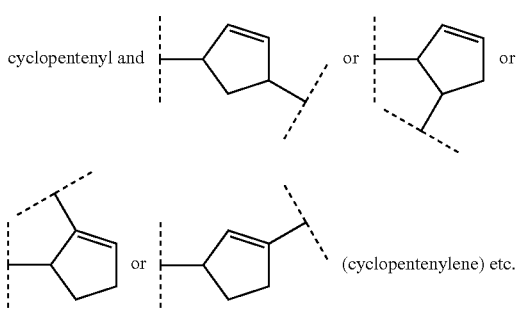

The above definition for cycloalkenylene also applies when cycloalkenylene is part of another group as in HO—$C_{x-y}$-cycloalkenyleneamino or $H_2N$—$C_{x-y}$-cycloalkenyleneoxy, for example.

Aryl denotes a mono-, bi- or tricyclic group with at least one aromatic carbocycle. Preferably it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated. If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies when aryl is part of another group as in arylamino or aryloxy, for example.

If the free valency of an aryl is saturated, then an aromatic croup is obtained.

The term arylene can also be derived from the previously defined aryl. Arylene, unlike aryl, is bivalent and requires two binding partners. Formally, the second valency is formed by removing a hydrogen atom from an aryl. Corresponding groups are e.g.

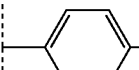

The above definition for arylene also applies when arylene is part of another group as in HO-aryleneamino or $H_2N$-aryleneoxy for example.

Heterocyclyl denotes ring systems, which are derived from the previously defined cycloalkyl, cycloalkenyl and aryl by replacing one or more of the groups —$CH_2$-independently of one another in the hydrocarbon rings by the groups —O—, —S— or —NH— or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO—, sulphone —$SO_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form. By unsaturated is meant that there is at least one double bond in the ring system in question, but no heteroaromatic system is formed. In bicyclic heterorings two rings are linked together so that they have at least two (hetero)atoms in common. In spiro-heterorings a carbon atom (spiroatom) belongs to two rings together. If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-5-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-5-oxide, tetrahydrothienyl-S,S-dioxide, homothiomorpholinyl-5-oxide, 2,3-dihydroazet, 2H-pyrrolyl, 4H-pyranyl, 1,4-dihydropyridinyl, 8-azabicyclo[3.2.1]octyl, 8-azabicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo-[2.2.1]heptyl, 1-aza-bicyclo[2.2.2]octyl, 3,8-diaza-bicyclo [3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro [5.5]undecyl, 2,8-diaza-spiro[4.5]decyl etc.

Further examples are the structures illustrated below, which may be attached via each hydrogen-carrying atom (exchanged for hydrogen):

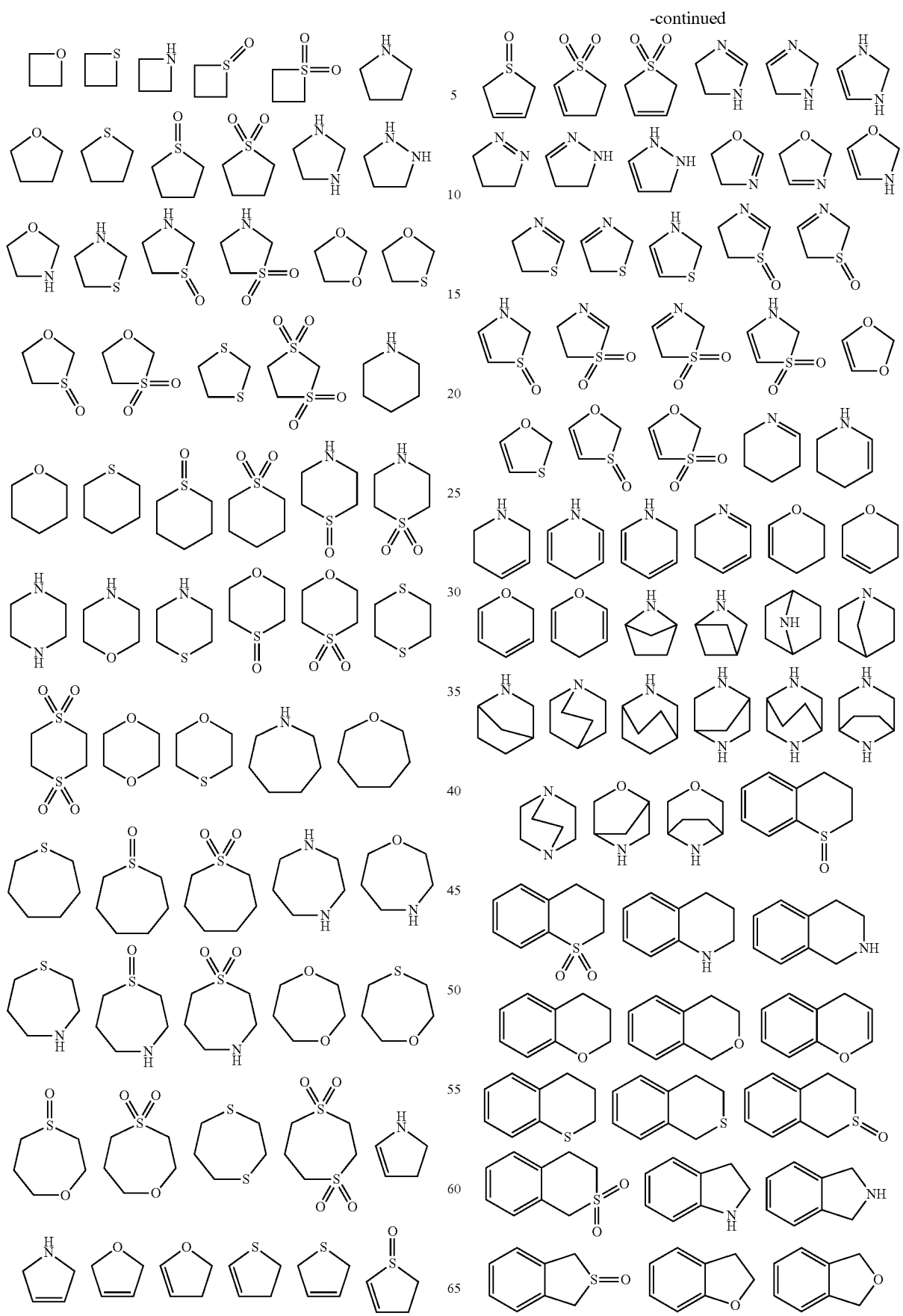

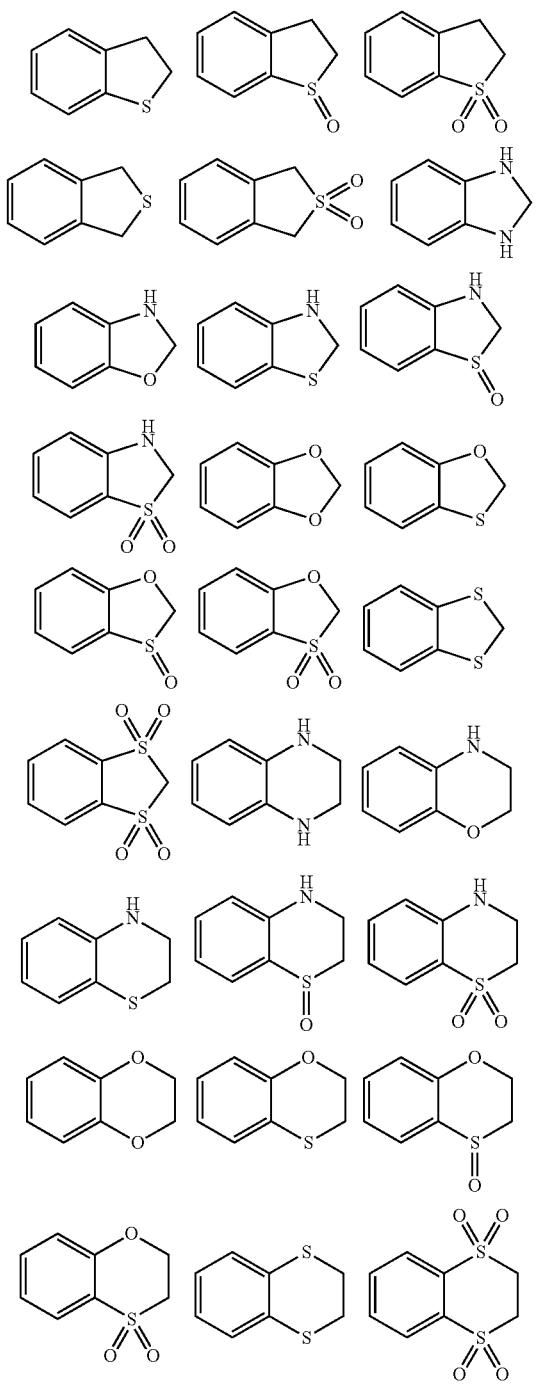

The above definition of heterocyclyl also applies if heterocyclyl is part of another group as in heterocyclylamino or heterocyclyloxy for example.

If the free valency of a heterocyclyl is saturated, then a heterocyclic croup is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example The above definition of heterocyclylene also applies if heterocyclylene is part of another group as in HO-heterocyclyleneamino or H$_2$N-heterocyclyleneoxy for example.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system. If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

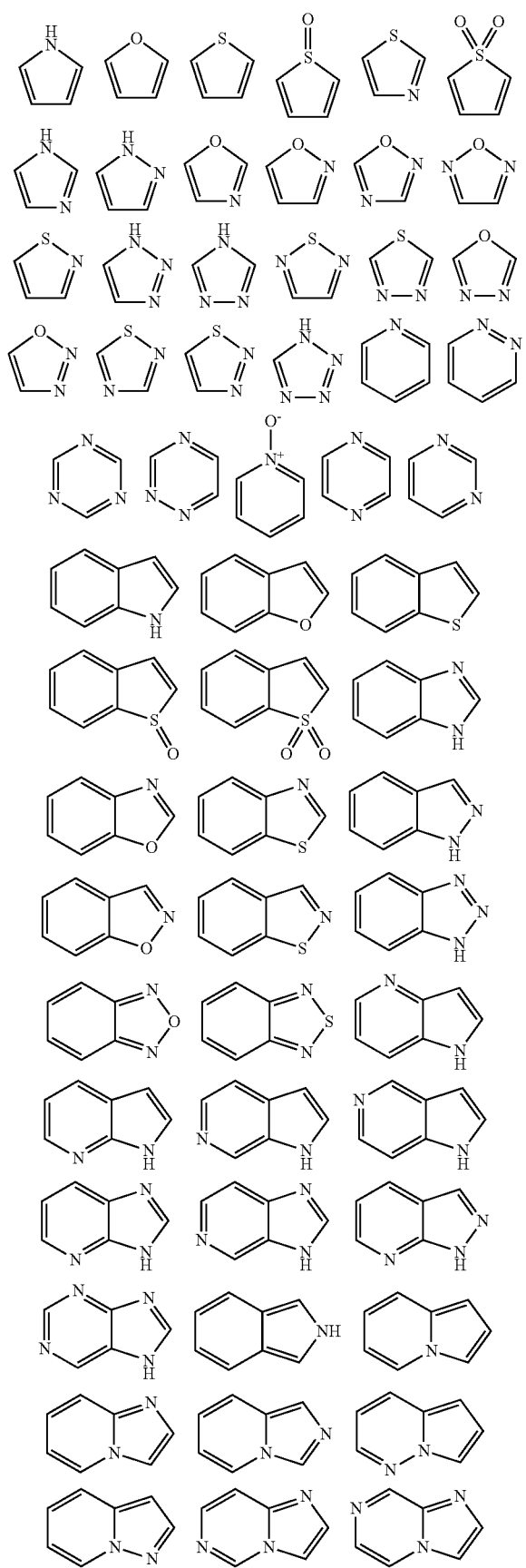

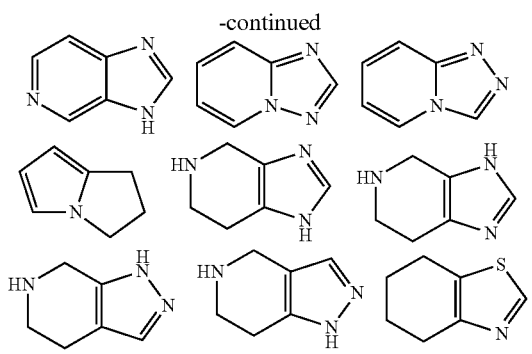

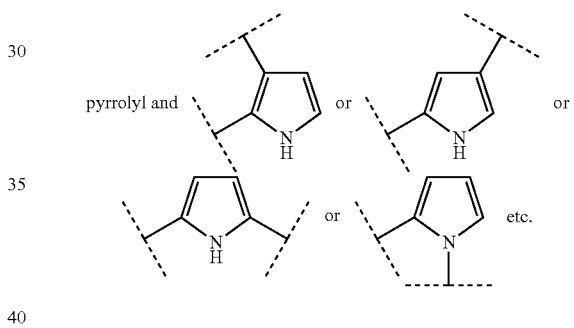

The above definition of heteroaryl also applies when heteroaryl is part of another group as in heteroarylamino or heteroaryloxy, for example.

If the free valency of a heteroaryl is saturated, a heteroaromatic croup is obtained.

The term heteroarylene can therefore be derived from the previously defined heteroaryl. Heteroarylene, unlike heteroaryl, is bivalent and requires two binding partners. Formally, the second valency is obtained by removing a hydrogen atom from a heteroaryl.

Corresponding groups are for example

The above definition of heteroarylene also applies when heteroarylene is part of another group as in HO-heteroaryleneamino or $H_2N$-heteroaryleneoxy, for example.

The above-mentioned bivalent groups (alkylene, alkenylene, alkynylene etc.) may also be a part of composite groups (e.g. $H_2N$—$C_{1-4}$alkylene or HO—$C_{1-4}$alkylene-). In this case one of the valencies is saturated by the attached group (in this case: —$NH_2$, —OH), so that a composite group of this kind in this nomenclature amounts in total to only a monovalent substituent.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =$N_2$ or the like, may only be substituents at carbon atoms, wherein the bivalent substituent =O may also be a substituent at sulphur. Generally, substitution may be carried out by a bivalent substituent only at ring systems and requires replacement by two geminal hydrogen atoms, i.e. hydrogen atoms that are bound to the same carbon atom that is saturated prior to the substitution. Substitution by a bivalent substituent is therefore only possible at the group —CH$_2$— or sulphur atoms of a ring system.

Stereochemistry/Solvates/Hydrates: Unless stated otherwise a structural formula given in the description or in the claims or a chemical name refers to the corresponding compound itself, but also encompasses the tautomers, stereoisomers, optical and geometric isomers (e.g. enantiomers, diastereomers, E/Z isomers, etc.), racemates, mixtures of separate enantiomers in any desired combinations, mixtures of diastereomers, mixtures of the forms mentioned hereinbefore (if such forms exist) as well as salts, particularly pharmaceutically acceptable salts thereof. The compounds and salts according to the invention may be present in solvated form (e.g. with pharmaceutically acceptable solvents such as e.g. water, ethanol etc.) or in unsolvated form. Generally, for the purposes of the present invention the solvated forms, e.g. hydrates, are to be regarded as of equal value to the unsolvated forms.

Salts: The term "pharmaceutically acceptable" is used herein to denote compounds, materials, compositions and/or formulations which are suitable, according to generally recognised medical opinion, for use in conjunction with human and/or animal tissue and do not have or give rise to any excessive toxicity, irritation or immune response or lead to other problems or complications, i.e. correspond overall to an acceptable risk/benefit ratio. The term "pharmaceutically acceptable salts" relates to derivatives of the chemical compounds disclosed in which the parent compound is modified by the addition of acid or base. Examples of pharmaceutically acceptable salts include (without being restricted thereto) salts of mineral or organic acids in relation to basic functional groups such as for example amines, alkali metal or organic salts of acid functional groups such as for example carboxylic acids, etc. These salts include in particular acetate, ascorbate, benzenesulphonate, benzoate, besylate, bicarbonate, bitartrate, bromide/hydrobromide, Ca-edetate/edetate, camsylate, carbonate, chloride/hydrochloride, citrate, edisylate, ethane disulphonate, estolate, esylate, fumarate, gluceptate, gluconate, glutamate, glycolate, glycollylarsnilate, hexylresorcinate, hydrabamine, hydroxymaleate, hydroxynaphthoate, iodide, isothionate, lactate, lactobionate, malate, maleate, mandelate, methanesulphonate, mesylate, methylbromide, methylnitrate, methylsulphate, mucate, napsylate, nitrate, oxalate, pamoate, pantothenate, phenyl acetate, phosphate/diphosphate, polygalacturonate, propionate, salicylate, stearate, subacetate, succinate, sulphamide, sulphate, tannate, tartrate, teoclate, toluenesulphonate, triethiodide, ammonium, benzathine, chloroprocaine, choline, diethanolamine, ethylenediamine, meglumin and procaine. Other pharmaceutically acceptable salts may be formed with cations of metals such as aluminium, calcium, lithium, magnesium, potassium, sodium, zinc, etc. (cf. also Pharmaceutical salts, Birge, S. M. et al., J. Pharm. Sci., (1977), 66, 1-19).

The pharmaceutically acceptable salts of the present invention may be prepared starting from the parent compound which carries a basic or acidic functionality, by conventional chemical methods. Generally, such salts may be synthesised by reacting the free acid or base form of these compounds with a sufficient amount of the corresponding base or acid in water or an organic solvent such as for example ether, ethyl acetate, ethanol, isopropanol, acetonitrile (or mixtures thereof).

Salts of acids other than those mentioned above, which are useful for example for purifying or isolating the compounds from the reaction mixtures (e.g. trifluoroacetates), are also to be regarded as part of the invention.

In a representation such as for example

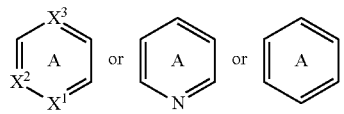

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets, where necessary for clarification purposes, as in the following representations:

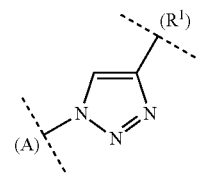

or (R$^2$)—C(O)NH— or (R$^2$)—NHC(O)—;

Groups or substituents are frequently selected from among a number of alternative groups/substituents with a corresponding group designation (e.g. R$^a$, R$^b$ etc). If such a group is used repeatedly to define a compound according to the invention in different molecular parts, it must always be borne in mind that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

| List of abbreviations | |
|---|---|
| aa | amino acid |
| Ac | acetyl |
| equiv. | equivalent(s) |
| Ar | aryl |
| ATP | adenosine triphosphate |
| Boc | tert-butyloxycarbonyl |
| BSA | bovine serum albumin |
| Bu | butyl |
| d | day(s) |
| TLC | thin layer chromatography |
| DCC | dicyclohexylcarbodiimide |
| DCM | dichloromethane |
| DEA | diethylamine |
| DIC | diisopropylcarbodiimide |
| DIPEA | N-ethyl-N,N-diisopropylamine (HÜNIG-base) |
| DMA | N,N-dimethylacetamide |
| DMAP | 4-dimethylaminopyridine |
| DMF | N,N-dimethylformamide |
| DMF-DMA | N,N-dimethylformamide-dimethylacetal |
| DMSO | dimethylsulphoxide |
| dppf | 1,1'-bis(diphenylphosphino)ferrocene |
| EDC | N-(3-dimethylaminopropyl)-N4-ethylcarbodiimide hydrochloride |
| ESI | electron spray ionization |
| Et | ethyl |
| EtOH | ethanol |
| h | hour(s) |
| HATU | O-(7-azabenzotriazol-1-yl)-N,N,N',N'-tetramethyluronium hexafluorophosphate |
| HCl | hydrochloric acid |
| het | hetero |
| HPLC | high performance liquid chromatography |

List of abbreviations

| | |
|---|---|
| HÜNIG base | N-ethyl-N,N-diisopropylamine |
| i | iso |
| iPr$_2$NEt | diisopropylethylamine (HÜNIG base) |
| iPrOH | isopropanol |
| cat. | catalyst, catalytic |
| conc. | concentrated |
| LC | liquid chromatography |
| sln. | solution |
| M | molar |
| Me | methyl |
| MeOH | methanol |
| min | minute(s) |
| mL | millilitres |
| MPLC | medium pressure liquid chromatography |
| MS | mass spectrometry |
| MW | microwave |
| N | normal |
| NMP | N-methylpyrrolidinone |
| PBS | phosphate-buffered saline |
| Pd-dppf | 1,1'-bis(diphenylphosphino)ferrocene palladium(II)-dichloride dichloromethane |
| Ph | phenyl |
| PK | pharmacokinetics |
| Pr | propyl |
| R$_f$(Rf) | retention factor |
| RP | reversed phase |
| RT | ambient temperature |
| s | second(s) |
| TBTU | O-(benzotriazol-1-yl)-N,N,N',N'-tetramethyl-uronium tetrafluoroborate |
| TEA | triethylamine |
| tert | tertiary |
| Tf | triflate |
| TFA | trifluoroacetic acid |
| THF | tetrahydrofuran |
| TMS | trimethylsilyl |
| Tos | tosyl |
| t$_{Ret.}$ | retention time (HPLC) |
| TRIS | tris(hydroxymethyl)-aminomethane |
| UV | ultraviolet |

Features and advantages of the present invention will become apparent from the following detailed Examples, which illustrate the fundamentals of the invention by way of example, without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds are named according to the Beilstein rules using the Autonom software (Beilstein). If a compound is to be represented both by a structural formula and by its nomenclature, in the event of a conflict the structural formula is decisive.

Microwave reactions are carried out in an initiator/reactor made by Biotage or Synthos 3000 and Monowave 300 made by the company Anton Paar in sealed containers (preferably 2, 5 or 20 mL), preferably with stirring.

Chromatography

Thin layer chromatography is carried out on ready-made TLC plates of silica gel 60 on glass (with fluorescence indicator F-254) made by Merck.

The preparative high pressure chromatography (HPLC) of the example compounds according to the invention is carried out with columns made by Waters (names: Sunfire C18, 5 μm, 30×100 mm Part. No. 186002572; X-Bridge C18, 5 μm, 30×100 mm Part. No. 186002982).

The compounds are eluted using either different gradients of H$_2$O/acetonitrile or H$_2$O/MeOH, wherein preferably 0.1% HCOOH is added to the water (acid conditions). For chromatography under basic conditions H$_2$O/acetonitrile gradients are also used, and the water is made basic according to the following recipe: 5 mL of an ammonium hydrogen carbonate solution (158 g to 1 L H$_2$O) and 2 mL ammonia (7M in MeOH) are made up to 1 L with H$_2$O.

The normal-phase preparative high pressure chromatography (HPLC) of the example compounds according to the invention is carried out with columns made by Macherey & Nagel (name: Nucleosil, 50-7, 40×250 mm) and VDSoptilab (name: Kromasil 100 NH$_2$, 10 μM, 50×250 mm). The compounds are eluted using different gradients of DCM/MeOH, with 0.1% NH$_3$ added to the MeOH.

The analytical HPLC (reaction monitoring) of intermediate compounds is carried out with columns made by Agilent, Waters and Phenomenex. The analytical equipment is also provided with a mass detector in each case.

HPLC Mass Spectroscopy/UV Spectrometry

The retention times/MS-ESI$^+$ for characterising the example compounds according to the invention are produced using an HPLC-MS apparatus (high performance liquid chromatography with mass detector) made by Agilent. Compounds that elute at the injection peak are given the retention time t$_{Ret.}$=0.00.

HPLC-Methods

Preparative prep. HPLC1
  HPLC: 333 and 334 Pumps
  Column: Waters X-Bridge C18, 5 μm, 30×100 mm, Part. No. 186002982
  Eluant: A: 10 mM NH$_4$HCO$_3$ in H$_2$O; B: acetonitrile (HPLC grade)
  Detection: UV/Vis-155
  Flow: 50 mL/min
  Gradient: 0.00 min: 5% B
    3.00-15.00 min: variable (see individual methods)
    15.00-17.00 min: 100% B prep. HPLC2
  HPLC: 333 and 334 Pumps
  Column: Waters Sunfire C18, 5 μm, 30×100 mm, Part. No. 186002572
  Eluant: A: H$_2$O+0.2% HCOOH; B: acetonitrile (HPLC grade)+0.2% HCOOH
  Detection: UV/Vis-155
  Flow: 50 mL/min
  Gradient: 0.00 min: 5% B
    3.00-15.00 min: variable (see individual methods)
    15.00-17.00 min: 100% B Analytical Method A

| | |
|---|---|
| HPLC | Agilent 1100 Series |
| MS | 1100 Series LC/MSD SL (MM-ES + APCI, +3000 V, Quadrupol, G1956B) |
| MSD signal settings | Scan pos 120-750 |
| column | Waters, XBridge, C18, 3.5 μm, 135 Å, 30 × 2.1 mm column, Part. No: 186003020 |
| eluant | A: 5 mM NH$_4$HCO$_3$/20 mM NH$_3$ (pH = 9.5) B: acetonitrile (HPLC grade) |
| detection signal | UV 254/214 nm (bandwidth 8, reference off) |
| spectrum | range: 190-400 nm; step: 2.0 nm |

-continued

| | |
|---|---|
| peak width | >00025 min (0.05 s) |
| injection | 2 µL standard injection |
| flow | 1.0 mL/min |
| column temperature | 35° C. |
| gradient | 0.0-1.0 min 15% → 95% B |
| | 1.0-1.6 min 95% B |
| | 1.6-1.7 min 95% → 15% B |
| | 1.7-2.3 min 15% B |

Method B

| | |
|---|---|
| HPLC | Agilent 1100 Series |
| MS | 1100 Series LC/MSD SL (MM-ES + APCI, +3000 V, Quadrupol, G1956B) |
| MSD signal settings | Scan pos 120-750 |
| column | Waters, XBridge, C18, 3.5 µm, 135 Å, 30 × 2.1 mm column, Part. No.: 186003020 |
| eluant | A: 5 mM NH$_4$HCO$_3$/20 mM NH$_3$ (pH = 9.5) B: MeOH (HPLC grade) |
| detection signal | UV 254/214 nm (bandwidth 8, reference off) |
| spectrum | range: 190-400 nm; step: 2.0 nm |
| peak width | >00025 min (0.05 s) |
| injection | 2 µL standard injection |
| flow | 1.0 mL/min |
| column temperature | 40° C. |
| gradient | 0.0-1.0 min 20% → 95% B |
| | 1.0-2.0 min 95% B |
| | 2.0-2.1 min 95% → 20% B |
| | 2.1-2.3 min 20% B |

Method C

| | |
|---|---|
| HPLC | Agilent 1100 Series |
| MS | 1200 Series LC/MSD (API-ES + 3000 V, Quadrupol, G6140A) |
| MSD signal settings | Scan pos 150-750 |
| column | Agilent. Zorbax SB, C8, 3.5 µm, 80 Å, 50 × 2.1 mm column, Part. No.: 871700-906 |
| eluant | A: water + 0.11% formic acid B: acetonitrile (HPLC grade) + 0.1% formic acid |
| detection signal | UV 254/214/230 nm (bandwidth 8, reference off) |
| spectrum | range: 190-450 nm; step: 4.0 nm |
| peak width | >0.01 min (0.2 s) |
| injection | 1.5 µL standard injection |
| flow | 1.1 mL/min |
| column temperature | 45° C. |
| gradient | 0.0-1.75 min 15% → 95% B |
| | 1.75-1.9 min 95% B |
| | 1.9-1.92 min 95% → 15% B |
| | 1.92-2.1 min 15% B |

Method D

| | |
|---|---|
| HPLC | Agilent 1100 Series |
| MS | 1100 Series LC/MSD SL (MM-ES + APCI, +2500 V, Quadrupol, G1956B) |
| MSD signal settings | Scan pos 70-500 |
| column | Agilent Zorbax SB, C8, 3.5 µm, 80 Å, 50 × 2.1 mm column, Part. No.: 871700-906 |
| eluant | A: water + 0.11% formic acid B: MeOH (HPLC grade) |
| detection signal | UV 254/214/230 nm (bandwidth 8, reference off) |
| spectrum | range: 190-450 nm; step: 4.0 nm |
| peak width | >0.01 min (0.2 s) |

-continued

| | |
|---|---|
| injection | 1.5 µL standard injection |
| flow | 1.0 mL/min |
| column temperature | 45° C. |
| gradient | 0.0-1.5 min 20% → 95% B |
| | 1.5-2.1 min 95% B |
| | 2.1-2.2 min 95% → 20% B |
| | 2.2-2.4 min 20% B |

Method E

| | |
|---|---|
| HPLC | Agilent 1100 Series |
| MS | 1100 Series LC/MSD SL (MM-ES + APCI, +3000 V, Quadrupol, G1956B) |
| MSD signal settings | Scan pos 100-750 |
| column | Waters, XBridge, C18, 3.5 µm, 135 Å, 30 × 2.1 mm column, Part. No.: 186003020 |
| eluant | A: 5 mM NH$_4$HCO$_3$/20 mM NH$_3$ (pH = 9.5) B: acetonitrile (HPLC grade) |
| detection signal | UV 254/214 nm (bandwidth 8, reference off) |
| spectrum | range: 190-400 nm; step: 2.0 nm |
| peak width | >0005 min (0.1 s) |
| injection | 2 µL standard injection |
| flow | 1.0 mL/min |
| column temperature | 35° C. |
| gradient | 0.0-1.0 min 15% → 95% B |
| | 1.0-1.6 min 95% B |
| | 1.6-1.7 min 95% → 15% B |
| | 1.7-2.3 min 15% B |

Method F

| | |
|---|---|
| HPLC | Agilent 1100 Series |
| MS | 1200 Series LC/MSD (API-ES + 2500 V, Quadrupol, G6140A) |
| MSD signal settings | Scan pos 75-500 |
| column | Agilent Zorbax SB, C8, 3.5 µm, 80 Å, 50 × 2.1 mm column, Part. No.: 871700-906 |
| eluant | A: water + 0.11% formic acid B: acetonitrile (HPLC grade) + 0.1% formic acid |
| detection signal | UV 254/214/230 nm (bandwidth 8, reference off) |
| spectrum | range: 190-450 nm; step: 4.0 nm |
| peak width | >0.01 min (0.2 s) |
| injection | 1.5 µL standard injection |
| flow | 1.1 mL/min |
| column temperature | 45° C. |
| gradient | 0.0-1.75 min 15% → 95% B |
| | 1.75-1.9 min 95% B |
| | 1.9-1.92 min 95% → 15% B |
| | 1.92-2.1 min 15% B |

Method G

| | |
|---|---|
| HPLC | Agilent 1100 Series |
| MS | 1100 Series LC/MSD (API-ES +/− 3000 V, Quadrupol, G1946D) |
| MSD signal settings | Scan pos 120-900, Scan neg 120-900 |
| column | phenomenex; Part. No. 00M-4439-BO-CE; Gemini 3 µm, C18, 110 Å; 20 × 2.0 mm column |
| eluant | A: 5 mM NH$_4$HCO$_3$/20 mM NH$_3$ (pH = 9.5) B: acetonitrile (HPLC grade) |
| detection signal | UV 254 nm (bandwidth 1, reference off) |
| spectrum | range: 250-400 nm; step: 1 nm |
| peak width | <0.01 min (0.1 s) |

-continued

| | | |
|---|---|---|
| injection | 10 µL standard injection | |
| flow | 1.0 mL/min | |
| column temperature | 40° C. | |
| gradient | 0.0-2.5 min | 5% → 95% B |
| | 2.5-2.8 min | 95% B |
| | 2.8-3.1 min | 95% → 5% B |

The compounds according to the invention are prepared by the methods of synthesis described hereinafter, in which the substituents of the general formulae have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

General formula scheme and summary of the synthesis route

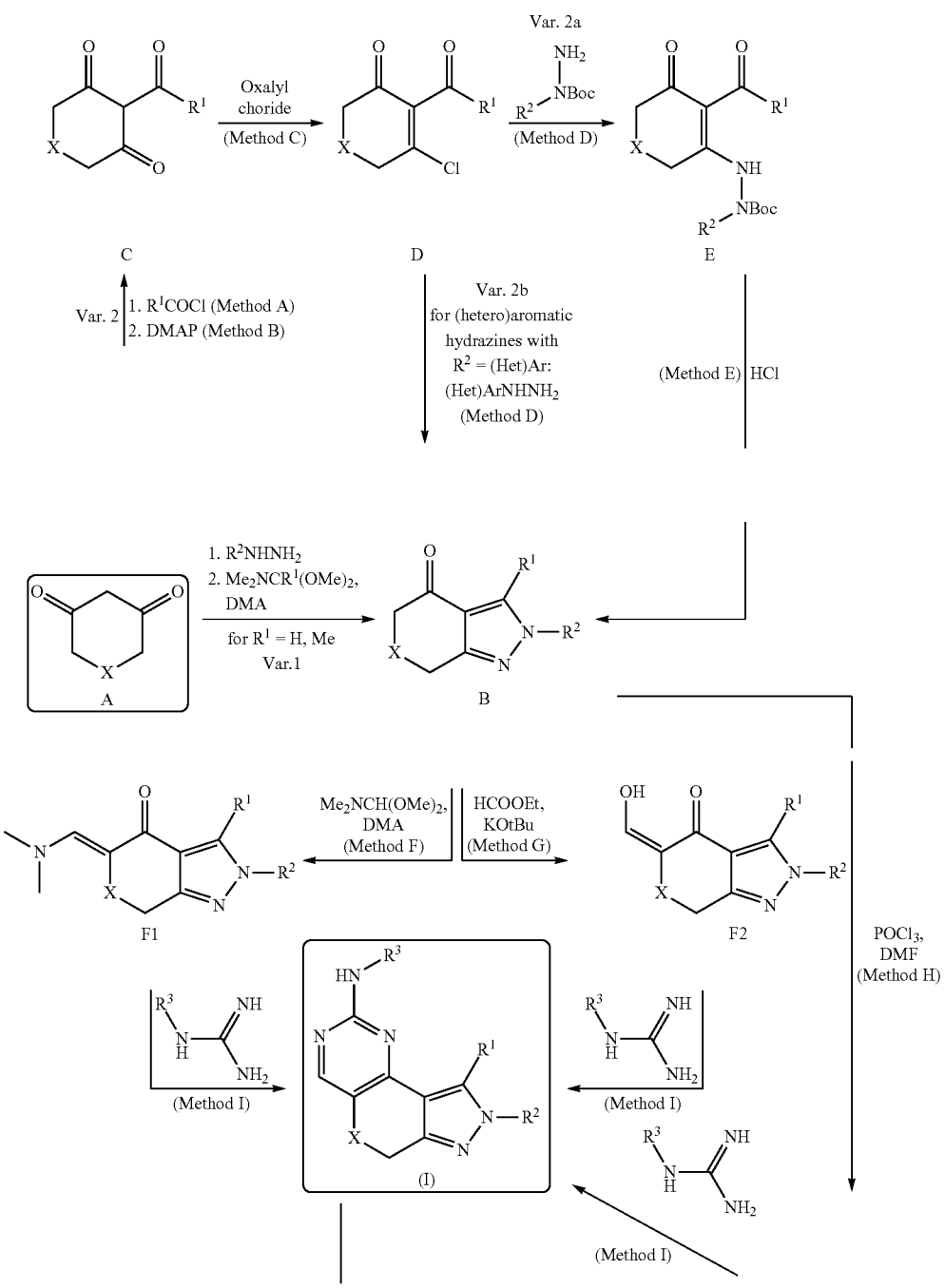

Novel compounds of general structure (I) may be prepared starting from cyclic 1,3-diketones A by two different synthesis routes leading to the central component B:

The first variant (Var. 1) makes the intermediates B available by the reaction of suitable diketones A with substituted hydrazines $R^1NHNH_2$ and dimethylformamide-dimethylacetal or analogous reagents.

The second variant (Var. 2) converts the starting compounds A by reaction with acid chlorides $R^1COCl$ and subsequent rearrangement of the intermediate enol esters into the triketones C, which can be converted with oxalyl chloride into the vinyl chlorides D. Substitution with protected hydrazines $R^2NHNH_2$ (Var. 2a) leads to the intermediates E, which cyclise in the hydrochloric acid medium after the cleaving of the protective group to form the central component B. When arylhydrazines are used there is no need for the protective group (Var. 2b). Here, the reaction of the chlorine compound D yields the intermediate B directly.

By reacting B with dimethylformamide-dimethylacetal or formic acid esters in the presence of bases the intermediate compounds F1 or F2 are obtained, which may in turn be reacted to form the end compounds (I) by reaction with guanidines available from amines using known methods. Alternatively B may be reacted with phosphorus oxychloride in the presence of DMF to form the intermediate F3 which may be cyclised with corresponding guanidines to form (I).

The compounds (I) may be on the one hand end compounds according to the invention or on the other hand may also be prepared using correspondingly protected components, deprotected by conventional methods and then converted into other compounds (I) according to the invention by derivatisation steps such as e.g. amide formation, alkylation or amination reactions. Instead of protected reagents it is also possible to use synthesis compounds which can be directly functionalised or derivatised without recourse to protective groups.

1. Preparation of the Pyrazole Fragments B
1.1. Preparation of the Pyrazole Fragments B Starting from Diketones A According to Variant 1

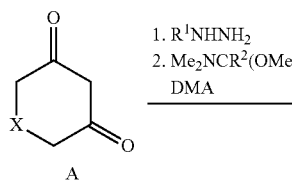

The pyrazole fragments B are prepared analogously to the method of Kennedy L. J., Lawrence J. *Synlett* 2008 (4), 600-604.

Preparation of B-01

Cyclohexane-1,3-dione (6.00 g, 53.5 mmol) in MeOH (15 mL) is combined at 0° C. with methylhydrazine (2.82 mL, 53.0 mmol) in THF (15 mL) and the mixture is stirred for 1.5 h. It is heated to RT, dimethylformamide-dimethylacetal (15 mL, 113.3 mmol) is added and the reaction mixture is heated in a microwave reactor (120° C., 10 min). The solvent is spun off in vacuo and the residue is purified by chromatography.

The liberation of hydrazinium salts is carried out either analogously to the Kennedy method with triethylamine or by the addition of potassium-tert-butoxide.

Reactions with dimethylacetamide-dimethylketal are carried out analogously to dimethylformamide-dimethylacetal. Optionally potassium-tert-butoxide may also be added to the cyclisation reaction here.

Analogously to B-01 further pyrazole fragments B are synthesised using the corresponding educts (Table 1).

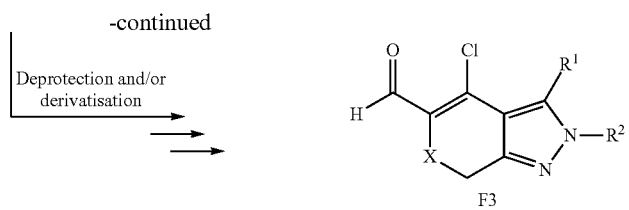

F3

TABLE 1

| No. | Structure | $t_{ret}$ [min] | $[M + H]^+$ | Method of analysis |
|---|---|---|---|---|
| B-01 | 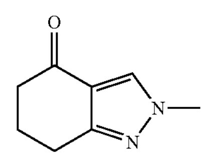 | 0.35 | 151.2 | C |
| B-02 | 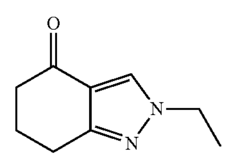 | 0.29 | 165.0 | A |
| B-03 | 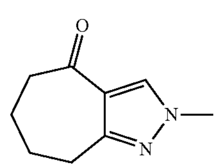 | 0.49 | 165.2 | F |
| B-04 | 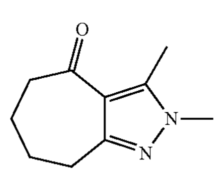 | 0.59 | 179.1 | C |
| B-05 | 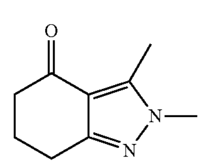 | 0.46 | 165.2 | F |

TABLE 1-continued

| No. | Structure | $t_{ret}$ [min] | [M + H]⁺ | Method of analysis |
|---|---|---|---|---|
| B-06 | (2-(dimethylamino)ethyl tetrahydroindazolone) | 0.24 | 208.0 | E |
| B-07 | (2-propyl tetrahydroindazolone) | 0.59 | 179.3 | F |
| B-08 | (2-ethyl-3-methyl tetrahydroindazolone) | 0.57 | 179.3 | F |
| B-09 | (2-(3-(dimethylamino)propyl)-3-methyl tetrahydroindazolone) | 0.35 | 236.2 | E |
| B-10 | (2-ethyl-3-methyl cycloheptapyrazolone) | 0.69 | 193.1 | F |
| B-11 | (2,6,6-trimethyl tetrahydroindazolone) | 0.58 | 179.3 | F |
| B-12 | (2,3,6,6-tetramethyl tetrahydroindazolone) | 0.67 | 193.1 | F |

1.2. Preparation of the Pyrazole Fragments B Via Triketones C (Variant 2/2a)

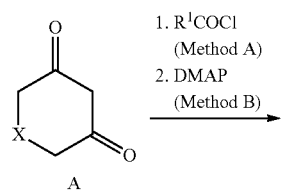

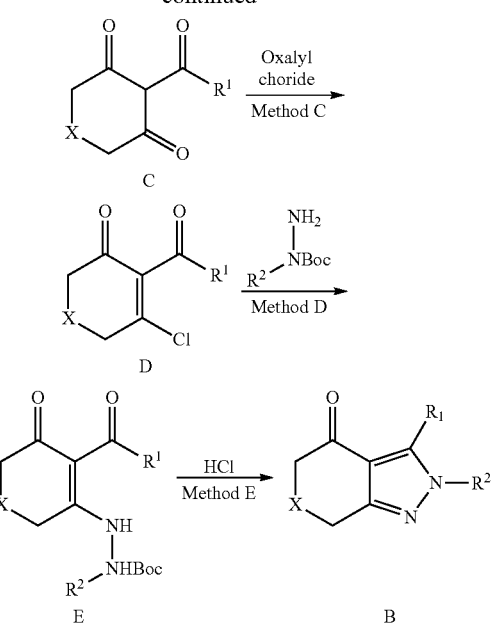

Preparation of C-01 (method A, method B)

Cyclohexane-1,3-dione (2.00 g, 17.3 mmol), propionic acid chloride (2.07 mL, 23.2 mmol) and DMAP (360 mg, 3.21 mmol) are stirred in anhydrous toluene (60 mL) for 30 min at RT and refluxed for 1 h. The cooled reaction mixture is washed 3× with water and once with saturated saline, dried on sodium sulphate, filtered and evaporated down. The residue is taken up in anhydrous toluene (100 mL), combined with DMAP (290 mg, 2.23 mmol) and refluxed for 3 h with stirring. The cooled reaction mixture is washed 3× with water and once with saturated saline, dried on sodium sulphate, filtered and evaporated down.

Alternatively the second partial step may be carried out in the presence of triethylamine with catalytic amounts of potassium cyanide or 1,2,4-triazole in acetonitrile.

Analogously to C-01 further triketones C are synthesised using the corresponding educts (Table 2).

TABLE 2

| No. | Structure | $t_{ret}$ [min] | [M + H]⁺ | Method of analysis |
|---|---|---|---|---|
| C-01 | (2-propanoyl cyclohexane-1,3-dione) | 0.77 | 169.1 | F |
| C-02 | (2-acetyl cycloheptane-1,3-dione) | 0.68 | 169.2 | C |

TABLE 2-continued

| No. | Structure | $t_{ret}$ [min] | $[M+H]^+$ | Method of analysis |
|---|---|---|---|---|
| C-03 | 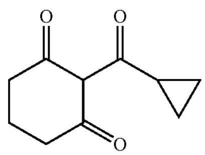 [SMILES: O=C1CCCC(=O)C1C(=O)C1CC1] | 0.84 | 181.2 | C |
| C-04 | 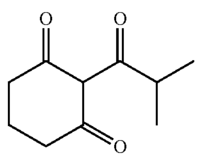 | 0.97 | 183.2 | F |
| C-05 | 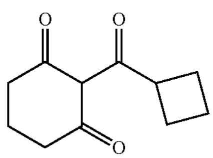 [SMILES: O=C1CCCC(=O)C1C(=O)C1CCC1] | 0.99 | 195.0 | C |
| C-06 | 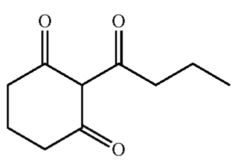 | 0.94 | 183.3 | C |
| C-07 | 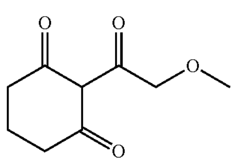 | 0.46 | 185.0 | F |
| C-08 | 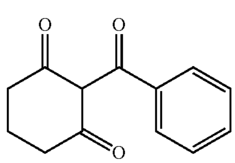 [SMILES: O=C1CCCC(=O)C1C(=O)c1ccccc1] | 0.74 | 217.2 | C |
| C-09 | 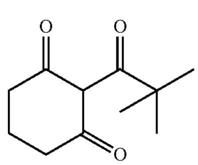 | 0.87 | 197.3 | D |
| C-10 | 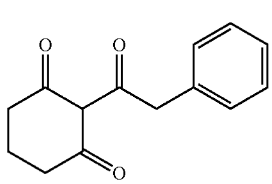 [SMILES: O=C1CCCC(=O)C1C(=O)Cc1ccccc1] | 1.09 | 231.2 | F |
| C-11 | 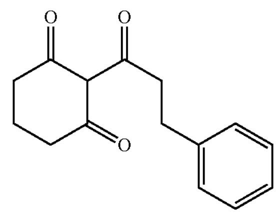 [SMILES: O=C1CCCC(=O)C1C(=O)CCc1ccccc1] | 1.16 | 245.0 | F |
| C-12 | 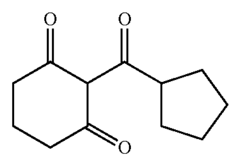 [SMILES: O=C1CCCC(=O)C1C(=O)C1CCCC1] | 1.12 | 209.1 | C |
| C-13 | 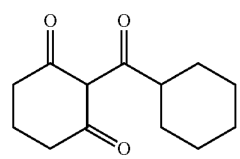 [SMILES: O=C1CCCC(=O)C1C(=O)C1CCCCC1] | 1.19 | 223.2 | C |
| C-14 | 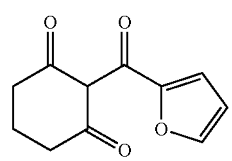 [SMILES: O=C1CCCC(=O)C1C(=O)c1ccco1] | 0.43 | 207.0 | C |
| C-15 | 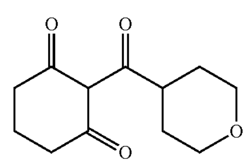 [SMILES: O=C1CCCC(=O)C1C(=O)C1CCOCC1] | 0.74 | 225.0 | C |
| C-16 | 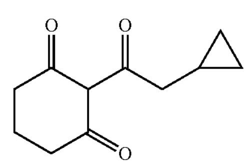 [SMILES: O=C1CCCC(=O)C1C(=O)CC1CC1] | 0.97 | 195.2 | F |
| C-17 | 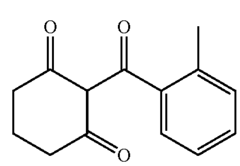 [SMILES: Cc1ccccc1C(=O)C1C(=O)CCCC1=O] | 0.97 | 231.2 | C |
| C-18 | 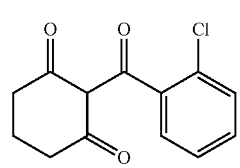 | 1.00 | 251.0 | C |

TABLE 2-continued

| No. | Structure | $t_{ret}$ [min] | [M + H]+ | Method of analysis |
|---|---|---|---|---|
| C-19 | 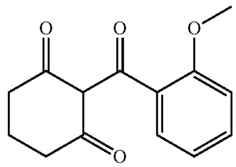 [SMILES: COc1ccccc1C(=O)C1C(=O)CCCC1=O] | 0.85 | 247.2 | C |
| C-20 | 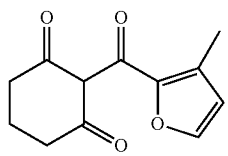 [SMILES: Cc1ccoc1C(=O)C1C(=O)CCCC1=O] | 0.89 | 221.0 | C |
| C-21 | 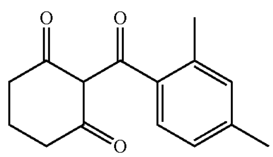 [SMILES: Cc1ccc(C(=O)C2C(=O)CCCC2=O)c(C)c1] | 1.09 | 245.2 | C |
| C-22 | 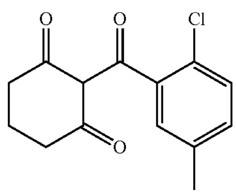 [SMILES: Cc1ccc(Cl)c(C(=O)C2C(=O)CCCC2=O)c1] | 1.11 | 265.2 | C |
| C-23 | 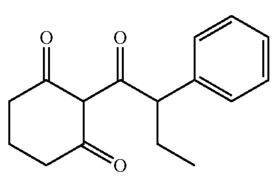 [SMILES: CCC(C(=O)C1C(=O)CCCC1=O)c1ccccc1] | 1.24 | 259.2 | C |
| C-24 | 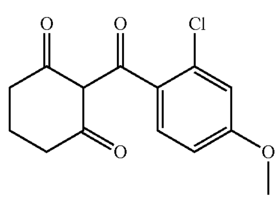 [SMILES: COc1ccc(C(=O)C2C(=O)CCCC2=O)c(Cl)c1] | 1.04 | 281.0 | C |
| C-25 | 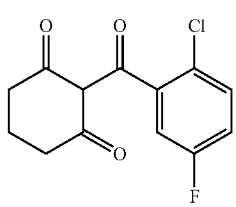 [SMILES: O=C1CCCC(=O)C1C(=O)c1cc(F)ccc1Cl] | 1.05 | 269.0 | C |
| C-26 | 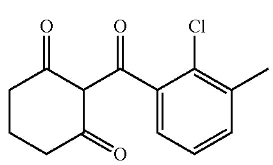 [SMILES: Cc1cccc(C(=O)C2C(=O)CCCC2=O)c1Cl] | 1.10 | 265.0 | C |
| C-27 | | 1.05 | 269.0 | C |
| C-28 | | 1.14 | 245.2 | C |
| C-29 | | 1.08 | 261.2 | C |
| C-30 | | 1.06 | 261.2 | C |
| C-31 | | 1.12 | 265.2 | C |
| C-32 | | 0.90 | 261.2 | C |

Preparation of D-01 by Chlorination (Method C)

C-01 (525 mg, 3.22 mmol) and oxalyl chloride (515 μL, 5.84 mmol) are stirred in anhydrous DCM for 12 h at RT. The reaction mixture is evaporated to dryness and further reacted immediately.

For the HPLC analysis the reaction mixture is mixed with morpholine and the product is detected as alkylated morpholine derivative. The [M+H]+ value found relates to this compound.

Analogously to D-01 further chlorinated diketones D are synthesised using the corresponding intermediate C (Table 3).

TABLE 3
| No. | Structure | $t_{ret}$ [min] | $[M+H]^+$ | Method of analysis |
|---|---|---|---|---|
| D-01 | 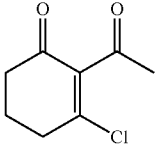 | 0.23 | 224.3 | F |
| D-02 | 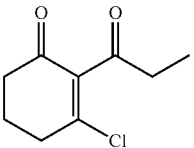 | 0.33 | 238.1 | F |
| D-03 | 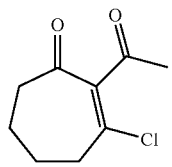 | 0.20 | 238.2 | C |
| D-04 | 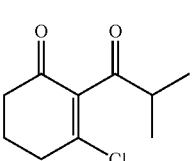 | 0.45 | 252.3 | C |
| D-05 | 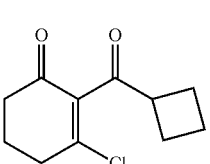 | 0.51 | 264.3 | C |
| D-06 | 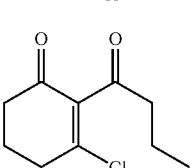 | 0.30 | 252.2 | E |
| D-07 | 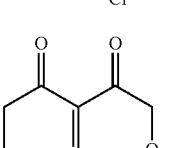 | 0.10 | 254.0 | A |
| D-08 | 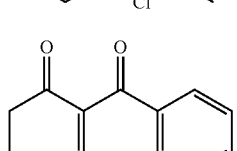 | 0.54 | 286.2 | C |
| D-09 | 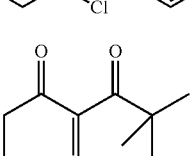 | 0.42 | 266.2 | A |
| D-10 | 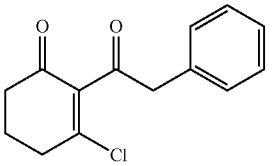 [SMILES: O=C1CCCC(Cl)=C1C(=O)Cc1ccccc1] | 0.66 | 300.2 | F |
| D-11 | 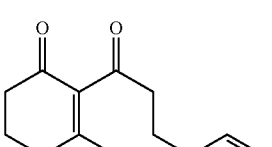 | 0.75 | 314.1 | C |
| D-12 | 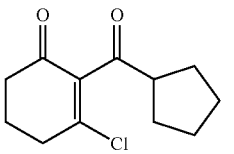 [SMILES: O=C1CCCC(Cl)=C1C(=O)C1CCCC1] | 0.64 | 278.2 | B |
| D-13 | 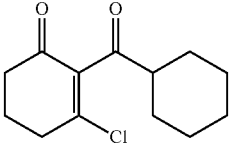 [SMILES: O=C1CCCC(Cl)=C1C(=O)C1CCCCC1] | 0.74 | 292.2 | B |
| D-14 | 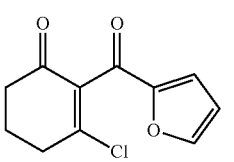 [SMILES: O=C1CCCC(Cl)=C1C(=O)c1ccco1] | 0.32 | 276.3 | C |
| D-15 | 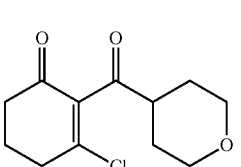 | 0.35 | 294.3 | C |
| D-16 | 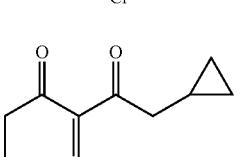 | 0.50 | 264.3 | C |
| D-17 | 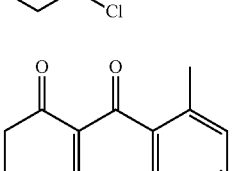 | 0.59 | 300.2 | C |

TABLE 3-continued

| No. | Structure | $t_{ret}$ [min] | $[M+H]^+$ | Method of analysis |
|---|---|---|---|---|
| D-18 | 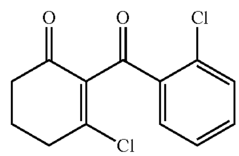 [SMILES: Cc1ccccc1C(=O)C1=C(Cl)CCCC1=O] | 0.76 | | C |
| D-19 | 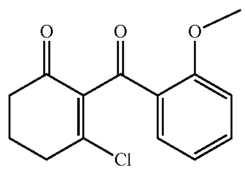 [SMILES: COc1ccccc1C(=O)C1=C(Cl)CCCC1=O] | 0.48 | 316.2 | C |
| D-20 | 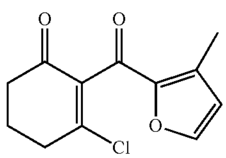 [SMILES: Cc1ccoc1C(=O)C1=C(Cl)CCCC1=O] | 0.43 | 290.2 | C |
| D-21 | 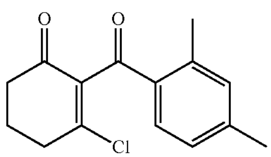 [SMILES: Cc1ccc(C(=O)C2=C(Cl)CCCC2=O)c(C)c1] | 0.73 | 314.2 | C |
| D-22 | 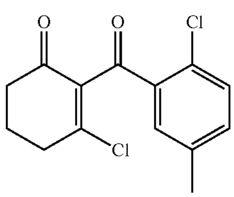 [SMILES: Cc1ccc(Cl)c(C(=O)C2=C(Cl)CCCC2=O)c1] | 0.67 | 334.2 | C |
| D-23 | 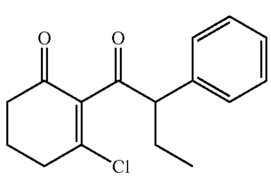 [SMILES: CCC(C(=O)C1=C(Cl)CCCC1=O)c1ccccc1] | 1.26 | 277.2 (product mass) | C |
| D-24 | 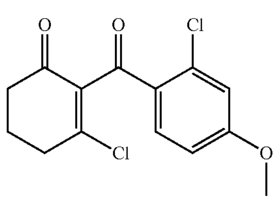 [SMILES: COc1ccc(C(=O)C2=C(Cl)CCCC2=O)c(Cl)c1] | 0.64 | 350.2 | C |
| D-25 | 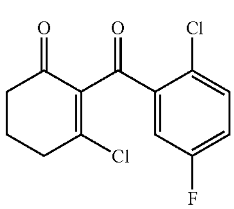 [SMILES: O=C1CCCC(Cl)=C1C(=O)c1cc(F)ccc1Cl] | 0.61 | 338.2 | C |

TABLE 3-continued

| No. | Structure | $t_{ret}$ [min] | $[M+H]^+$ | Method of analysis |
|---|---|---|---|---|
| D-26 | | 0.65 | 334.2 | C |
| D-27 | | 0.62 | 338.2 | C |
| D-28 | | 0.76 | 314.2 | C |
| D-29 | | 0.68 | 330.2 | C |
| D-30 | | 0.66 | 330.2 | C |
| D-31 | | 0.67 | 334.2 | C |
| D-32 | | 0.57 | 330.2 | C |

Preparation of E-01 by Substitution with Boc-Protected Hydrazines (Method D, Variant 2a)

Chlorine compound D-01 (1.20 g, 6.43 mmol) in anhydrous THF (10 mL) is combined at −35° C. with N-ethyldiisopropylamine (1.10 mL, 6.43 mmol) and 1-Boc-1-methylhydrazine (0.969 mL, 6.43 mmol), heated to RT and stirred for 12 h at RT. The reaction mixture is evaporated down, the residue is taken up in EtOAc, washed with saturated ammonium chloride solution, water and saturated sodium chloride solution, dried (Na$_2$SO$_4$), filtered and evaporated down. Optionally the crude product may be purified by chromatography.

Analogously to E-01 further intermediate compounds E are synthesised using the corresponding intermediate D and a hydrazine component (Table 4).

TABLE 4

| No. | Structure | $t_{ret}$ [min] | [M + H]$^+$ | Method of analysis |
|---|---|---|---|---|
| E-01 | 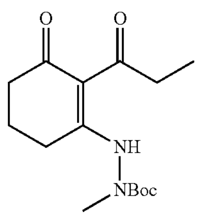 [SMILES: CCC(=O)C1=C(NN(C)C(=O)OC(C)(C)C)CCCC1=O] | 1.03 | 297.3 | C |
| E-02 | 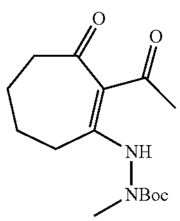 [SMILES: CC(=O)C1=C(NN(C)C(=O)OC(C)(C)C)CCCCC1=O] | 0.96 | 297.3 | C |
| E-03 | 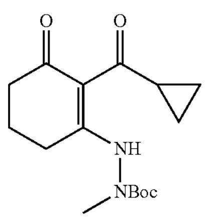 [SMILES: CN(NC1=C(C(=O)C2CC2)C(=O)CCC1)C(=O)OC(C)(C)C] | 1.02 | 309.3 | C |
| E-04 | 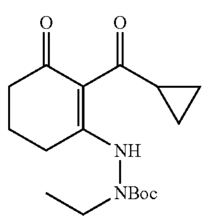 [SMILES: CCN(NC1=C(C(=O)C2CC2)C(=O)CCC1)C(=O)OC(C)(C)C] | 1.13 | 323.4 | C |
| E-05 | 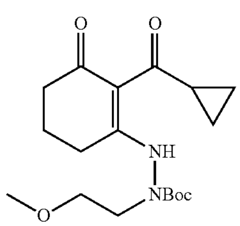 [SMILES: COCCN(NC1=C(C(=O)C2CC2)C(=O)CCC1)C(=O)OC(C)(C)C] | 1.07 | 353.4 | C |
| E-06 | 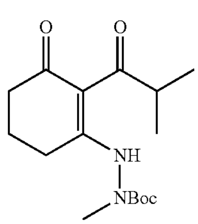 [SMILES: CC(C)C(=O)C1=C(NN(C)C(=O)OC(C)(C)C)CCCC1=O] | 1.11 | 311.1 | C |
| E-07 | 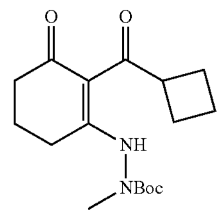 [SMILES: CN(NC1=C(C(=O)C2CCC2)C(=O)CCC1)C(=O)OC(C)(C)C] | 1.15 | 323.1 | C |
| E-08 | 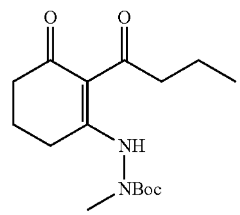 [SMILES: CCCC(=O)C1=C(NN(C)C(=O)OC(C)(C)C)CCCC1=O] | 1.11 | 311.4 | C |
| E-09 | 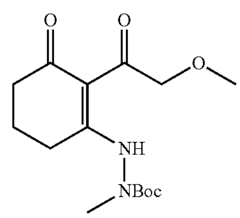 [SMILES: COCC(=O)C1=C(NN(C)C(=O)OC(C)(C)C)CCCC1=O] | 0.84 | 313.1 | F |
| E-10 | 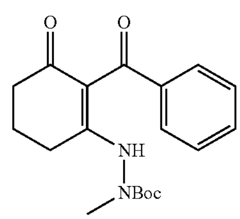 [SMILES: CN(NC1=C(C(=O)c2ccccc2)C(=O)CCC1)C(=O)OC(C)(C)C] | 0.67 | 345.2 | A |
| E-11 | 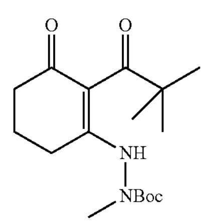 [SMILES: CN(NC1=C(C(=O)C(C)(C)C)C(=O)CCC1)C(=O)OC(C)(C)C] | 1.07 | 325.1 | F |
| E-12 | 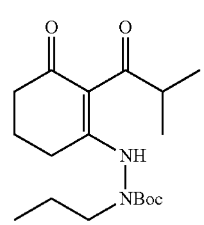 [SMILES: CCCN(NC1=C(C(=O)C(C)C)C(=O)CCC1)C(=O)OC(C)(C)C] | 1.36 | 339.2 | F |

TABLE 4-continued

| No. | Structure | $t_{ret}$ [min] | $[M+H]^+$ | Method of analysis |
|---|---|---|---|---|
| E-13 | 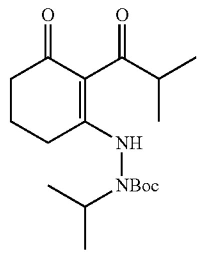 [SMILES: CC(C)C(=O)C1=C(NN(C(=O)OC(C)(C)C)C(C)C)CCCC1=O] | 1.31 | 339.3 | C |
| E-14 | 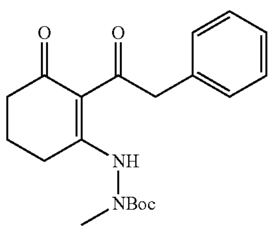 [SMILES: CN(NC1=C(C(=O)Cc2ccccc2)C(=O)CCC1)C(=O)OC(C)(C)C] | 1.26 | 359.3 | F |
| E-15 | 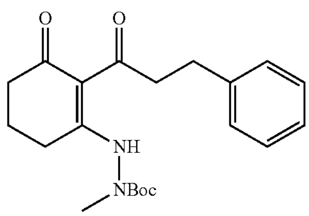 [SMILES: CN(NC1=C(C(=O)CCc2ccccc2)C(=O)CCC1)C(=O)OC(C)(C)C] | 1.31 | 373.1 | F |
| E-16 | 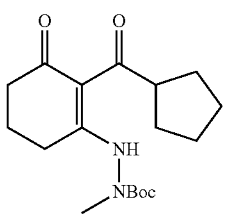 [SMILES: CN(NC1=C(C(=O)C2CCCC2)C(=O)CCC1)C(=O)OC(C)(C)C] | 1.24 | 337.2 | C |
| E-17 | 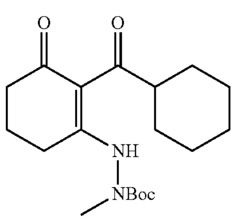 [SMILES: CN(NC1=C(C(=O)C2CCCCC2)C(=O)CCC1)C(=O)OC(C)(C)C] | 1.28 | 351.3 | C |
| E-18 | 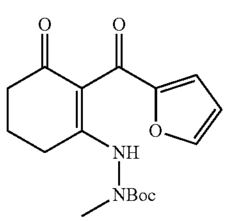 [SMILES: CN(NC1=C(C(=O)c2ccco2)C(=O)CCC1)C(=O)OC(C)(C)C] | 0.76 | 335.1 | C |
| E-19 | | 0.92 | 353.4 | C |
| E-20 | | 1.16 | 311.2 | F |
| E-21 | | 0.95 | 327.3 | C |
| E-22 | | 1.10 | 341.3 | F |
| E-23 | | 1.22 | 325.2 | C |
| E-24 | | 1.12 | 323.3 | F |

TABLE 4-continued

| No. | Structure | $t_{ret}$ [min] | [M+H]⁺ | Method of analysis |
|---|---|---|---|---|
| E-25 | (2-methylbenzoyl cyclohexenone with NH-NBoc) | 1.10 | 359.2 | C |
| E-26 | (2-chlorobenzoyl cyclohexenone with NH-NBoc) | 1.14 | 379.2 | C |
| E-27 | (2-methoxybenzoyl cyclohexenone with NH-NBoc) | 1.02 | 375.2 | C |
| E-28 | (3-methylfuroyl cyclohexenone with NH-NBoc) | 0.84 | 349.2 | C |
| E-29 | (2,4-dimethylbenzoyl cyclohexenone with NH-NBoc) | 1.19 | 373.2 | C |
| E-30 | (2-chloro-5-methylbenzoyl cyclohexenone with NH-NBoc) | 1.21 | 393.2 | C |
| E-31 | (2-phenylbutanoyl cyclohexenone with NH-NBoc) | 1.37 | 387.2 | C |
| E-32 | (2-chloro-4-methoxybenzoyl cyclohexenone with NH-NBoc) | 1.15 | 409.2 | C |
| E-33 | (2-chloro-5-fluorobenzoyl cyclohexenone with NH-NBoc) | 1.19 | 397.2 | C |
| E-34 | (2-chloro-3-methylbenzoyl cyclohexenone with NH-NBoc) | 1.21 | 393.2 | C |
| E-35 | (2-chloro-4-fluorobenzoyl cyclohexenone with NH-NBoc) | 1.19 | 397.2 | C |
| E-36 | (2-phenylpropanoyl cyclohexenone with NH-NBoc) | 1.26 | 373.2 | C |

TABLE 4-continued

| No. | Structure | $t_{ret}$ [min] | [M + H]$^+$ | Method of analysis |
|---|---|---|---|---|
| E-37 | 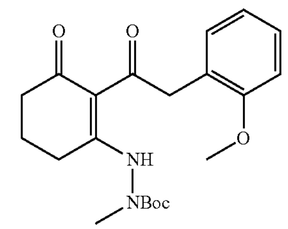 [SMILES: COc1ccccc1CC(=O)C1=C(NN(C)C(=O)OC(C)(C)C)CCCC1=O] | 1.21 | 389.2 | C |
| E-38 | 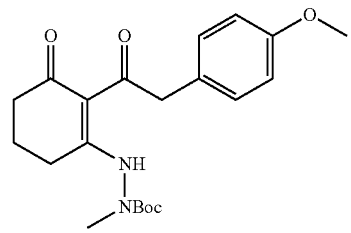 [SMILES: COc1ccc(CC(=O)C2=C(NN(C)C(=O)OC(C)(C)C)CCCC2=O)cc1] | 1.20 | 389.2 | C |
| E-39 | 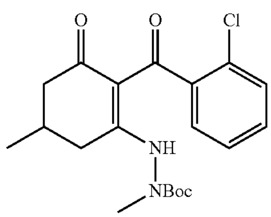 [SMILES: CC1CC(=O)C(C(=O)c2ccccc2Cl)=C(NN(C)C(=O)OC(C)(C)C)C1] | 1.22 | 393.2 | C |
| E-40 | 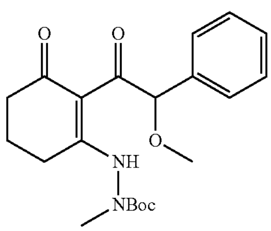 | 1.07 | 389.2 | C |

[1] Brosse, Nicolas et al., "Preparation of multiply protected alkylhydrazine derivatives by Mitsunobu and PTC approaches"; Europ. J. Org. Chem. 2003, 4757-4764;

[2] Bross, Nicolas et al., "New synthesis of 1,1-substituted hydrazines by alkylation of N-acyl or N-[(alkyloxycarbonyl)amino]phthalimide using the Mitsunobu protocol"; J. Org. Chem. 2000, 4370-4374.

Preparation of B-13 by Cyclisation (Method E)

The protected hydrazine E-01 (1.5 g, 5.06 mmol) in anhydrous dioxane (3 mL) is combined with 4 N HCl in dioxane (5 mL) and stirred for 1 h at RT. The reaction mixture is evaporated down, the residue is taken up in DCM, washed with saturated potassium carbonate solution and saturated sodium chloride solution, dried (Na$_2$SO$_4$), filtered and evaporated down. Optionally the crude product may be purified by chromatography.

Analogously to B-13 further intermediate compounds E are cyclised (Table 5).

TABLE 5

| No. | Structure | $t_{ret}$ [min] | [M + H]$^+$ | Method of analysis |
|---|---|---|---|---|
| B-13 | 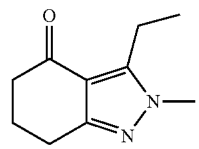 | 0.60 | 179.1 | C |
| B-14 | 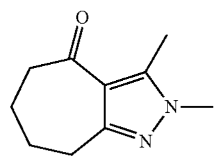 | 0.60 | 179.1 | C |
| B-15 | 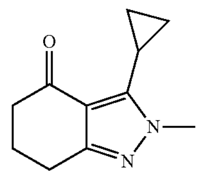 | 0.62 | 191.1 | C |
| B-16 | 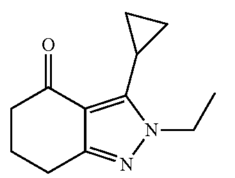 | 0.72 | 205.2 | C |
| B-17 | 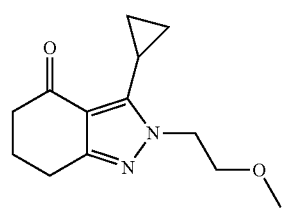 [SMILES: COCCn1nc2c(c1C1CC1)C(=O)CCC2] | 0.66 | 235.2 | C |
| B-18 | 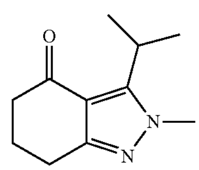 | 0.74 | 193.2 | C |
| B-19 | 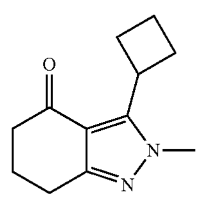 | 0.81 | 205.2 | C |
| B-20 | 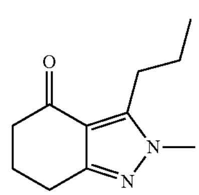 | 0.71 | 193.2 | C |

TABLE 5-continued

| No. | Structure | $t_{ret}$ [min] | [M + H]+ | Method of analysis |
|---|---|---|---|---|
| B-21 | | 0.48 | 195.2 | F |
| B-22 | | 0.79 | 227.1 | C |
| B-23 | | 0.87 | 207.2 | C |
| B-24 | | 0.95 | 221.1 | C |
| B-25 | | 0.95 | 221.1 | C |
| B-26 | | 0.892 | 241.2 | C |
| B-27 | | 0.96 | 255.3 | C |
| B-28 | 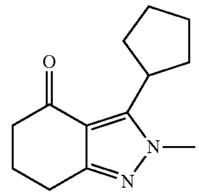 [SMILES: Cn1nc2c(c1C1CCCC1)C(=O)CCC2] | 0.91 | 219.3 | C |
| B-29 | 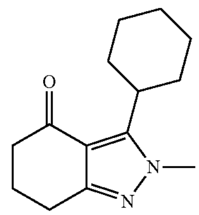 [SMILES: Cn1nc2c(c1C1CCCCC1)C(=O)CCC2] | 1.02 | 233.1 | C |
| B-30 | 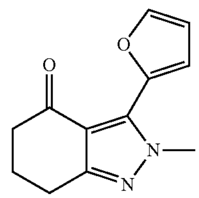 [SMILES: Cn1nc2c(c1-c1ccco1)C(=O)CCC2] | 0.79 | 217.2 | C |
| B-31 | 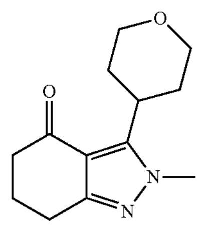 [SMILES: Cn1nc2c(c1C1CCOCC1)C(=O)CCC2] | 0.59 | 235.2 | C |
| B-32 | 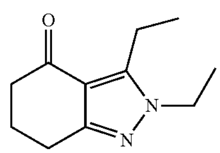 | 0.68 | 193.2 | C |
| B-33 | 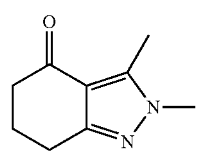 | 0.46 | 165.2 | F |
| B-34 | 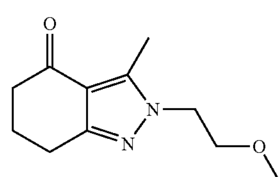 | 0.53 | 209.1 | C |
| B-35 | 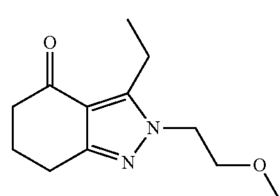 | 0.64 | 223.2 | C |

TABLE 5-continued

| No. | Structure | $t_{ret}$ [min] | [M + H]$^+$ | Method of analysis |
|---|---|---|---|---|
| B-36 | 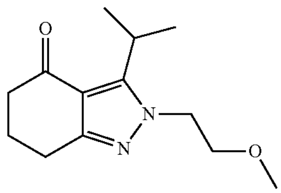 [SMILES: COCCn1nc2c(c1C(C)C)C(=O)CCC2] | 0.80 | 237.3 | C |
| B-37 | 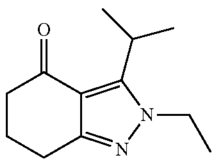 | 0.84 | 207.3 | C |
| B-38 | 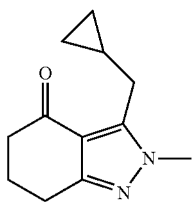 | 0.95 | 205.2 | C |
| B-39 | 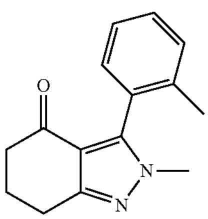 [SMILES: Cc1ccccc1-c1c2c(nn1C)CCCC2=O] | 0.85 | 241.2 | C |
| B-40 | 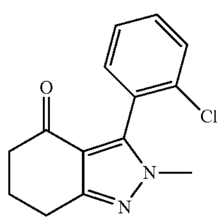 [SMILES: Cn1nc2c(c1-c1ccccc1Cl)C(=O)CCC2] | 0.88 | 261.2 | C |
| B-41 | 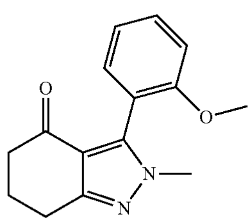 [SMILES: COc1ccccc1-c1c2c(nn1C)CCCC2=O] | 0.80 | 257.2 | C |
| B-42 | 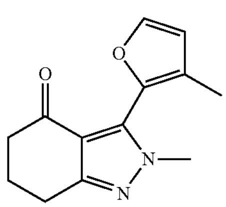 [SMILES: Cc1ccoc1-c1c2c(nn1C)CCCC2=O] | 0.80 | 231.2 | C |
| B-43 | 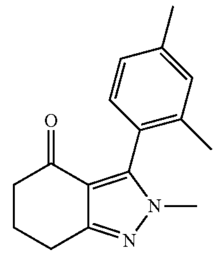 [SMILES: Cc1ccc(-c2c3c(nn2C)CCCC3=O)c(C)c1] | 1.00 | 255.2 | C |
| B-44 | 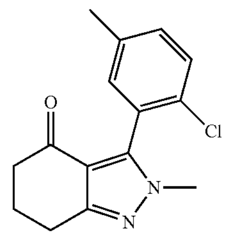 [SMILES: Cc1ccc(Cl)c(-c2c3c(nn2C)CCCC3=O)c1] | 1.00 | 275.2 | C |
| B-45 | 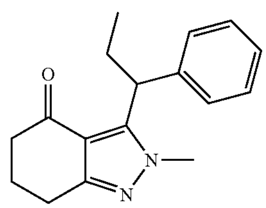 [SMILES: CCC(c1ccccc1)c1c2c(nn1C)CCCC2=O] | 1.08 | 269.2 | C |
| B-46 | 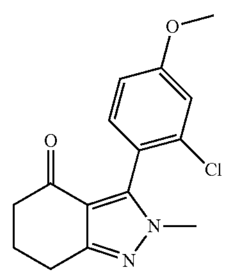 [SMILES: COc1ccc(-c2c3c(nn2C)CCCC3=O)c(Cl)c1] | 0.94 | 291.0 | C |
| B-47 | 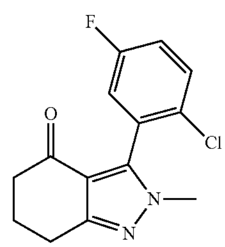 [SMILES: Cn1nc2c(c1-c1cc(F)ccc1Cl)C(=O)CCC2] | 0.92 | 279.2 | C |
| B-48 | 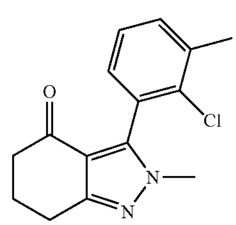 [SMILES: Cc1cccc(-c2c3c(nn2C)CCCC3=O)c1Cl] | 0.99 | 275.2 | C |

TABLE 5-continued

| No. | Structure | $t_{ret}$ [min] | [M + H]⁺ | Method of analysis |
|---|---|---|---|---|
| B-49 | 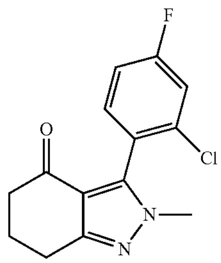 [SMILES: Cn1nc2c(c1-c1ccc(F)cc1Cl)C(=O)CCC2] | 0.92 | 279.0 | C |
| B-50 | 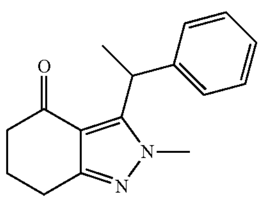 [SMILES: CC(c1ccccc1)c1c2c(nn1C)CCCC2=O] | 0.98 | 255.2 | C |
| B-51 | 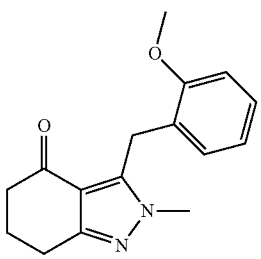 [SMILES: COc1ccccc1Cc1c2c(nn1C)CCCC2=O] | 0.95 | 271.2 | C |
| B-52 | 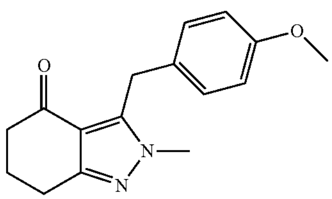 [SMILES: COc1ccc(Cc2c3c(nn2C)CCCC3=O)cc1] | 0.90 | 271.2 | C |
| B-53 | 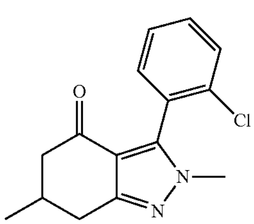 [SMILES: CC1CC(=O)c2c(nn(C)c2-c2ccccc2Cl)C1] | 0.99 | 275.2 | C |
| B-54 | 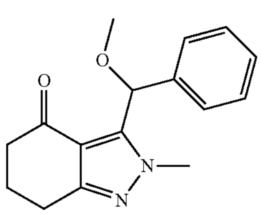 [SMILES: COC(c1ccccc1)c1c2c(nn1C)CCCC2=O] | 1.00 | 271.2 | C |

1.3. Preparation of (Hetero)Arylpyrazole Fragments B Via Triketones C (Variant 2/2B)

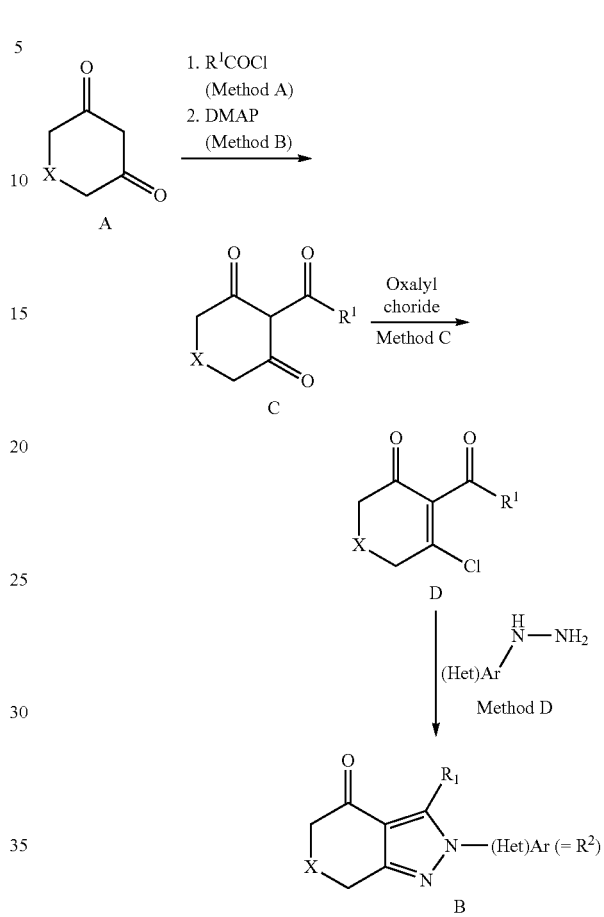

Preparation of Pyrazole Fragment B-55 by Cyclisation with (Hetero)Arylhydrazine (Method D)

The reaction of the chlorinated diketones with (hetero)arylhydrazines is carried out according to method E and yields the corresponding (hetero)arylpyrazole fragment directly.

TABLE 6

| No. | Structure | $t_{ret}$ [min] | [M + H]⁺ | Method of analysis |
|---|---|---|---|---|
| B-55 | 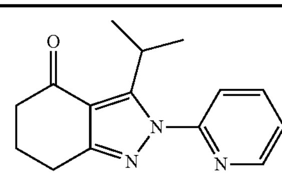 | 0.93 | 256.2 | C |
| B-56 | 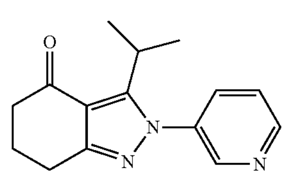 [SMILES: CC(C)c1c2c(nn1-c1cccnc1)CCCC2=O] | 0.85 | 256.2 | C |

2. Preparation of the Starting Compounds for the Pyrimidine Cyclisation Reaction 2.1. Reaction of B to Obtain Intermediates F1 and F2

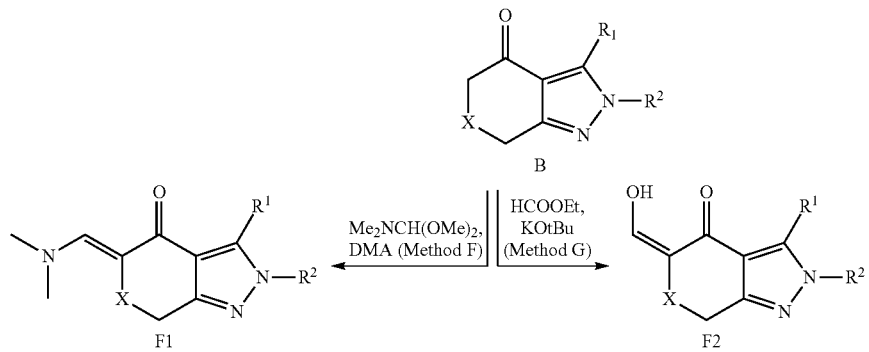

Preparation of F1-01: Condensation with Dimethylformamide-Dimethylacetal (Method F)

Pyrazole fragment B-01 (7.5 g, 49.9 mmol) and DMF-DMA (15 mL, 113.3 mmol) in DMA (15 mL) are stirred in a microwave reactor for 30 min at 180° C. The solvent is spun off in vacuo and the residue is purified by chromatography.

Analogously to F1-01 further intermediate compounds F1 are obtained by condensation of pyrazole fragments B with DMF-DMA (Table 7).

TABLE 7

| No. | Structure | $t_{ret}$ [min] | $[M + H]^+$ | Method of analysis |
|---|---|---|---|---|
| F1-01 | 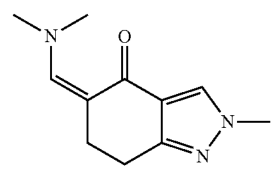 | 0.45 | 179.0 (hydrolysis) | C |
| F1-02 | 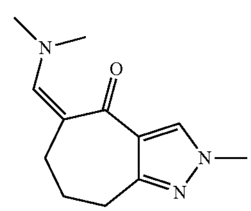 | 0.74 | 193.1 (hydrolysis) | F |
| F1-03 | 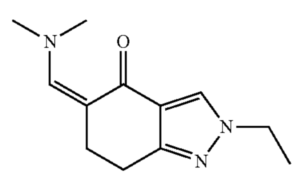 [SMILES: CCn1cc2c(n1)CC/C(=C/N(C)C)C2=O] | 0.34 | 220.2 | E |
| F1-04 | 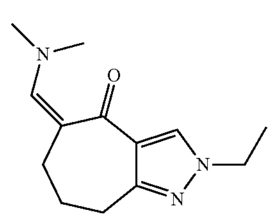 [SMILES: CCn1cc2c(n1)CCC/C(=C/N(C)C)C2=O] | 0.42 | 234.2 | E |

TABLE 7-continued

| No. | Structure | t_ret [min] | [M + H]+ | Method of analysis |
|---|---|---|---|---|
| F1-05 | 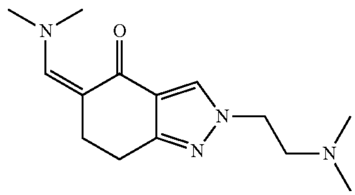 | 0.33 | 263.2 | E |
| F1-06 | 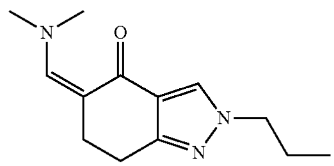 [SMILES: CCCn1cc2c(n1)CC/C(=C/N(C)C)C2=O] | 0.67 | 207.3 | C |
| F1-07 | 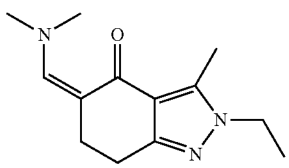 [SMILES: CCn1nc2c(c1C)C(=O)/C(=C\N(C)C)CC2] | 0.39 | 234.2 | E |
| F1-08 | 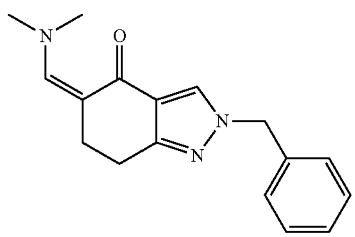 [SMILES: CN(C)/C=C1/CCc2nn(Cc3ccccc3)cc2C1=O] | 0.56 | 282.0 | A |
| F1-09 | 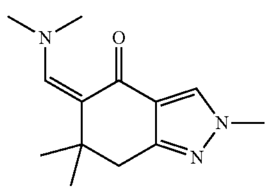 | 0.40 | 234.2 | E |
| F1-10 | 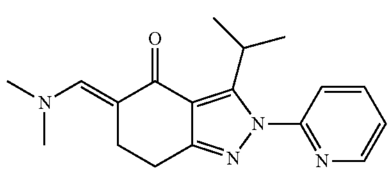 [SMILES: CC(C)c1c2c(nn1-c1ccccn1)CC/C(=C\N(C)C)C2=O] | 0.81 | 311.2 | B |
| F1-11 | 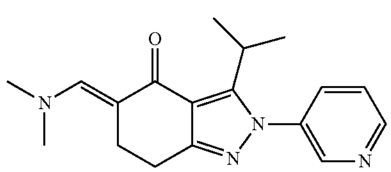 [SMILES: CC(C)c1c2c(nn1-c1cccnc1)CC/C(=C\N(C)C)C2=O] | 0.75 | 311.2 | B |
| F1-12 | 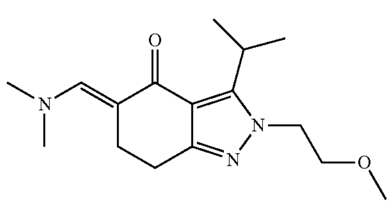 | 0.53 | 292.2 | A |

TABLE 7-continued

| No. | Structure | t_ret [min] | [M + H]+ | Method of analysis |
|---|---|---|---|---|
| F1-13 | 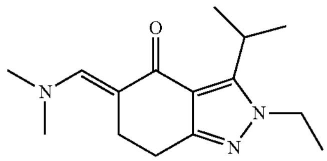 [SMILES: CCn1nc2c(c1C(C)C)C(=O)/C(=C/N(C)C)CC2] | 0.84 | 262.2 | B |
| F1-14 | 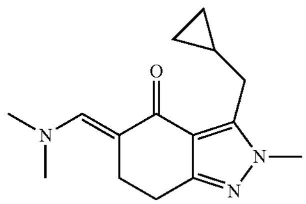 | 0.74 | 260.2 | B |
| F1-15 | 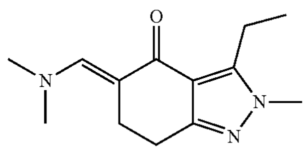 | 0.64 | 234.3 | B |
| F1-16 | 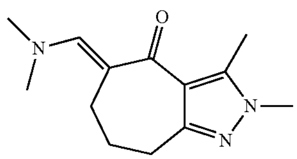 | 0.45 | 234.3 | A |
| F1-17 | 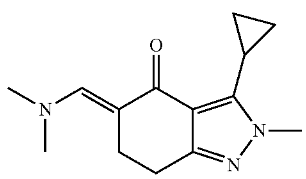 | 0.41 | 246.2 | A |
| F1-18 | 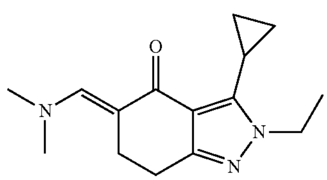 [SMILES: CCn1nc2c(c1C1CC1)C(=O)/C(=C/N(C)C)CC2] | 0.48 | 260.2 | A |
| F1-19 | 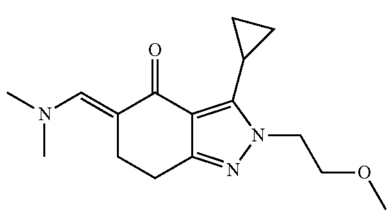 | 0.45 | 290.2 | A |
| F1-20 | 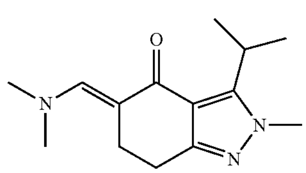 | 0.49 | 248.2 | A |

TABLE 7-continued
| No. | Structure | $t_{ret}$ [min] | $[M + H]^+$ | Method of analysis |
|---|---|---|---|---|
| F1-21 | 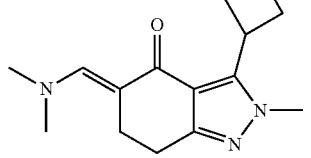 | 0.76 | 260.2 | B |
| F1-22 | 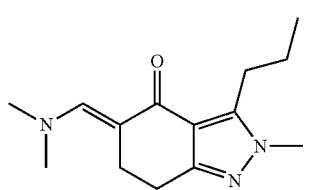 | 0.49 | 248.2 | A |
| F1-23 | 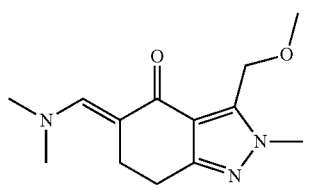 | 0.34 | 250.2 | A |
| F1-24 | 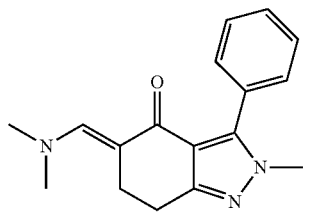 | 0.52 | 282.2 | A |
| F1-25 | 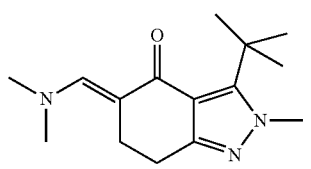 | 0.60 | 262.2 | A |
| F1-26 | 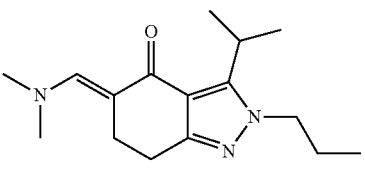 [SMILES: CCCn1nc2c(c1C(C)C)C(=O)/C(=C/N(C)C)CC2] | 0.64 | 276.2 | A |
| F1-27 | 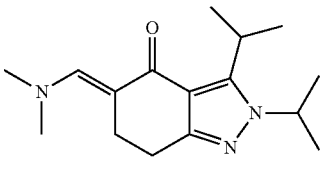 [SMILES: CC(C)c1c2c(nn1C(C)C)CC/C(=C\N(C)C)C2=O] | 0.86 | 276.2 | B |
| F1-28 | 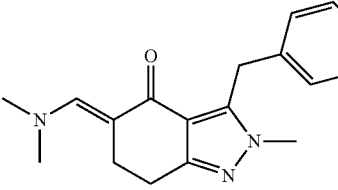 | 0.82 | 296.2 | B |

TABLE 7-continued

| No. | Structure | t_ret [min] | [M + H]+ | Method of analysis |
|---|---|---|---|---|
| F1-29 | 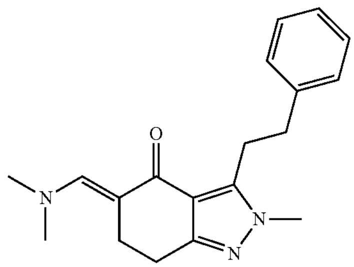 [SMILES: CN(C)/C=C1\CCc2nn(C)c(CCc3ccccc3)c2C1=O] | 0.87 | 310.2 | B |
| F1-30 | 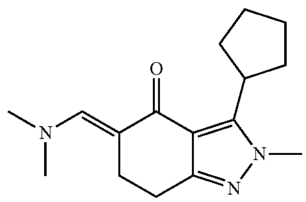 | 1.11 | 247.2 (hydrolysis) | C |
| F1-31 | 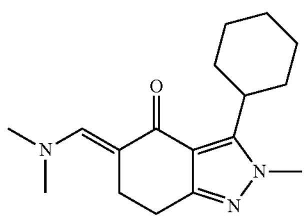 | 1.21 | 261.2 (hydrolysis) | C |
| F1-32 | 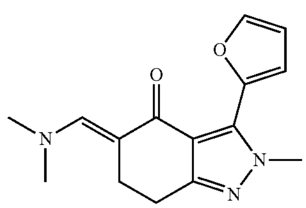 | 0.75 | 272.0 | B |
| F1-33 | 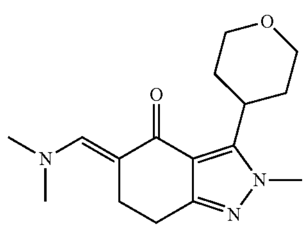 | 0.66 | 290.2 | B |
| F1-34 | 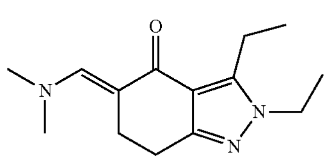 [SMILES: CCc1c2c(nn1CC)CC/C(=C\N(C)C)C2=O] | 0.71 | 248.2 | B |
| F1-35 | 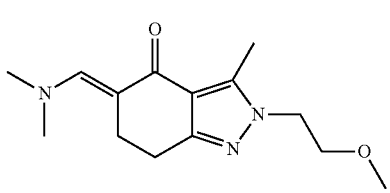 | 0.37 | 264.2 | A |

TABLE 7-continued

| No. | Structure | $t_{ret}$ [min] | $[M + H]^+$ | Method of analysis |
|---|---|---|---|---|
| F1-36 | 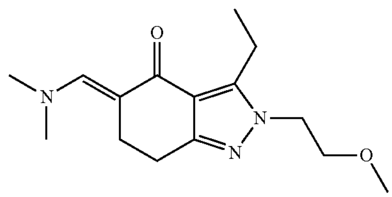 | 0.43 | 278.2 | A |

Preparation of F2-01: Reaction with Formic Acid Esters (Method G)

KOtBu (100 mg, 0.89 mmol) is added at 0° C. to pyrazole fragment B-09 (100 mg, 0.43 mmol) in anhydrous dioxane (0.5 mL) and stirred for 5 min. Ethyl formate (60 μL) is added and the mixture is stirred until the starting compound is completely reacted. KOtBu and ethyl formate are optionally metered in subsequently. The crude product may be reacted further directly in the next step.

Analogously to F2-01 further intermediate compounds F2 are obtained by reacting formic acid esters with pyrazole fragments B (Table 8).

TABLE 8

| No. | product | $t_{ret}$ [min] | $[M + H]^+$ | Method of analysis |
|---|---|---|---|---|
| F2-01 | | 0.84 | 207.3 | C |
| F2-02 | | 0.13 | 264.2 | E |

2.2. Formylation and Chlorination of B to Form Intermediates F3

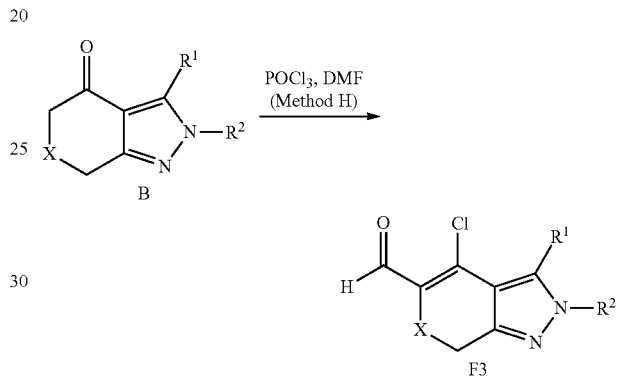

Preparation of F3-01 by Reaction with Phosphorus Oxychloride/Dmf (Method H)

DMF (2.7 mL) is added at 0° C. to POCl$_3$ (2.4 mL) in anhydrous DCM (10 mL) and stirred for 20 min. Pyrazole fragment B-22 (2.0 g, 8.8 mmol) is added, the mixture is stirred for 20 min at RT and for 10 min at 100° C. in a microwave reactor. The reaction mixture is added dropwise to semisaturated potassium carbonate solution and the product is extracted with DCM. The organic phase is washed with water, dried on sodium sulphate, filtered and evaporated down.

Analogously to F3-01 further intermediate compounds F3 are obtained by reacting pyrazole fragments B with POCl$_3$/DMF (Table 9).

TABLE 9

| No. | Structure | $t_{ret}$ [min] | $[M + H]^+$ | Method of analysis |
|---|---|---|---|---|
| F3-01 | 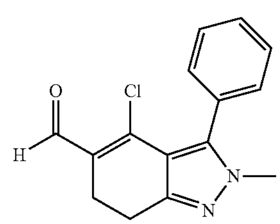 [SMILES: Cn1nc2c(c1-c1ccccc1)C(Cl)=C(C=O)CC2] | 1.15 | 273.2 | C |

TABLE 9-continued

| No. | Structure | t_ret [min] | [M + H]+ | Method of analysis |
|---|---|---|---|---|
| F3-02 | 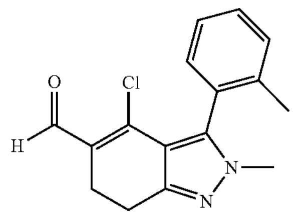 [SMILES: Cc1ccccc1-c1c2c(nn1C)CCC(C=O)=C2Cl] | 1.22 | 287.2 | C |
| F3-03 | 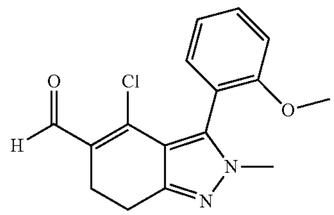 [SMILES: COc1ccccc1-c1c2c(nn1C)CCC(C=O)=C2Cl] | 1.11 | 303.2 | C |
| F3-04 | 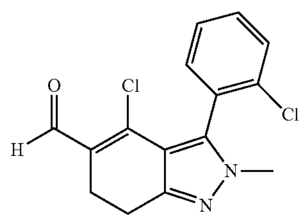 [SMILES: Cn1nc2c(c1-c1ccccc1Cl)C(Cl)=C(C=O)CC2] | 1.20 | 307.0 | C |
| F3-05 | 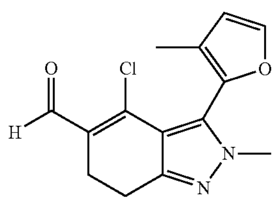 [SMILES: Cc1ccoc1-c1c2c(nn1C)CCC(C=O)=C2Cl] | 1.14 | 277.2 | C |
| F3-06 | 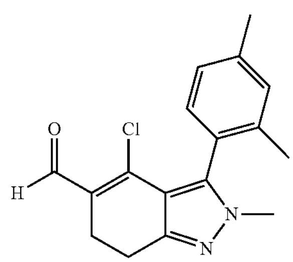 [SMILES: Cc1ccc(-c2c3c(nn2C)CCC(C=O)=C3Cl)c(C)c1] | 1.32 | 301.2 | C |
| F3-07 | 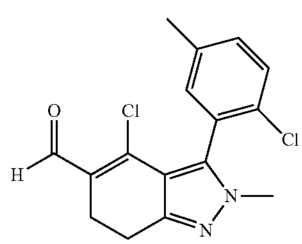 [SMILES: Cc1ccc(Cl)c(-c2c3c(nn2C)CCC(C=O)=C3Cl)c1] | 1.32 | 321.0 | C |
| F3-08 | 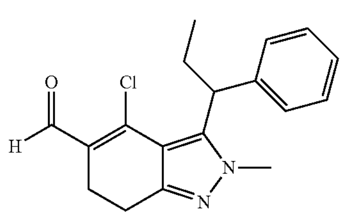 [SMILES: CCC(c1ccccc1)c1c2c(nn1C)CCC(C=O)=C2Cl] | 1.36 | 315.2 | C |

TABLE 9-continued

| No. | Structure | t$_{ret}$ [min] | [M + H]$^+$ | Method of analysis |
|---|---|---|---|---|
| F3-09 | 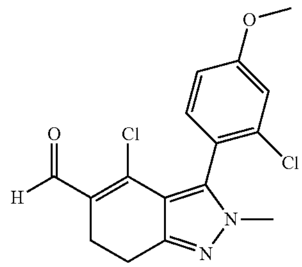 [SMILES: COc1ccc(-c2c3c(nn2C)CCC(C=O)=C3Cl)c(Cl)c1] | 1.24 | 337.0 | C |
| F3-10 | 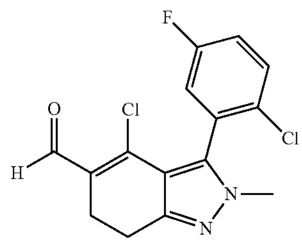 [SMILES: Cn1nc2c(c1-c1cc(F)ccc1Cl)C(Cl)=C(C=O)CC2] | 1.23 | 325.0 | C |
| F3-11 | 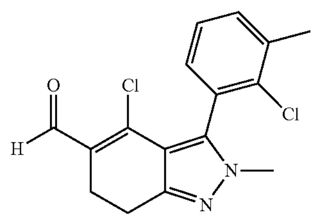 [SMILES: Cc1cccc(-c2c3c(nn2C)CCC(C=O)=C3Cl)c1Cl] | 1.30 | 321.0 | C |
| F3-12 | 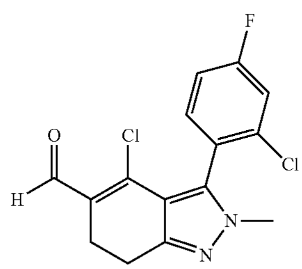 [SMILES: Cn1nc2c(c1-c1ccc(F)cc1Cl)C(Cl)=C(C=O)CC2] | 1.24 | 325.0 | C |
| F3-13 | 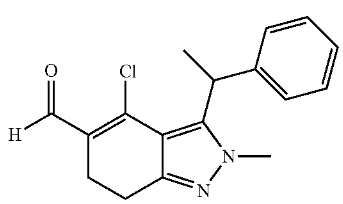 [SMILES: CC(c1ccccc1)c1c2c(nn1C)CCC(C=O)=C2Cl] | 1.25 | 301.0 | C |
| F3-14 | 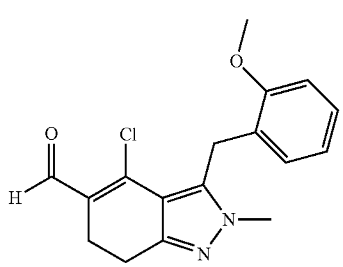 [SMILES: COc1ccccc1Cc1c2c(nn1C)CCC(C=O)=C2Cl] | 1.21 | 317.2 | C |

TABLE 9-continued

| No. | Structure | $t_{ret}$ [min] | $[M + H]^+$ | Method of analysis |
|---|---|---|---|---|
| F3-15 | 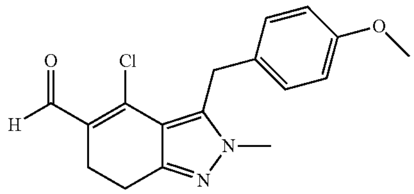 [SMILES: COc1ccc(Cc2c3c(nn2C)CCC(C=O)=C3Cl)cc1] | 1.16 | 317.2 | C |
| F3-16 | 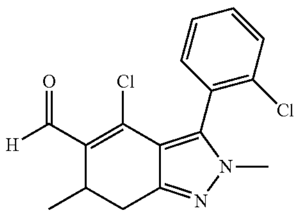 [SMILES: CC1Cc2nn(C)c(-c3ccccc3Cl)c2C(Cl)=C1C=O] | 1.26 | 321.0 | C |
| F3-17 | 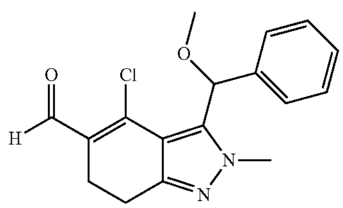 | 1.27 | 317.2 | C |

3. Guanidine Syntheses

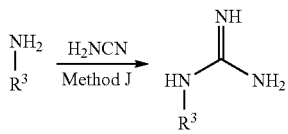

The preparation of the guanidine compounds (method J) takes place in the Parallel Synthesis Microwave Reactor (Synthos 3000, Anton Paar GmbH). The aniline (0.5 mmol) in dioxane (300 µL) is combined with cyanamide (1.5 mmol) in dioxane (125 µL) and HCl (4 N in dioxane, 188 µL) and stirred for 1 h at 120° C.

The reaction solutions are used in the next step without any further purification.

Complexly substituted guanidines are prepared analogously to or using the methods of C. E. Stephens, *J. Med. Chem.* 2001, 1741-1748 and H. Ube, *J. Organomet. Chem.* 2007, 545-549 using isothiourea components.

4. Preparation of Novel Compounds (I) by Pyrimidine Cyclisation and Optionally Derivatisation 4.1. Pyrimidine Cyclisation on Intermediates F1, F2 and F3 Using Guanidine (Method I, Type I)

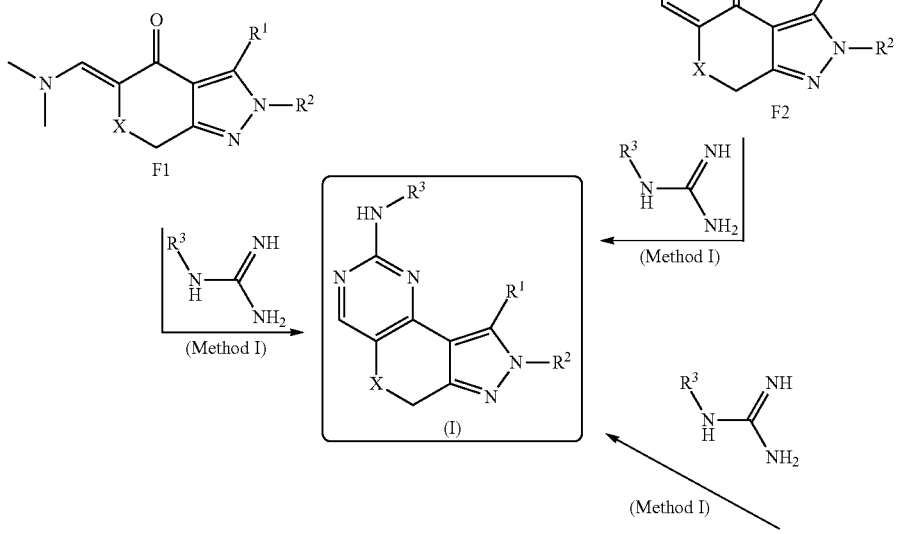

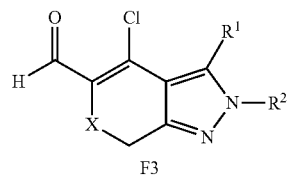

F3

Method I: The reaction mixture of the guanidine synthesis is combined with pyridine (200 μL) and the corresponding pyrazole component F1, F2 or F3 (0.5 mmol) in dioxane (150 μL) and stirred for 1 h at 120° C. in a parallel synthesis microwave reactor. The reaction mixture is purified by preparative HPLC-MS. The fractions containing the reaction product are freeze-dried. The compounds I-1 to I-295 according to the invention (Table 10) are prepared in this way.

Protected intermediate stages or guanidine intermediates intended for further derivatisation are prepared analogously and purified by conventional methods. The synthesis components required for this are synthesised from commercial reactants using standard methods.

TABLE 10

| No. | Structure | $t_{ret}$ [min] | $[M + H]^+$ | Method of analysis |
|---|---|---|---|---|
| I-1 | 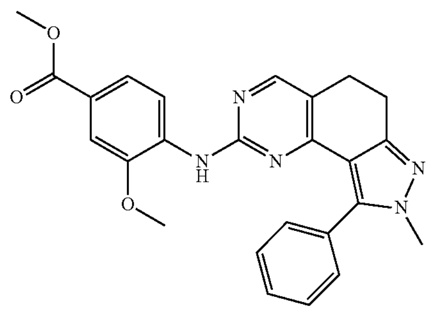 [SMILES: COC(=O)c1ccc(Nc2ncc3c(n2)-c2c(nn(C)c2-c2ccccc2)CC3)c(OC)c1] | 1.33 | 442.2 | C |
| I-2 | 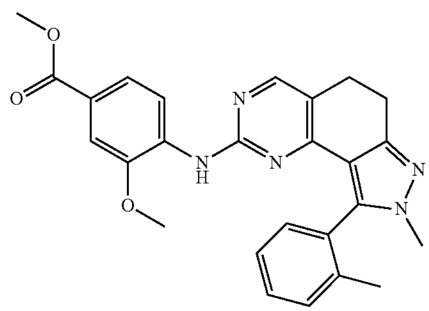 [SMILES: COC(=O)c1ccc(Nc2ncc3c(n2)-c2c(nn(C)c2-c2ccccc2C)CC3)c(OC)c1] | 1.39 | 456.2 | C |
| I-3 | 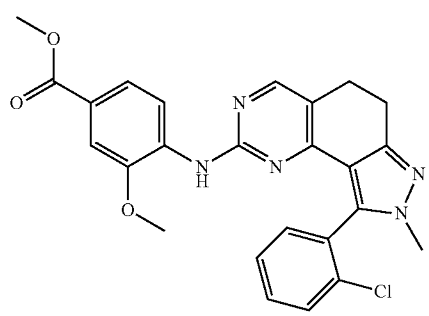 [SMILES: COC(=O)c1ccc(Nc2ncc3c(n2)-c2c(nn(C)c2-c2ccccc2Cl)CC3)c(OC)c1] | 1.36 | 476.2 | C |

TABLE 10-continued
| I-4 | 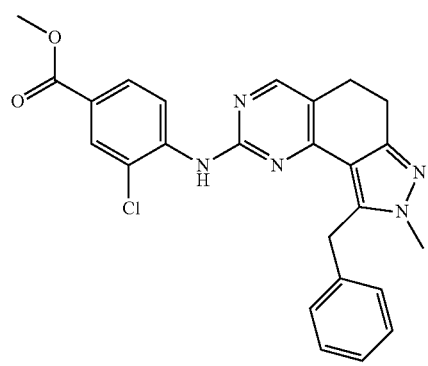 [SMILES: COC(=O)c1ccc(Nc2ncc3c(n2)-c2c(nn(C)c2Cc2ccccc2)CC3)c(Cl)c1] | 1.50 | 460.2 | C |
| I-5 | 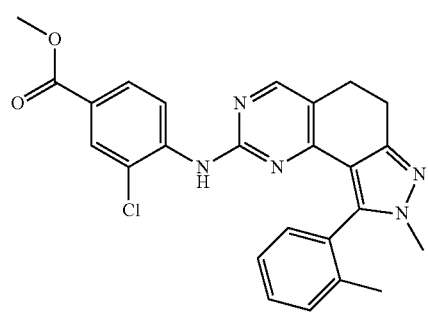 [SMILES: COC(=O)c1ccc(Nc2ncc3c(n2)-c2c(nn(C)c2-c2ccccc2C)CC3)c(Cl)c1] | 1.54 | 460.2 | C |
| I-6 | 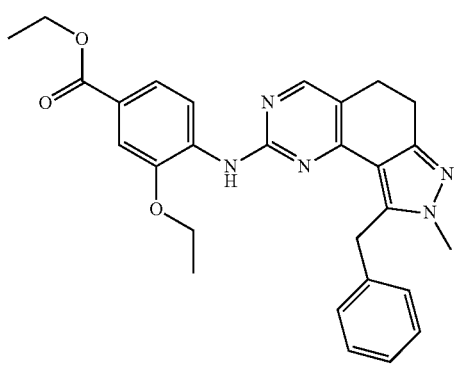 [SMILES: CCOC(=O)c1ccc(Nc2ncc3c(n2)-c2c(nn(C)c2Cc2ccccc2)CC3)c(OCC)c1] | 1.53 | 484.2 | C |
| I-7 | 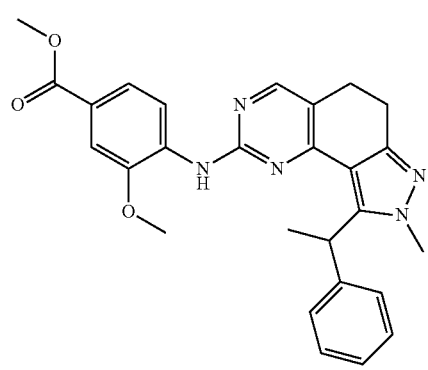 [SMILES: COC(=O)c1ccc(Nc2ncc3c(n2)-c2c(nn(C)c2C(C)c2ccccc2)CC3)c(OC)c1] | 1.46 | 470.2 | C |

TABLE 10-continued

| ID | Structure | | | |
|---|---|---|---|---|
| I-8* | (structure) | 1.40 | 490.2 | C |
| I-9 | (structure) | 2.07 | 456.3 | G |
| I-10 | (structure) | 2.05 | 476.3 | G |
| I-11 | (structure) | 1.25 | 482.2 | C |
| I-12 | (structure) | 2.04 | 482.0 | G |

TABLE 10-continued
| | | | | |
|---|---|---|---|---|
| I-13 | 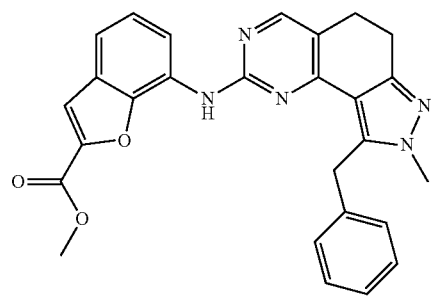 [SMILES: COC(=O)c1cc2cccc(Nc3ncc4c(n3)-c3c(nn(C)c3Cc3ccccc3)CC4)c2o1] | 2.05 | 466.0 | G |
| I-14 | 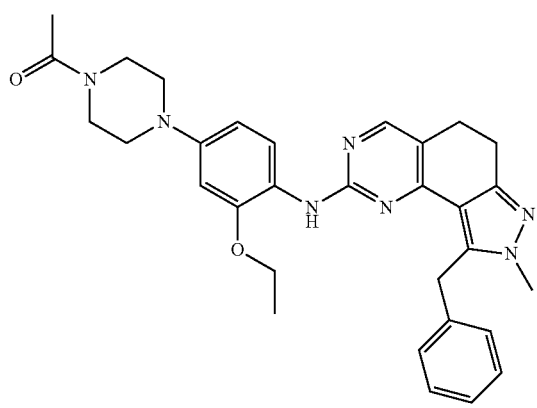 [SMILES: CCOc1cc(N2CCN(C(C)=O)CC2)ccc1Nc1ncc2c(n1)-c1c(nn(C)c1Cc1ccccc1)CC2] | 0.90 | 538.4 | C |
| I-15 | 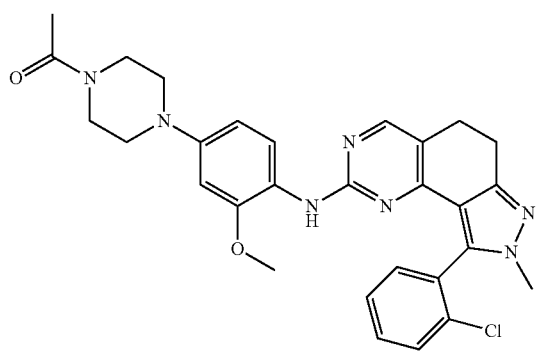 [SMILES: COc1cc(N2CCN(C(C)=O)CC2)ccc1Nc1ncc2c(n1)-c1c(nn(C)c1-c1ccccc1Cl)CC2] | 0.93 | 544.2 | C |
| I-16 | 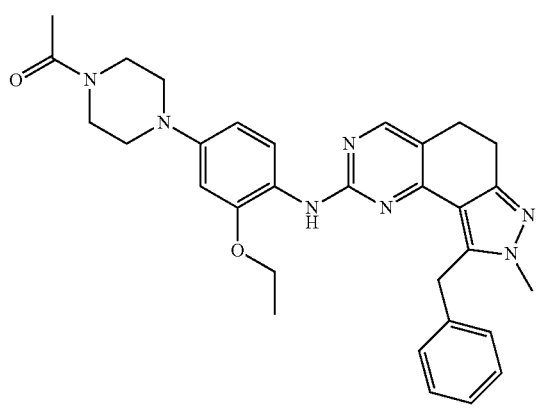 [SMILES: CCOc1cc(N2CCN(C(C)=O)CC2)ccc1Nc1ncc2c(n1)-c1c(nn(C)c1Cc1ccccc1)CC2] | 1.84 | 538.3 | G |

TABLE 10-continued

| | | | | |
|---|---|---|---|---|
| I-17 | | 1.66 | 528.2 | C |
| I-18 | | 1.88 | 354.3 | G |
| I-19 | | 1.66 | 420.3 | G |
| I-20 | | 1.99 | 384.3 | G |
| I-21 | | 1.91 | 388.3 | G |
| I-22 | | 2.04 | 418.3 | G |

TABLE 10-continued

| | | | | |
|---|---|---|---|---|
| I-23 | | 1.54 | 392.3 | G |
| I-24 | | 2.05 | 497.3 | G |
| I-25 | | 1.97 | 396.0 | G |
| I-26 | | 1.83 | 482.3 | G |
| I-27 | | 2.11 | 531.2 | G |
| I-28 | | 2.14 | 388.0 | G |

TABLE 10-continued
| | | | | |
|---|---|---|---|---|
| I-29* | 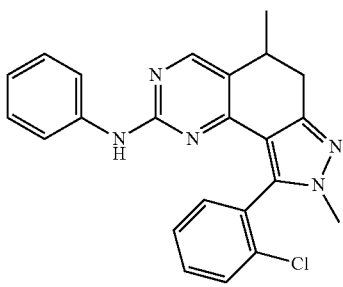 [SMILES: CC1Cc2nn(C)c(-c3ccccc3Cl)c2-c2nc(Nc3ccccc3)ncc21] | 1.96 | 402.3 | G |
| I-30 | 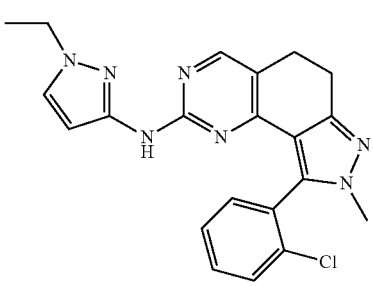 [SMILES: CCn1ccc(Nc2ncc3c(n2)-c2c(nn(C)c2-c2ccccc2Cl)CC3)n1] | 1.65 | 406.3 | G |
| I-31 | 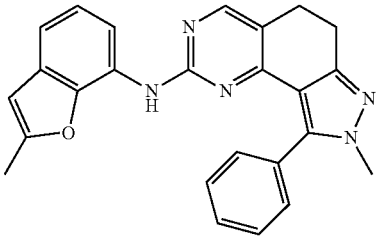 | 2.11 | 408.0 | G |
| I-32 | 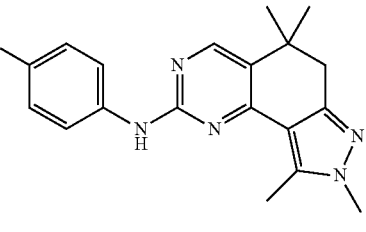 | 1.79 | 350.3 | G |
| I-33 | 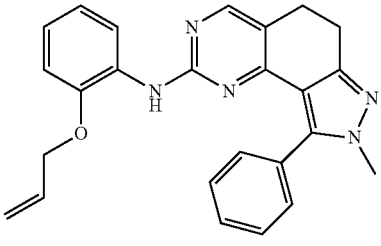 [SMILES: C=CCOc1ccccc1Nc1ncc2c(n1)-c1c(nn(C)c1-c1ccccc1)CC2] | 2.15 | 410.3 | G |
| I-34 | 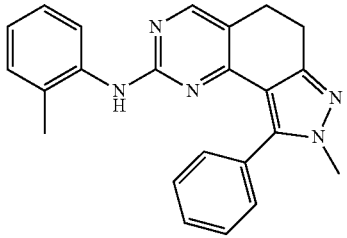 [SMILES: Cc1ccccc1Nc1ncc2c(n1)-c1c(nn(C)c1-c1ccccc1)CC2] | 1.97 | 368.0 | G |

TABLE 10-continued
| | | | | |
|---|---|---|---|---|
| I-35 | 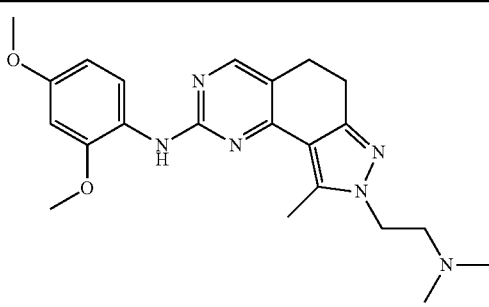 | 1.83 | 409.3 | G |
| I-36 | 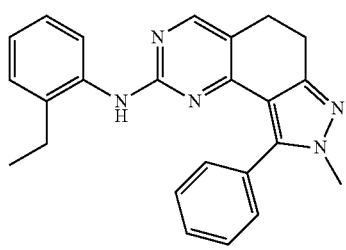 [SMILES: CCc1ccccc1Nc1ncc2c(n1)-c1c(nn(C)c1-c1ccccc1)CC2] | 2.08 | 382.0 | G |
| I-37 | 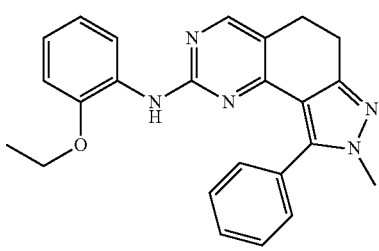 [SMILES: CCOc1ccccc1Nc1ncc2c(n1)-c1c(nn(C)c1-c1ccccc1)CC2] | 2.13 | 398.0 | G |
| I-38 | 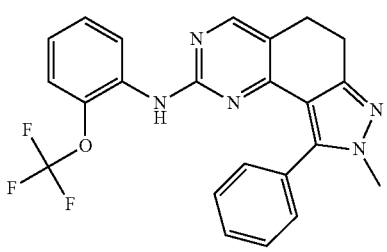 [SMILES: Cn1nc2c(c1-c1ccccc1)-c1nc(Nc3ccccc3OC(F)(F)F)ncc1CC2] | 2.21 | 438.0 | G |
| I-39 | 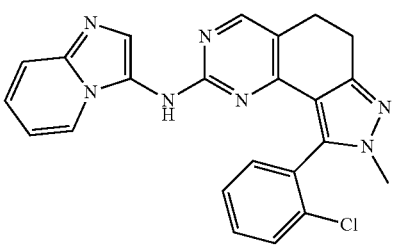 [SMILES: Cn1nc2c(c1-c1ccccc1Cl)-c1nc(Nc3cnc4ccccn34)ncc1CC2] | 1.51 | 428.3 | G |
| I-40* | 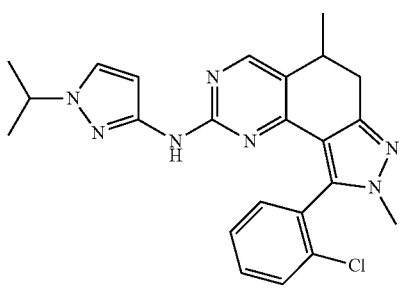 [SMILES: CC1Cc2nn(C)c(-c3ccccc3Cl)c2-c2nc(Nc3ccn(C(C)C)n3)ncc21] | 1.82 | 434.3 | G |

TABLE 10-continued
| | | | | |
|---|---|---|---|---|
| I-41* | 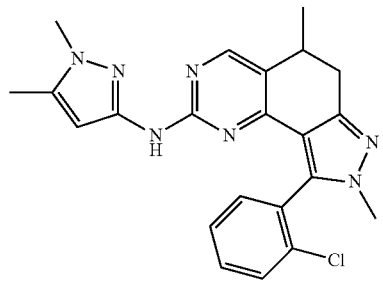 | 1.69 | 420.3 | G |
| I-42* | 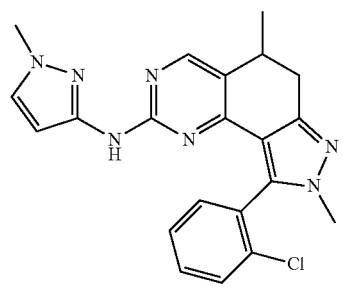 [SMILES: CC1Cc2nn(C)c(-c3ccccc3Cl)c2-c2nc(Nc3ccn(C)n3)ncc21] | 1.64 | 406.3 | G |
| I-43* | 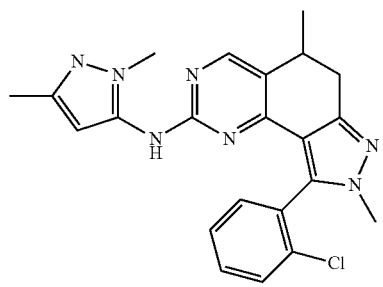 | 1.64 | 420.3 | G |
| I-44 | 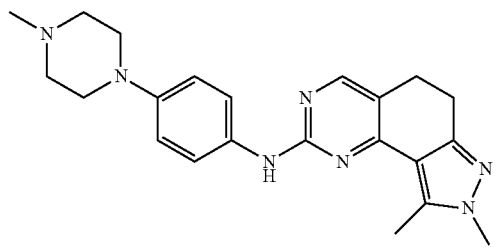 | 1.53 | 390.3 | G |
| I-45 | 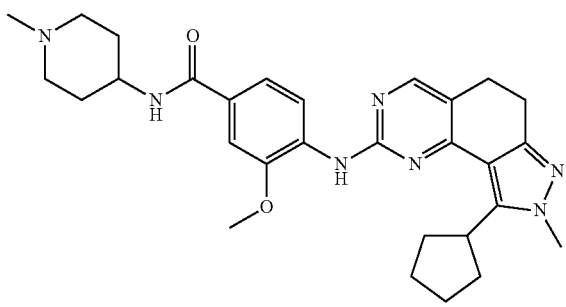 | 2.16 | 516.3 | G |

TABLE 10-continued

| | | | | |
|---|---|---|---|---|
| I-46 | | 2.28 | 530.5 | G |
| I-47 | Chiral | 1.78 | 510.5 | G |
| I-48 | Chiral | 1.94 | 510.3 | G |
| I-49 | | 1.77 | 538.3 | G |

TABLE 10-continued
| | | | | |
|---|---|---|---|---|
| I-50 | 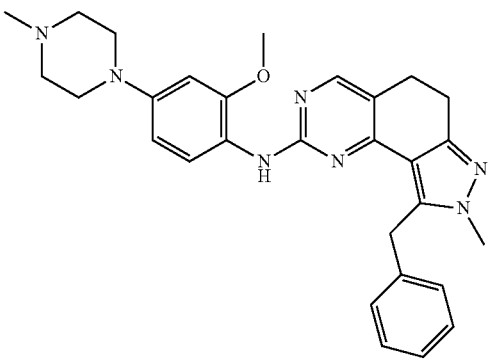 | 1.86 | 496.3 | G |
| I-51 | 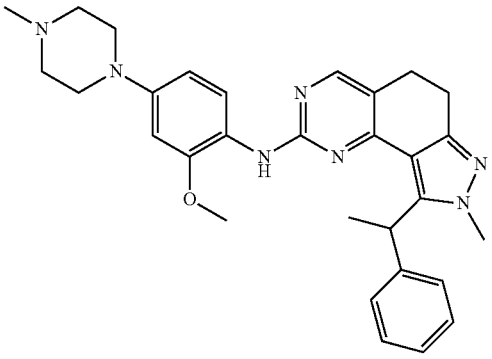 | 1.94 | 510.3 | G |
| I-52 | 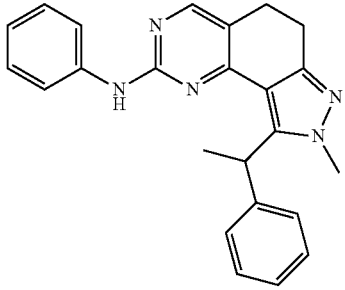 [SMILES: CC(c1ccccc1)c1c2c(nn1C)CCc1cnc(Nc3ccccc3)nc1-2] | 2.05 | 382.3 | G |
| I-53 | 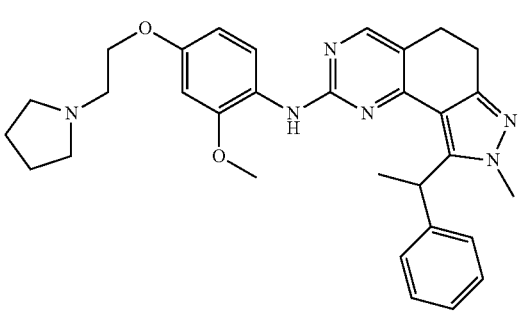 [SMILES: COc1cc(OCCN2CCCC2)ccc1Nc1ncc2c(n1)-c1c(nn(C)c1C(C)c1ccccc1)CC2] | 2.16 | 525.3 | G |
| I-54 | 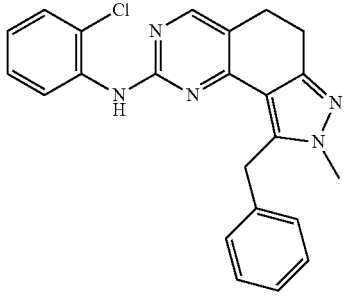 [SMILES: Cn1nc2c(c1Cc1ccccc1)-c1nc(Nc3ccccc3Cl)ncc1CC2] | 2.01 | 402.2 | G |

TABLE 10-continued

| ID | Structure | A | B | C |
|---|---|---|---|---|
| I-55 | 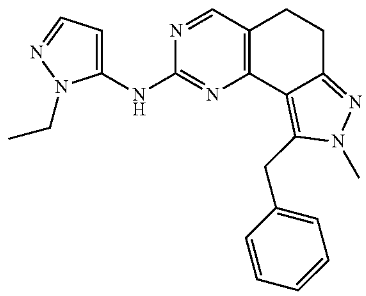 [SMILES: CCn1nccc1Nc1ncc2c(n1)-c1c(nn(C)c1Cc1ccccc1)CC2] | 1.64 | 386.0 | G |
| I-56 | 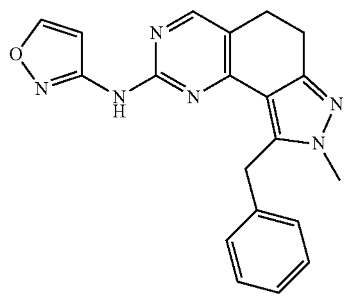 [SMILES: Cn1nc2c(c1Cc1ccccc1)-c1nc(Nc3ccon3)ncc1CC2] | 1.67 | 359.0 | G |
| I-57 | 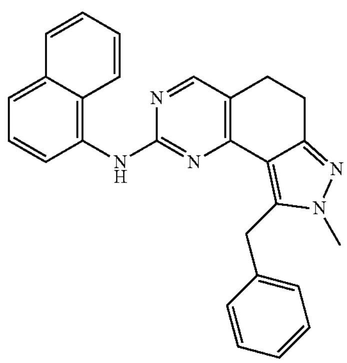 [SMILES: Cn1nc2c(c1Cc1ccccc1)-c1nc(Nc3cccc4ccccc34)ncc1CC2] | 2.11 | 418.0 | G |
| I-58 | 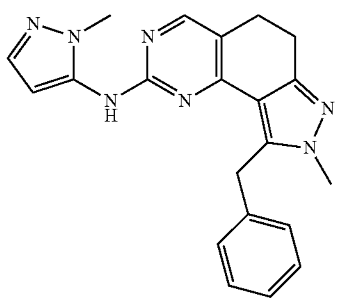 [SMILES: Cn1nccc1Nc1ncc2c(n1)-c1c(nn(C)c1Cc1ccccc1)CC2] | 1.56 | 372.3 | G |
| I-59 | 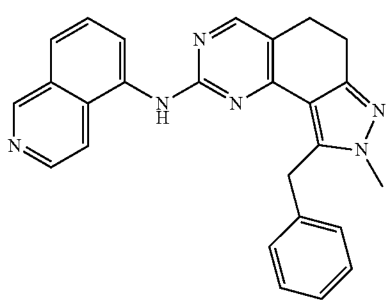 [SMILES: Cn1nc2c(c1Cc1ccccc1)-c1nc(Nc3cccc4cnccc34)ncc1CC2] | 1.77 | 419.0 | G |

TABLE 10-continued
| | | | | |
|---|---|---|---|---|
| I-60 | 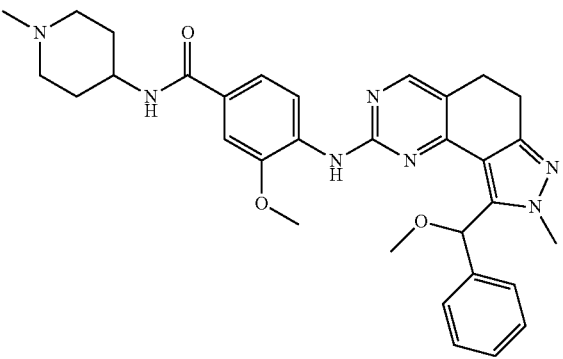 | 1.90 | 568.2 | G |
| I-61 | 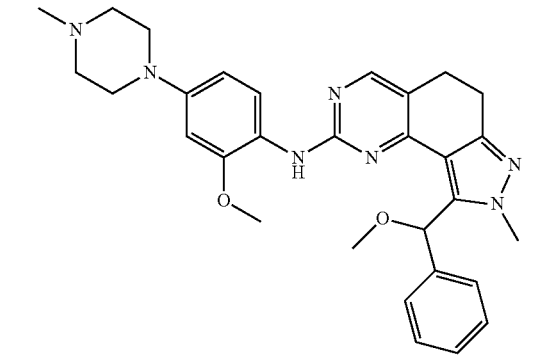 | 1.94 | 526.2 | G |
| I-62 | 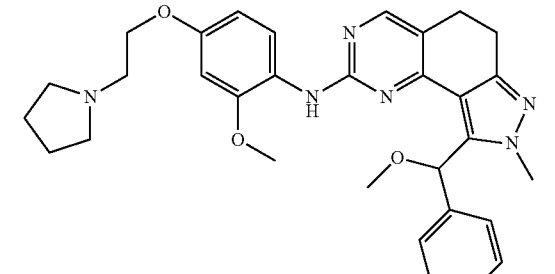 | 2.16 | 541.3 | G |
| I-63 | 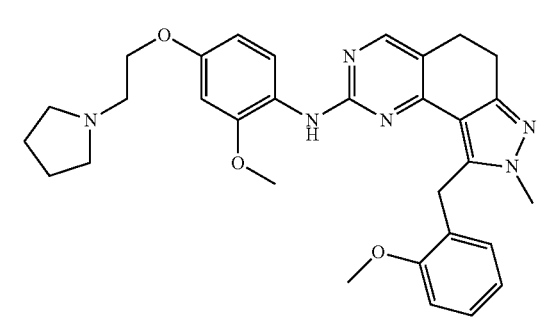 [SMILES: COc1ccccc1Cc1c2c(nn1C)CCc1cnc(Nc3ccc(OCCN4CCCC4)cc3OC)nc1-2] | 2.01 | 541.5 | G |
| I-64 | 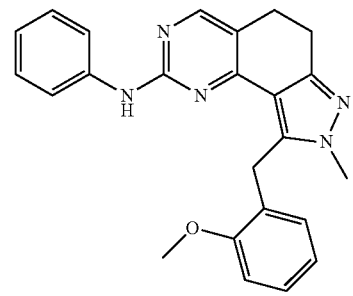 [SMILES: COc1ccccc1Cc1c2c(nn1C)CCc1cnc(Nc3ccccc3)nc1-2] | 1.77 | 398.3 | G |

TABLE 10-continued
| I-65 | 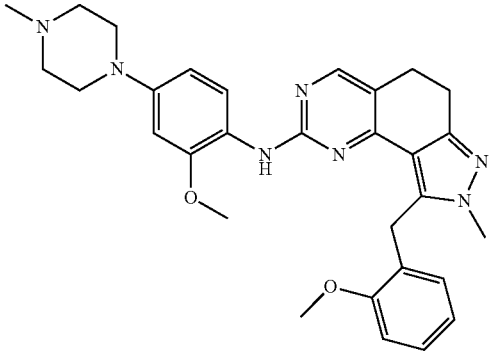 | 1.73 | 526.5 | G |
| I-66 | 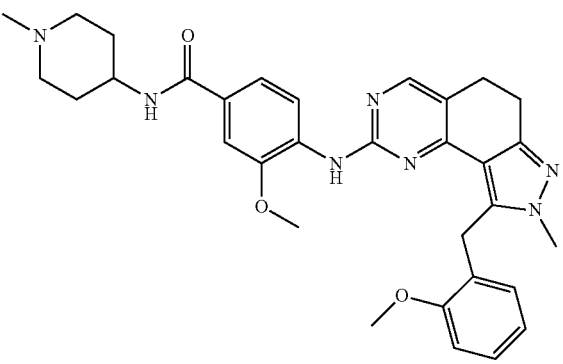 | 1.80 | 568.5 | G |
| I-67 | 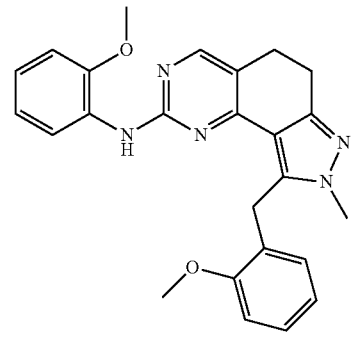 [SMILES: COc1ccccc1Cc1c2c(nn1C)CCc1cnc(Nc3ccccc3OC)nc1-2] | 1.87 | 428.5 | G |
| I-68 | 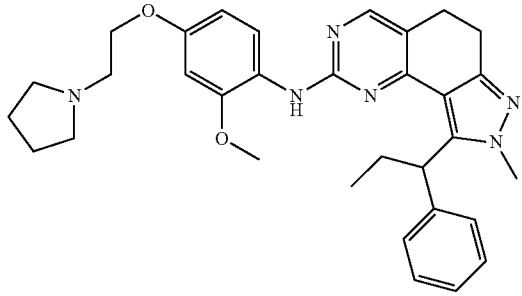 [SMILES: CCC(c1ccccc1)c1c2c(nn1C)CCc1cnc(Nc3ccc(OCCN4CCCC4)cc3OC)nc1-2] | 2.21 | 539.2 | G |

TABLE 10-continued
| | | | | |
|---|---|---|---|---|
| I-69 | 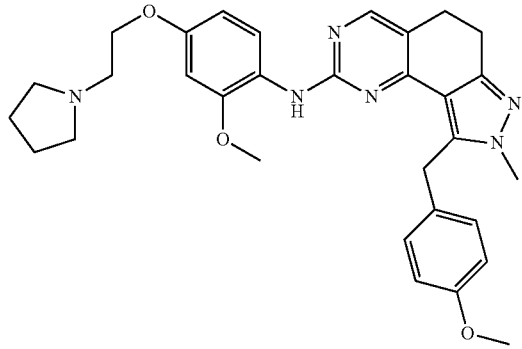 [SMILES: COc1ccc(Cc2c3c(nn2C)CCc2cnc(Nc4ccc(OCCN5CCCC5)cc4OC)nc2-3)cc1] | 2.07 | 541.3 | G |
| I-70 | 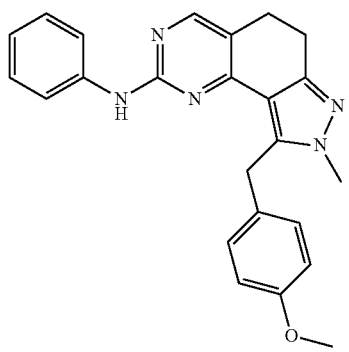 [SMILES: COc1ccc(Cc2c3c(nn2C)CCc2cnc(Nc4ccccc4)nc2-3)cc1] | 1.93 | 398.3 | G |
| I-71 | 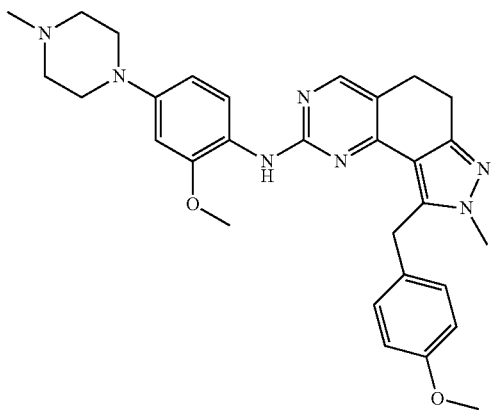 | 1.86 | 526.2 | G |
| I-72 | 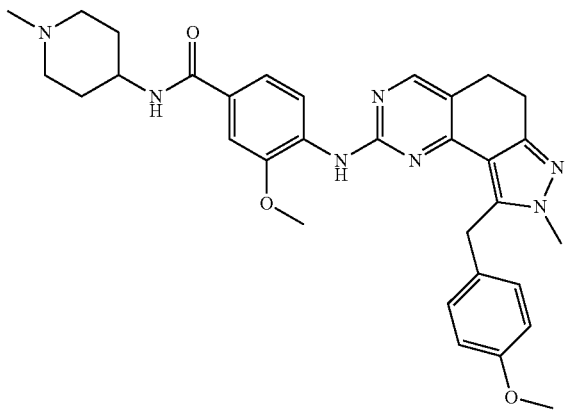 | 1.81 | 568.2 | G |

TABLE 10-continued
| | | | | |
|---|---|---|---|---|
| I-73 | 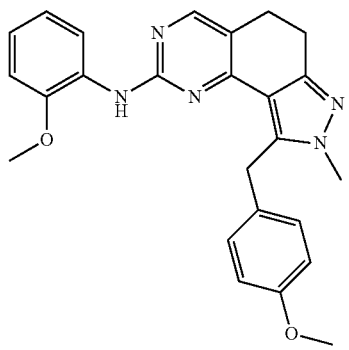 [SMILES: COc1ccc(Cc2c3c(nn2C)CCc2cnc(Nc4ccccc4OC)nc2-3)cc1] | 2.02 | 428.3 | G |
| I-74 | 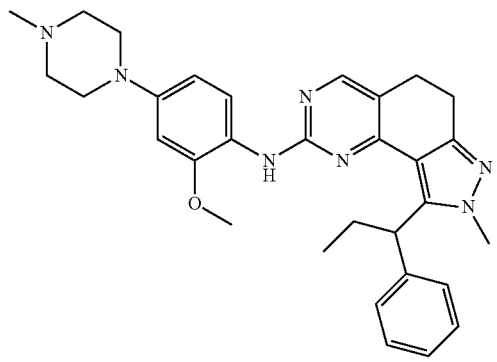 | 2.00 | 524.3 | G |
| I-75 | 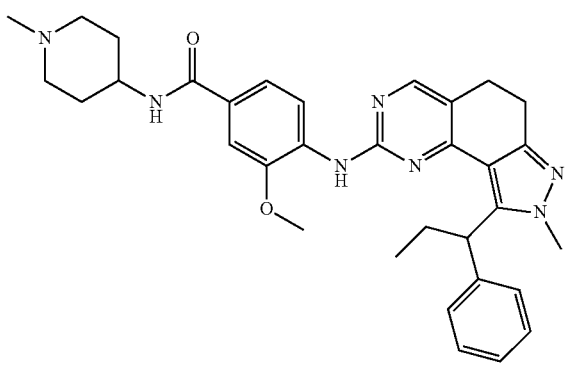 | 1.95 | 566.2 | G |
| I-76 | 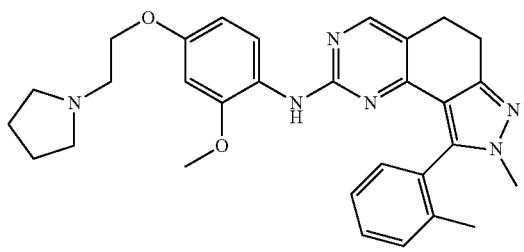 [SMILES: COc1cc(OCCN2CCCC2)ccc1Nc1ncc2c(n1)-c1c(nn(C)c1-c1ccccc1C)CC2] | 2.14 | 511.3 | G |
| I-77 | 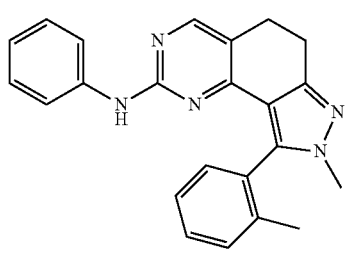 [SMILES: Cc1ccccc1-c1c2c(nn1C)CCc1cnc(Nc3ccccc3)nc1-2] | 1.97 | 368.0 | G |

TABLE 10-continued
| | | | | |
|---|---|---|---|---|
| I-78 | 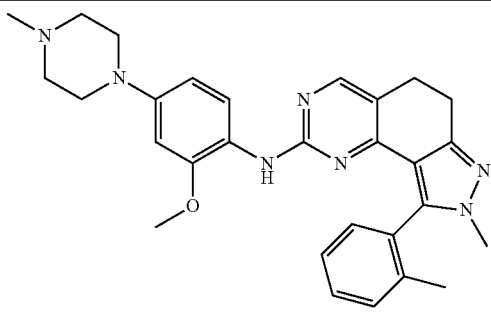 | 1.91 | 496.3 | G |
| I-79 | 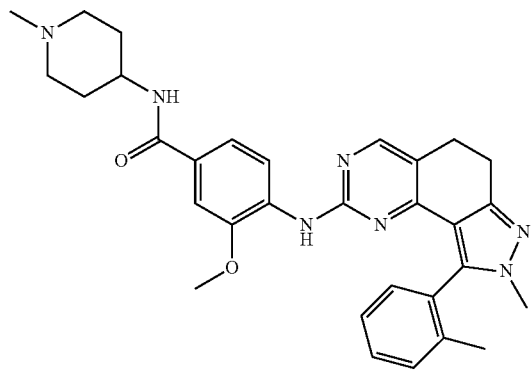 | 1.84 | 538.3 | G |
| I-80 | 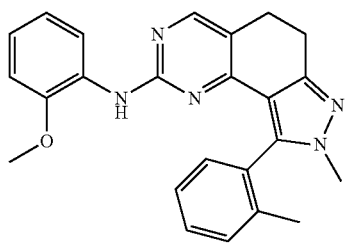 [SMILES: COc1ccccc1Nc1ncc2c(n1)-c1c(nn(C)c1-c1ccccc1C)CC2] | 2.08 | 398.3 | G |
| I-81 | 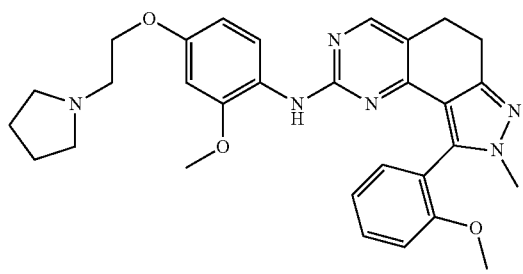 [SMILES: COc1cc(OCCN2CCCC2)ccc1Nc1ncc2c(n1)-c1c(nn(C)c1-c1ccccc1OC)CC2] | 2.05 | 527.2 | G |
| I-82 | 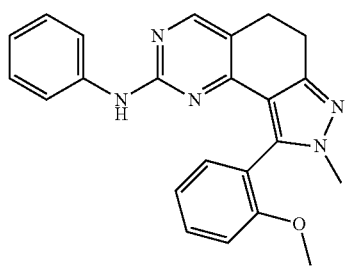 [SMILES: COc1ccccc1-c1c2c(nn1C)CCc1cnc(Nc3ccccc3)nc1-2] | 1.87 | 384.3 | G |

| | | | | |
|---|---|---|---|---|
| I-83 | 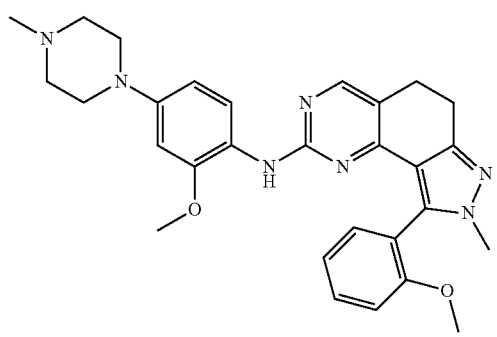 | 1.82 | 512.3 | G |
| I-84 | 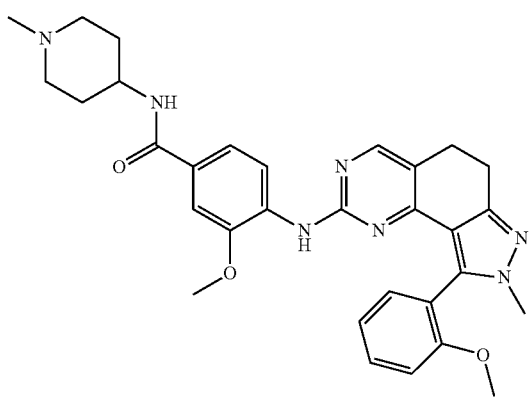 | 1.76 | 554.2 | G |
| I-85 | 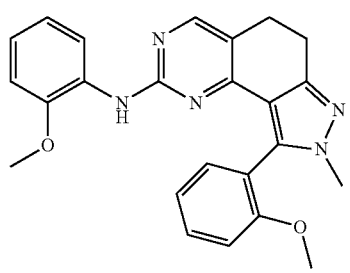 [SMILES: COc1ccccc1Nc1ncc2c(n1)-c1c(nn(C)c1-c1ccccc1OC)CC2] | 1.98 | 414.0 | G |
| I-86 | 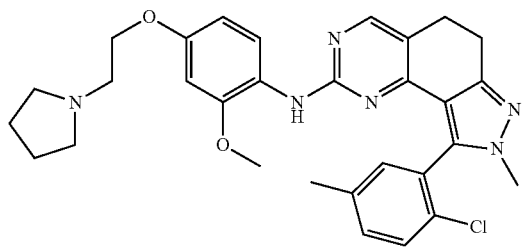 [SMILES: COc1cc(OCCN2CCCC2)ccc1Nc1ncc2c(n1)-c1c(nn(C)c1-c1cc(C)ccc1Cl)CC2] | 2.12 | 545.3 | G |
| I-87 | 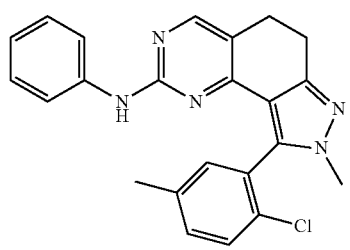 [SMILES: Cc1ccc(Cl)c(-c2c3c(nn2C)CCc2cnc(Nc4ccccc4)nc2-3)c1] | 1.98 | 402.0 | G |

TABLE 10-continued
| | | | | |
|---|---|---|---|---|
| I-88 | 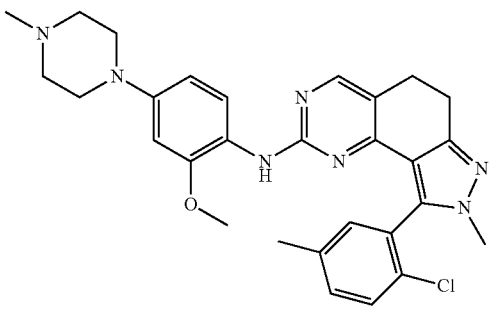 | 1.92 | 530.2 | G |
| I-89 | 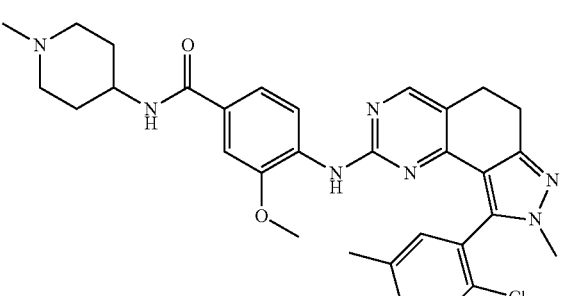 | 1.82 | 572.3 | G |
| I-90 | 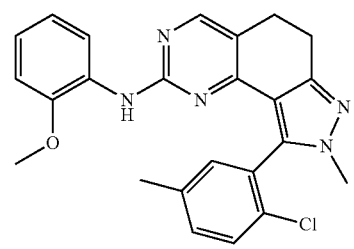 [SMILES: COc1ccccc1Nc1ncc2c(n1)-c1c(nn(C)c1-c1cc(C)ccc1Cl)CC2] | 2.09 | 432.3 | G |
| I-91 | 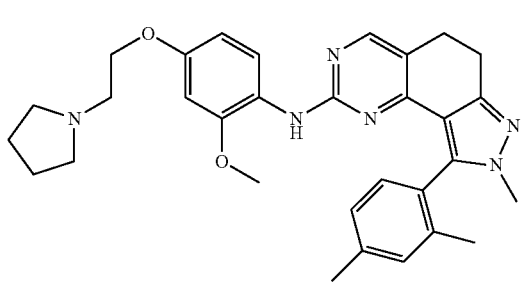 [SMILES: COc1cc(OCCN2CCCC2)ccc1Nc1ncc2c(n1)-c1c(nn(C)c1-c1ccc(C)cc1C)CC2] | 2.25 | 525.3 | G |
| I-92 | 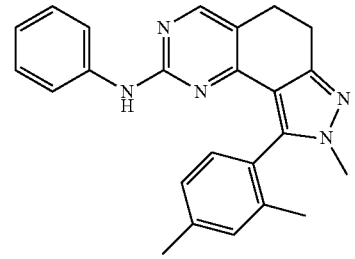 [SMILES: Cc1ccc(-c2c3c(nn2C)CCc2cnc(Nc4ccccc4)nc2-3)c(C)c1] | 2.01 | 382.3 | G |

| | | | | |
|---|---|---|---|---|
| I-93 | 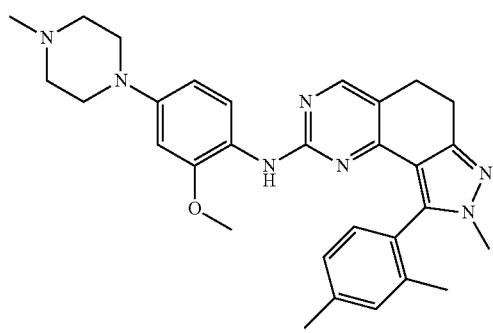 | 1.94 | 510.3 | G |
| I-94 | 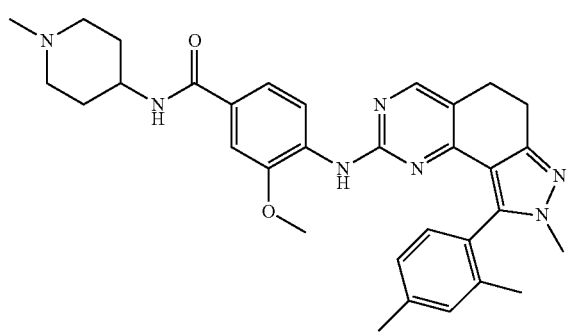 | 1.82 | 552.2 | G |
| I-95 | 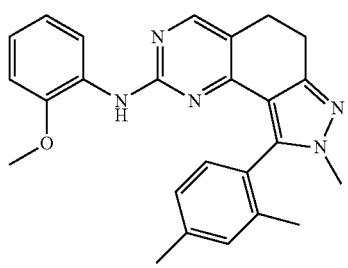 [SMILES: COc1ccccc1Nc1ncc2c(n1)-c1c(nn(C)c1-c1ccc(C)cc1C)CC2] | 2.12 | 412.3 | G |
| I-96* | 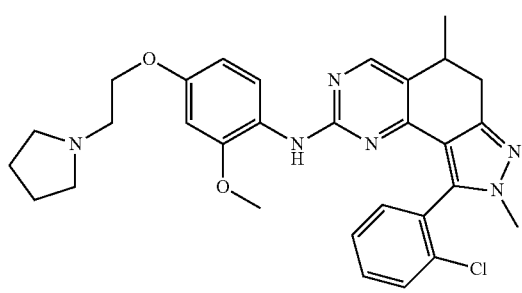 [SMILES: COc1cc(OCCN2CCCC2)ccc1Nc1ncc2c(n1)-c1c(nn(C)c1-c1ccccc1Cl)CC2C] | 2.12 | 545.3 | G |
| I-97* | 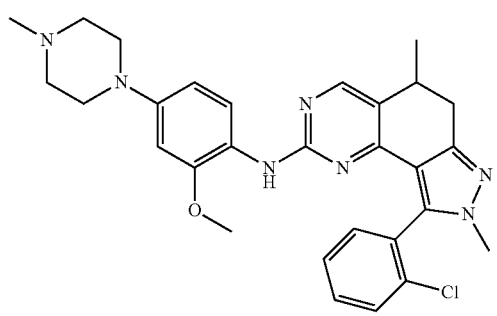 | 1.91 | 530.2 | G |

TABLE 10-continued

| ID | Structure | | | |
|---|---|---|---|---|
| I-98* | 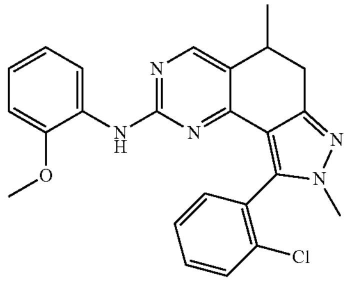 [SMILES: COc1ccccc1Nc1ncc2c(n1)-c1c(nn(C)c1-c1ccccc1Cl)CC2C] | 2.08 | 432.3 | G |
| I-99 | 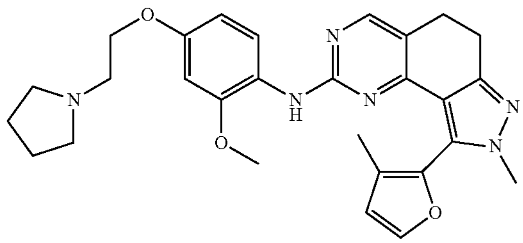 [SMILES: COc1cc(OCCN2CCCC2)ccc1Nc1ncc2c(n1)-c1c(nn(C)c1-c1occc1C)CC2] | 2.04 | 501.3 | G |
| I-100 | 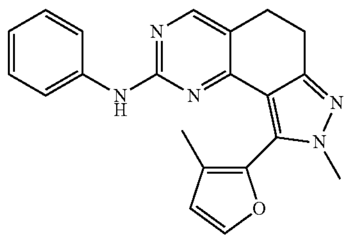 | 1.86 | 358.3 | G |
| I-101 | 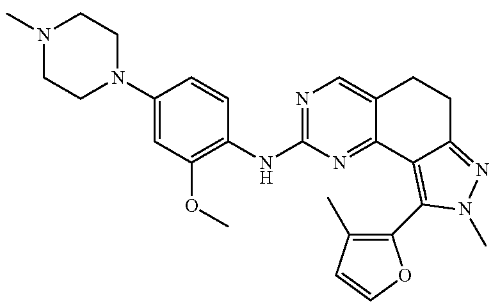 | 1.81 | 486.3 | G |
| I-102 | 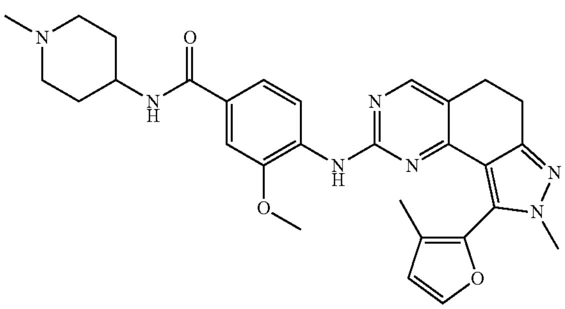 | 1.73 | 528.3 | G |
| I-103 | 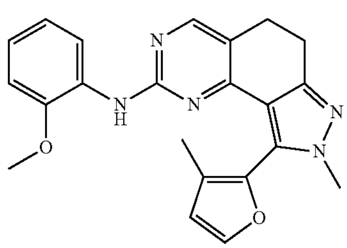 [SMILES: COc1ccccc1Nc1ncc2c(n1)-c1c(nn(C)c1-c1occc1C)CC2] | 1.99 | 388.3 | G |

TABLE 10-continued

| | | | | |
|---|---|---|---|---|
| I-104 | | 1.58 | 406.3 | G |
| I-105 | | 1.89 | 448.3 | G |
| I-106 | | 1.62 | 407.3 | G |
| I-107 | | 1.69 | 432.3 | G |
| I-108 | | 1.75 | 442.3 | G |
| I-109 | | 1.62 | 406.3 | G |

TABLE 10-continued

| | | | | |
|---|---|---|---|---|
| I-110 | | 1.88 | 516.3 | G |
| I-111 | | 1.55 | 372.3 | G |
| I-112 | | 1.80 | 558.5 | G |
| I-113 | | 1.94 | 368.3 | G |
| I-114 | | 2.13 | 360.3 | G |
| I-115 | | 1.85 | 320.3 | G |

TABLE 10-continued

| I-116 | | 1.90 | 336.3 | G |
| --- | --- | --- | --- | --- |
| I-117 | | 1.88 | 413.0 | G |
| I-118 | | 1.89 | 326.3 | G |
| I-119 | | 1.66 | 322.3 | G |
| I-120 | | 2.04 | 413.0 | G |
| I-121 | | 1.88 | 383.0 | G |

TABLE 10-continued

| | | | | |
|---|---|---|---|---|
| I-122 | | 1.97 | 413.0 | G |
| I-123 | | 1.98 | 413.0 | G |
| I-124 | | 1.97 | 320.3 | G |
| I-125 | | 1.94 | 334.3 | G |
| I-126 | | 1.90 | 332.3 | G |
| I-127 | | 1.82 | 460.3 | G |

TABLE 10-continued
| | | | | |
|---|---|---|---|---|
| I-128 | 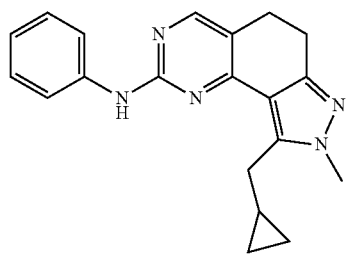 [SMILES: Cn1nc2c(c1CC1CC1)-c1nc(Nc3ccccc3)ncc1CC2] | 1.87 | 332.0 | G |
| I-129 | 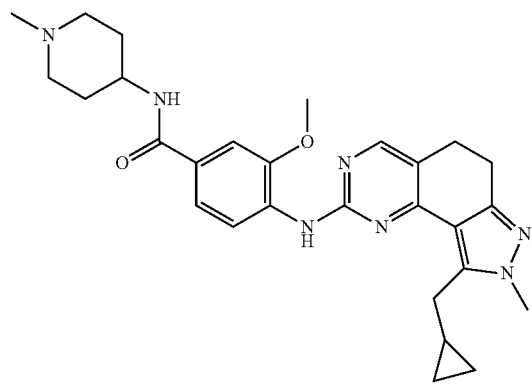 | 1.74 | 502.0 | G |
| I-130 | 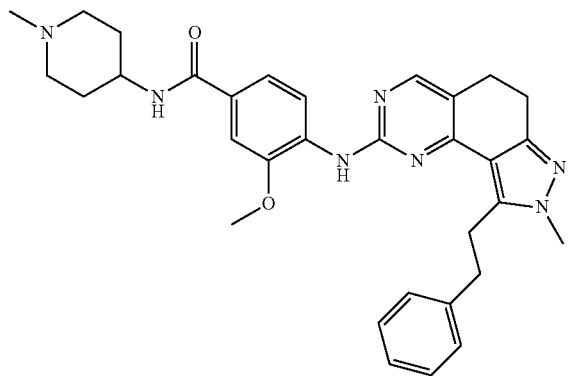 | 2.15 | 552.5 | G |
| I-131 | 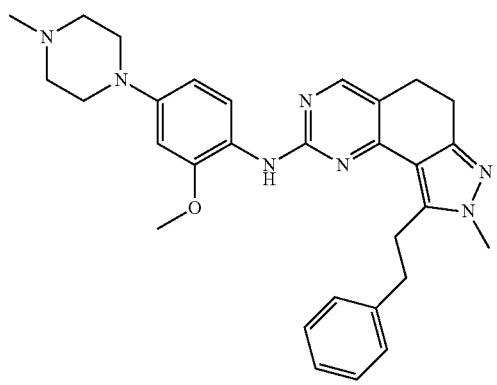 | 2.03 | 510.20 | G |

TABLE 10-continued
| I-132 | 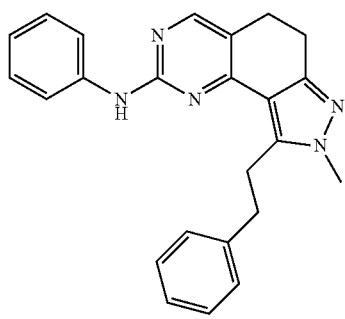 [SMILES: Cn1nc2c(c1CCc1ccccc1)-c1nc(Nc3ccccc3)ncc1CC2] | 2.06 | 382.3 | G |
| I-133 | 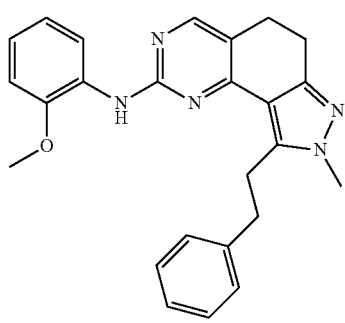 [SMILES: COc1ccccc1Nc1ncc2c(n1)-c1c(nn(C)c1CCc1ccccc1)CC2] | 2.19 | 412.3 | G |
| I-134 | 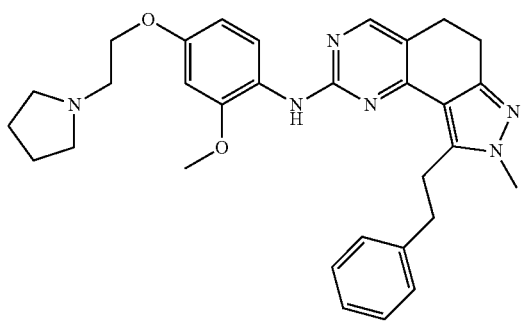 [SMILES: COc1cc(OCCN2CCCC2)ccc1Nc1ncc2c(n1)-c1c(nn(C)c1CCc1ccccc1)CC2] | 2.14 | 525.5 | G |
| I-135 | 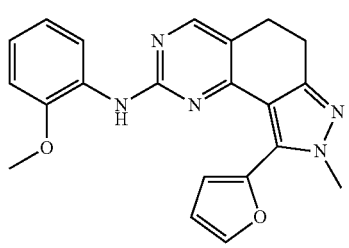 [SMILES: COc1ccccc1Nc1ncc2c(n1)-c1c(nn(C)c1-c1ccco1)CC2] | 1.97 | 374.2 | G |
| I-136 | 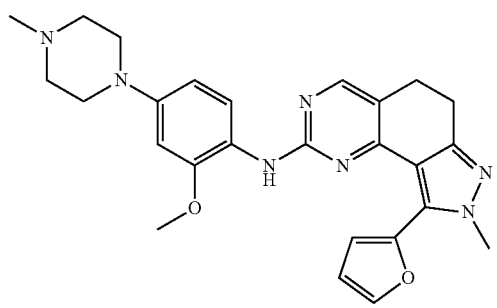 | 1.81 | 472.30 | G |

TABLE 10-continued
| | | | | |
|---|---|---|---|---|
| I-137 | 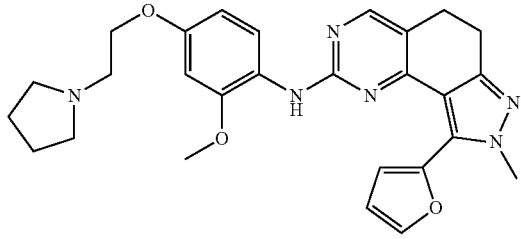 [SMILES: COc1cc(OCCN2CCCC2)ccc1Nc1ncc2c(n1)-c1c(nn(C)c1-c1ccco1)CC2] | 2.04 | 487.3 | G |
| I-138 | 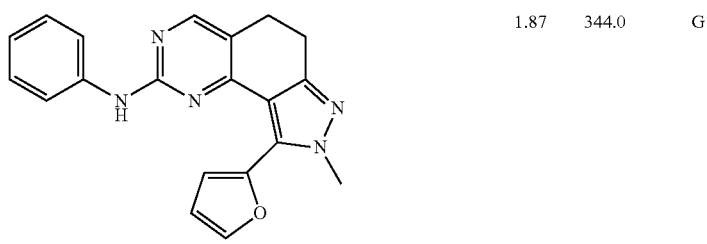 | 1.87 | 344.0 | G |
| I-139 | 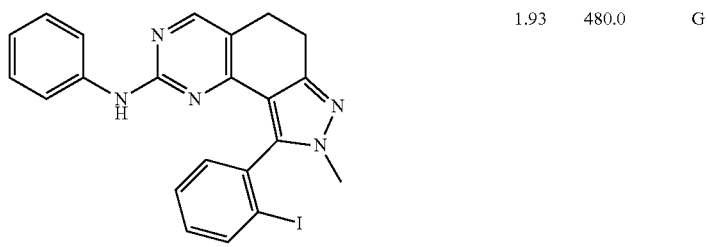 | 1.93 | 480.0 | G |
| I-140 | 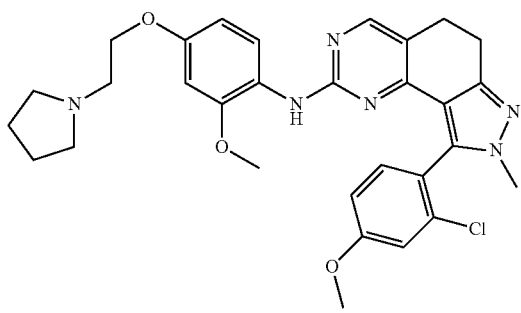 [SMILES: COc1ccc(-c2c3c(nn2C)CCc2cnc(Nc4ccc(OCCN5CCCC5)cc4OC)nc2-3)c(Cl)c1] | 2.08 | 561.3 | G |
| I-141 | 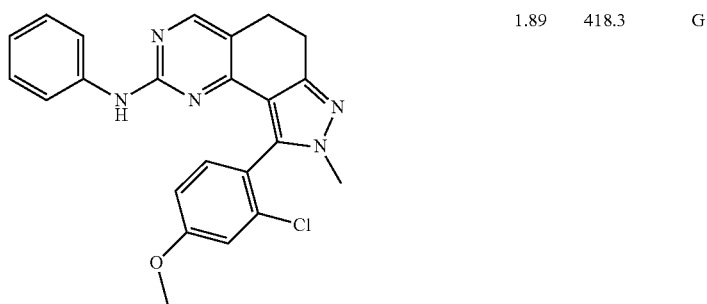 | 1.89 | 418.3 | G |

TABLE 10-continued
| | | | | |
|---|---|---|---|---|
| I-142 | 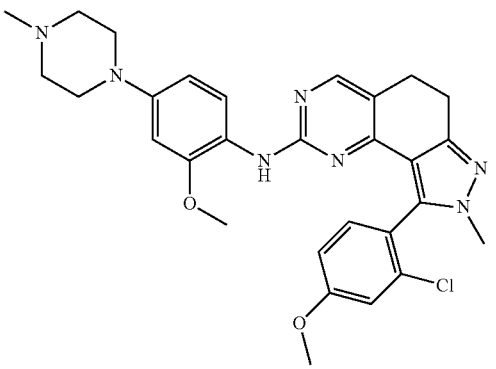 | 1.86 | 546.3 | G |
| I-143 | 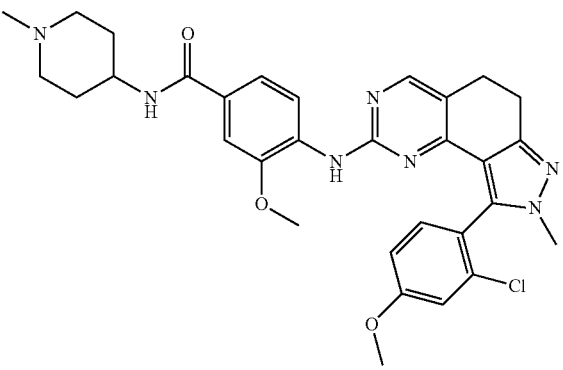 | 1.78 | 588.3 | G |
| I-144 | 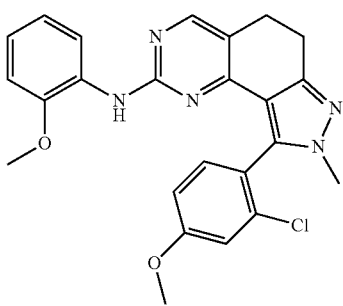 [SMILES: COc1ccc(-c2c3c(nn2C)CCc2cnc(Nc4ccccc4OC)nc2-3)c(Cl)c1] | 2.00 | 448.3 | G |
| I-145 | 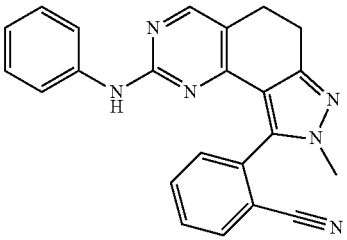 [SMILES: Cn1nc2c(c1-c1ccccc1C#N)-c1nc(Nc3ccccc3)ncc1CC2] | 1.68 | 379.0 | G |
| I-146 | 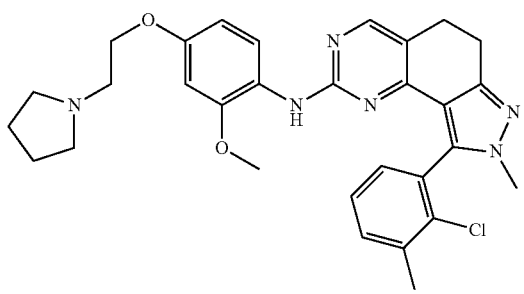 [SMILES: COc1cc(OCCN2CCCC2)ccc1Nc1ncc2c(n1)-c1c(nn(C)c1-c1cccc(C)c1Cl)CC2] | 2.02 | 545.3 | G |

TABLE 10-continued
| | | | | |
|---|---|---|---|---|
| I-147 | 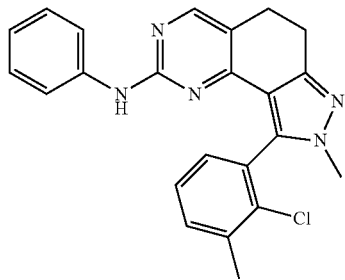 [SMILES: Cc1cccc(-c2c3c(nn2C)CCc2cnc(Nc4ccccc4)nc2-3)c1Cl] | 1.84 | 402.2 | G |
| I-148 | 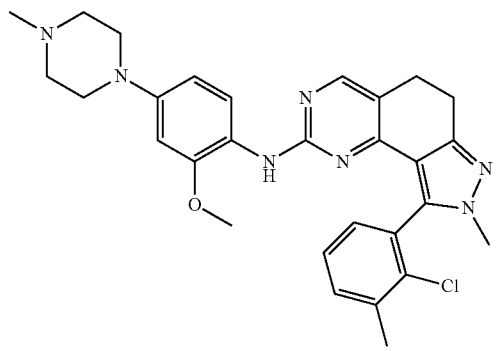 | 1.77 | 530.5 | G |
| I-149 | 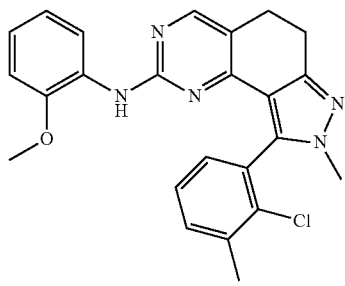 [SMILES: COc1ccccc1Nc1ncc2c(n1)-c1c(nn(C)c1-c1cccc(C)c1Cl)CC2] | 1.93 | 432.0 | G |
| I-150 | 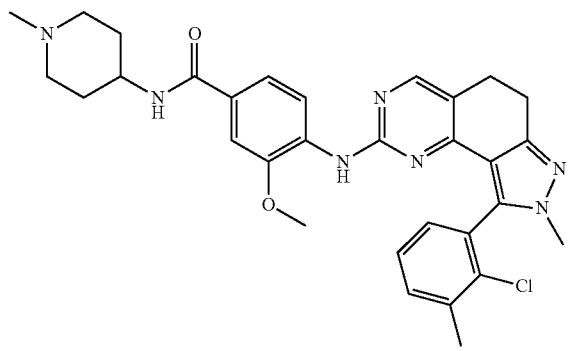 | 1.69 | 572.3 | G |
| I-151 | 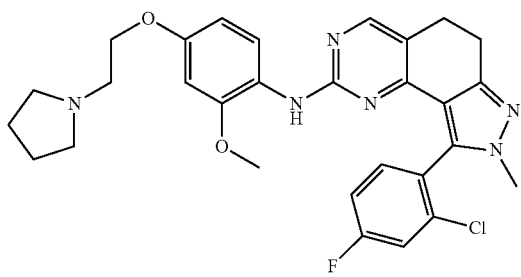 [SMILES: COc1cc(OCCN2CCCC2)ccc1Nc1ncc2c(n1)-c1c(nn(C)c1-c1ccc(F)cc1Cl)CC2] | 1.94 | 549.3 | G |

TABLE 10-continued
| | | | | |
|---|---|---|---|---|
| I-152 | 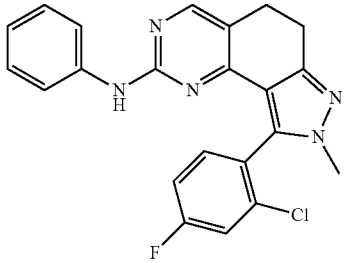 [SMILES: Cn1nc2c(c1-c1ccc(F)cc1Cl)-c1nc(Nc3ccccc3)ncc1CC2] | 1.76 | 406.2 | G |
| I-153 | 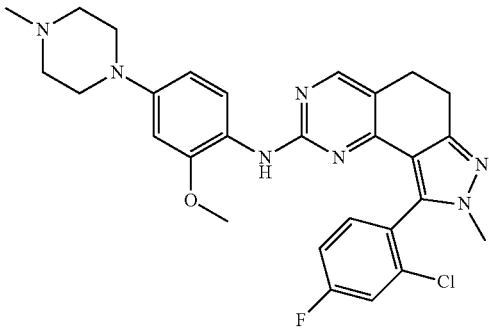 | 1.71 | 534.5 | G |
| I-154 | 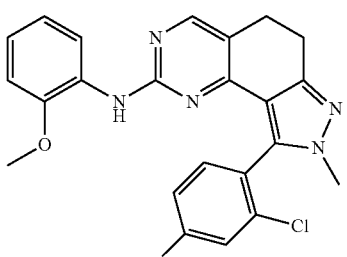 | 1.87 | 436.2 | G |
| I-155 | 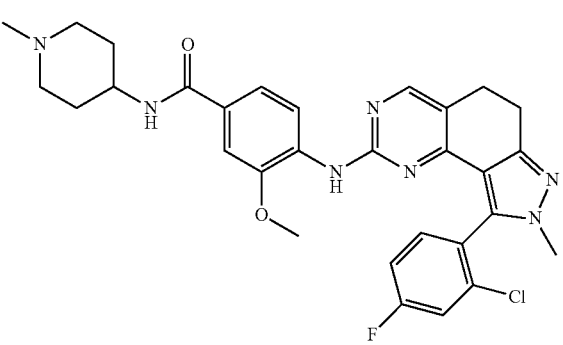 | 1.64 | 576.2 | G |
| I-156 | 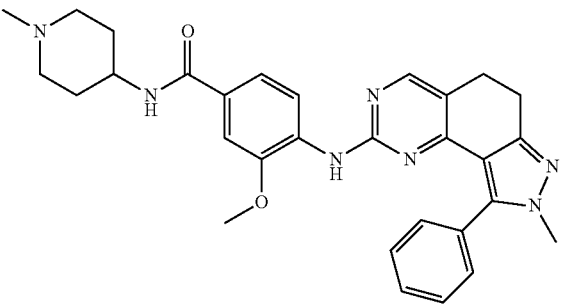 | 1.75 | 524.3 | G |

TABLE 10-continued

| | | | | |
|---|---|---|---|---|
| I-157* | (structure) | 1.82 | 572.3 | G |
| I-158 | (structure) | 1.72 | 490.3 | G |
| I-159 | (structure) | 1.70 | 488.3 | G |
| I-160 | (structure) | 1.72 | 490.3 | G |
| I-161 | (structure) | 1.72 | 476.3 | G |

TABLE 10-continued

| No. | Structure | t_ret [min] | [M + H]+ | Analysis |
|-----|-----------|-------------|----------|----------|
| I-162 | 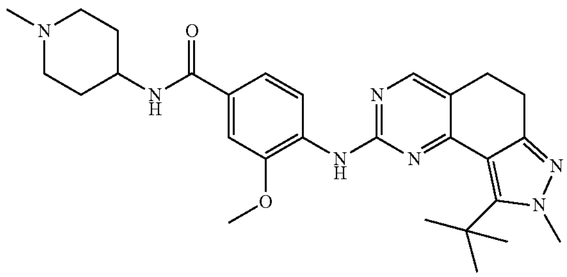 | 1.80 | 504.3 | G |
| I-163 | 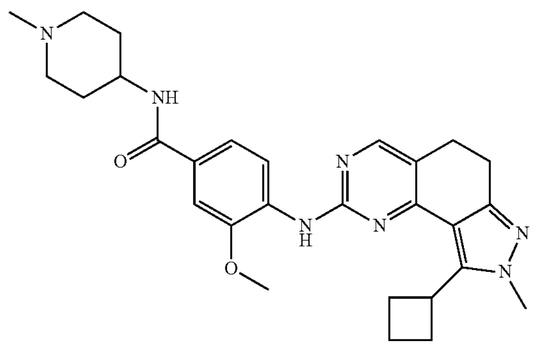 | 1.78 | 502.3 | G |
| I-164 | 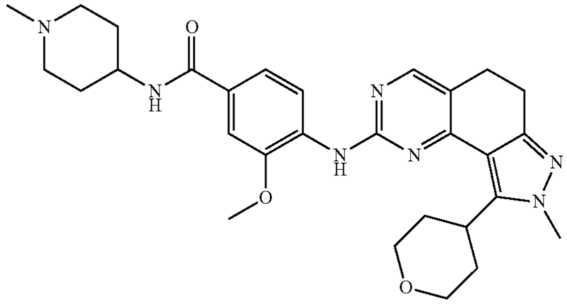 | 1.66 | 532.3 | G |
| I-165 | 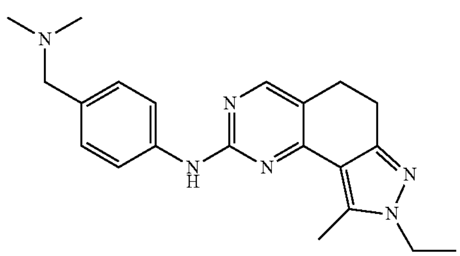 [SMILES: CCn1nc2c(c1C)-c1nc(Nc3ccc(CN(C)C)cc3)ncc1CC2] | 1.76 | 363.3 | G |
| I-166 | | 1.07 | 500 | G |

TABLE 10-continued
| I-167 | 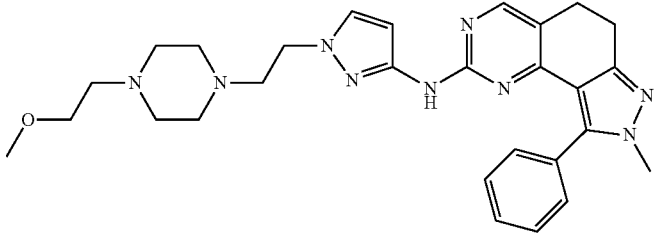 | 1.17 | 514 | G |
| I-168 | 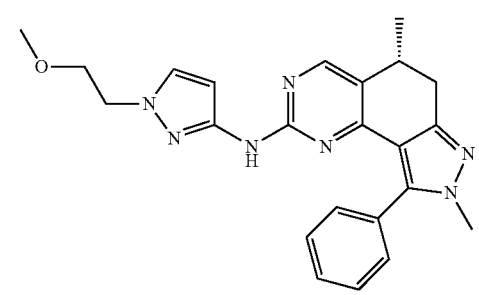 | 1.67 | 416 | G |
| I-169 | 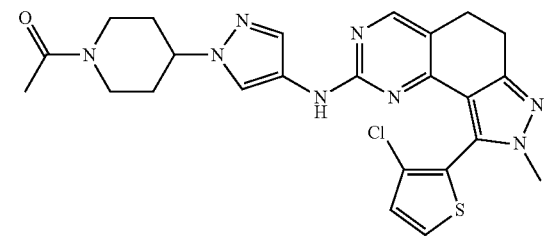 [SMILES: CC(=O)N1CCC(n2cc(Nc3ncc4c(n3)-c3c(nn(C)c3-c3sccc3Cl)CC4)cn2)CC1] | 1.25 | 509 | G |
| I-170 | 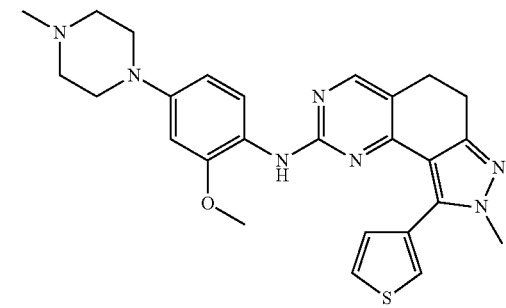 | 1.76 | 488 | G |
| I-171 | 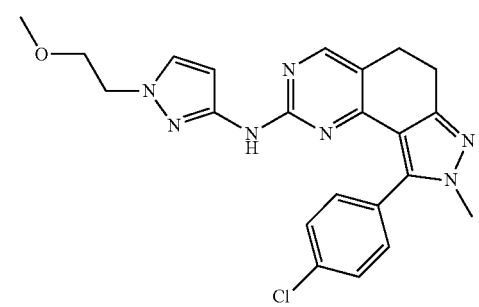 | 1.29 | 436 | G |

TABLE 10-continued
| | | | | |
|---|---|---|---|---|
| I-172 | 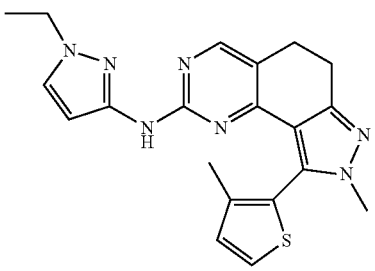 [SMILES: CCn1ccc(Nc2ncc3c(n2)-c2c(nn(C)c2-c2sccc2C)CC3)n1] | 1.37 | 392 | G |
| I-173 | 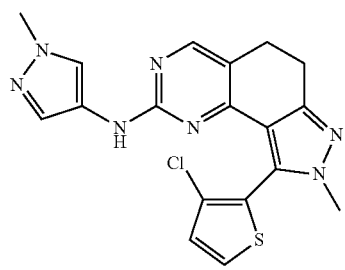 | 1.25 | 398 | G |
| I-174 | 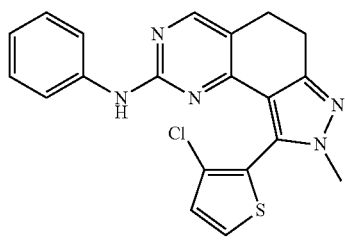 | 1.54 | 394 | G |
| I-175 | 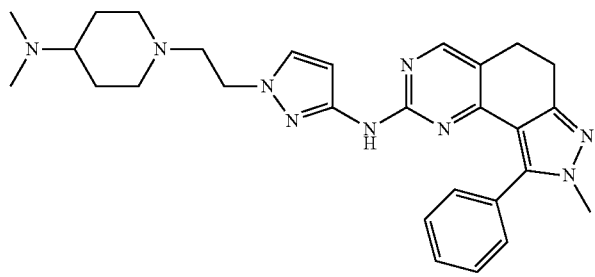 | 1.29 | 498 | G |
| I-176 | 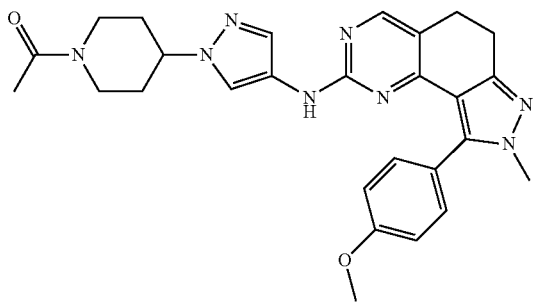 [SMILES: COc1ccc(-c2c3c(nn2C)CCc2cnc(Nc4cnn(C5CCN(C(C)=O)CC5)c4)nc2-3)cc1] | 1.14 | 499 | G |
| I-177 | 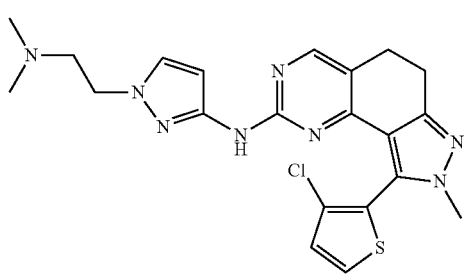 | 1.35 | 455 | G |

TABLE 10-continued
| | | | | |
|---|---|---|---|---|
| I-178 | 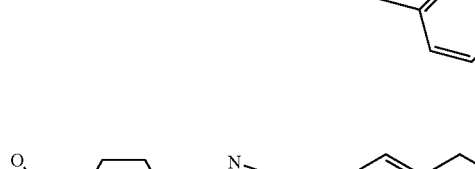 | 1.19 | 497 | G |
| I-179 | 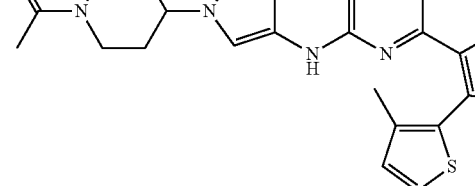 | 1.24 | 489 | G |
| I-180 | 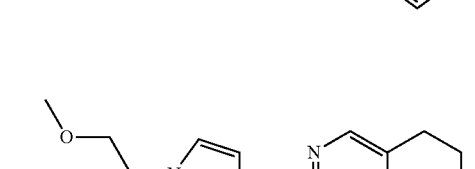 | 1.33 | 442 | G |
| I-181 | 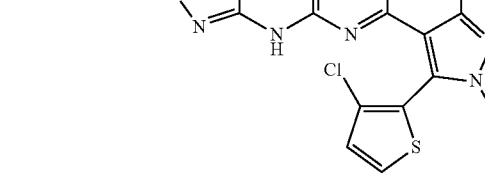 | 1.37 | 412 | G |
| I-182 | 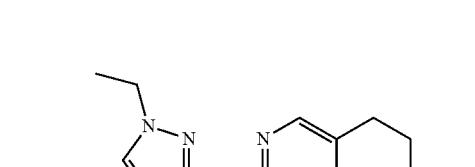 | 1.10 | 456 | G |

TABLE 10-continued
| | | | | |
|---|---|---|---|---|
| I-183 | 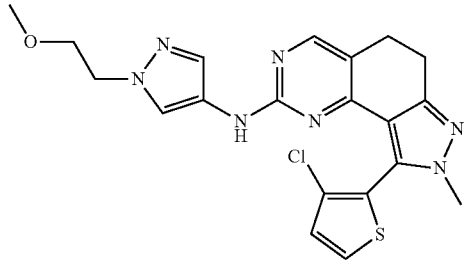 | 1.28 | 442 | G |
| I-184 | 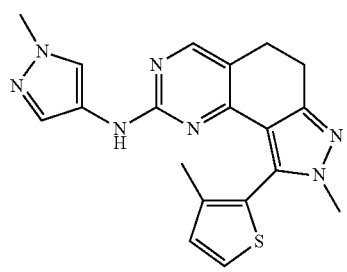 [SMILES: Cc1ccsc1-c1c2c(nn1C)CCc1cnc(Nc3cnn(C)c3)nc1-2] | 1.24 | 378 | G |
| I-185 | 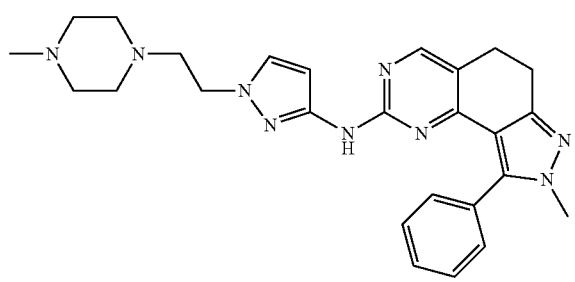 | 1.14 | 470 | G |
| I-186* | 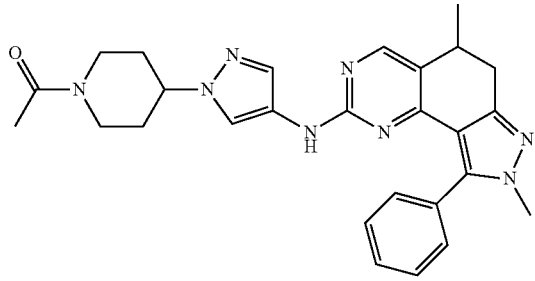 [SMILES: CC(=O)N1CCC(n2cc(Nc3ncc4c(n3)-c3c(nn(C)c3-c3ccccc3)CC4C)cn2)CC1] | 1.18 | 483 | G |
| I-187 | 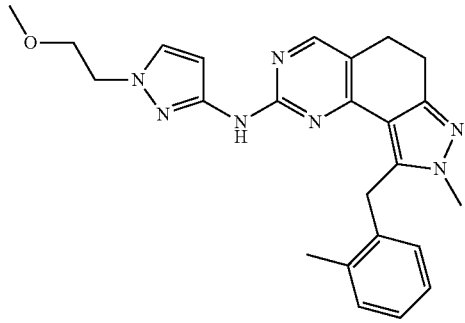 | 1.29 | 430 | G |

TABLE 10-continued
| I-188 | 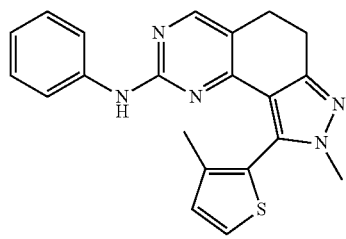 | 1.55 | 374 | G |
| I-189 | 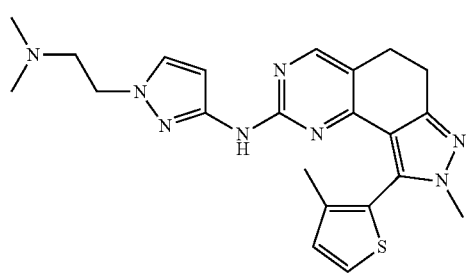 | 1.34 | 435 | G |
| I-190 | 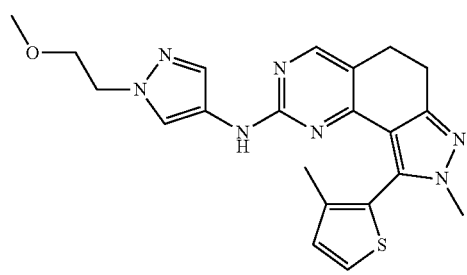 | 1.28 | 422 | G |
| I-191 | 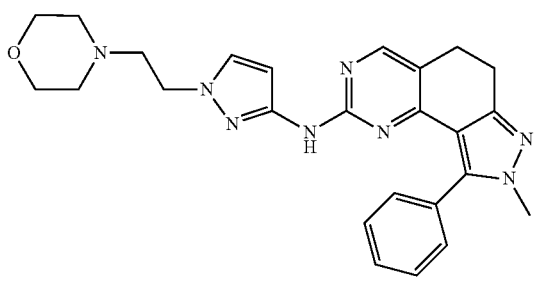 [SMILES: Cn1nc2c(c1-c1ccccc1)-c1nc(Nc3ccn(CCN4CCOCC4)n3)ncc1CC2] | 1.16 | 457 | G |
| I-192 | 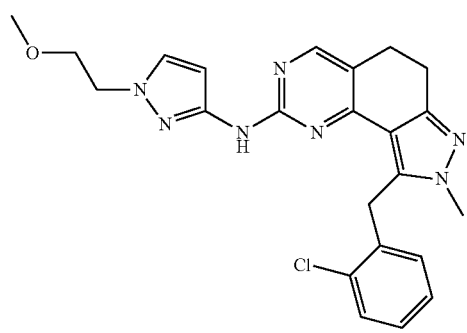 | 1.30 | 450/452 | G |

TABLE 10-continued
| | | | | |
|---|---|---|---|---|
| I-193 | 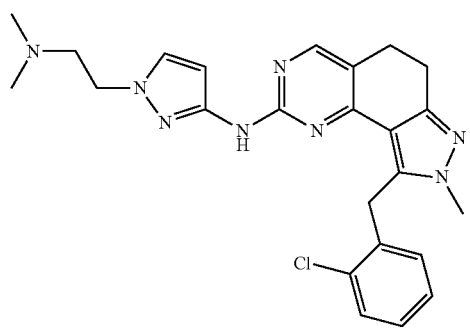 | 1.29 | 463 | G |
| I-194* | 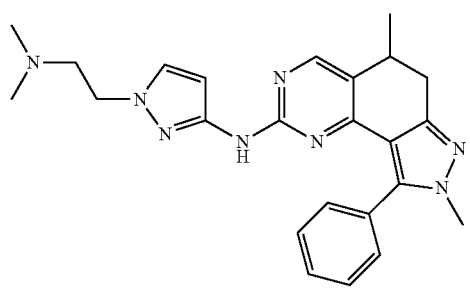 | 1.25 | 429 | G |
| I-195 | 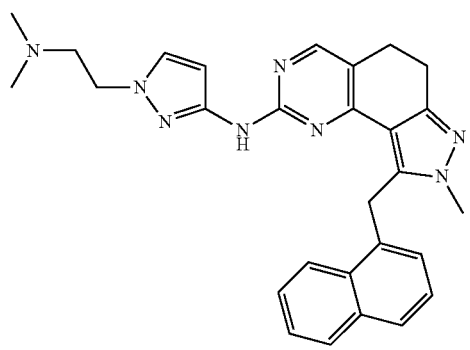 | 1.32 | 479 | G |
| I-196 | 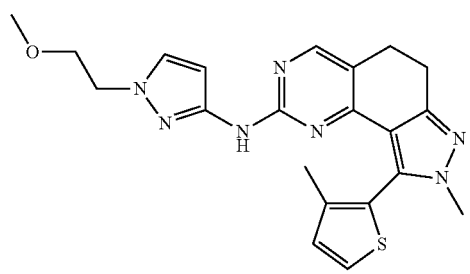 | 1.32 | 422 | G |
| I-197 | 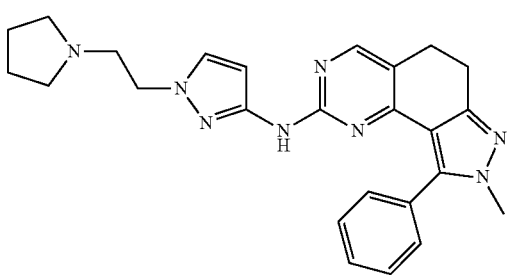 [SMILES: Cn1nc2c(c1-c1ccccc1)-c1nc(Nc3ccn(CCN4CCCC4)n3)ncc1CC2] | 1.26 | 441 | G |

TABLE 10-continued
| | | | | |
|---|---|---|---|---|
| I-198 | 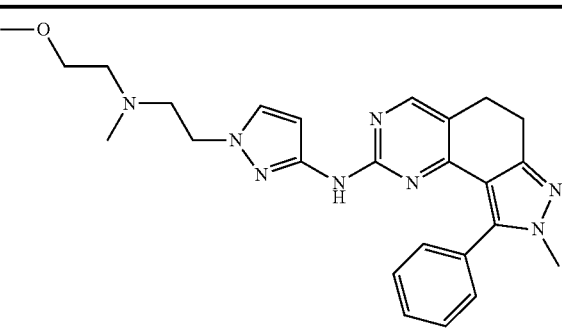 | 1.22 | 459 | G |
| I-199 | 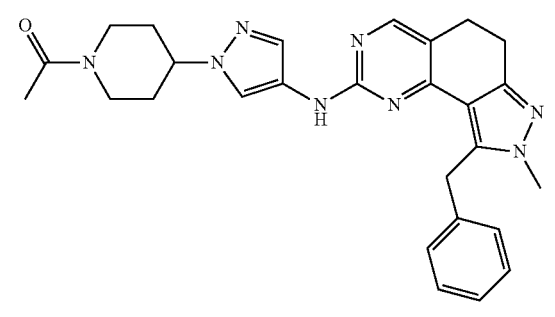 [SMILES: CC(=O)N1CCC(n2cc(Nc3ncc4c(n3)-c3c(nn(C)c3Cc3ccccc3)CC4)cn2)CC1] | 1.16 | 483 | G |
| I-200 | 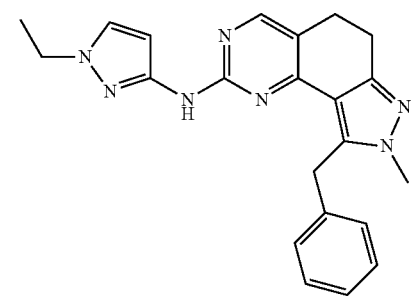 [SMILES: CCn1ccc(Nc2ncc3c(n2)-c2c(nn(C)c2Cc2ccccc2)CC3)n1] | 1.30 | 386 | G |
| I-201 | 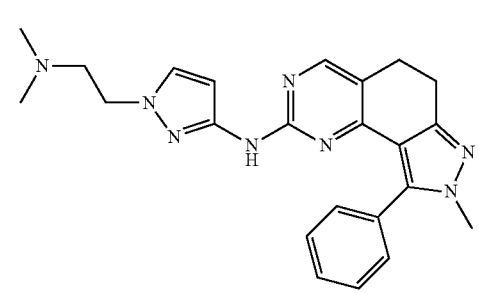 | 1.19 | 415 | G |
| I-202 | 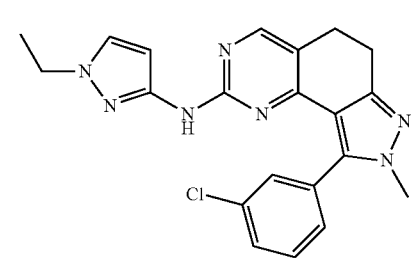 [SMILES: CCn1ccc(Nc2ncc3c(n2)-c2c(nn(C)c2-c2cccc(Cl)c2)CC3)n1] | 1.34 | 420/422 | G |

TABLE 10-continued

| ID | Structure | A | B | C |
|---|---|---|---|---|
| I-203 | 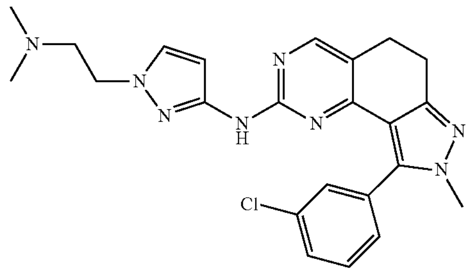 | 1.27 | 463/465 | G |
| I-204* | 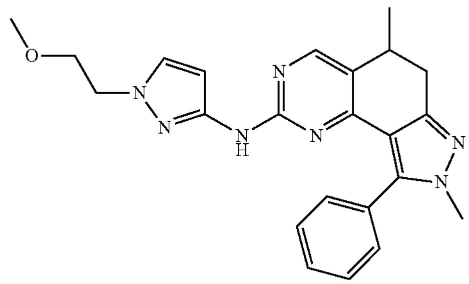 | 1.25 | 416 | G |
| I-205 | 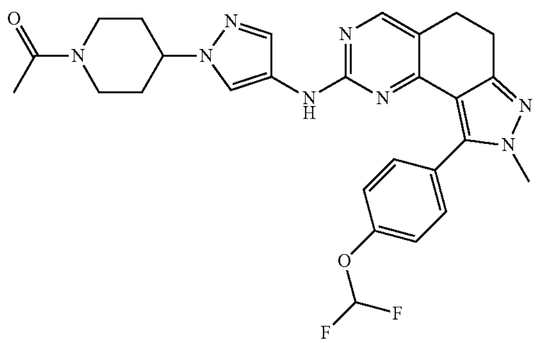 [SMILES: CC(=O)N1CCC(n2cc(Nc3ncc4c(n3)-c3c(nn(C)c3-c3ccc(OC(F)F)cc3)CC4)cn2)CC1] | 1.65 | 535 | G |
| I-206 | 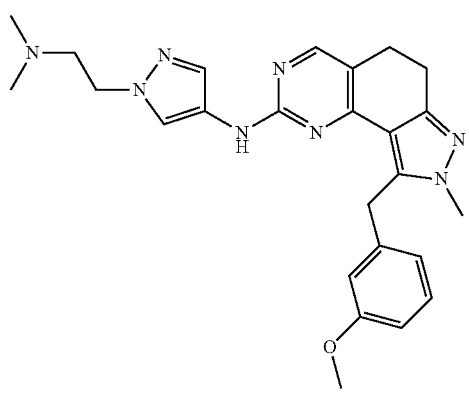 | 1.19 | 459 | G |
| I-207 | 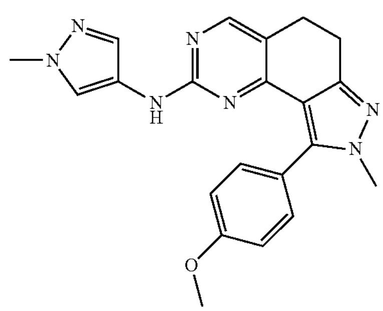 | 1.14 | 388 | G |

TABLE 10-continued

| ID | Structure | | | |
|---|---|---|---|---|
| I-208 | 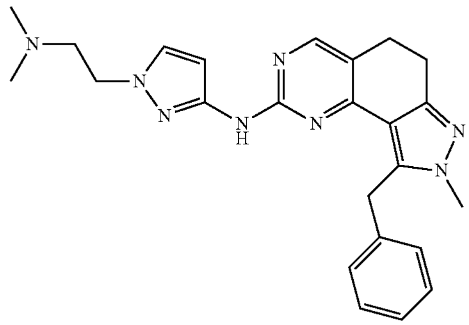 | 1.26 | 429 | G |
| I-209 | 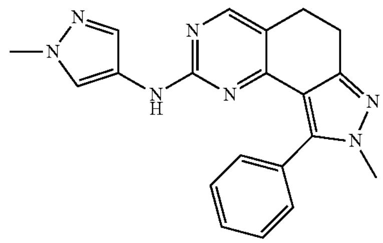 | 1.12 | 358 | G |
| I-210 | 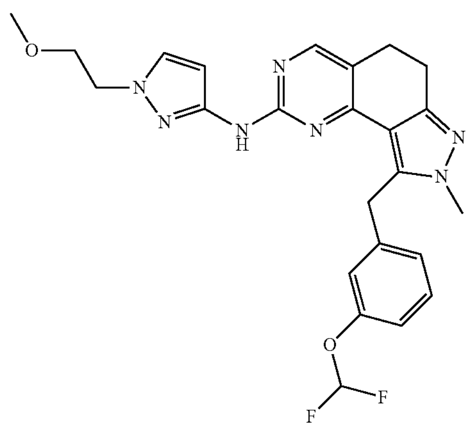 | 1.72 | 468 | G |
| I-211 | 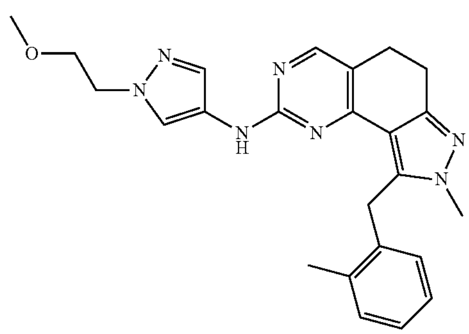 | 1.26 | 430 | G |
| I-212 | 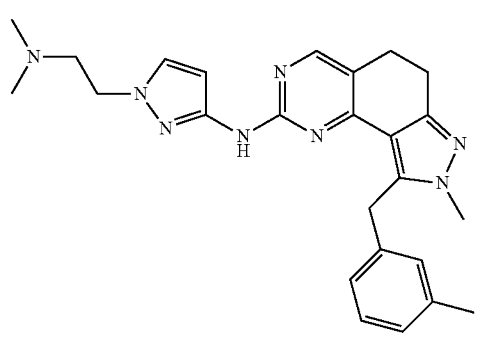 | 1.52 | 443 | G |

TABLE 10-continued
| | | | | |
|---|---|---|---|---|
| I-213 | 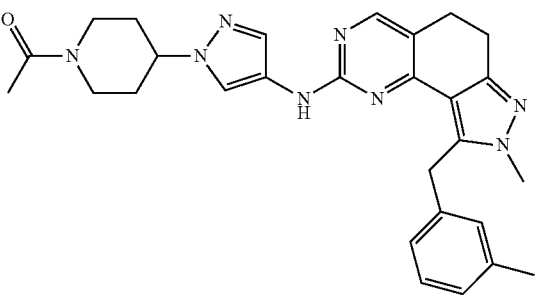 [SMILES: CC(=O)N1CCC(n2cc(Nc3ncc4c(n3)-c3c(nn(C)c3Cc3cccc(C)c3)CC4)cn2)CC1] | 1.35 | 497 | G |
| I-214 | 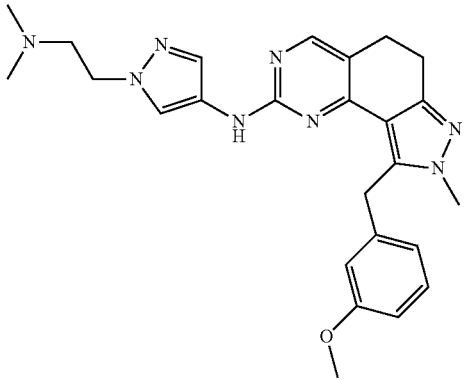 | 1.18 | 445 | G |
| I-215 | 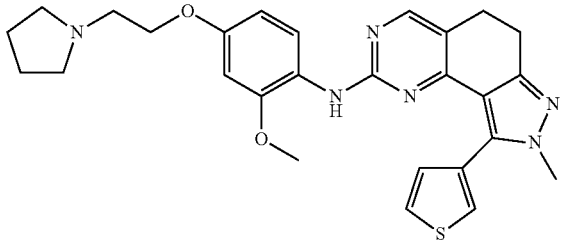 [SMILES: COc1cc(OCCN2CCCC2)ccc1Nc1ncc2c(n1)-c1c(nn(C)c1-c1ccsc1)CC2] | 1.99 | 503 | G |
| I-216* | 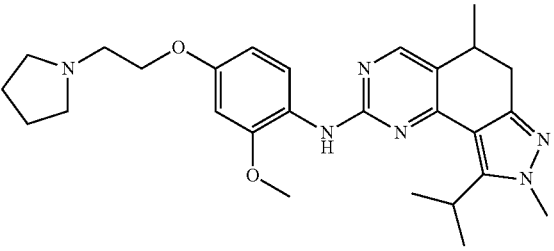 [SMILES: COc1cc(OCCN2CCCC2)ccc1Nc1ncc2c(n1)-c1c(nn(C)c1C(C)C)CC2C] | 2.05 | 477 | G |
| I-217 | 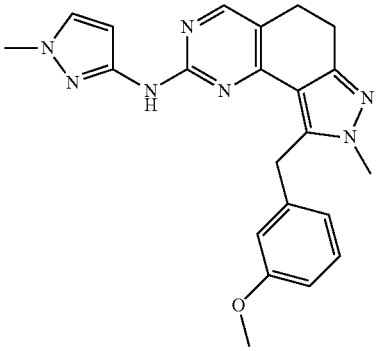 | 1.20 | 402 | G |

TABLE 10-continued
| | | | | |
|---|---|---|---|---|
| I-218 | 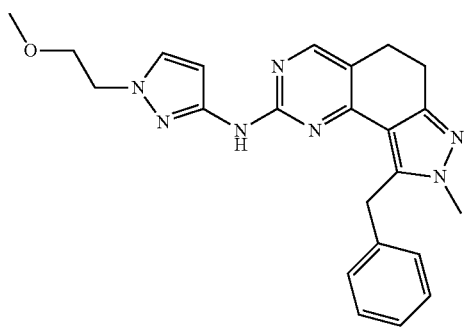 | 1.26 | 416 | G |
| I-219 | 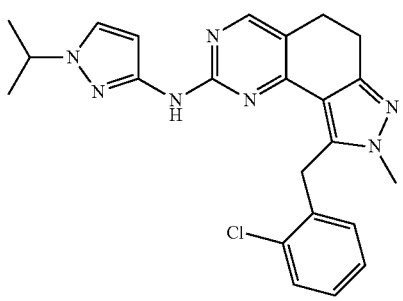 [SMILES: CC(C)n1ccc(Nc2ncc3c(n2)-c2c(nn(C)c2Cc2ccccc2Cl)CC3)n1] | 1.41 | 434/436 | G |
| I-220 | 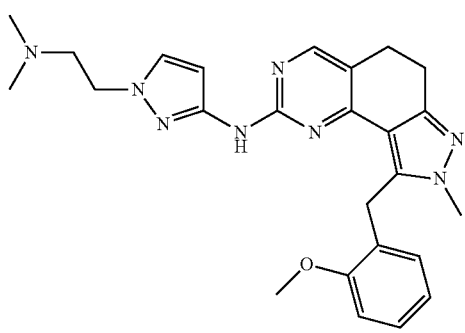 | 1.25 | 459 | G |
| I-221* | 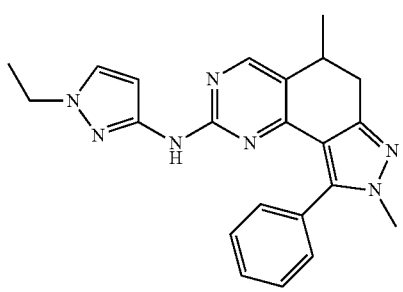 [SMILES: CCn1ccc(Nc2ncc3c(n2)-c2c(nn(C)c2-c2ccccc2)CC3C)n1] | 1.27 | 386 | G |
| I-222 | 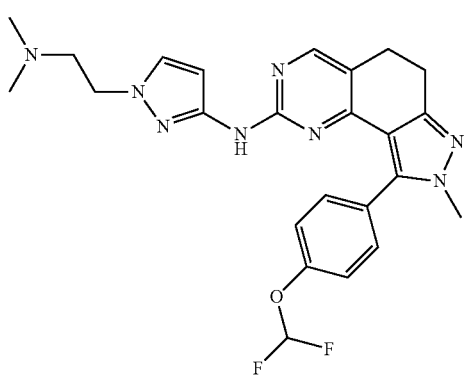 | 1.72 | 481 | G |

TABLE 10-continued
| | | | | |
|---|---|---|---|---|
| I-223 | 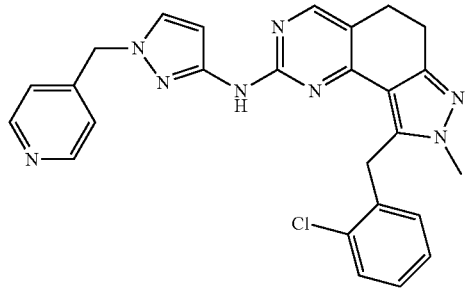 [SMILES: Cn1nc2c(c1Cc1ccccc1Cl)-c1nc(Nc3ccn(Cc4ccncc4)n3)ncc1CC2] | 1.25 | 483 | G |
| I-224 | 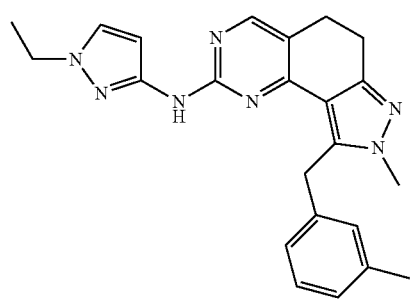 [SMILES: CCn1ccc(Nc2ncc3c(n2)-c2c(nn(C)c2Cc2cccc(C)c2)CC3)n1] | 1.57 | 400 | G |
| I-225 | 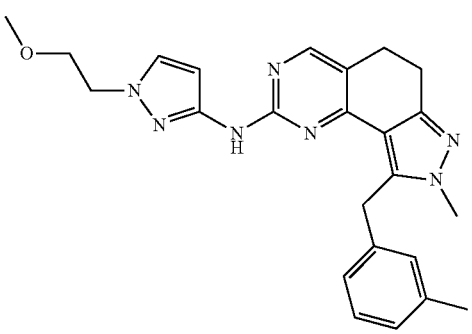 | 1.54 | 430 | G |
| I-226 | 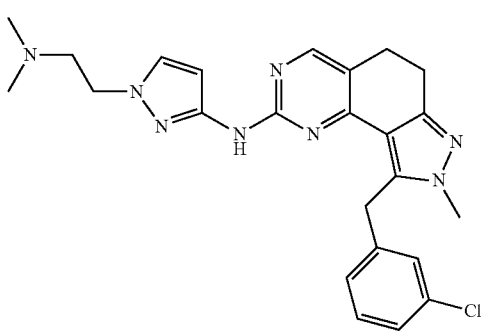 [SMILES: CN(C)CCn1ccc(Nc2ncc3c(n2)-c2c(nn(C)c2Cc2cccc(Cl)c2)CC3)n1] | 1.54 | 463 | G |
| I-227 | 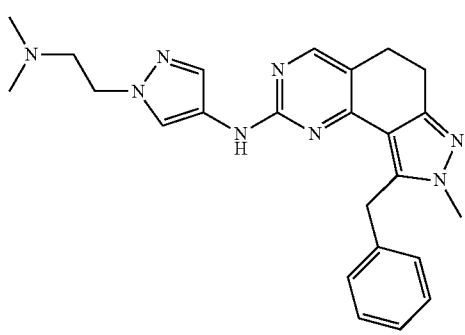 | 1.24 | 429 | G |

TABLE 10-continued

| ID | Structure | | | |
|---|---|---|---|---|
| I-228 | [structure] | 1.25 | 416 | G |
| I-229 | [structure] | 1.37 | 400 | G |
| I-230 | [structure] | 1.19 | 402 | G |
| I-231 | [structure] | 1.16 | 513 | G |
| I-232 | [structure] | 1.19 | 503/505 | G |

TABLE 10-continued

| | | | | |
|---|---|---|---|---|
| I-233 | | 1.17 | 483 | G |
| I-234 | | 1.24 | 433 | G |
| I-235 | | 1.16 | 388 | G |
| I-236 | | 1.71 | 481 | G |
| I-237 | | 1.76 | 438 | G |

TABLE 10-continued
| | | | | |
|---|---|---|---|---|
| I-238 | 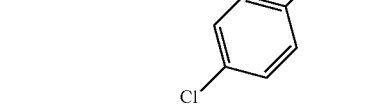 | 1.21 | 392 | G |
| I-239 | 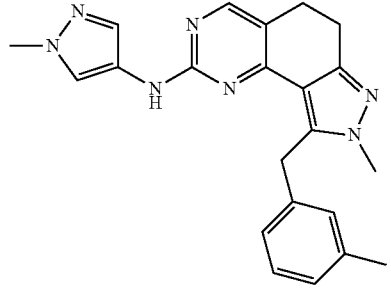 | 1.44 | 386 | G |
| I-240 | 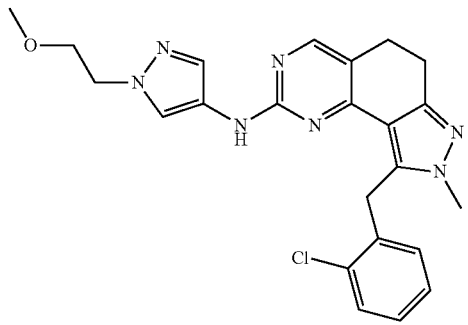 | 1.27 | 450/452 | G |
| I-241 | 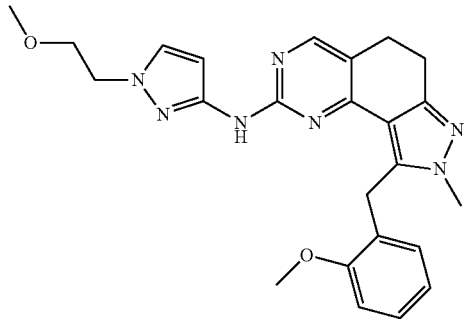 | 1.25 | 446 | G |
| I-242 | 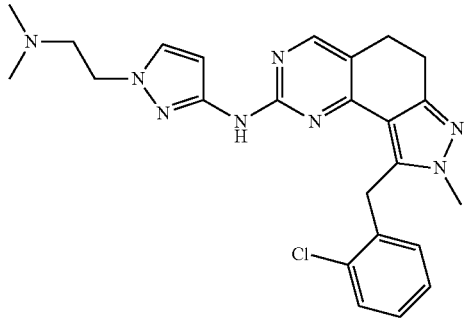 | 1.26 | 449/451 | G |

TABLE 10-continued
| I-243 | 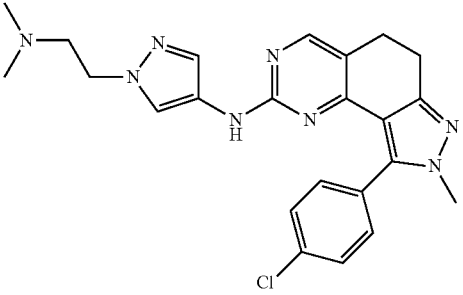 | 1.24 | 449 | G |
| I-244 | 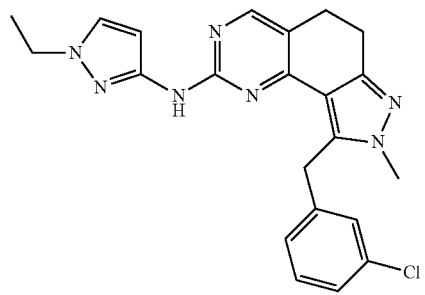 [SMILES: CCn1ccc(Nc2ncc3c(n2)-c2c(nn(C)c2Cc2cccc(Cl)c2)CC3)n1] | 1.58 | 420 | G |
| I-245 | 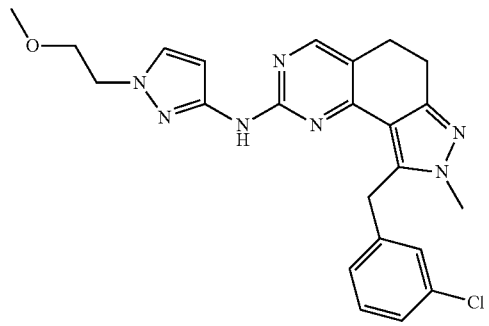 [SMILES: COCCn1ccc(Nc2ncc3c(n2)-c2c(nn(C)c2Cc2cccc(Cl)c2)CC3)n1] | 1.54 | 450 | G |
| I-246 | 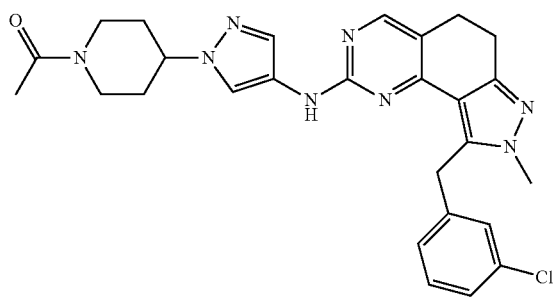 [SMILES: CC(=O)N1CCC(n2cc(Nc3ncc4c(n3)-c3c(nn(C)c3Cc3cccc(Cl)c3)CC4)cn2)CC1] | 1.39 | 517 | G |
| I-247 | 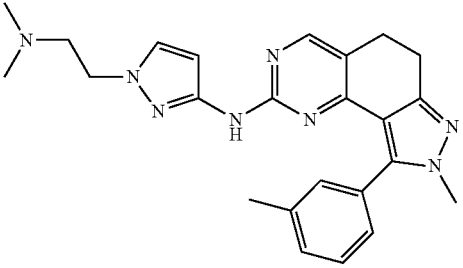 | 1.24 | 429 | G |

TABLE 10-continued

| | | | | |
|---|---|---|---|---|
| I-248 | | 1.23 | 420 | G |
| I-249 | | 1.31 | 416 | G |
| I-250 | | 1.20 | 432 | G |
| I-251 | | 1.11 | 459 | G |
| I-252 | | 1.49 | 386 | G |

TABLE 10-continued

| | | | | |
|---|---|---|---|---|
| I-253 | (structure) | 1.61 | 497 | G |
| I-254 | (structure) | 1.33 | 479 | G |
| I-255 | (structure) | 1.22 | 446 | G |
| I-256 | (structure) | 1.13 | 499 | G |

TABLE 10-continued
| I-257 | 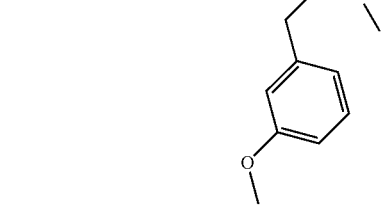 | 1.71 | 416 | G |
| I-258 | 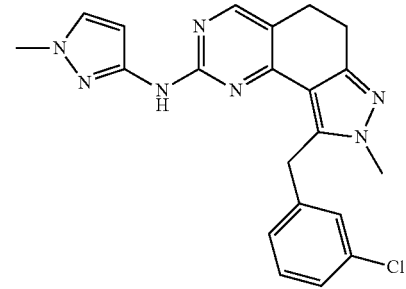 [SMILES: Cn1ccc(Nc2ncc3c(n2)-c2c(nn(C)c2Cc2cccc(Cl)c2)CC3)n1] | 1.49 | 406 | G |
| I-259 | 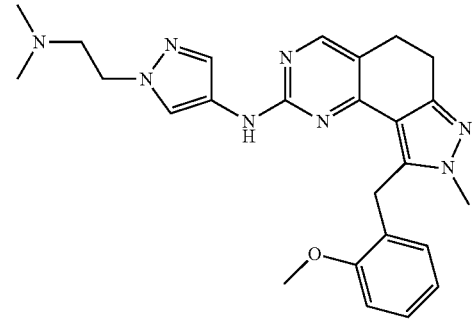 | 1.22 | 459 | G |
| I-260 | 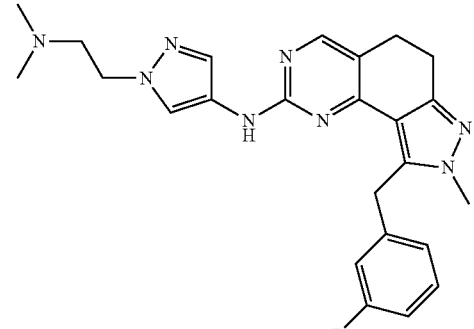 | 1.22 | 433 | G |
| I-261* | 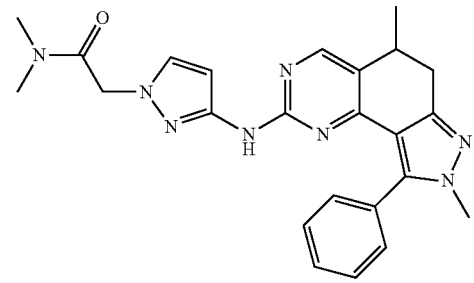 | 1.15 | 443 | G |

TABLE 10-continued
| | | | | |
|---|---|---|---|---|
| I-262 | 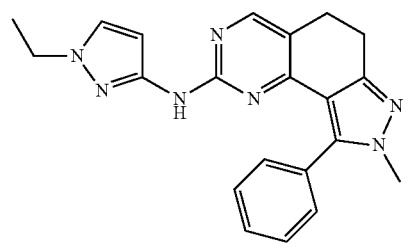 [SMILES: CCn1ccc(Nc2ncc3c(n2)-c2c(nn(C)c2-c2ccccc2)CC3)n1] | 1.22 | 372 | G |
| I-263 | 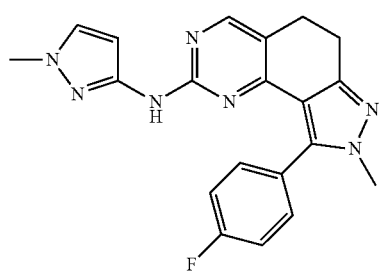 | 1.20 | 376 | G |
| I-264* | 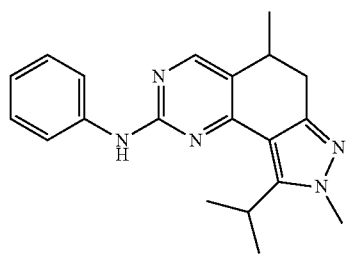 [SMILES: CC(C)c1c2c(nn1C)CC(C)c1cnc(Nc3ccccc3)nc1-2] | 1.92 | 334 | G |
| I-265 | 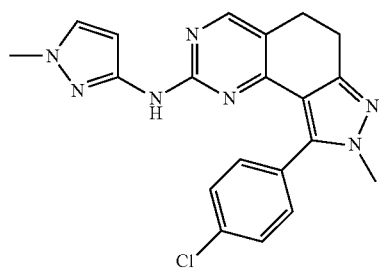 | 1.25 | 392 | G |
| I-266 | 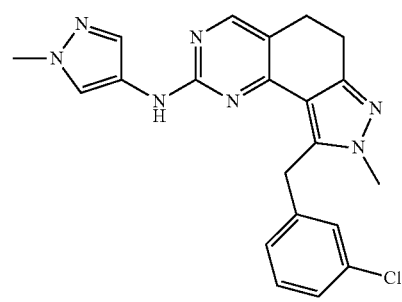 [SMILES: Cn1cc(Nc2ncc3c(n2)-c2c(nn(C)c2Cc2cccc(Cl)c2)CC3)cn1] | 1.45 | 406 | G |

TABLE 10-continued
| | | | | |
|---|---|---|---|---|
| I-267 | 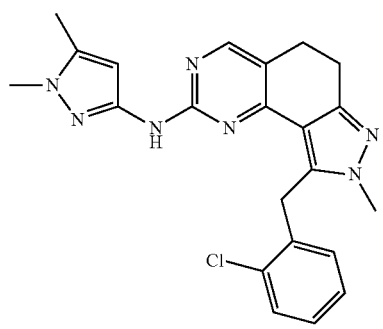 | 1.33 | 420 | G |
| I-268 | 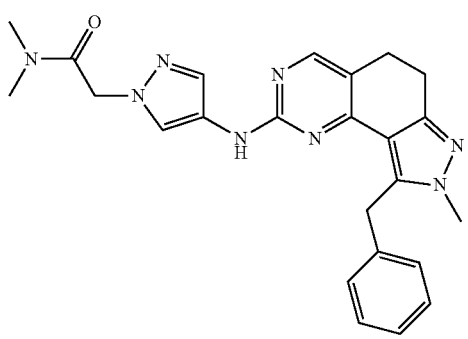 | 1.08 | 443 | G |
| I-269 | 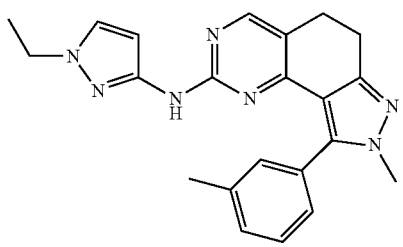 [SMILES: CCn1ccc(Nc2ncc3c(n2)-c2c(nn(C)c2-c2cccc(C)c2)CC3)n1] | 1.29 | 386 | G |
| I-270 | 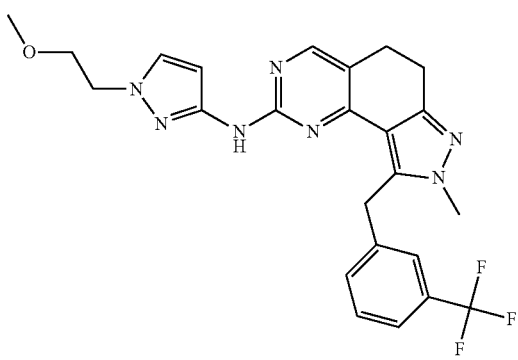 [SMILES: COCCn1ccc(Nc2ncc3c(n2)-c2c(nn(C)c2Cc2cccc(C(F)(F)F)c2)CC3)n1] | 1.58 | 484 | G |
| I-271 | 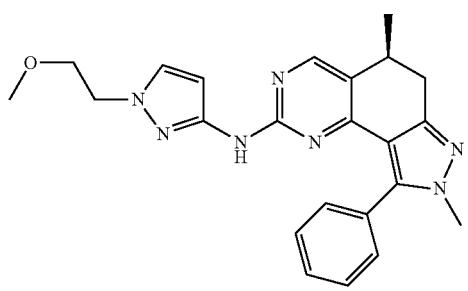 | 1.67 | 416 | G |

TABLE 10-continued

| | | | | |
|---|---|---|---|---|
| I-272 | | 1.30 | 406/408 | G |
| I-273 | | 1.20 | 445 | G |
| I-274 | | 1.18 | 477 | G |
| I-275 | | 1.26 | 551 | G |
| I-276 | | 1.25 | 416 | G |

TABLE 10-continued

| ID | Structure | | | |
|---|---|---|---|---|
| I-277 | 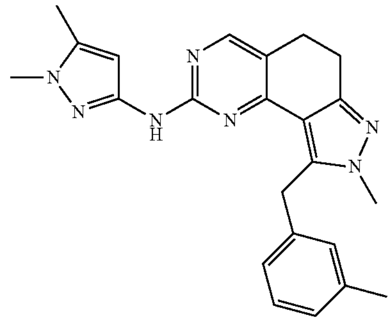 | 1.55 | 400 | G |
| I-278 | 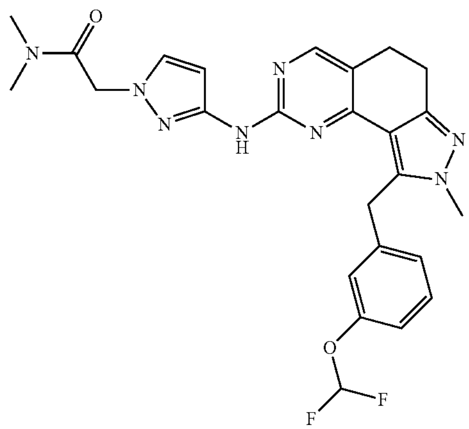 | 1.60 | 495 | G |
| I-279 | 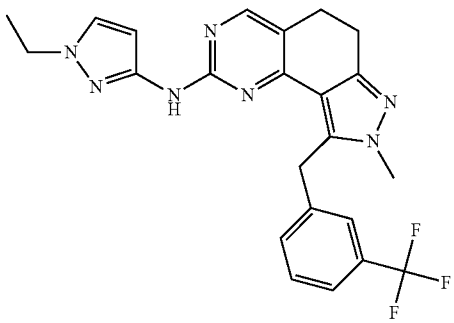 [SMILES: CCn1ccc(Nc2ncc3c(n2)-c2c(nn(C)c2Cc2cccc(C(F)(F)F)c2)CC3)n1] | 1.64 | 454 | G |
| I-280 | 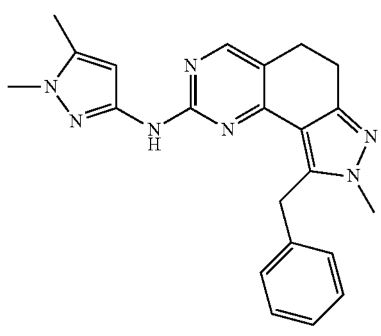 | 1.28 | 386 | G |
| I-281 | 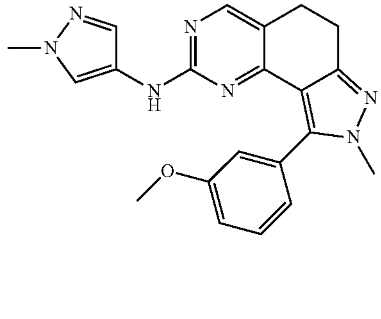 | 1.13 | 388 | G |

TABLE 10-continued
| I-282 | 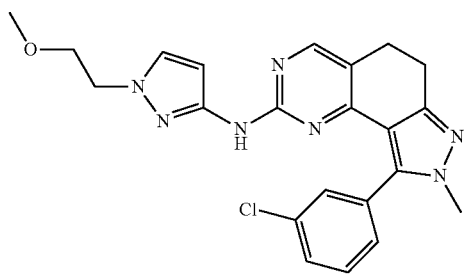 | 1.26 | 436/438 | G |
| I-283 | 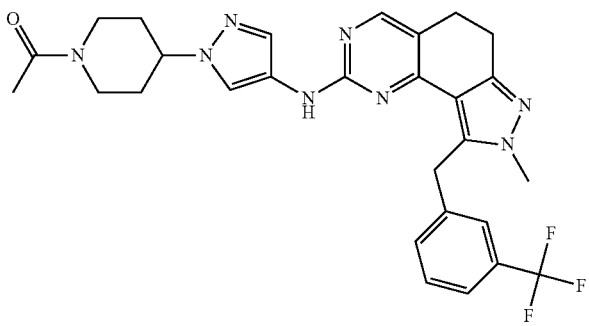 [SMILES: CC(=O)N1CCC(n2cc(Nc3ncc4c(n3)-c3c(nn(C)c3Cc3cccc(C(F)(F)F)c3)CC4)cn2)CC1] | 1.45 | 551 | G |
| I-284 | 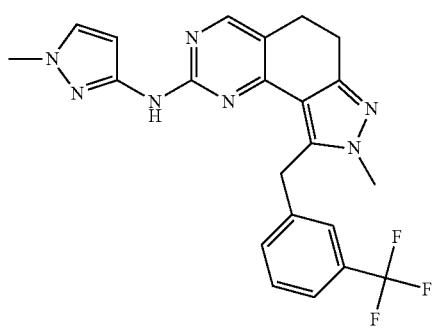 [SMILES: Cn1ccc(Nc2ncc3c(n2)-c2c(nn(C)c2Cc2cccc(C(F)(F)F)c2)CC3)n1] | 1.57 | 440 | G |
| I-285* | 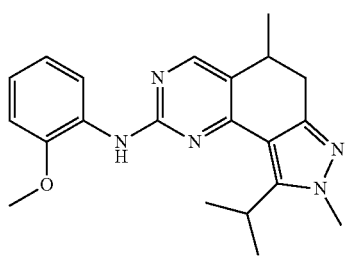 [SMILES: COc1ccccc1Nc1ncc2c(n1)-c1c(nn(C)c1C(C)C)CC2C] | 2.04 | 364 | G |
| I-286 | 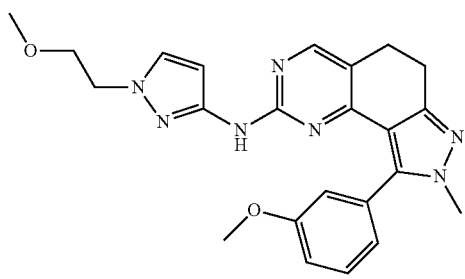 | 1.19 | 432 | G |

TABLE 10-continued

| ID | Structure | | | |
|---|---|---|---|---|
| I-287 | 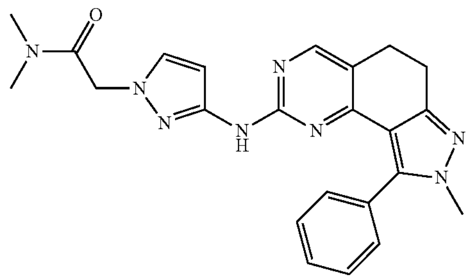 | 1.09 | 429 | G |
| I-288 | 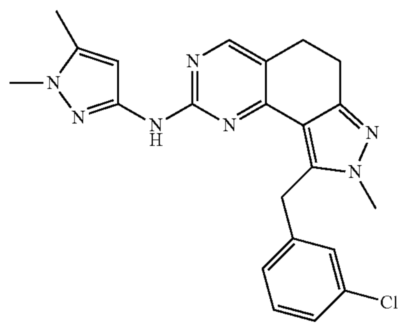 [SMILES: Cc1cc(Nc2ncc3c(n2)-c2c(nn(C)c2Cc2cccc(Cl)c2)CC3)nn1C] | 1.55 | 420 | G |
| I-289 | 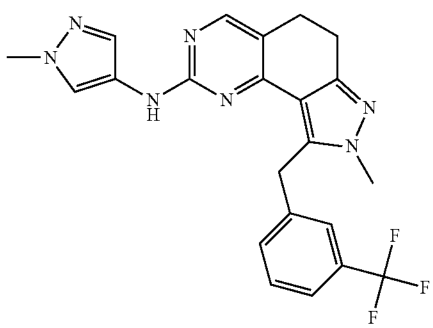 [SMILES: Cn1cc(Nc2ncc3c(n2)-c2c(nn(C)c2Cc2cccc(C(F)(F)F)c2)CC3)cn1] | 1.52 | 440 | G |
| I-290 | 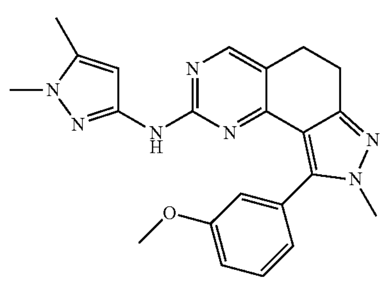 | 1.29 | 416 | G |
| I-291 | 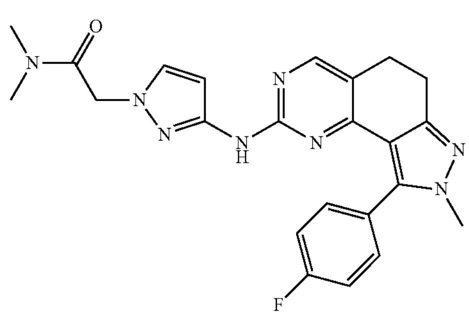 | 1.13 | 447 | G |

TABLE 10-continued
| | | | | |
|---|---|---|---|---|
| I-292 | 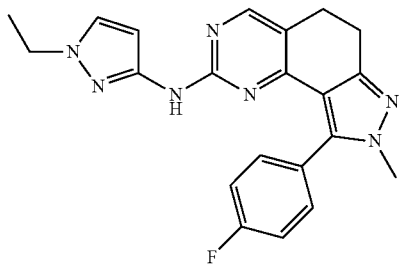 [SMILES: CCn1ccc(Nc2ncc3c(n2)-c2c(nn(C)c2-c2ccc(F)cc2)CC3)n1] | 1.26 | 390 | G |
| I-293 | 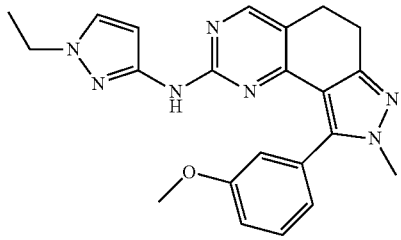 [SMILES: CCn1ccc(Nc2ncc3c(n2)-c2c(nn(C)c2-c2cccc(OC)c2)CC3)n1] | 1.22 | 402 | G |
| I-294 | 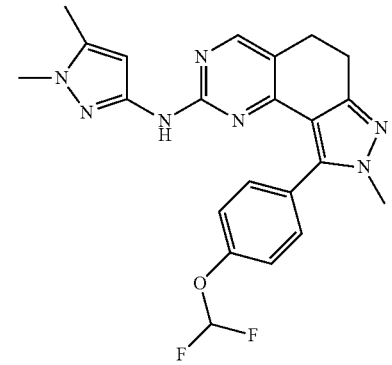 | 1.73 | 438 | G |
| I-295 | 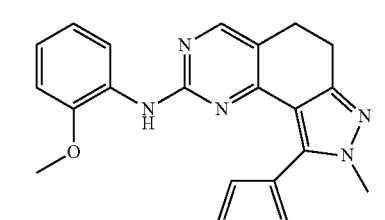 | 1.94 | 390 | G |
*Structure includes both enantiomers in each case, i.e.
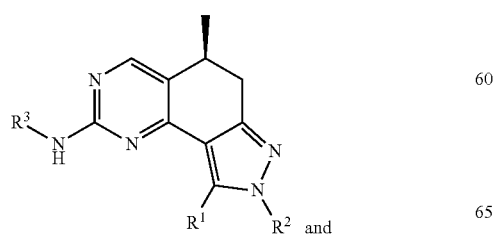 and 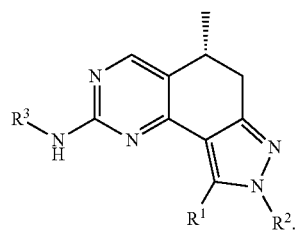.

4.2. Preparation of Other Novel Compounds (I) by Derivatisation of Carboxylic Acids (Method K/Method L)

Preparation of Compound II-1 by Ester Cleaving

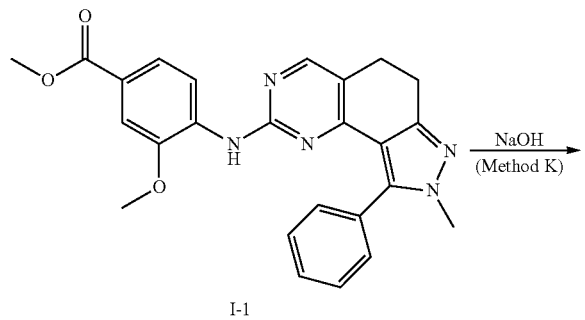

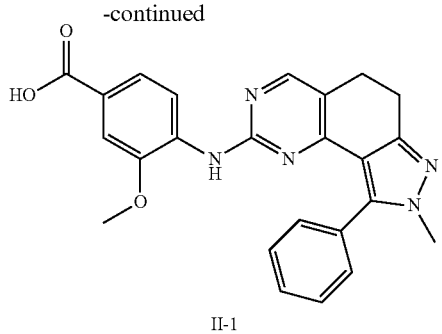

Ester Cleaving (Method K). Compound I-1 (2.5 g, 5.66 mmol) in MeOH (25 mL) is combined with 10 N NaOH (2.8 mL, 28 mmol) and stirred at 50° C. until the reaction is complete. The reaction mixture is acidified with conc. hydrochloric acid (pH=3). The precipitated solid is isolated by filtration, digested several times with water and dried.

Analogously to II-1 further free acids are obtained by ester cleaving (Table 11). The product may optionally be isolated by extraction and purified by chromatography.

TABLE 11

| No. | Structure | $t_{ret}$ [min] | $[M + H]^+$ | Method of analysis |
|---|---|---|---|---|
| II-1 | 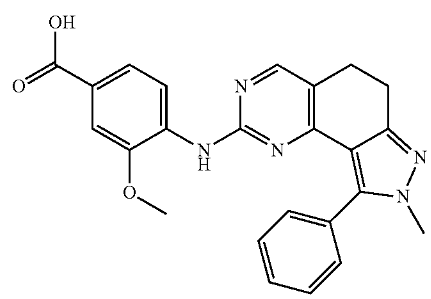 [SMILES: COc1cc(C(=O)O)ccc1Nc1ncc2c(n1)-c1c(nn(C)c1-c1ccccc1)CC2] | 1.06 | 428.2 | C |
| II-2 | 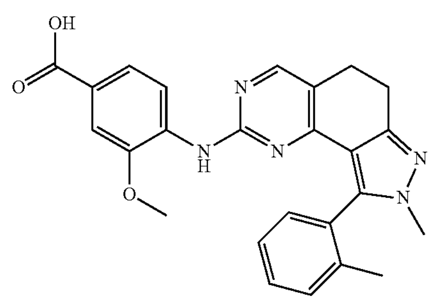 [SMILES: COc1cc(C(=O)O)ccc1Nc1ncc2c(n1)-c1c(nn(C)c1-c1ccccc1C)CC2] | 1.10 | 442.2 | C |
| II-3 | 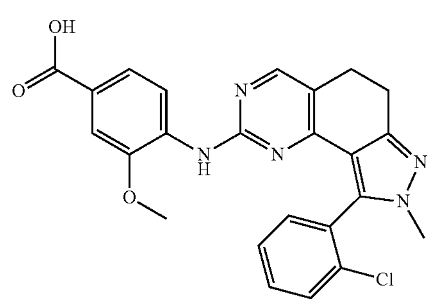 [SMILES: COc1cc(C(=O)O)ccc1Nc1ncc2c(n1)-c1c(nn(C)c1-c1ccccc1Cl)CC2] | 1.11 | 462.2 | C |

TABLE 11-continued

| No. | Structure | $t_{ret}$ [min] | $[M + H]^+$ | Method of analysis |
|---|---|---|---|---|
| II-4 | 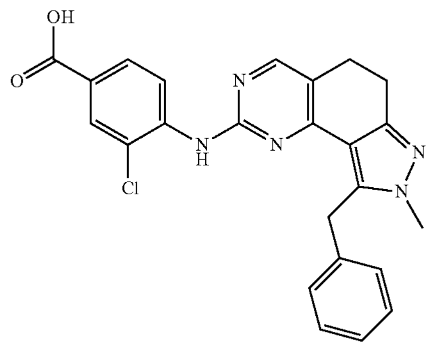 [SMILES: Cn1nc2c(c1Cc1ccccc1)-c1nc(Nc3ccc(C(=O)O)cc3Cl)ncc1CC2] | 1.21 | 446.2 | C |
| II-5 | 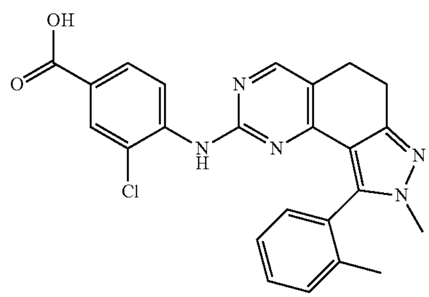 [SMILES: Cc1ccccc1-c1c2c(nn1C)CCc1cnc(Nc3ccc(C(=O)O)cc3Cl)nc1-2] | 1.25 | 446.2 | C |
| II-6 | 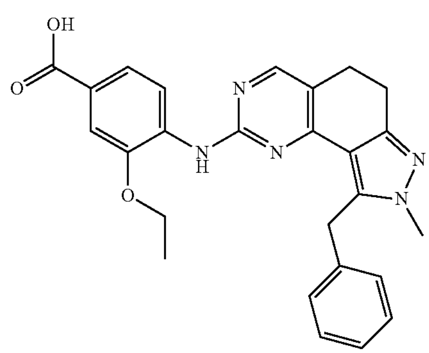 [SMILES: CCOc1cc(C(=O)O)ccc1Nc1ncc2c(n1)-c1c(nn(C)c1Cc1ccccc1)CC2] | 1.17 | 456.3 | C |
| II-7 | 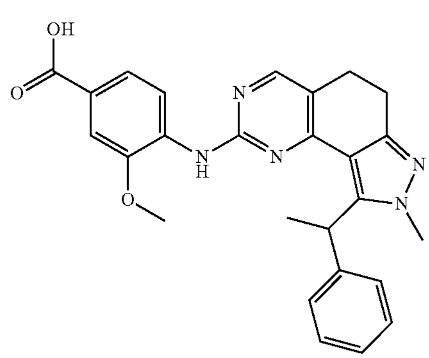 [SMILES: COc1cc(C(=O)O)ccc1Nc1ncc2c(n1)-c1c(nn(C)c1C(C)c1ccccc1)CC2] | 1.18 | 456.2 | C |

TABLE 11-continued

| No. | Structure | t_ret [min] | [M + H]+ | Method of analysis |
|---|---|---|---|---|
| II-8* | 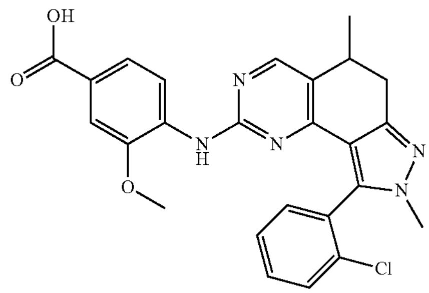 [SMILES: COc1cc(C(=O)O)ccc1Nc1ncc2c(n1)-c1c(nn(C)c1-c1ccccc1Cl)CC2C] | 1.14 | 476.2 | C |
| II-9 | 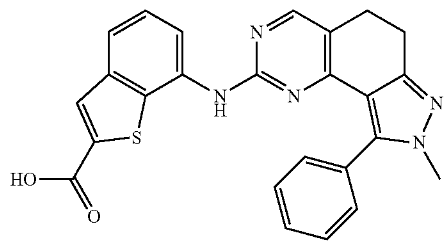 [SMILES: Cn1nc2c(c1-c1ccccc1)-c1nc(Nc3cccc4cc(C(=O)O)sc34)ncc1CC2] | 0.97 | 468.2 | C |
| II-10 | 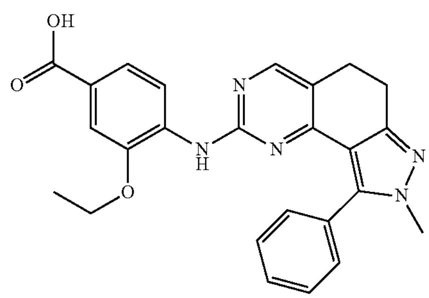 [SMILES: CCOc1cc(C(=O)O)ccc1Nc1ncc2c(n1)-c1c(nn(C)c1-c1ccccc1)CC2] | 1.13 | 442.0 | G |
| II-11* | 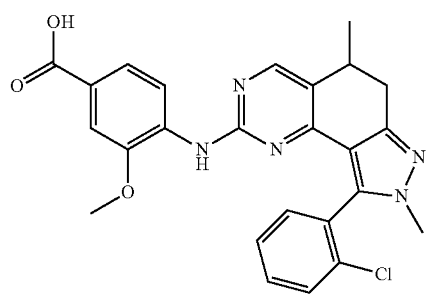 [SMILES: COc1cc(C(=O)O)ccc1Nc1ncc2c(n1)-c1c(nn(C)c1-c1ccccc1Cl)CC2C] | 1.16 | 476.3 | G |
| II-12 | 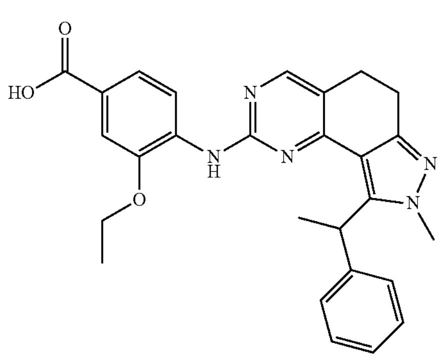 [SMILES: CCOc1cc(C(=O)O)ccc1Nc1ncc2c(n1)-c1c(nn(C)c1C(C)c1ccccc1)CC2] | 1.29 | 470.3 | G |

TABLE 11-continued

| No. | Structure | $t_{ret}$ [min] | $[M + H]^+$ | Method of analysis |
|---|---|---|---|---|
| II-13 | 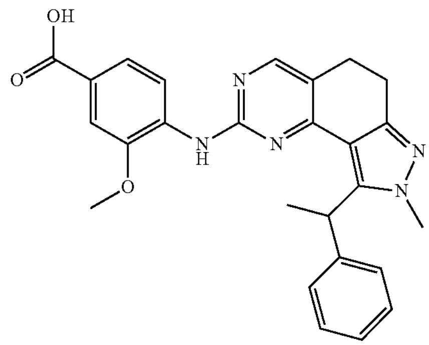 [SMILES: COc1cc(C(=O)O)ccc1Nc1ncc2c(n1)-c1c(nn(C)c1C(C)c1ccccc1)CC2] | 1.24 | 456.3 | G |
| II-14 | 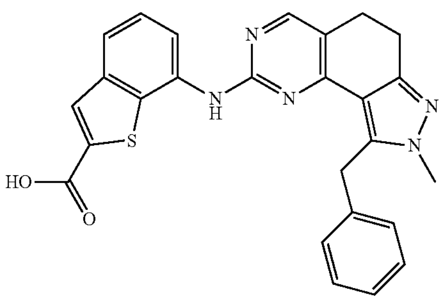 [SMILES: Cn1nc2c(c1Cc1ccccc1)-c1nc(Nc3cccc4cc(C(=O)O)sc34)ncc1CC2] | 1.21 | 468.3 | G |
| II-15 | 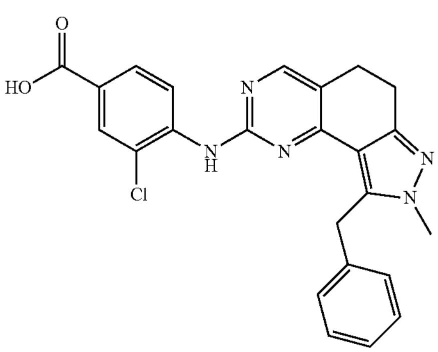 [SMILES: Cn1nc2c(c1Cc1ccccc1)-c1nc(Nc3ccc(C(=O)O)cc3Cl)ncc1CC2] | 1.20 | 446.0 | G |
| II-16 | 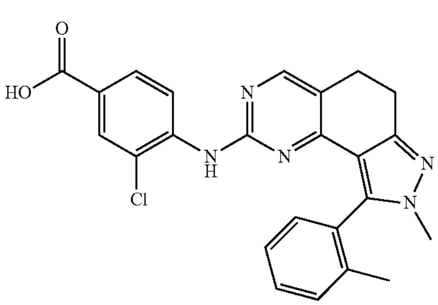 [SMILES: Cc1ccccc1-c1c2c(nn1C)CCc1cnc(Nc3ccc(C(=O)O)cc3Cl)nc1-2] | 1.18 | 446.3 | G |

TABLE 11-continued

| No. | Structure | $t_{ret}$ [min] | $[M+H]^+$ | Method of analysis |
|---|---|---|---|---|
| II-17 | 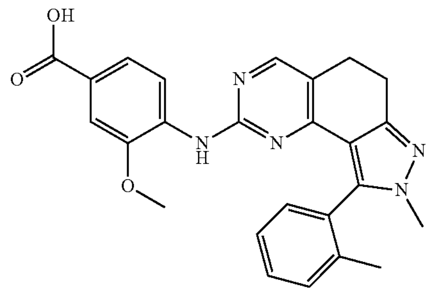 [SMILES: COc1cc(C(=O)O)ccc1Nc1ncc2c(n1)-c1c(nn(C)c1-c1ccccc1C)CC2] | 1.06 | 442.3 | G |
| II-18 | 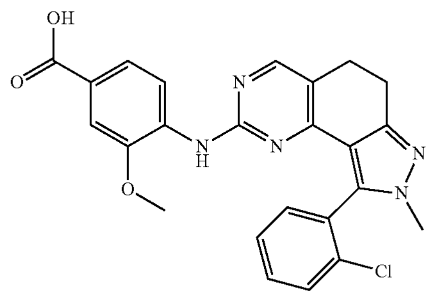 [SMILES: COc1cc(C(=O)O)ccc1Nc1ncc2c(n1)-c1c(nn(C)c1-c1ccccc1Cl)CC2] | 1.07 | 462.0 | G |

*Structure includes both enantiomers in each case, i.e.

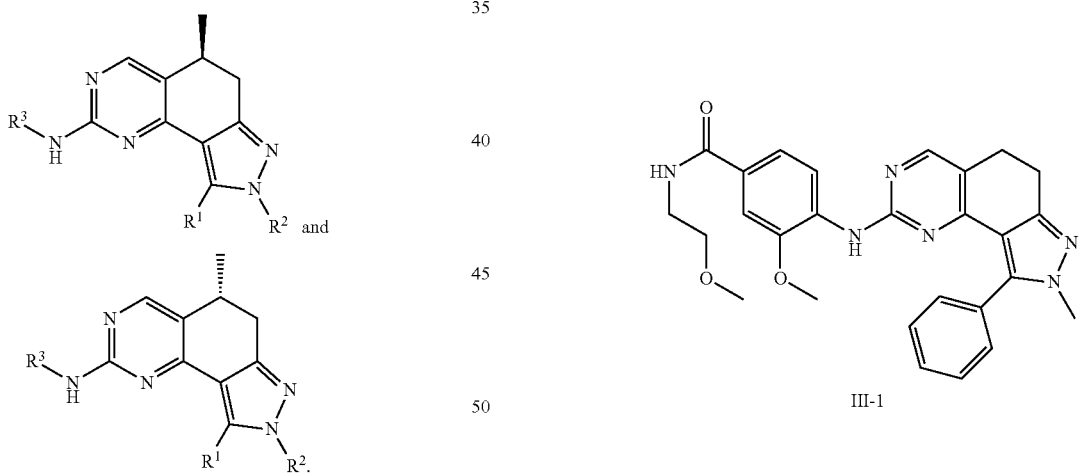

Preparation of Compound III-1 by Amidation

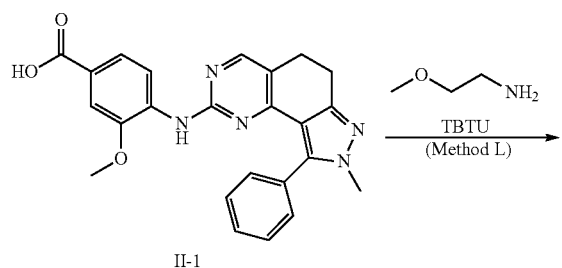

Amide Formation (Method L). The starting compound II-1 (75 mg, 0.18 mmol) and TBTU (87 mg, 0.27 mmol) in anhydrous DMSO (0.5 mL) are combined with triethylamine (124 µL, 0.90 mmol) and 2-methoxyethylamine (17 mg, 0.23 mmol) and stirred at RT until the reaction is complete. The reaction mixture is purified by preparative HPLC-MS. The fractions containing the reaction product are freeze-dried.

Analogously to III-1 further novel compounds are obtained by amidation or esterification (Table 12).

TABLE 12

| No. | Structure | t_ret [min] | [M + H]+ | Method of analysis |
|---|---|---|---|---|
| III-1 | 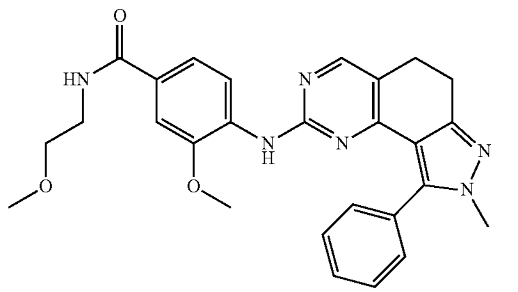 | 1.73 | 485.3 | G |
| III-2 | 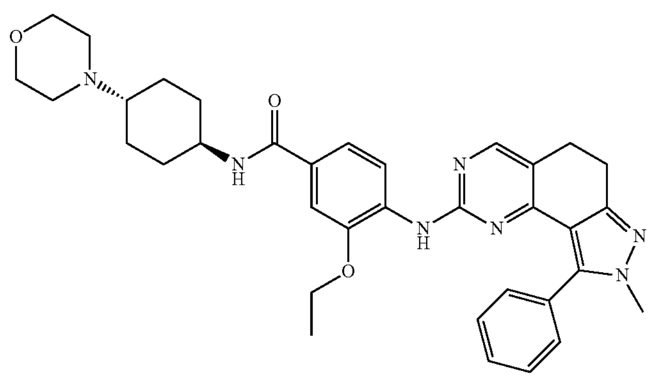 [SMILES: CCOc1cc(C(=O)N[C@H]2CC[C@H](N3CCOCC3)CC2)ccc1Nc1ncc2c(n1)-c1c(nn(C)c1-c1ccccc1)CC2] | 1.89 | 608.0 | G |
| III-3 | 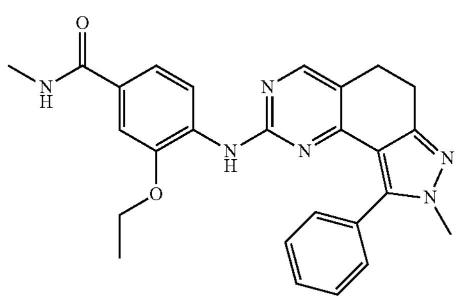 | 1.76 | 455.0 | G |
| III-4 | 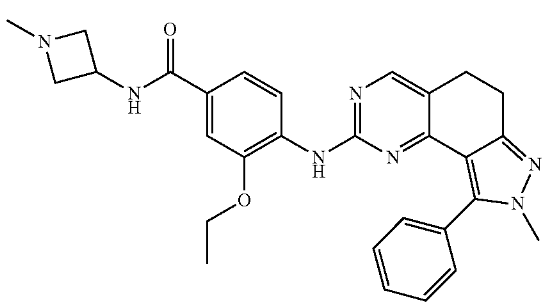 | 1.81 | 510.3 | G |

TABLE 12-continued

| | | | | |
|---|---|---|---|---|
| III-5 | (structure) | 2.00 | 564.3 | G |
| III-6 | (structure) | 1.85 | 538.0 | G |
| III-7 | (structure) | 1.86 | 608.3 | G |
| III-8 | (structure) | 1.78 | 498.3 | G |
| III-9 | (structure, Chiral) | 1.84 | 536.2 | G |

TABLE 12-continued

| | | | | |
|---|---|---|---|---|
| III-10 | (structure) | 1.91 | 524.3 | G |
| III-11 | (structure) | 1.85 | 512.3 | G |
| III-12 | (structure) Chiral | 1.96 | 647.5 | G |
| III-13 | (structure) | 1.86 | 538.3 | G |
| III-14 | (structure) Chiral | 1.93 | 550.2 | G |

TABLE 12-continued
| | | | | |
|---|---|---|---|---|
| III-15 | 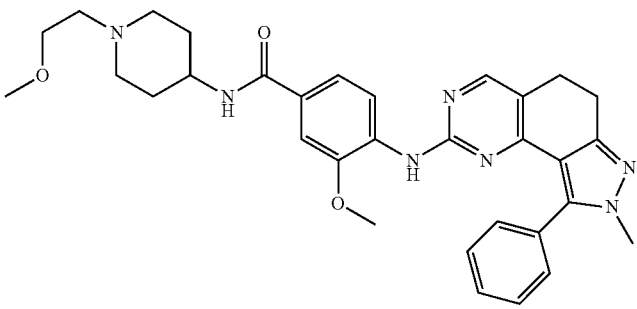 | 1.79 | 568.2 | G |
| III-16 | 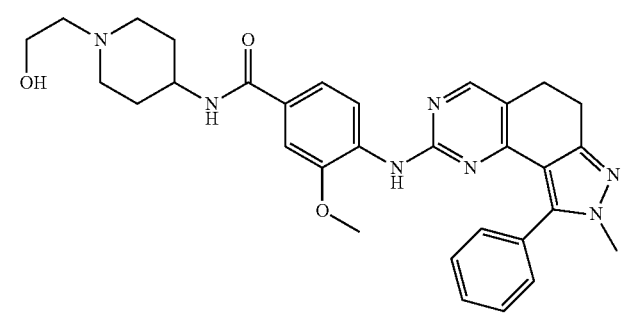 [SMILES: COc1cc(C(=O)NC2CCN(CCO)CC2)ccc1Nc1ncc2c(n1)-c1c(nn(C)c1-c1ccccc1)CC2] | 1.66 | 554.2 | G |
| III-17 | 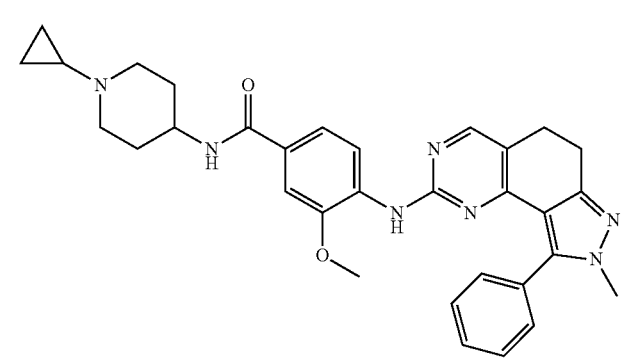 [SMILES: COc1cc(C(=O)NC2CCN(C3CC3)CC2)ccc1Nc1ncc2c(n1)-c1c(nn(C)c1-c1ccccc1)CC2] | 1.92 | 550.2 | G |
| III-18 | 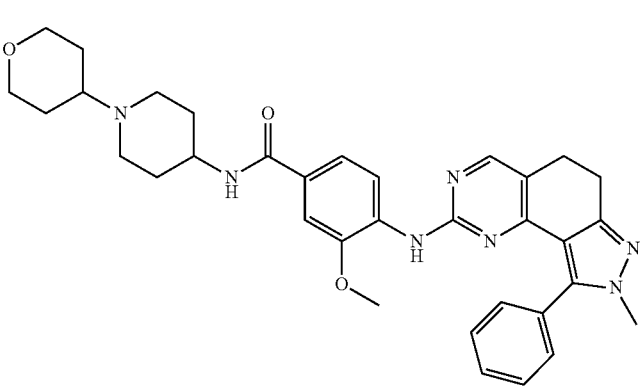 [SMILES: COc1cc(C(=O)NC2CCN(C3CCOCC3)CC2)ccc1Nc1ncc2c(n1)-c1c(nn(C)c1-c1ccccc1)CC2] | 1.78 | 594.2 | G |
| III-19 | 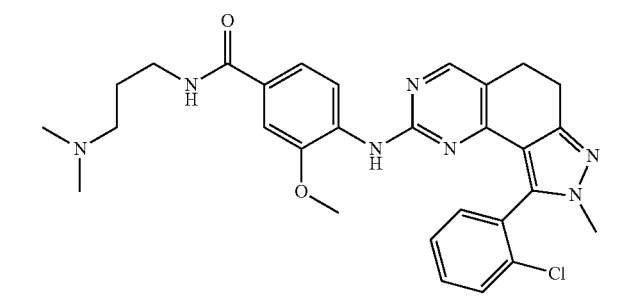 | 1.87 | 546.5 | G |

TABLE 12-continued

| | | | | |
|---|---|---|---|---|
| III-20 | | 1.81 | 628.7 | G |
| III-21 | | 1.68 | 588.5 | G |
| III-22 | | 1.84 | 628.5 | G |
| III-23 | | 1.95 | 584.5 | G |

TABLE 12-continued

| ID | Structure | col1 | col2 | col3 |
|---|---|---|---|---|
| III-24 | 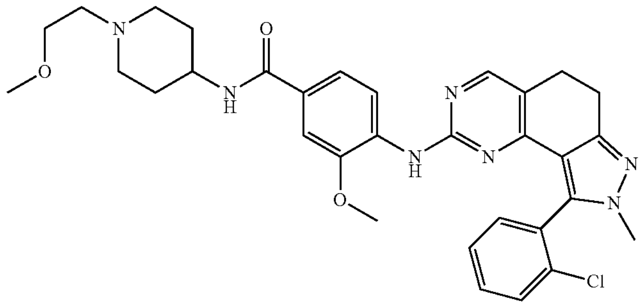 | 1.81 | 602.5 | G |
| III-25 | 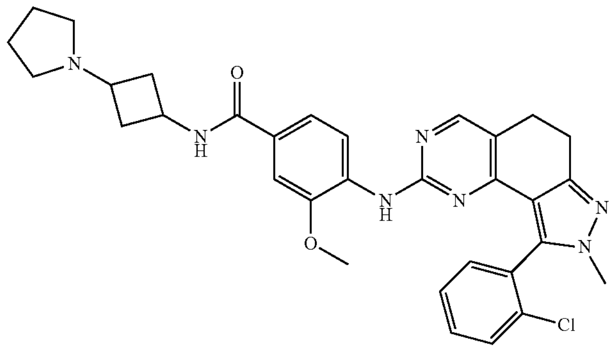 [SMILES: COc1cc(C(=O)NC2CC(N3CCCC3)C2)ccc1Nc1ncc2c(n1)-c1c(nn(C)c1-c1ccccc1Cl)CC2] | 1.91 | 584.2 | G |
| III-26 | (Chiral) | 1.83 | 627.2 | G |
| III-27 | 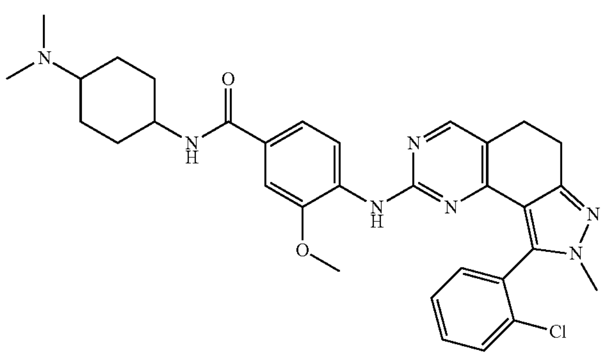 | 1.92 | 586.2 | G |
| III-28 | 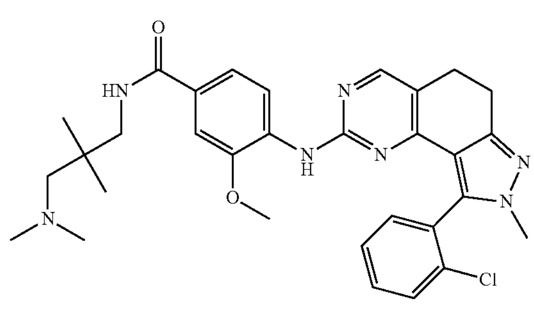 | 2.10 | 574.2 | G |

TABLE 12-continued
| | | | | |
|---|---|---|---|---|
| III-29 | 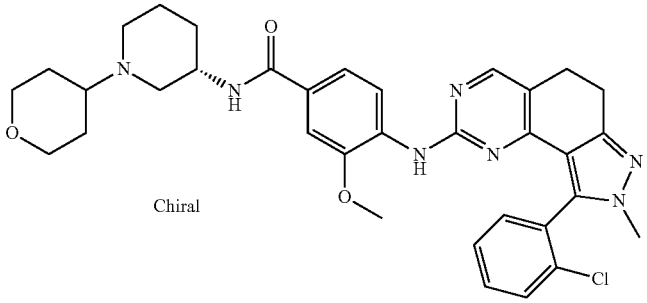 [SMILES: COc1cc(C(=O)N[C@H]2CCCN(C3CCOCC3)C2)ccc1Nc1ncc2c(n1)-c1c(nn(C)c1-c1ccccc1Cl)CC2] Chiral | 1.88 | 628.3 | G |
| III-30 | 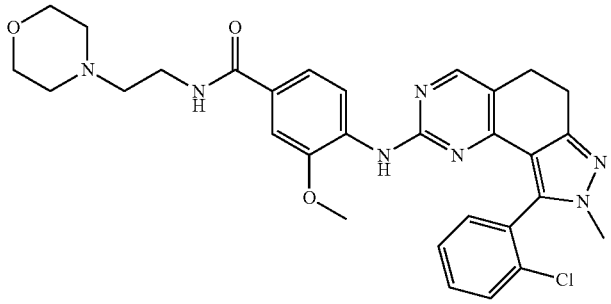 [SMILES: COc1cc(C(=O)NCCN2CCOCC2)ccc1Nc1ncc2c(n1)-c1c(nn(C)c1-c1ccccc1Cl)CC2] | 1.71 | 574.2 | G |
| III-31 | 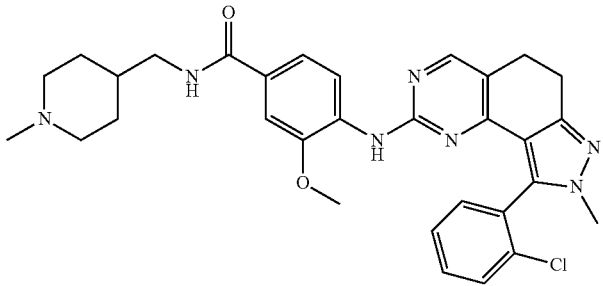 | 1.83 | 572.3 | G |
| III-32 | 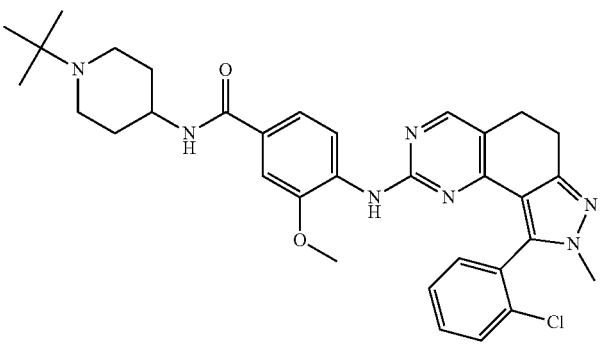 [SMILES: COc1cc(C(=O)NC2CCN(C(C)(C)C)CC2)ccc1Nc1ncc2c(n1)-c1c(nn(C)c1-c1ccccc1Cl)CC2] | 2.01 | 600.2 | G |
| III-33 | 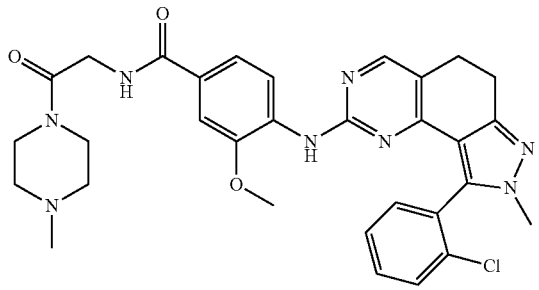 [SMILES: COc1cc(C(=O)NCC(=O)N2CCN(C)CC2)ccc1Nc1ncc2c(n1)-c1c(nn(C)c1-c1ccccc1Cl)CC2] | 1.68 | 601.3 | G |

TABLE 12-continued

| | | | | |
|---|---|---|---|---|
| III-34 | | 1.82 | 635.2 | G |
| III-35 | | 1.74 | 645.3 | G |
| III-36 | | 1.81 | 635.2 | G |
| III-37 | | 1.95 | 598.2 | G |
| III-38 | | 1.71 | 613.3 | G |

TABLE 12-continued

| | | | | |
|---|---|---|---|---|
| III-39 | (structure) | 1.74 | 600.2 | G |
| III-40* | (structure) | 2.07 | 614.2 | G |
| III-41* | (structure) | 2.20 | 612.3 | G |
| III-42* | (structure) | 1.91 | 586.2 | G |
| III-43* | (structure) | 1.85 | 616.2 | G |

TABLE 12-continued
| III-44* | 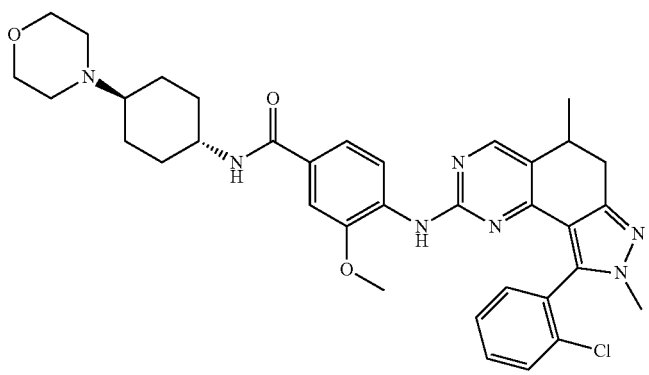 [SMILES: COc1cc(C(=O)N[C@H]2CC[C@H](N3CCOCC3)CC2)ccc1Nc1ncc2c(n1)-c1c(nn(C)c1-c1ccccc1Cl)CC2C] | 1.88 | 642.3 | G |
| III-45* | 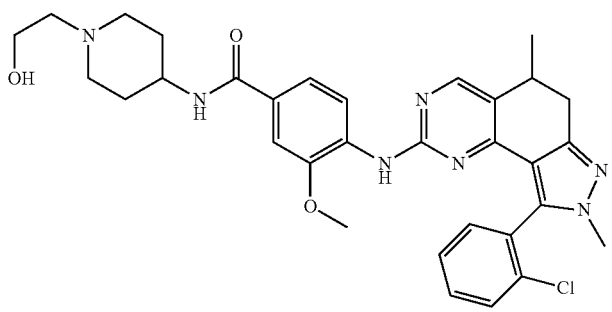 [SMILES: COc1cc(C(=O)NC2CCN(CCO)CC2)ccc1Nc1ncc2c(n1)-c1c(nn(C)c1-c1ccccc1Cl)CC2C] | 1.72 | 602.2 | G |
| III-46* | 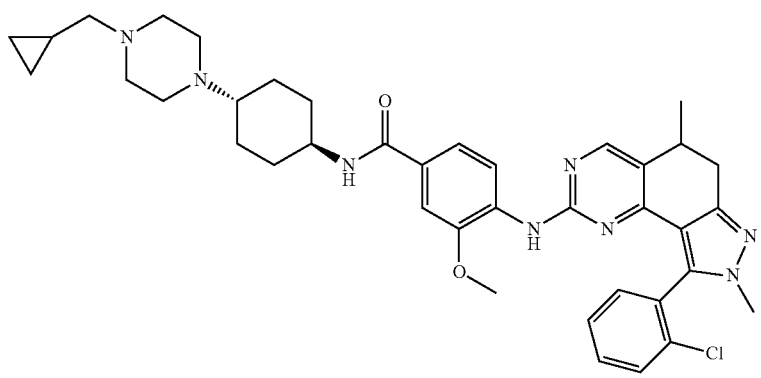 [SMILES: COc1cc(C(=O)N[C@H]2CC[C@H](N3CCN(CC4CC4)CC3)CC2)ccc1Nc1ncc2c(n1)-c1c(nn(C)c1-c1ccccc1Cl)CC2C] | 2.00 | 696.3 | G |
| III-47* | 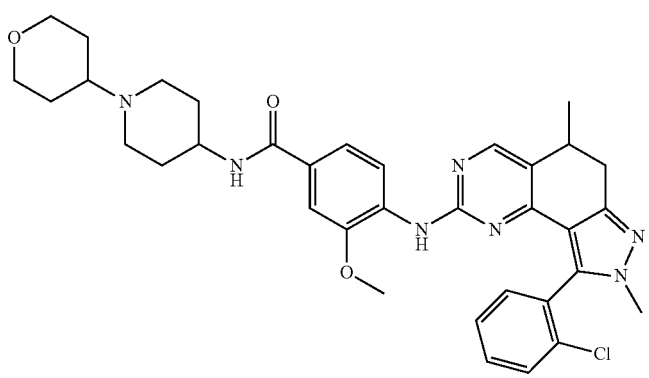 [SMILES: COc1cc(C(=O)NC2CCN(C3CCOCC3)CC2)ccc1Nc1ncc2c(n1)-c1c(nn(C)c1-c1ccccc1Cl)CC2C] | 1.84 | 642.3 | G |

TABLE 12-continued
| | | | | |
|---|---|---|---|---|
| III-48* | 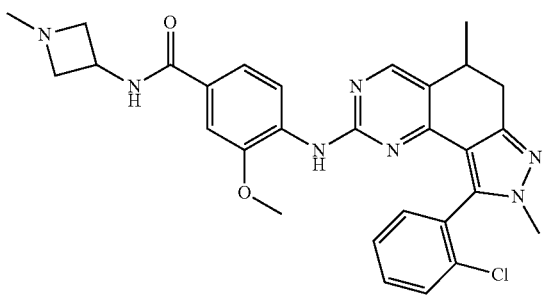 | 1.78 | 544.2 | G |
| III-49* | 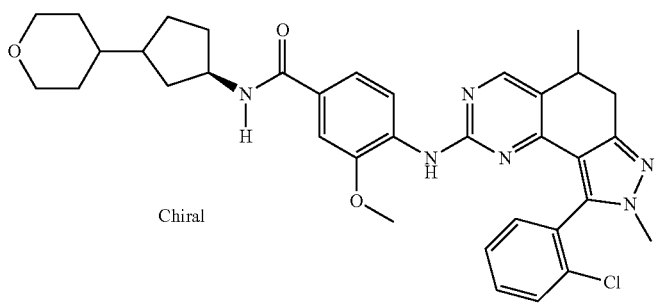 [SMILES: COc1cc(C(=O)N[C@@H]2CCC(C3CCOCC3)C2)ccc1Nc1ncc2c(n1)-c1c(nn(C)c1-c1ccccc1Cl)CC2C]<br>Chiral | 1.84 | 628.3 | G |
| III-50 | 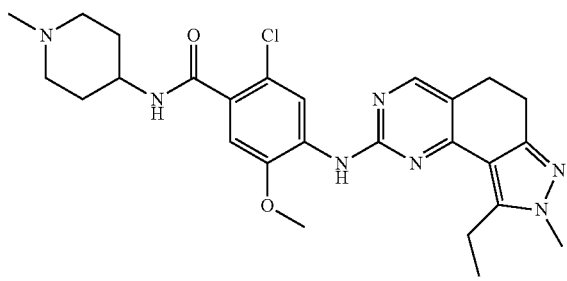 | 1.73 | 510.3 | G |
| III-51 | 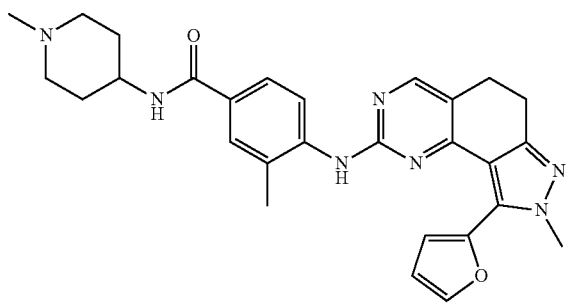 | 1.69 | 498.3 | G |
| III-52 | 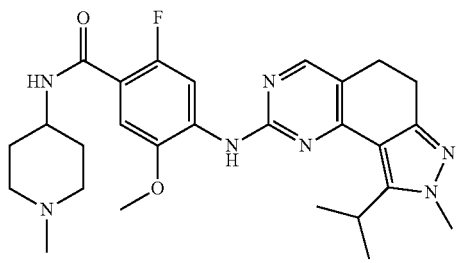 [SMILES: COc1cc(C(=O)NC2CCN(C)CC2)c(Cl)cc1Nc1ncc2c(n1)-c1c(nn(C)c1C(C)C)CC2] | 1.86 | 508.0 | G |

TABLE 12-continued

| | | | | |
|---|---|---|---|---|
| III-53 | | 1.72 | 504.3 | G |
| III-54 | | 1.74 | 548.3 | G |
| III-55 | | 1.79 | 524.3 | G |
| III-56 | | 1.81 | 568.3 | G |
| III-57 | | 2.13 | 539.2 | G |

TABLE 12-continued
| | | | | |
|---|---|---|---|---|
| III-58 | 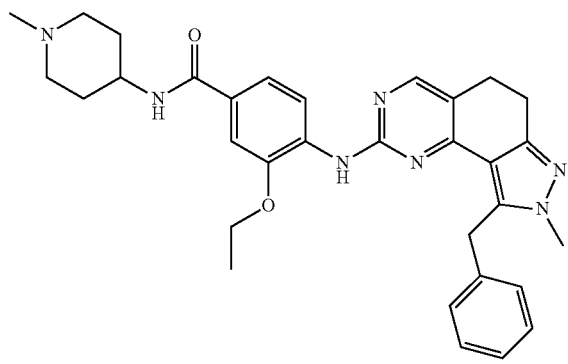 | 1.86 | 552.2 | G |
| III-59 | 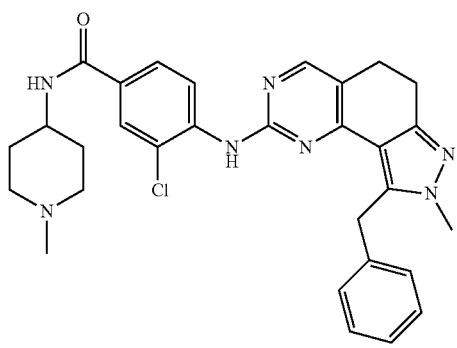 [SMILES: CN1CCC(NC(=O)c2ccc(Nc3ncc4c(n3)-c3c(nn(C)c3Cc3ccccc3)CC4)c(Cl)c2)CC1] | 1.96 | 542.0 | G |
| III-60 | 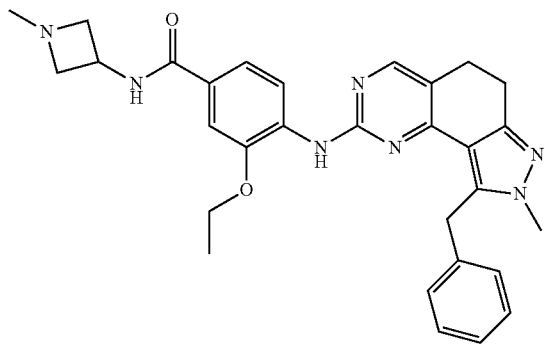 | 1.86 | 524.3 | G |
| III-61 | 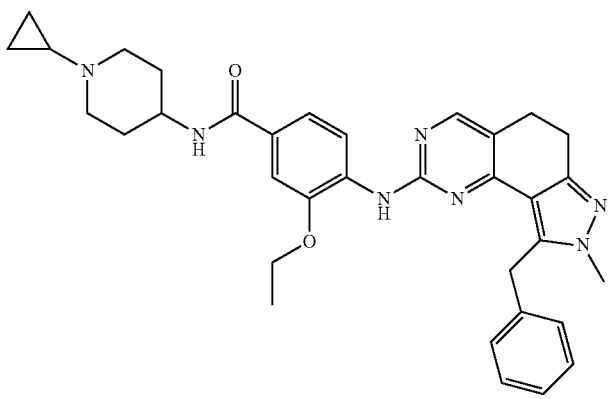 [SMILES: CCOc1cc(C(=O)NC2CCN(C3CC3)CC2)ccc1Nc1ncc2c(n1)-c1c(nn(C)c1Cc1ccccc1)CC2] | 2.02 | 578.3 | G |

TABLE 12-continued
| III-62 | 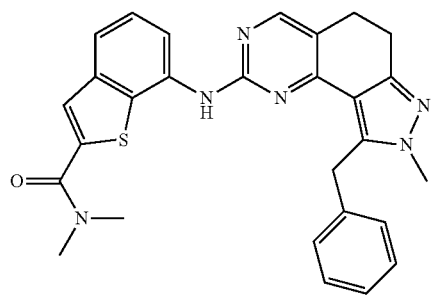 [SMILES: CN(C)C(=O)c1cc2cccc(Nc3ncc4c(n3)-c3c(nn(C)c3Cc3ccccc3)CC4)c2s1] | 1.86 | 495.0 | G |
| III-63 | 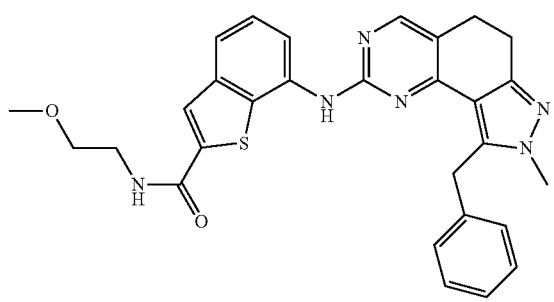 | 1.81 | 525.0 | G |
| III-64 | 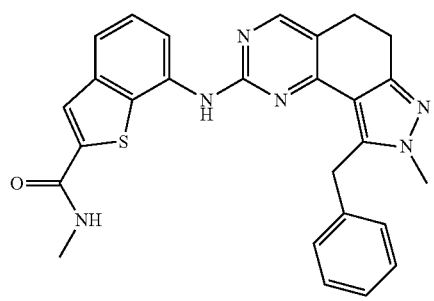 [SMILES: CNC(=O)c1cc2cccc(Nc3ncc4c(n3)-c3c(nn(C)c3Cc3ccccc3)CC4)c2s1] | 1.76 | 481.0 | G |
| III-65 | 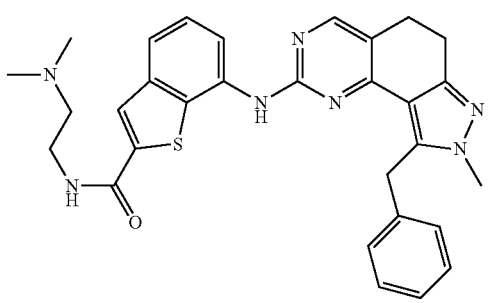 | 1.84 | 538.3 | G |
| III-66 | 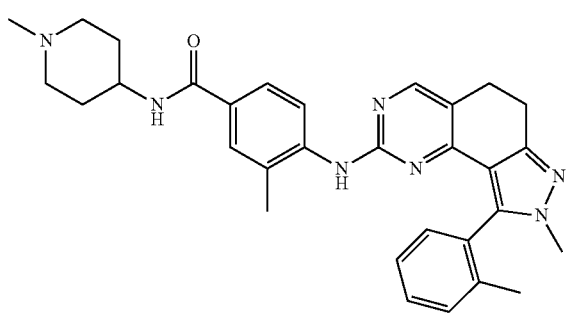 | 1.78 | 522.2 | G |

TABLE 12-continued
| | | | | |
|---|---|---|---|---|
| III-67 | 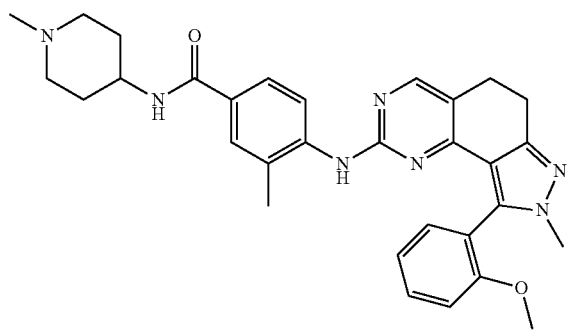 | 1.71 | 538.3 | G |
| III-68 | 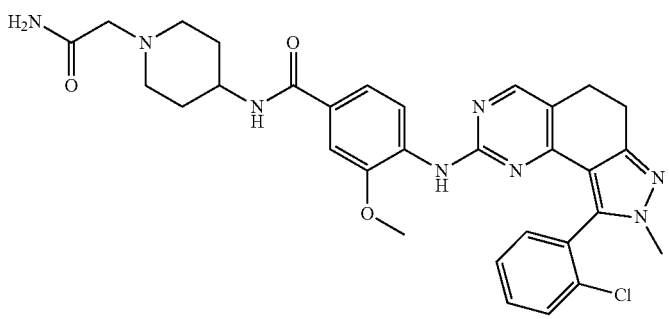 [SMILES: COc1cc(C(=O)NC2CCN(CC(N)=O)CC2)ccc1Nc1ncc2c(n1)-c1c(nn(C)c1-c1ccccc1Cl)CC2] | 1.65 | 601.3 | G |
| III-69 | 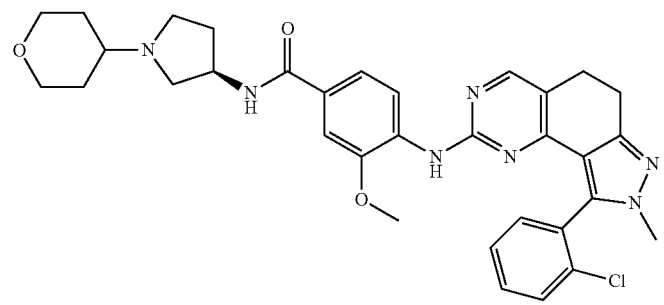 [SMILES: COc1cc(C(=O)N[C@@H]2CCN(C3CCOCC3)C2)ccc1Nc1ncc2c(n1)-c1c(nn(C)c1-c1ccccc1Cl)CC2] | 1.78 | 614.2 | G |
| III-70 | 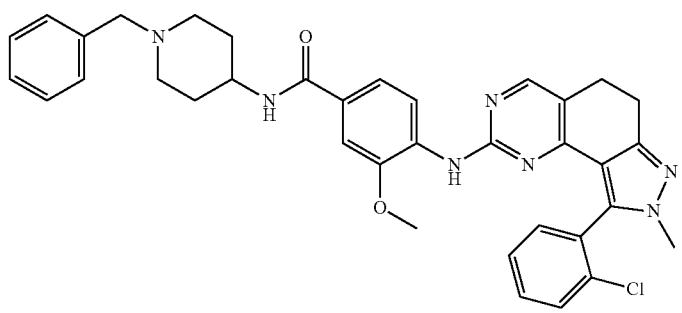 [SMILES: COc1cc(C(=O)NC2CCN(Cc3ccccc3)CC2)ccc1Nc1ncc2c(n1)-c1c(nn(C)c1-c1ccccc1Cl)CC2] | 2.09 | 634.2 | G |
| III-71 | 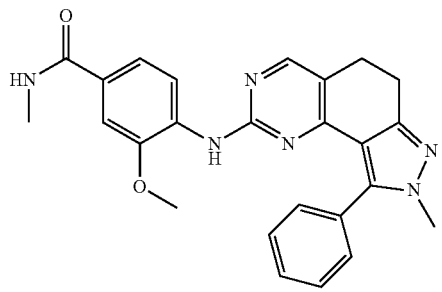 [SMILES: CNC(=O)c1ccc(Nc2ncc3c(n2)-c2c(nn(C)c2-c2ccccc2)CC3)c(OC)c1] | 1.67 | 441.3 | G |

TABLE 12-continued

| | | | | |
|---|---|---|---|---|
| III-72 | | 1.75 | 496.3 | G |
| III-73 | | 1.84 | 608.5 | G |
| III-74 | | 1.82 | 512.5 | G |
| III-75 | | 1.68 | 568.5 | G |
| III-76 | | 1.98 | 661.5 | G |

TABLE 12-continued

| | | | | |
|---|---|---|---|---|
| III-77 | | 1.82 | 582.5 | G |
| III-78 | | 1.81 | 608.5 | G |
| III-79 | | 1.78 | 499.5 | G |
| III-80 | | 1.87 | 526.5 | G |
| III-81 | | 1.76 | 510.5 | G |

TABLE 12-continued

| | | | | |
|---|---|---|---|---|
| III-82 | | 1.96 | 564.5 | G |
| III-83 | | 1.81 | 532.5 | G |
| III-84 | | 1.98 | 681.7 | G |
| III-85 | | 1.78 | 519.5 | G |
| III-86 | | 1.76 | 530.5 | G |

TABLE 12-continued

| ID | Structure | | | |
|---|---|---|---|---|
| III-87 | (structure) | 1.90 | 542.3 | G |
| III-88 | (structure) | 1.96 | 530.2 | G |
| III-89 | (structure) | 1.92 | 516.3 | G |
| III-90 | (structure) | 2.06 | 568.2 | G |
| III-91 | (structure) | 1.90 | 612.3 | G |

TABLE 12-continued
| | | | | |
|---|---|---|---|---|
| III-92 | 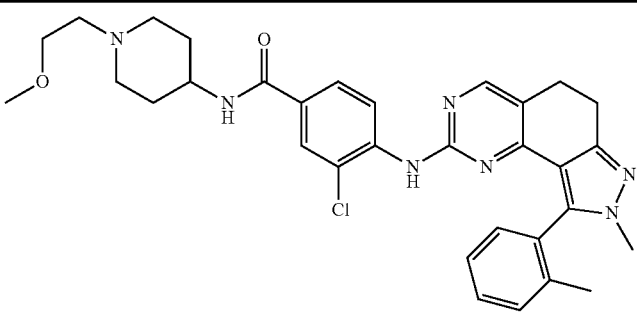 | 1.91 | 586.2 | G |
| III-93 | 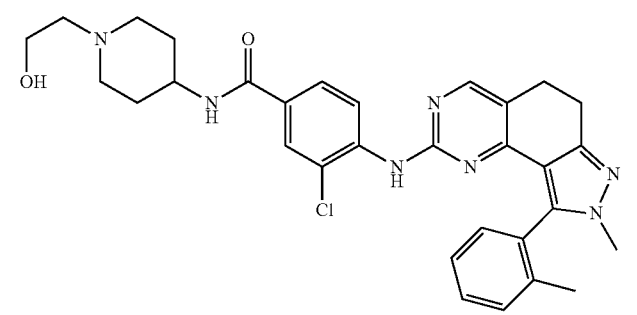 [SMILES: Cc1ccccc1-c1c2c(nn1C)CCc1cnc(Nc3ccc(C(=O)NC4CCN(CCO)CC4)cc3Cl)nc1-2] | 1.76 | 572.3 | G |
| III-94 | 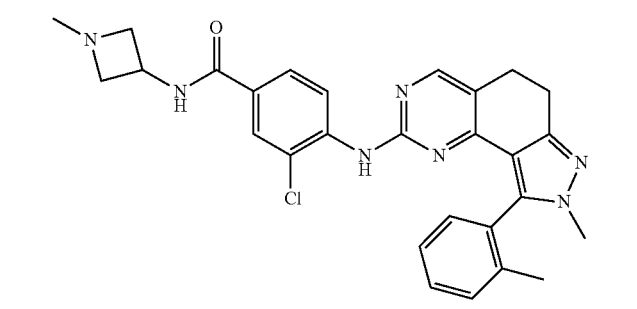 | 1.97 | 514.2 | G |
| III-95 | 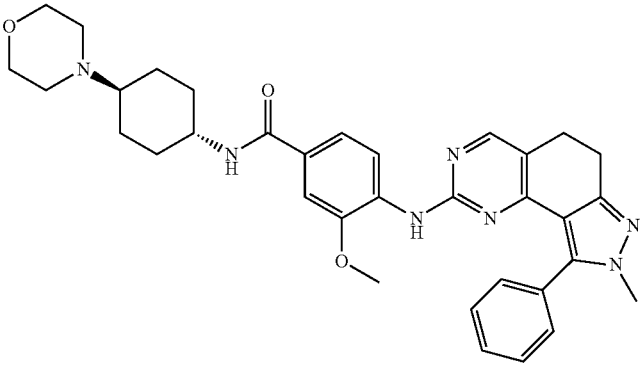 [SMILES: COc1cc(C(=O)N[C@H]2CC[C@H](N3CCOCC3)CC2)ccc1Nc1ncc2c(n1)-c1c(nn(C)c1-c1ccccc1)CC2] | 1.81 | 594.2 | G |
| III-96 | 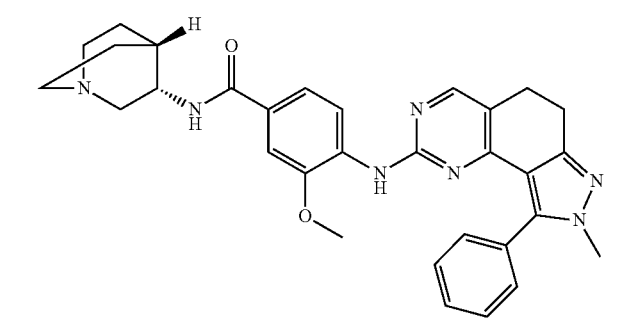 | 1.83 | 536.2 | G |

TABLE 12-continued
| | | | | |
|---|---|---|---|---|
| III-97 | 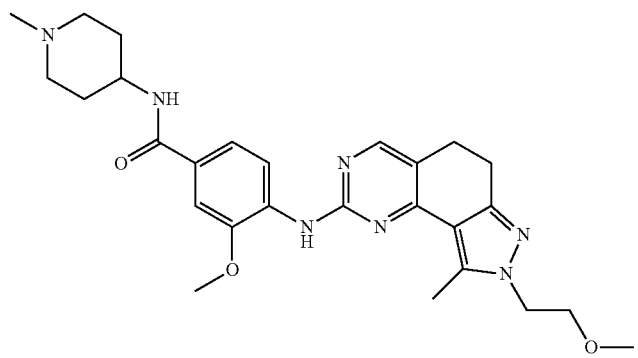 | 1.61 | 506.3 | G |
| III-98 | 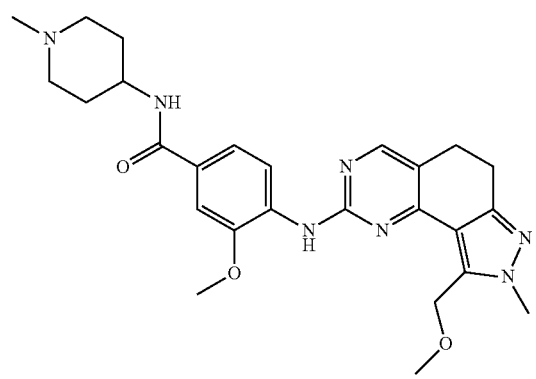 | 1.57 | 492.3 | G |
| III-99 | 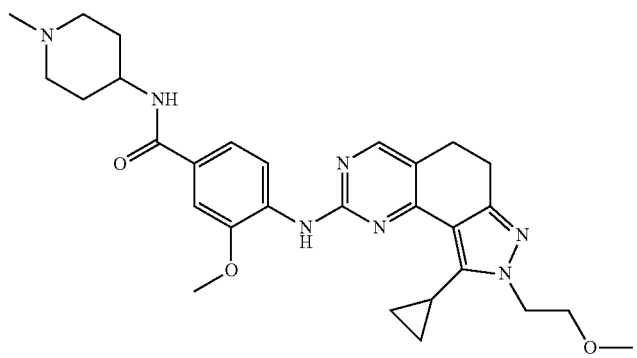 | 1.71 | 532.3 | G |
| III-100 | 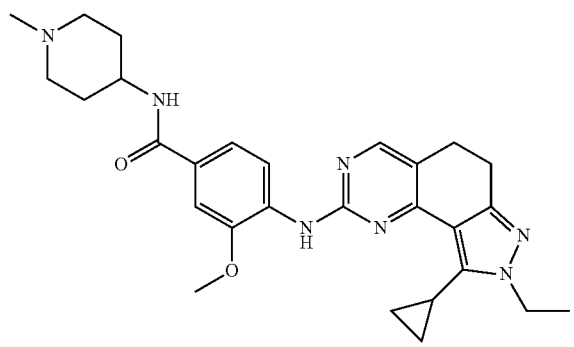 [SMILES: CCn1nc2c(c1C1CC1)-c1nc(Nc3ccc(C(=O)NC4CCN(C)CC4)cc3OC)ncc1CC2] | 1.77 | 502.3 | G |

TABLE 12-continued

| No. | Structure | t_ret [min] | [M + H]+ | Analysis |
|---|---|---|---|---|
| III-101 | (structure) | 1.95 | 476.3 | G |
| III-102 | (structure) | 1.92 | 518.2 | G |
| III-103 | (structure) | 1.48 | 564 | G |
| III-104 | (structure) | 1.37 | 572 | G |

TABLE 12-continued
| | | | | |
|---|---|---|---|---|
| III-105 | (structure) | 1.47 | 544 | G |
| III-106* | (structure) | 1.78 | 504 | G |
| III-107 | (structure) | 1.51 | 606 | G |
| III-108 | (structure) | 1.7 | 530 | G |
*Structure includes both enantiomers in each case, i.e.
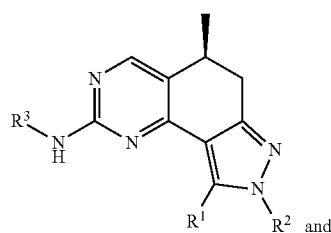 and 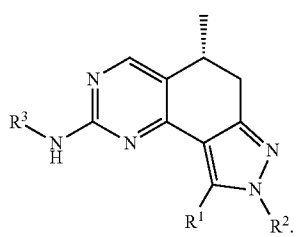

4.3. Preparation of Other Novel Compounds (I) by Derivatisation of Amines (Method M/method N/method O/method P)

Preparation of Compound IV-1 by Amide Cleaving

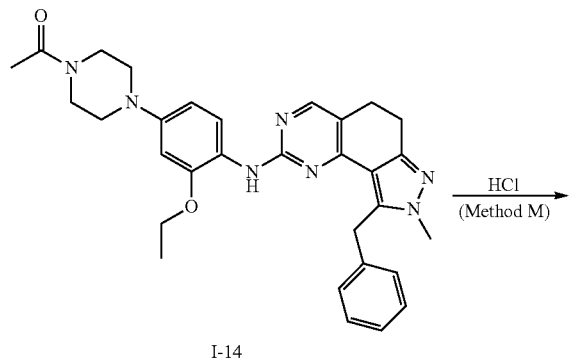

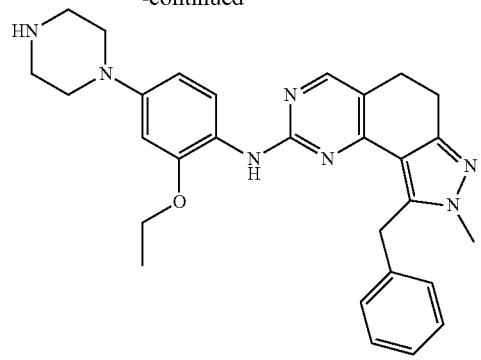

Amide Cleaving (Method M). The starting compound I-14 (1.2 g, 2.23 mmol) is stirred in conc. HCl (3 mL)/EtOH (3 mL) for 10 min. at 120° C. in a microwave reactor. The reaction mixture is made basic with potassium carbonate solution and exhaustively extracted with DCM. The organic phase is washed with water, dried on sodium sulphate, filtered and evaporated down. The crude product is purified by column chromatography.

Analogously to IV-1 further free amines are obtained by amide cleaving (Table 13).

TABLE 13

| No. | Structure | $t_{ret}$ [min] | $[M+H]^+$ | Method of analysis |
|---|---|---|---|---|
| IV-1 | 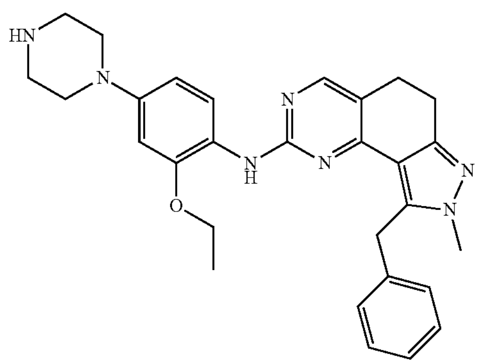 [SMILES: CCOc1cc(N2CCNCC2)ccc1Nc1ncc2c(n1)-c1c(nn(C)c1Cc1ccccc1)CC2] | 1.85 | 496.3 | G |
| IV-2 | 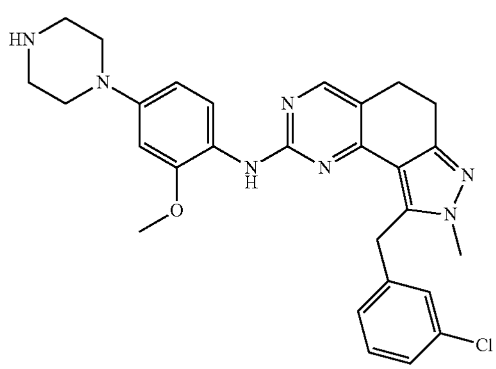 [SMILES: COc1cc(N2CCNCC2)ccc1Nc1ncc2c(n1)-c1c(nn(C)c1Cc1cccc(Cl)c1)CC2] | 0.71 | 502.2 | A |

TABLE 13-continued

| No. | Structure | $t_{ret}$ [min] | $[M + H]^+$ | analysis |
|---|---|---|---|---|
| IV-2a* | 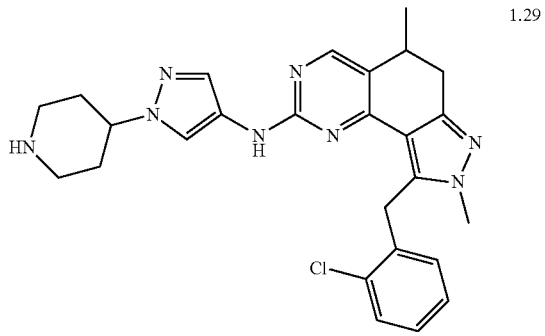 | 1.29 | 489 | G |

*Structure includes both enantiomers in each case, i.e.

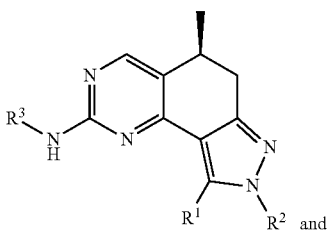

and

Preparation of Compound IV-3 by Reductive Amination (Method N)

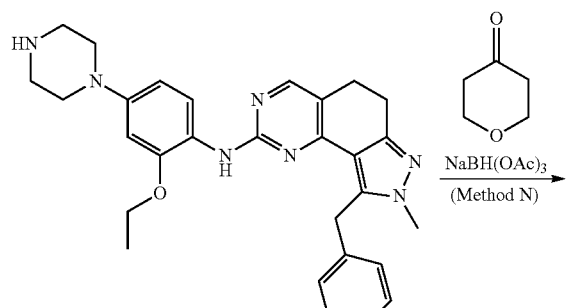

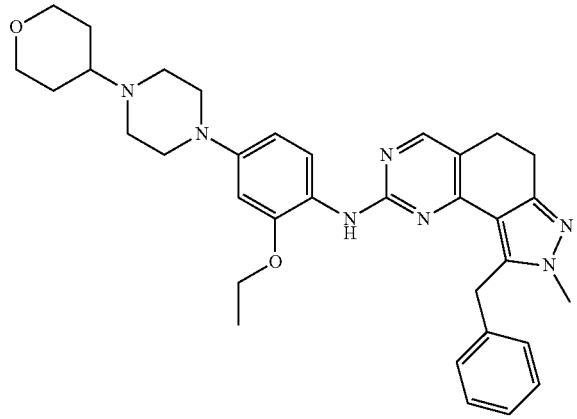

IV-3

Reductive Amination (Method N). The starting compound IV-1 (80 mg, 0.16 mmol) in anhydrous NMP (500 µL) is combined with tetrahydro-4H-pyran-4-one (45 µL, 0.48 mmol) and sodium triacetoxyborohydride (107 mg, 0.48 mmol) and stirred for 1.5 h at RT. The reaction mixture is purified by preparative HPLC-MS. The fractions containing the reaction product are freeze-dried.

Analogously to IV-3 further novel compounds are obtained by reductive amination (Table 14).

TABLE 14
| No. | Structure | t_ret [min] | [M + H]+ | Method of analysis |
|---|---|---|---|---|
| IV-3 | 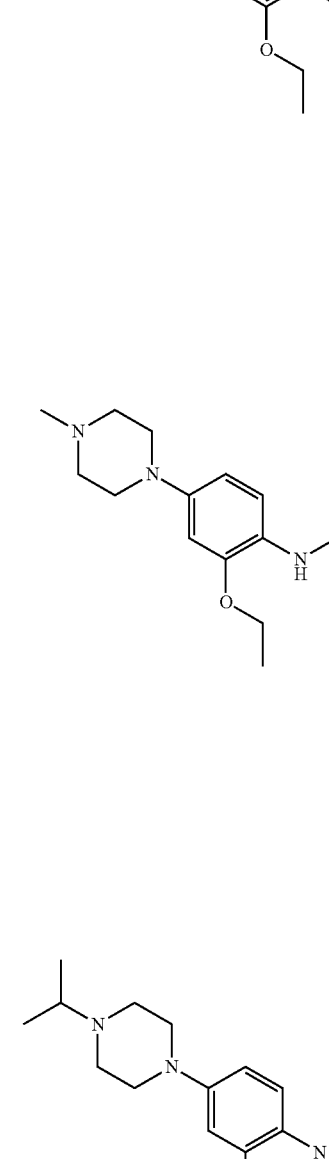 | 1.99 | 580.3 | G |
| IV-4 | 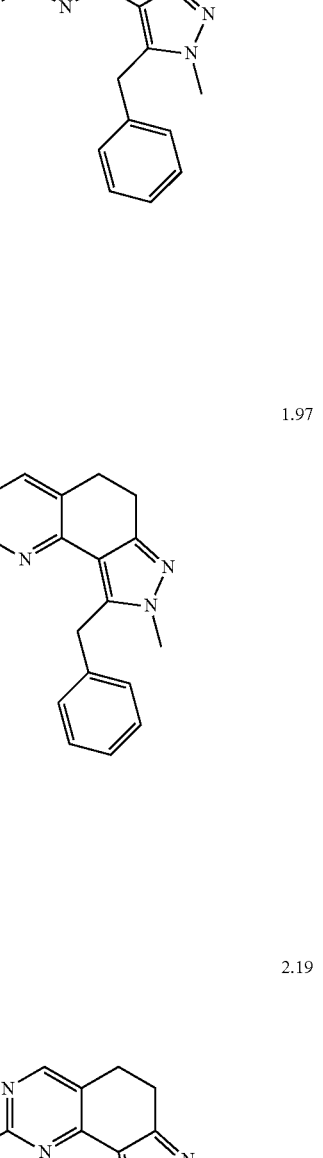 | 1.97 | 510.3 | G |
| IV-5 | 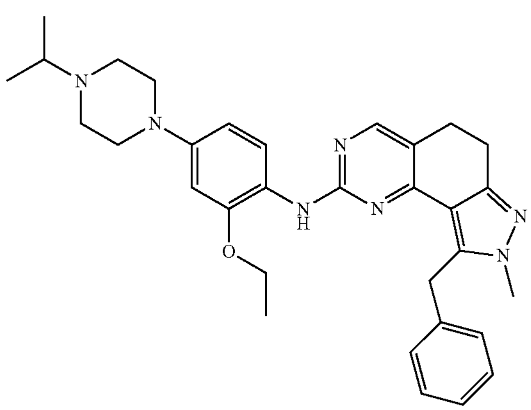 [SMILES: CCOc1cc(N2CCN(C(C)C)CC2)ccc1Nc1ncc2c(n1)-c1c(nn(C)c1Cc1ccccc1)CC2] | 2.19 | 538.3 | G |

TABLE 14-continued
| IV-6 | 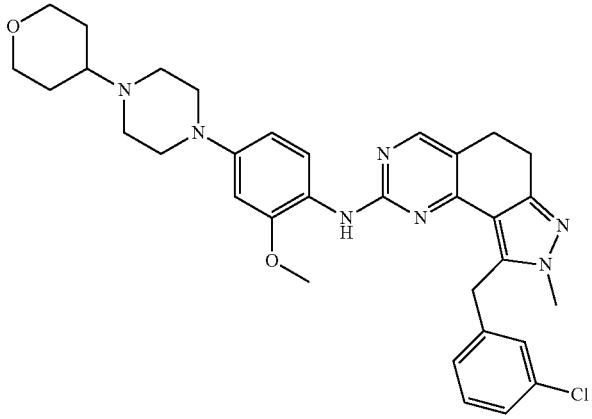 [SMILES: COc1cc(N2CCN(C3CCOCC3)CC2)ccc1Nc1ncc2c(n1)-c1c(nn(C)c1Cc1cccc(Cl)c1)CC2] | 1.58 | 586.2 | G |
| IV-7 | 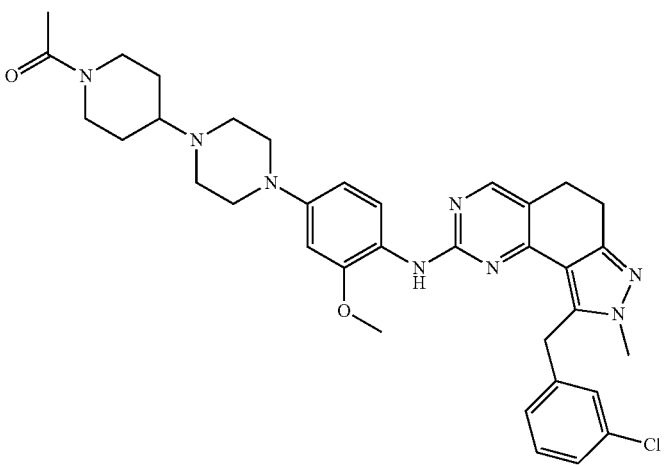 [SMILES: COc1cc(N2CCN(C3CCN(C(C)=O)CC3)CC2)ccc1Nc1ncc2c(n1)-c1c(nn(C)c1Cc1cccc(Cl)c1)CC2] | 1.48 | 627.5 | G |
| IV-8 | 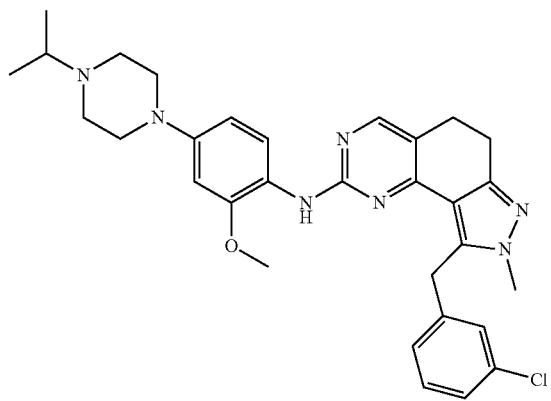 [SMILES: COc1cc(N2CCN(C(C)C)CC2)ccc1Nc1ncc2c(n1)-c1c(nn(C)c1Cc1cccc(Cl)c1)CC2] | 1.92 | 544.5 | G |
| IV-9 | 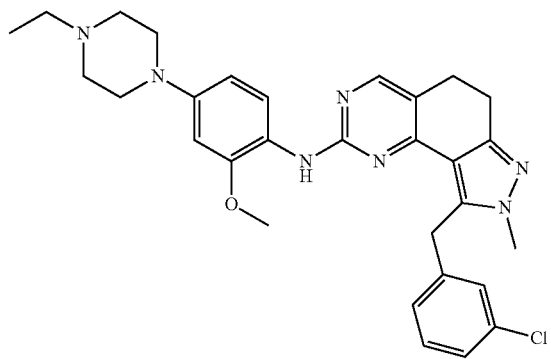 [SMILES: CCN1CCN(c2ccc(Nc3ncc4c(n3)-c3c(nn(C)c3Cc3cccc(Cl)c3)CC4)c(OC)c2)CC1] | 1.81 | 530.2 | G |

TABLE 14-continued
| No. | Structure | t_ret [min] | [M + H]+ | Analysis |
|---|---|---|---|---|
| IV-9a | 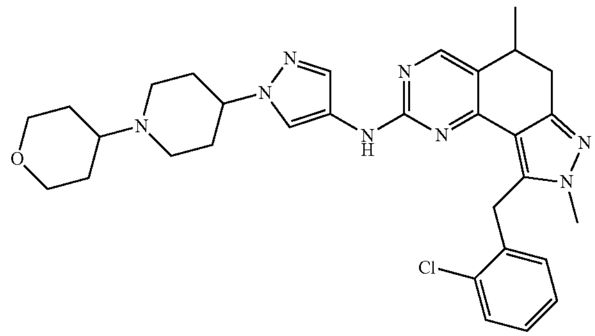 [SMILES: CC1Cc2nn(C)c(Cc3ccccc3Cl)c2-c2nc(Nc3cnn(C4CCN(C5CCOCC5)CC4)c3)ncc21] | 1.46 | 573 | G |
| IV-9b | 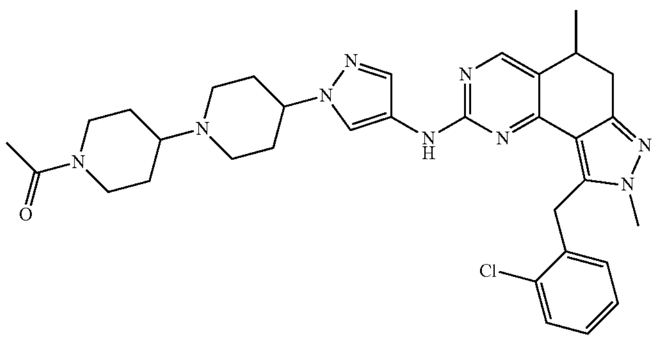 [SMILES: CC(=O)N1CCC(N2CCC(n3cc(Nc4ncc5c(n4)-c4c(nn(C)c4Cc4ccccc4Cl)CC5C)cn3)CC2)CC1] | 1.33 | 614 | G |
| IV-9c | 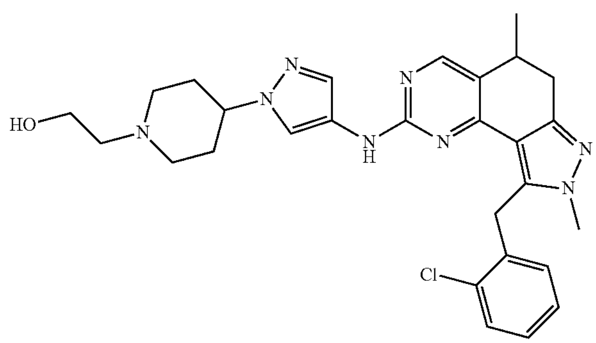 [SMILES: CC1Cc2nn(C)c(Cc3ccccc3Cl)c2-c2nc(Nc3cnn(C4CCN(CCO)CC4)c3)ncc21] | 1.37 | 533 | G |
*Structure includes both enantiomers in each case, i.e.
Preparation of Compound IV-10 by Sulphonamidation (Method O)
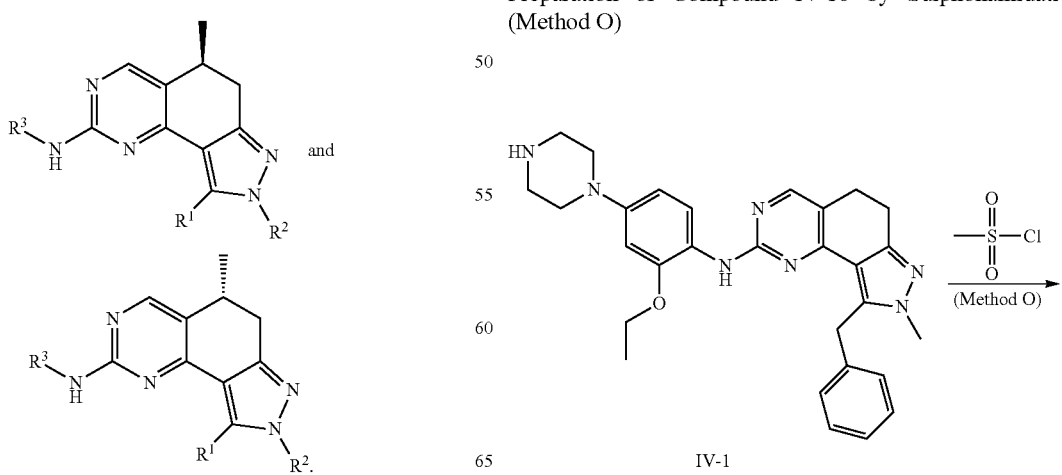

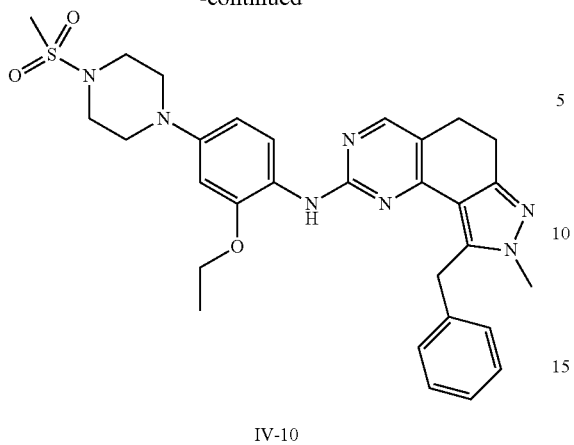

IV-10

Sulphonamide Formation (Method O). The starting compound IV-1 (100 mg, 0.20 mmol) in anhydrous DCM (0.5 mL) is combined with methanesulphonic acid chloride (22 µL, 0.28 mmol) and triethylamine (90 µL, 0.62 mmol) and stirred for 3 h at RT. The reaction mixture is evaporated down, the residue is taken up in DMSO (500 µL) and purified by preparative HPLC-MS. The fractions containing the reaction product are freeze-dried.

Analogously to IV-10 further novel compounds are obtained by reaction with sulphonic acid chlorides.

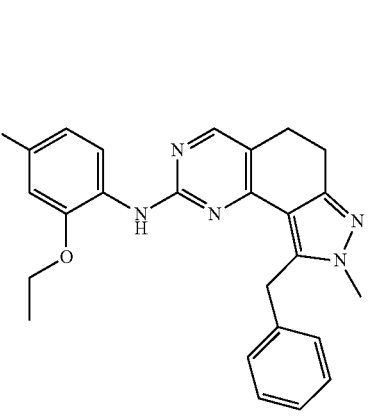

IV-11

TABLE 15

| No. | Structure | $t_{ret}$ [min] | $[M + H]^+$ | Method of analysis |
|---|---|---|---|---|
| IV-10 | 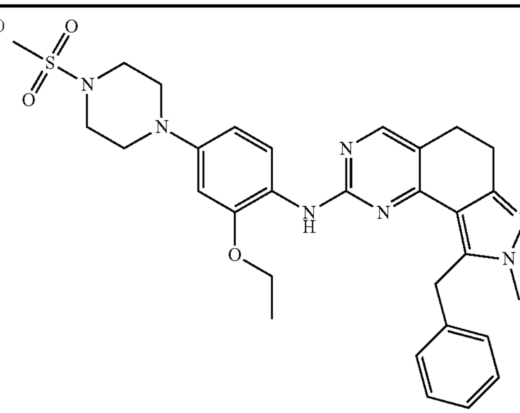 | 1.94 | 574.0 | G |

Preparation of Compound IV-11 by Amidation (Method P)

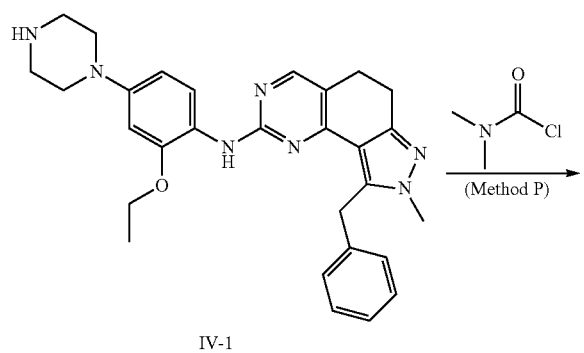

IV-1

Amide formation (method P). The starting compound IV-1 (100 mg, 0.20 mmol) in anhydrous DCM (0.5 mL) is combined with dimethylcarbamyl chloride (30 mg, 0.28 mmol) and triethylamine (90 µL, 0.62 mmol) and stirred for 3 h at RT. The reaction mixture is evaporated down, the residue is taken up in DMSO (0.5 mL) and purified by preparative HPLC-MS. The fractions containing the reaction product are freeze-dried. Alternatively method L may be used for the amide linking.

Analogously to IV-11 further novel compounds may be obtained by reaction with acid chlorides or amide coupling of acids.

TABLE 16

| No. | Structure | $t_{ret}$ [min] | $[M + H]^+$ | Method of analysis |
|---|---|---|---|---|
| IV-11 | 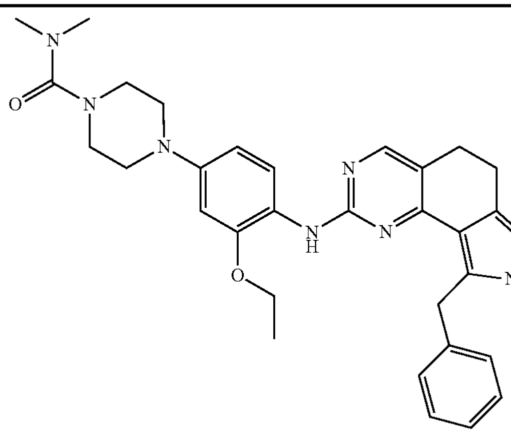 | 1.96 | 567.3 | G |

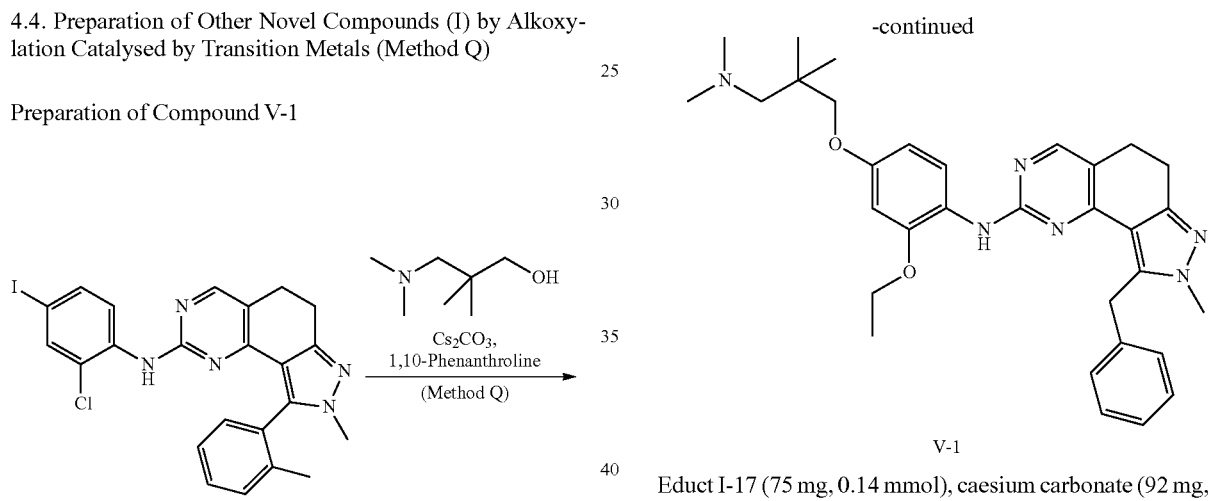

4.4. Preparation of Other Novel Compounds (I) by Alkoxylation Catalysed by Transition Metals (Method Q)

Preparation of Compound V-1

Educt I-17 (75 mg, 0.14 mmol), caesium carbonate (92 mg, 0.28 mmol), 1,10-phenanthroline (5 mg, 0.03 mmol) and copper-I-iodide (3 mg, 0.015 mmol) are stirred in 3-dimethylamino-2,2-dimethyl-1-propanol (95 mg, 0.71 mmol) for 60 h at 100° C. under argon. The reaction mixture is taken up in DMSO, filtered and purified by preparative HPLC-MS. The fractions containing the reaction product are freeze-dried.

Analogously to V-1 further novel compounds (I) are obtained (Table 17).

TABLE 17

| No. | Structure | $t_{ret}$ [min] | $[M + H]^+$ | Method of analysis |
|---|---|---|---|---|
| V-1 | 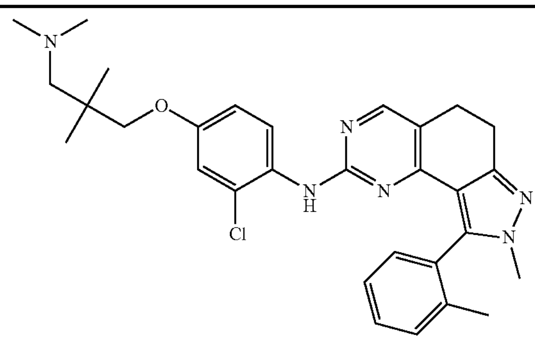 | 2.63 | 531.2 | G |

TABLE 17-continued

| No. | Structure | $t_{ret}$ [min] | $[M + H]^+$ | Method of analysis |
|---|---|---|---|---|
| V-2 | 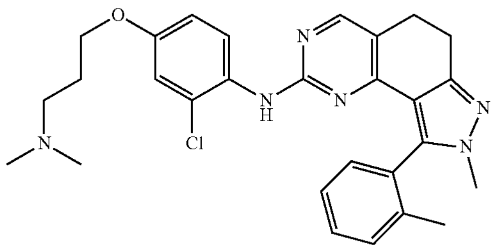 [SMILES: Cc1ccccc1-c1c2c(nn1C)CCc1cnc(Nc3ccc(OCCCN(C)C)cc3Cl)nc1-2] | 2.21 | 503.3 | G |
| V-3 | 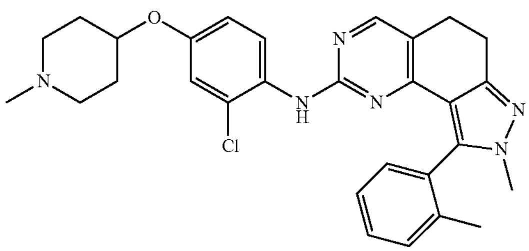 [SMILES: Cc1ccccc1-c1c2c(nn1C)CCc1cnc(Nc3ccc(OC4CCN(C)CC4)cc3Cl)nc1-2] | 2.16 | 515.2 | G |
| V-4 | 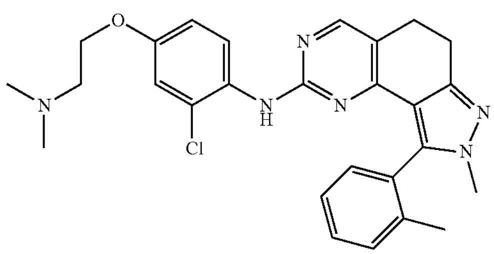 [SMILES: Cc1ccccc1-c1c2c(nn1C)CCc1cnc(Nc3ccc(OCCN(C)C)cc3Cl)nc1-2] | 2.11 | 489.3 | G |
| V-5 | 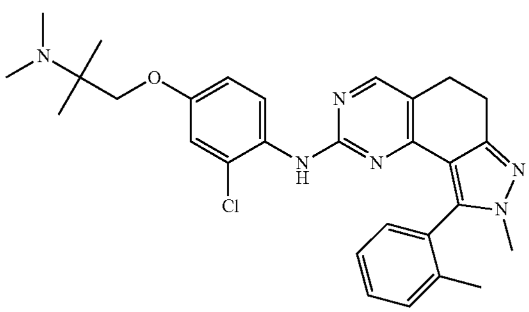 [SMILES: Cc1ccccc1-c1c2c(nn1C)CCc1cnc(Nc3ccc(OCC(C)(C)N(C)C)cc3Cl)nc1-2] | 2.26 | 517.3 | G |
| V-6 | 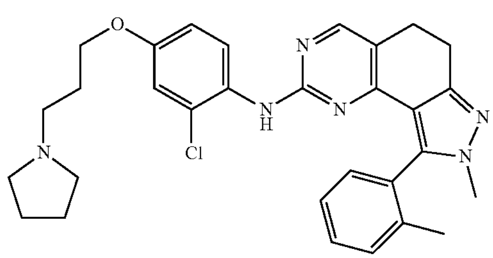 [SMILES: Cc1ccccc1-c1c2c(nn1C)CCc1cnc(Nc3ccc(OCCCN4CCCC4)cc3Cl)nc1-2] | 2.38 | 529.3 | G |
| V-7 | 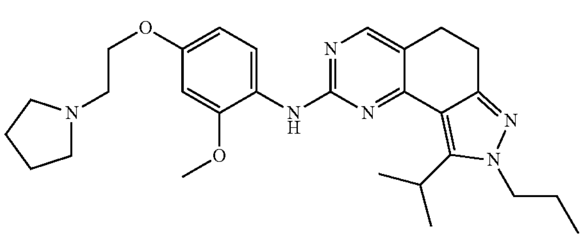 [SMILES: CCCn1nc2c(c1C(C)C)-c1nc(Nc3ccc(OCCN4CCCC4)cc3OC)ncc1CC2] | 2.17 | 491.3 | G |

TABLE 17-continued

| No. | Structure | $t_{ret}$ [min] | $[M + H]^+$ | Method of analysis |
|---|---|---|---|---|
| V-8 | 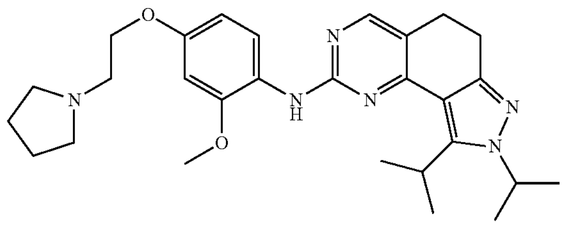 [SMILES: COc1cc(OCCN2CCCC2)ccc1Nc1ncc2c(n1)-c1c(nn(C(C)C)c1C(C)C)CC2] | 2.18 | 491.3 | G |

The following Examples describe the biological activity of the compounds according to the invention, without restricting the invention to these Examples.

Compounds of general formula (I) are characterised by their many possible applications in the therapeutic field. Particular mention should be made of those applications in which the inhibiting effect on the proliferation of cultivated human tumour cells but also on the proliferation of other cells such as endothelial cells, for example, are involved.

Insulin-Like Growth Factor-1 Receptor (IGF-1R)-Kinase Assay

The kinase activity is measured by DELFIA® assay (dissociation-enhanced lanthanide fluorescence immunoassay, Perkin Elmer). The cytoplasmic kinase domain of human IGF-1R (amino acids 964-1370) is expressed as a fusion protein with a glutathione-S-transferase tag (IGF-1R-GST) in High Five™ Cells (Invitrogen). Enzyme activity is measured in the presence of substances and a control substance. Polyglutamate-tyrosine peptide (pEY, Sigma Aldrich) and biotinylated pEY (bio-pEY) are used as reaction substrates.

10 μL of substance in 25% DMSO are mixed with 30 μL of IGF-1R-GST solution (67 mM HEPES pH 7.4, 15 μg/mL pEY, 1.7 μg/mL bio-pEY, 13.3 mM $MgCl_2$, 3.3 mM dithiothreitol, 0.0033% Brij 35, 2 ng IGF-1R-GST) in 96-well plates. The reactions are started with 10 μL of a 750 μM ATP solution. After 40 min at RT the reactions are stopped with 50 μL of stop solution (250 mM EDTA, 20 mM HEPES pH 7.4). 90 μL from each reaction are transferred onto streptavidin-coated 96-well plates. After 120 min incubation at RT the plates are washed three times with 200 μL phosphate-buffered saline (PBS) per well. The plates are incubated for 60 min with 100 μL of europium-coupled antibody against phospho-tyrosine (diluted 1/2000 in Perkin Elmer DELFIA assay buffer) per well. The plates are washed three times with 200 μL per well of DELFIA washing buffer. 100 μL DELFIA Enhancement Solution (Perkin Elmer) is added to each well, and the plates are incubated for 10 min. The fluorescence signal is measured with a Wallac Victor TRF Reader. $IC_{50}$ values for the inhibition of the IGF-1R-kinase activity are calculated using the programmes Fifty (Version 2) and GraphPad (Version 3.0).

Table 18 shows the $IC_{50}$ values of the example compounds determined using the above assay.

TABLE 18

| No. | IGF1R $IC_{50}$ [nM] |
|---|---|
| I-2 | 73 |
| I-3 | 25 |
| I-9 | 73 |
| I-10 | 25 |
| I-12 | 14 |
| I-13 | 13 |
| I-14 | 4 |
| I-15 | 3 |
| I-16 | 4 |
| I-18 | 15 |
| I-19 | 50 |
| I-20 | 62 |
| I-21 | 2 |
| I-22 | 12 |
| I-23 | 2 |
| I-24 | 5 |
| I-25 | 48 |
| I-26 | 2 |
| I-27 | 0.18 |
| I-28 | 179 |
| I-29 | 5 |
| I-30 | 2 |
| I-31 | 34 |
| I-32 | 433 |
| I-33 | 398 |
| I-34 | 226 |
| I-35 | 242 |
| I-36 | 409 |
| I-37 | 264 |
| I-38 | 299 |
| I-39 | 63 |
| I-40 | 3 |
| I-41 | 4 |
| I-42 | 1 |
| I-43 | 3 |
| I-44 | 196 |
| I-45 | 11 |
| I-46 | 9 |
| I-47 | 89 |
| I-48 | 0.69 |
| I-49 | 2 |
| I-50 | 1 |
| I-51 | 4 |
| I-52 | 475 |
| I-53 | 11 |
| I-54 | 91 |
| I-55 | 22 |
| I-56 | 120 |
| I-57 | 91 |
| I-58 | 11 |
| I-59 | 36 |
| I-60 | 226 |
| I-61 | 207 |
| I-62 | 155 |
| I-63 | 1 |
| I-64 | 37 |
| I-65 | 1 |
| I-66 | 2 |
| I-67 | 30 |
| I-68 | 219 |
| I-69 | 9 |

TABLE 18-continued

| No. | IGF1R IC$_{50}$ [nM] |
|---|---|
| I-70 | 231 |
| I-71 | 5 |
| I-72 | 11 |
| I-73 | 208 |
| I-74 | 169 |
| I-75 | 219 |
| I-76 | 1 |
| I-77 | 7 |
| I-78 | 0.92 |
| I-79 | 2 |
| I-80 | 43 |
| I-81 | 20 |
| I-82 | 56 |
| I-83 | 21 |
| I-84 | 38 |
| I-85 | 437 |
| I-86 | 15 |
| I-87 | 60 |
| I-88 | 11 |
| I-89 | 20 |
| I-90 | 700 |
| I-91 | 2 |
| I-92 | 23 |
| I-93 | 1 |
| I-94 | 2 |
| I-95 | 106 |
| I-96 | 0.8 |
| I-97 | 0.19 |
| I-98 | 13 |
| I-99 | 13 |
| I-100 | 50 |
| I-101 | 11 |
| I-102 | 17 |
| I-103 | 169 |
| I-104 | 11 |
| I-105 | 500 |
| I-106 | 1000 |
| I-107 | 17 |
| I-108 | 1000 |
| I-109 | 6 |
| I-110 | 0.19 |
| I-111 | 12 |
| I-112 | 0.87 |
| I-113 | 29 |
| I-114 | 140 |
| I-115 | 471 |
| I-116 | 785 |
| I-117 | 922 |
| I-118 | 1939 |
| I-119 | 2035 |
| I-120 | 2354 |
| I-121 | 2612 |
| I-122 | 2613 |
| I-123 | 2976 |
| I-124 | 135 |
| I-125 | 27 |
| I-126 | 77 |
| I-127 | 7 |
| I-128 | 96 |
| I-129 | 11 |
| I-130 | 54 |
| I-131 | 22 |
| I-132 | 1132 |
| I-133 | 1000 |
| I-134 | 46 |
| I-135 | 264 |
| I-136 | 23 |
| I-137 | 108 |
| I-138 | 131 |
| I-139 | 63 |
| I-140 | 0.5 |
| I-141 | 4 |
| I-142 | 0.3 |
| I-143 | 0.4 |
| I-144 | 15 |
| I-145 | 277 |
| I-146 | 1 |
| I-147 | 13 |
| I-148 | 1 |
| I-149 | 39 |
| I-150 | 2 |
| I-151 | 2 |
| I-152 | 13 |
| I-153 | 1 |
| I-154 | 71 |
| I-155 | 2 |
| I-156 | 16 |
| I-157 | 1 |
| I-158 | 4 |
| I-159 | 42 |
| I-160 | 25 |
| I-161 | 148 |
| I-162 | 8 |
| I-163 | 13 |
| I-164 | 71 |
| I-165 | 105 |
| II-2 | 73 |
| II-3 | 21 |
| II-7 | 246 |
| II-8 | 29 |
| II-10 | 282 |
| II-11 | 29 |
| II-12 | 244 |
| II-13 | 246 |
| II-14 | 94 |
| II-15 | 61 |
| II-16 | 500 |
| II-17 | 73 |
| II-18 | 21 |
| III-1 | 10 |
| III-2 | 17 |
| III-3 | 92 |
| III-4 | 17 |
| III-5 | 44 |
| III-6 | 13 |
| III-7 | 21 |
| III-8 | 7 |
| III-9 | 4 |
| III-10 | 8 |
| III-11 | 4 |
| III-12 | 11 |
| III-13 | 3 |
| III-14 | 3 |
| III-15 | 5 |
| III-16 | 5 |
| III-17 | 5 |
| III-18 | 9 |
| III-19 | 0.75 |
| III-20 | 1 |
| III-21 | 0.54 |
| III-22 | 0.27 |
| III-23 | 2 |
| III-24 | 2 |
| III-25 | 1 |
| III-26 | 2 |
| III-27 | 2 |
| III-28 | 1 |
| III-29 | 1 |
| III-30 | 2 |
| III-31 | 1 |
| III-32 | 1 |
| III-33 | 2 |
| III-34 | 4 |
| III-35 | 3 |
| III-36 | 3 |
| III-37 | 3 |
| III-38 | 1 |
| III-39 | 2 |
| III-40 | 1 |
| III-41 | 2 |
| III-42 | 1 |
| III-43 | 1 |
| III-44 | 2 |
| III-45 | 1 |

TABLE 18-continued

| No. | IGF1R IC$_{50}$ [nM] |
|---|---|
| III-46 | 3 |
| III-47 | 1 |
| III-48 | 1 |
| III-49 | 2 |
| III-50 | 26 |
| III-51 | 183 |
| III-52 | 6 |
| III-53 | 8 |
| III-54 | 11 |
| III-55 | 7 |
| III-56 | 8 |
| III-57 | 36 |
| III-58 | 5 |
| III-59 | 2 |
| III-60 | 0.57 |
| III-61 | 5 |
| III-62 | 76 |
| III-63 | 22 |
| III-64 | 21 |
| III-65 | 4 |
| III-66 | 6 |
| III-67 | 117 |
| III-68 | 3 |
| III-69 | 2 |
| III-70 | 6 |
| III-71 | 15 |
| III-72 | 2 |
| III-73 | 6 |
| III-74 | 3 |
| III-75 | 4 |
| III-76 | 10 |
| III-77 | 5 |
| III-78 | 4 |
| III-79 | 12 |
| III-80 | 3 |
| III-81 | 4 |
| III-82 | 8 |
| III-83 | 1 |
| III-84 | 2 |
| III-85 | 3 |
| III-86 | 0.87 |
| III-87 | 7 |
| III-88 | 6 |
| III-89 | 6 |
| III-90 | 13 |
| III-91 | 11 |
| III-92 | 10 |
| III-93 | 10 |
| III-94 | 7 |
| III-95 | 9 |
| III-96 | 4 |
| III-97 | 387 |
| III-98 | 34 |
| III-99 | 193 |
| III-100 | 21 |
| III-101 | 64 |
| III-102 | 54 |
| IV-1 | 0.63 |
| IV-3 | 0.43 |
| IV-4 | 0.31 |
| IV-5 | 0.26 |
| IV-6 | 1 |
| IV-7 | 1 |
| IV-8 | 0.5 |
| IV-9 | 1 |
| IV-10 | 14 |
| IV-11 | 2 |
| V-1 | 12 |
| V-2 | 13 |
| V-3 | 5 |
| V-4 | 7 |
| V-5 | 8 |
| V-6 | 7 |
| V-7 | 180 |
| V-8 | 109 |
| I-166 | 0.6 |
| I-167 | 0.6 |
| I-168 | 1 |
| I-169 | 0.2 |
| I-170 | 3 |
| I-171 | 0.2 |
| I-172 | 0.3 |
| I-173 | 0.3 |
| I-174 | 0.4 |
| I-175 | 0.4 |
| I-176 | 0.4 |
| I-177 | 0.5 |
| I-178 | 0.5 |
| I-179 | 0.6 |
| I-180 | 0.6 |
| I-181 | 0.6 |
| I-182 | 0.6 |
| I-183 | 0.7 |
| I-184 | 1 |
| I-185 | 1 |
| I-186* | 1 |
| I-187 | 1 |
| I-188 | 2 |
| I-189 | 2 |
| I-190 | 2 |
| I-191 | 2 |
| I-192 | 2 |
| I-193 | 2 |
| I-194* | 2 |
| I-195 | 2 |
| I-196 | 3 |
| I-197 | 3 |
| I-198 | 3 |
| I-199 | 3 |
| I-200 | 3 |
| I-201 | 3 |
| I-202 | 3 |
| I-203 | 3 |
| I-204* | 3 |
| I-205 | 3 |
| I-206 | 3 |
| I-207 | 3 |
| I-208 | 4 |
| I-209 | 4 |
| I-210 | 4 |
| I-211 | 4 |
| I-212 | 4 |
| I-213 | 4 |
| I-214 | 4 |
| I-215 | 5 |
| I-216* | 5 |
| I-217 | 5 |
| I-218 | 5 |
| I-219 | 5 |
| I-220 | 5 |
| I-221* | 5 |
| I-222 | 5 |
| I-223 | 5 |
| I-224 | 5 |
| I-225 | 5 |
| I-226 | 5 |
| I-227 | 6 |
| I-228 | 6 |
| I-229 | 6 |
| I-230 | 6 |
| I-231 | 6 |
| I-232 | 6 |
| I-233 | 6 |
| I-234 | 6 |
| I-235 | 6 |
| I-236 | 6 |
| I-237 | 6 |
| I-238 | 6 |
| I-239 | 7 |
| I-240 | 8 |
| I-241 | 8 |
| I-242 | 8 |
| I-243 | 8 |
| I-244 | 8 |

TABLE 18-continued

| No. | IGF1R IC$_{50}$ [nM] |
|---|---|
| I-245 | 8 |
| I-246 | 8 |
| I-247 | 9 |
| I-248 | 9 |
| I-249 | 10 |
| I-250 | 10 |
| I-251 | 10 |
| I-252 | 10 |
| I-253 | 10 |
| I-254 | 10 |
| I-255 | 12 |
| I-256 | 12 |
| I-257 | 12 |
| I-258 | 12 |
| I-259 | 13 |
| I-260 | 13 |
| I-261* | 13 |
| I-262 | 14 |
| I-263 | 14 |
| I-264* | 15 |
| I-265 | 15 |
| I-266 | 15 |
| I-267 | 16 |
| I-268 | 16 |
| I-269 | 17 |
| I-270 | 17 |
| I-271 | 18 |
| I-272 | 18 |
| I-273 | 18 |
| I-274 | 18 |
| I-275 | 18 |
| I-276 | 19 |
| I-277 | 19 |
| I-278 | 21 |
| I-279 | 22 |
| I-280 | 23 |
| I-281 | 23 |
| I-282 | 23 |
| I-283 | 23 |
| I-284 | 25 |
| I-285* | 28 |
| I-286 | 31 |
| I-287 | 36 |
| I-288 | 48 |
| I-289 | 51 |
| I-290 | 57 |
| I-291 | 58 |
| I-292 | 59 |
| I-293 | 70 |
| I-294 | 70 |
| I-295 | 89 |
| III-103 | 0.3 |
| III-104 | 0.4 |
| III-105 | 1 |
| III-106* | 5 |
| III-107 | 5 |
| III-108 | 8 |
| IV-2a* | 2 |
| IV-9a | 1 |
| IV-9b | 1 |
| IV-9c | 1 |

Cellular IGF-1R-Phosphorylation Assay

The activity of substances against the phosphorylation of IGF-1R in activated cells is measured as follows: mouse fibroblast cells (transfected with human IGF-1R, Fibro-hIGF-1R) are cultivated in standard medium (DMEM, 10% foetal calf serum (FCS, Gibco), 1×MEM Non-Essential Amino Acids (NEAA, Gibco), 7.5% sodium hydrogen carbonate (Gibco) and 0.3 mg/mL Puromycin (Sigma)) in a humid incubator at 37° C. with 5% CO$_2$/95% air.

10000 Fibro-hIGF-1R cells per well in 200 µL of standard medium are seeded into 96-well plates and cultivated overnight. The next day, the medium is suction filtered and the cells are cultivated in 90 µL serum-reduced medium (DMEM, 0.5% FCS, 1×MEM NEAA, 7.5% sodium hydrogen carbonate) for a further 24 h. 10 µL of substance solution (diluted in serum-reduced medium) is added thereto, and the cells are incubated for a further 120 min in the incubator. The phosphorylation of IGF-1R is activated for 30 min by the addition of IGF-1 (20 ng/mL in serum-reduced medium). All further incubations are carried out at RT. The supernatant is suction filtered from the wells, and the cells are fixed in 100 µL per well of 4% paraformaldehyde (diluted in PBS). The supernatant in the well is suction filtered and the cells are permeabilised for 5 min in 300 µL per well of 0.1% TritonX-100 (diluted in PBS). The supernatants are suction filtered once again and the cells are incubated for 20 min in quenching buffer (PBS with 0.1% TritonX-100 and 1.2 hydrogen peroxide), to inhibit the endogenous peroxidase of the cells. The cells are washed for 5 min with 300 µL per well of PBS with 0.1% TritonX-100 and then incubated for 60 min with 100 µL per well of blocking buffer (PBS with 0.1% TritonX-100 and 5 Bovine Serum Albumin (BSA)). The blocking buffer is exchanged for 50 µL of the first antibody buffer (1/1000 dilute anti-phospho-IGF-1 receptor β (Tyr1135/1136)/insulin receptor β (Tyr1150/1151) (19H7) rabbit monoclonal antibody from Cell Signaling Technology in blocking buffer) and the plates are incubated overnight at 4° C. The next day the plates are washed for 5 min with 300 µL PBS/0.1% TritonX-100 at RT and then incubated for 60 min with 50 µL per well of the second antibody buffer (1/500 diluted Goat Anti-Rabbit Immunoglobulin-Horseradish Peroxidase (HRP) (Dako) in blocking buffer) at RT. The plates are washed first for 5 min with 300 µL PBS/0.1% TritonX-100 and then for a further 5 min with 300 µL PBS at RT. The plates are developed for 10 min with 100 µL per well of a peroxidase solution (1:1 mixture of TMB Peroxidase Substrate and Peroxidase Solution B from Kirkegaard & Perry Laboratories, Inc.). The reactions are stopped with 100 µL per well of stop solution (1M phosphoric acid). The absorbance in each well is measured at 450 nm with a SpectraMax Absorbance Reader. EC$_{50}$ values for inhibiting the phosphorylation of the IGF-1R in activated cells are calculated using the programmes Fifty (Version 2) and GraphPad (Version 3.0).

Compounds (I) according to the invention generally display a good inhibitory effect in the cellular assay described above, i.e. for example an EC$_{50}$ value of less than 5 µmol/L, often less than 3 µmol/L.

Cell Proliferation Assays

Compounds were tested for their anti-proliferative effects in the TC-71 (Ewing's sarcoma) and HCT 116 (colorectal carcinoma) cancer cell lines in vitro. Published scientific data has described that interference with the Insulin-like Growth Factor-1 Receptor (IGF-1R) signaling pathway reduces the proliferation of TC-71 cells [1]. Therefore TC-71 cells served as a positive control cell line for monitoring the activity of compounds against IGF-1R-mediated cell proliferation. In contrast, published data has demonstrated that the proliferation of HCT 116 cells is independent of IGF-1R signaling [2]. Therefore the HCT 116 cell line served as a negative control.

2000 TC-71 cells or 1000 HCT 116 cells were seeded per well in 180 µL IMDM+10% foetal calf serum (FCS)+penicillin/streptomycin into 96-well microtitre plates. The plates were placed in a cell culture incubator (37° C. in a humidified atmosphere of 95% O$_2$/5 CO$_2$) overnight. The following day, serial dilutions of compounds, prepared in duplicates, were transferred onto the cell layers (controls without compound). The cells were cultivated for a further 72 h in the cell culture incubator. 20 µL of Alamar Bluet™ (Serotec Ltd, Düsseldorf, Germany) was added to each well and the plates incubated for 7 h in the cell culture incubator. Fluorescence (extinction wavelength of 544 nm and emission at 590 nm) was then measured and the normalized data fitted by iterative calculation with a sigmoidal curve analysis program (Graph Pad Prism) with a variable Hill slope to determine the $IC_{50}$ values.

The $EC_{50}$ values of the following compounds were determined on TC-71 cells: I-23, I-30, I-40, I-42, I-97, I-109, I-112, I-147, I-157, I-166-I-168, I-171, I-172, I-175-I-178, I-180-I-182, I-185-I-187, I-189, I-191-I-214, I-217-I-263, I-265-I-284, I-286-I-289, I-293, I-294, I-3, II-18, III-38, III-105, III-107, IV-2a, IV-9a, IV-9b and IV-9c.

The $EC_{50}$ values for all these compounds are less than 3 µM, very often less than 500 nM.

In addition to TC-71, several other cancer cell lines from diverse tissue origins, which have previously been demonstrated to be sensitive to IGF-1R inhibition, were shown to be sensitive to compounds (I). Examples include COLO 205 (colorectal cancer) [3], LP-1 (multiple myeloma) [4] and HL-60 (acute myeloid leukemia) [5].

Reference List

1 Manara, M. C., Landuzzi, L., Nanni, P., Nicoletti, G., Zambelli, D., Lollini, P. L., Nanni, C., Hofmann, F., Garcia-Echeverria, C., Picci, P. and Scotlandi, K. (2007) Preclinical in vivo study of new insulin-like growth factor-I receptor—specific inhibitor in Ewing's sarcoma. Clin. Cancer Res., 13, 1322-1330.

2 Pitts, T. M., Tan, A. C., Kulikowski, G. N., Tentler, J. J., Brown, A. M., Flanigan, S. A., Leong, S., Coldren, C. D., Hirsch, F. R., Varella-Garcia, M., Korch, C. and Eckhardt, S. G. (2010) Development of an integrated genomic classifier for a novel agent in colorectal cancer: approach to individualized therapy in early development. Clin Cancer Res., 16, 3193-3204.

3 Haluska, P., carboni, J. M., Loegering, D. A., Lee, F. Y., Wittman, M., Saulnier, M. G., Frennesson, D. B., Kalli, K. R., Conover, C. A., Attar, R. M., Kaufmann, S. H., Gottardis, M. and Erlichman, C. (2006) In vitro and in vivo antitumor effects of the dual insulin-like growth factor-I/insulin receptor inhibitor, BMS-554417. Cancer Res., 66, 362-371.

4 Georgii-Hemming, P., Wiklund, H. J., Ljunggren, O. and Nilsson, K. (1996) Insulin-like growth factor I is a growth and survival factor in human multiple myeloma cell lines. Blood, 88, 2250-2258.

5 Wahner Hendrickson, A. E., Haluska, P., Schneider, P. A., Loegering, D. A., Peterson, K. L., Attar, R., Smith, B. D., Erlichman, C., Gottardis, M., Karp, J. E., carboni, J. M. and Kaufmann, S. H. (2009) Expression of insulin receptor isoform A and insulin-like growth factor-1 receptor in human acute myelogenous leukemia: effect of the dual-receptor inhibitor BMS-536924 in vitro. Cancer Res., 69, 7635-7643.

On the basis of their biological properties the compounds of general formula (I) according to the invention, their tautomers, racemates, enantiomers, diastereomers, mixtures thereof and the salts of all the above-mentioned forms are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy). They are also suitable for protecting proliferating cells (e.g. hair, intestinal, blood and progenitor cells) from DNA damage caused by radiation, UV treatment and/or cytostatic treatment.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as e.g. tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as e.g. kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma; vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (I) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Other possible combination partners are 2-chlorodesoxyadenosine, 2-fluorodesoxycytidine, 2-methoxyoestradiol, 2C4,3-alethine, 131-I-TM-601, 3CPA, 7-ethyl-10-hydroxy-camptothecin, 16-aza-epothilone B, A 105972, A 204197, aldesleukin, alitretinoin, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, ARRY-300, ARRY-142886/AZD-6244, ARRY-704/AZD-8330, AS-703026, azacytidine, azaepothilone B, azonafide, BAY-43-9006, BBR-3464, BBR-3576, bevacizumab, biricodar dicitrate, BCX-1777, bleocin, BLP-25, BMS-184476, BMS-247550, BMS-188797, BMS-275291, BNP-1350, BNP-7787, BIBW 2992, BIBF 1120, bleomycinic acid, bleomycin A, bleomycin B, bryostatin-1, bortezomib, brostallicin, busulphan, CA-4 prodrug, CA-4, CapCell, calcitriol, canertinib, canfosfamide, capecitabine, carboxyphthalatoplatin, CCI-779, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, clofarabin, colchicin, combretastatin A4, CHS-828, CLL-Thera, CMT-3 cryptophycin 52, CTP-37, CP-461, CV-247, cyanomorpholinodoxorubicin, cytarabine, D 24851, decitabine, deoxyrubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, E7010, E-6201, edatrexat, edotreotide, efaproxiral, eflornithine, EKB-569, EKB-509, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, floxuridine, folic acid, FOLFOX, FOLFIRI, formestane, galarubicin, gallium maltolate, gefinitib, gemtuzumab, gimatecan, glufosfamide, GCS-100, G17DT immunogen, GMK, GPX-100, GSK-5126766, GSK-1120212, GW2016, granisetron, hexamethylmelamine, histamine, homoharringtonine, hyaluronic acid, hydroxyurea, hydroxyprogesterone caproate, ibandronate, ibritumomab, idatrexate, idenestrol, IDN-5109, IMC-1C11, immunol, indisulam, interferon alpha-2a, interferon alpha-2b, interleukin-2, ionafarnib, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, lobaplatin, leflunomide, lenograstim, leuprolide, leuporelin, lexidronam, LGD-1550, linezolid, lutetium texaphyrin, lometrexol, losoxantrone, LU 223651, lurtotecan, mafosfamide, marimastat, mechloroethamine, methyltestosteron, methylprednisolone, MEN-10755, MDX-H210, MDX-447, MGV, midostaurin, minodronic acid, mitomycin, mivobulin, MK-2206, MLN518, motexafin gadolinium, MS-209, MS-275, MX6, neridronate, neovastat, nimesulide, nitroglycerin, nolatrexed, norelin, N-acetylcysteine, 06-benzylguanine, omeprazole, oncophage, ormiplatin, ortataxel, oxantrazole, oestrogen, patupilone, pegfilgrastim, PCK-3145, pegfilgrastim, PBI-1402, PEG-paclitaxel, PEP-005, P-04, PKC412, P54, PI-88, pelitinib, pemetrexed, pentrix, perifosine, perillylalcohol, PG-TXL, PG2, PLX-4032/RO-5185426, PT-100, picoplatin, pivaloyloxymethylbutyrate, pixantrone, phenoxodiol O, PK1166, plevitrexed, plicamycin, polyprenic acid, porfiromycin, prednisone, prednisolone, quinamed, quinupristin, RAF-265, ramosetron, ranpirnase, RDEA-119/BAY 869766, rebeccamycin analogues, revimid, RG-7167, rhizoxin, rhuMAb, risedronate, rituximab, rofecoxib, Ro-31-7453, RO-5126766, RPR 109881A, rubidazone, rubitecan, R-flurbiprofen, S-9788, sabarubicin, SAHA, sargramostim, satraplatin, SB 408075, SU5416, SU6668, SDX-101, semustin, seocalcitol, SM-11355, SN-38, SN-4071, SR-27897, SR-31747, SRL-172, sorafenib, spiroplatin, squalamine, suberanilohydroxamic acid, sutent, T 900607, T 138067, TAS-103, tacedinaline, talaporfin, tariquitar, taxotere, taxoprexin, tazarotene, tegafur, temozolamide, tesmilifene, testosterone, testosterone propionate, tetraplatin, tetrodotoxin, tezacitabine, thalidomide, theralux, therarubicin, thymectacin, tiazofurin, tipifarnib, tirapazamine, tocladesine, tomudex, toremofin, trabectedin, TransMID-107, transretinic acid, traszutumab, tretinoin, triacetyluridine, triapine, trimetrexate, TLK-286TXD 258, urocidin, valrubicin, vatalanib, vincristine, vinflunine, virulizin, WX-UK1, vectibix, xeloda, XELOX, XL-281, XL-518/R-7420, YM-511, YM-598, ZD-4190, ZD-6474, ZD-4054, ZD-0473, ZD-6126, ZD-9331, ZD1839, zoledronat and zosuquidar.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) | Tablets | per tablet |
|---|---|---|
| | active substance according to formula (I) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formula (I) | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance according to formula (I) | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of the formula (I)

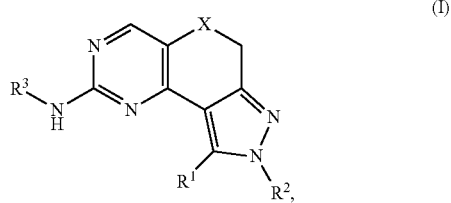

(I)

wherein $R^1$ denotes hydrogen or a group optionally substituted by one or more identical or different $R^a$ and/or $R^b$, selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

$R^2$ denotes hydrogen or a group optionally substituted by one or more identical or different $R^a$ and/or $R^b$, selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

$R^3$ denotes a group

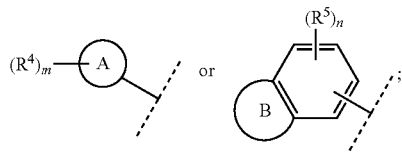

A is selected from among $C_{6-10}$aryl and 5-12 membered heteroaryl;

B denotes a 5- to 7-membered, non-aromatic hetero ring with at least one heteroatom, selected from among nitrogen, sulphur and oxygen, which optionally carries one or more substituents selected from among $C_{1-6}$alkyl and =O;

each $R^4$ is independently selected from among $R^a$ and $R^b$;

m denotes 0, 1, 2 or 3;

$R^5$ is selected from among $R^a$ and $R^b$;

n denotes 0 or 1;

X denotes a bond or is selected from among —$CH_2$— and —$CH_2$—$CH_2$— and in the above-mentioned —$CH_2$— and —$CH_2$—$CH_2$— one or two hydrogen atoms are optionally substituted independently of one another by $C_{1-4}$alkyl, $C_{1-4}$haloalkyl, —O—$C_{1-4}$alkyl or halogen;

each $R^a$ independently denotes a group optionally substituted by one or more identical or different $R^b$ and/or $R^c$, selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^b$ is independently selected from among —$OR^c$, —$SR^c$, —$NR^cR^c$, halogen, —CN, —$NO_2$, —$C(O)R^c$, —$C(O)OR^c$, —$C(O)NR^cR^c$, —$C(NR^h)NR^cR^c$, —$OC(O)R^c$, —$OC(O)OR^c$, —$S(O)_2R^c$, —$S(O)_2NR^cR^c$, —$NR^hC(O)R^c$, —$NR^hC(O)OR^c$, —$NR^hC(O)NR^cR^c$, —$NR^hC(NR^h)NR^cR^c$ and —$NR^hS(O)_2R^c$, as well as the bivalent substituent =O, while the latter may only be a substituent in non-aromatic ring systems;

each $R^c$ independently denotes hydrogen or a group optionally substituted by one or more identical or different $R^d$ and/or $R^e$, selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^d$ is independently selected from among —$OR^e$, —$SR^e$, —$NR^eR^e$, halogen, —CN, —$NO_2$, —$C(O)R^e$, —$C(O)OR^e$, —$C(O)NR^eR^e$, —$C(NR^h)NR^eR^e$, —$OC(O)R^e$, —$OC(O)OR^e$, —$S(O)_2R^e$, —$S(O)_2NR^eR^e$, —$NR^hC(O)R^e$, —$NR^hC(O)OR^e$, —$NR^hC(O)NR^eR^e$, —$NR^hC(NR^h)NR^eR^e$ and —$NR^hS(O)_2R^e$, as well as the bivalent substituent =O, while the latter may only be a substituent in non-aromatic ring systems;

each $R^e$ independently denotes hydrogen or a group optionally substituted by one or more identical or different $R^f$ and/or $R^g$, selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^f$ is independently selected from among —$OR^g$, —$SR^g$, —$NR^gR^g$, halogen, —CN, —$NO_2$, —$C(O)R^g$, —$C(O)OR^g$, —$C(O)NR^gR^g$, —$C(NR^h)NR^gR^g$, —$OC(O)R^g$, —$OC(O)OR^g$, —$S(O)_2R^g$, —$S(O)_2NR^gR^g$, —$NR^hC(O)R^g$, —$NR^hC(O)OR^g$, —$NR^hC(O)NR^gR^g$, —$NR^hC(NR^h)NR^gR^g$ and —$NR^hS(O)_2R^g$, as well as the bivalent substituent =O, while the latter may only be a substituent in non-aromatic ring systems;

each $R^g$ is independently selected from among hydrogen, $C_{1-6}$alkyl, $C_{2-6}$alkenyl, $C_{2-6}$alkynyl, $C_{1-6}$haloalkyl, $C_{3-10}$cycloalkyl, $C_{4-10}$cycloalkylalkyl, $C_{4-10}$cycloalkenyl, $C_{6-10}$aryl, 5-12 membered heteroaryl and 3- to 14-membered heterocyclyl, and each $R^h$ is independently selected from among hydrogen and $C_{1-6}$alkyl, or a tautomer or salt thereof.

2. A compound according to claim 1, wherein
$R^1$ is a group optionally substituted by one or more identical or different $R^{a1}$ and/or $R^{b1}$, selected from among $C_{1-6}$alkyl, $C_{3-10}$cycloalkyl, $C_{6-10}$aryl, 5-12 membered heteroaryl and 3- to 14-membered heterocyclyl;
each $R^{a1}$ independently denotes a group optionally substituted by one or more identical or different $R^{b1}$ and/or $C_{1-6}$alkyl, selected from among $C_{1-6}$alkyl, $C_{3-10}$cycloalkyl and $C_{6-10}$aryl, and
each $R^{b1}$ is independently selected from among —OH, —O—$C_{1-6}$alkyl, halogen and —CN.

3. A compound according to claim 1, wherein
$R^1$ is a group optionally substituted by one or more identical or different $R^{a1}$ and/or $R^{b1}$, selected from among $C_{1-4}$alkyl, $C_{3-6}$cycloalkyl, phenyl, 5- to 6-membered heteroaryl and 3-7 membered heterocyclyl;
each $R^{a1}$ independently denotes a group optionally substituted by one or more identical or different $R^{b1}$ and/or $C_{1-4}$alkyl, selected from among $C_{1-4}$alkyl, $C_{3-6}$cycloalkyl and phenyl, and
each $R^{b1}$ is independently selected from among —O—$C_{1-4}$alkyl, halogen and —CN.

4. A compound according to claim 1, wherein
$R^1$ denotes $C_{3-6}$alkyl.

5. A compound according to claim 1, wherein
$R^1$ denotes phenyl or benzyl, wherein the above-mentioned phenyl and benzyl optionally carry one or more substituents selected from among $C_{1-6}$alkyl, halogen, —O—$C_{1-6}$alkyl and —CN.

6. A compound according to claim 1, wherein
$R^1$ denotes phenyl or benzyl, wherein the above-mentioned phenyl and benzyl optionally carry one or more substituents selected from among $C_{1-4}$alkyl, $C_{1-4}$haloalkyl, halogen, —O—$C_{1-4}$alkyl, —O—$C_{1-4}$haloalkyl and —CN.

7. A compound according to claim 1, wherein
$R^1$ denotes thienyl, wherein this thienyl optionally carries one or more substituents selected from among $C_{1-4}$alkyl and halogen.

8. A compound according to claim 1, wherein
$R^2$ is hydrogen or a group optionally substituted by one or more identical or different $R^{b2}$ and/or $C_{6-10}$aryl selected from among $C_{1-6}$alkyl, $C_{2-6}$alkenyl and 5- to 12-membered heteroaryl;
each $R^{b2}$ is independently selected from among —OH, —O—$C_{1-6}$alkyl, —$NH_2$, —$NH(C_{1-6}$alkyl) and —$N(C_{1-6}$alkyl$)_2$.

9. A compound according to claim 1, wherein
$R^2$ is a group optionally substituted by one or more identical or different $R^{b2}$ and/or phenyl, selected from among $C_{1-4}$alkyl, and 5- to 6-membered heteroaryl;
each $R^{b2}$ is independently selected from among —O—$C_{1-4}$alkyl and —$N(C_{1-4}$alkyl$)_2$.

10. A compound according to claim 1, wherein
$R^2$ denotes methyl or ethyl.

11. A compound according to claim 1, wherein
X denotes a bond or is selected from among —$CH_2$— and —$CH_2$—$CH_2$— and in the above-mentioned —$CH_2$— and —$CH_2$—$CH_2$— one or two hydrogen atoms are optionally substituted by $C_{1-4}$alkyl.

12. A compound according to claim 1, wherein
X is selected from among —$CH_2$— and —$CH_2$—$CH_2$— and in the above-mentioned —$CH_2$— and —$CH_2$—$CH_2$— one or two hydrogen atoms are optionally substituted by $C_{1-4}$alkyl.

13. A compound according to claim 1, wherein
X is selected from among —$CH_2$, —$CH(CH_3)$—, —$C(CH_3)_2$— and —$CH_2$—$CH_2$—.

14. A compound according to claim 1, wherein
X denotes —$CH_2$ or —$CH(CH_3)$—.

15. A compound according to claim 1, wherein
A is selected from among phenyl, naphthyl, 5- to 6-membered monocyclic heteroaryl and 9- to 10-membered bicyclic heteroaryl.

16. A compound according to claim 1, wherein
A is selected from among phenyl, benzofuryl, benzothienyl, naphthyl, isoquinolinyl, pyrazolyl, indazolyl, isoxazolyl and imidazo[1,2-a]pyridyl.

17. A compound according to claim 1, wherein
A denotes phenyl.

18. A compound according to claim 1, wherein
A denotes pyrazolyl.

19. A compound according to claim 1, wherein
each $R^4$ is independently selected from among $R^{a3}$ and $R^{b3}$;
m denotes 0, 1, 2 or 3;
each $R^{a3}$ independently denotes a group optionally substituted by one or more identical or different $R^{b3}$ and/or $R^{c3}$, selected from among $C_{1-6}$alkyl, $C_{3-10}$cycloalkyl and 3- to 14-membered heterocyclyl;
each $R^{b3}$ is independently selected from among —$OR^{c3}$, —$NR^{c3}R^{c3}$, halogen, —$C(O)R^{c3}$, —$C(O)OR^{c3}$, —$C(O)NR^{c3}R^{c3}$ and —$S(O)_2R^{c3}$;
each $R^{c3}$ independently denotes hydrogen or a group optionally substituted by one or more identical or different $R^{d3}$ and/or $R^{e3}$ selected from among $C_{1-6}$alkyl, $C_{2-6}$alkenyl, $C_{3-10}$cycloalkyl and 3- to 14-membered heterocyclyl;
each $R^{d3}$ is independently selected from among —$OR^{e3}$, —$NR^{e3}R^{e3}$, halogen, —$C(O)R^{e3}$, —$C(O)OR^{e3}$ and —$C(O)NR^{e3}R^{e3}$;
each $R^{e3}$ independently denotes hydrogen or a group optionally substituted by one or more identical or different $R^{f3}$ and/or $R^{g3}$ selected from among $C_{1-6}$alkyl, $C_{3-10}$cycloalkyl and 3- to 14-membered heterocyclyl;
each $R^{f3}$ is independently selected from among —$OR^{g3}$, —$NR^{g3}R^{g3}$, halogen, —$C(O)R^{g3}$, —$C(O)OR^{g3}$ and —$C(O)NR^{g3}R^{g3}$ and
each $R^{g3}$ is independently selected from among hydrogen, $C_{1-6}$alkyl, $C_{1-6}$haloalkyl, $C_{3-10}$cycloalkyl, $C_{4-10}$cycloalkylalkyl, $C_{6-10}$aryl, and 5-12 membered heteroaryl.

20. A compound according to claim 19, wherein
m denotes 1, 2 or 3.

21. A compound according to claim 19, wherein
m denotes 2.

22. A compound according to claim 1, wherein
$R^3$ denotes a group

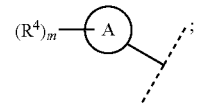

A is selected from among $C_{6\text{-}10}$aryl and 5-12 membered heteroaryl;

each $R^4$ is independently selected from among $R^a$ and $R^b$;

m denotes 0, 1, 2 or 3 and $R^a$ and $R^b$ are defined as in claim 1.

23. A compound according to claim 1, wherein $R^3$ denotes a group

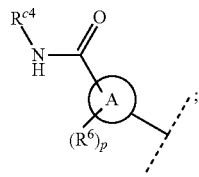

A is selected from among $C_{6\text{-}10}$aryl and 5-12 membered heteroaryl;

each $R^6$ is independently selected from among $C_{1\text{-}4}$alkyl, —O—$C_{1\text{-}4}$alkyl and halogen;

p denotes 0, 1 or 2;

$R^{c4}$ denotes hydrogen or a group optionally substituted by one or more identical or different $R^{d4}$ and/or $R^{e4}$ selected from among $C_{1\text{-}6}$alkyl, $C_{2\text{-}6}$alkenyl, $C_{2\text{-}6}$alkynyl, $C_{3\text{-}10}$cycloalkyl, $C_{4\text{-}10}$cycloalkenyl, $C_{6\text{-}10}$aryl, 5-12 membered heteroaryl and 3- to 14-membered heterocyclyl;

each $R^{d4}$ is independently selected from among —$OR^{e4}$, —$SR^{e4}$, —$NR^{e4}R^{e4}$, halogen, —CN, —$NO_2$, —C(O)$R^{e4}$, —C(O)$OR^{e4}$, —C(O)$NR^{e4}R^{e4}$, —C($NR^{h4}$)$NR^{e4}R^{e4}$, —OC(O)$R^{e4}$, —OC(O)$OR^{e4}$, —$S(O)_2R^{e4}$, —$S(O)_2NR^{e4}R^{e4}$, —$NR^{h4}$C(O)$R^{e4}$, —$NR^{h4}$C(O)$OR^{e4}$, —$NR^{h4}$C(O)$NR^{e4}R^{e4}$, —$NR^{h4}$C($NR^{h4}$)$NR^{e4}R^{e4}$ and —$NR^{h4}S(O)_2R^{e4}$, as well as the bivalent substituent =O, while the latter may only be a substituent in non-aromatic ring systems;

each $R^{e4}$ independently denotes hydrogen or a group optionally substituted by one or more identical or different $R^{f4}$ and/or $R^{g4}$ selected from among $C_{1\text{-}6}$alkyl, $C_{2\text{-}6}$alkenyl, $C_{2\text{-}6}$alkynyl, $C_{3\text{-}10}$cycloalkyl, $C_{4\text{-}10}$cycloalkenyl, $C_{6\text{-}10}$aryl, 5-12 membered heteroaryl and 3- to 14-membered heterocyclyl;

each $R^{f4}$ is independently selected from among —$OR^{g4}$, —$SR^{g4}$, —$NR^{g4}R^{g4}$, halogen, —CN, —$NO_2$, —C(O)$R^{g4}$, —C(O)$OR^{g4}$, —C(O)$NR^{g4}R^{g4}$, —C($NR^{h4}$)$NR^{g4}R^{g4}$, —OC(O)$R^{g4}$, —OC(O)$OR^{g4}$, —$S(O)_2R^{g4}$, —$S(O)_2NR^{g4}R^{g4}$, —$NR^{h4}$C(O)$R^{g4}$, —$NR^{h4}$C(O)$OR^{g4}$, —$NR^{h4}$C(O)$NR^{g4}R^{g4}$, —$NR^{h4}$C($NR^{h4}$)$NR^{g4}R^{g4}$ and —$NR^{h4}S(O)_2R^{g4}$, as well as the bivalent substituent =O, while the latter may only be a substituent in non-aromatic ring systems;

each $R^{g4}$ is independently selected from among hydrogen, $C_{1\text{-}6}$alkyl, $C_{2\text{-}6}$alkenyl, $C_{2\text{-}6}$alkynyl, $C_{1\text{-}6}$haloalkyl, $C_{3\text{-}10}$cycloalkyl, $C_{4\text{-}10}$cycloalkylalkyl, $C_{4\text{-}10}$cycloalkenyl, $C_{6\text{-}10}$aryl, 5-12 membered heteroaryl and 3- to 14-membered heterocyclyl and each $R^{h4}$ is independently selected from among hydrogen and $C_{1\text{-}4}$alkyl.

24. A compound according to claim 1, wherein $R^3$ denotes a group

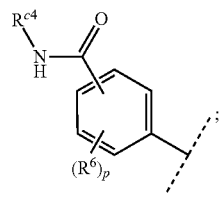

each $R^6$ is independently selected from among $C_{1\text{-}4}$alkyl, —O—$C_{1\text{-}4}$alkyl and halogen;

p denotes 0, 1 or 2;

$R^{c4}$ denotes hydrogen or a group optionally substituted by one or more identical or different $R^{d4}$ and/or $R^{e4}$ selected from among $C_{1\text{-}6}$alkyl, $C_{2\text{-}6}$alkenyl, $C_{2\text{-}6}$alkynyl, $C_{3\text{-}10}$cycloalkyl, $C_{4\text{-}10}$cycloalkenyl, $C_{6\text{-}10}$aryl, 5-12 membered heteroaryl and 3- to 14-membered heterocyclyl;

each $R^{d4}$ is independently selected from among —$OR^{e4}$, —$SR^{e4}$, —$NR^{e4}R^{e4}$, halogen, —CN, —$NO_2$, —C(O)$R^{e4}$, —C(O)$OR^{e4}$, —C(O)$NR^{e4}R^{e4}$, —C($NR^{h4}$)$NR^{e4}R^{e4}$, —OC(O)$R^{e4}$, —OC(O)$OR^{e4}$, —$S(O)_2R^{e4}$, —$S(O)_2NR^{e4}R^{e4}$, —$NR^{h4}$C(O)$R^{e4}$, —$NR^{h4}$C(O)$OR^{e4}$, —$NR^{h4}$C(O)$NR^{e4}R^{e4}$, —$NR^{h4}$C($NR^{h4}$)$NR^{e4}R^{e4}$ and —$NR^{h4}S(O)_2R^{e4}$, as well as the bivalent substituent =O, while the latter may only be a substituent in non-aromatic ring systems;

each $R^{e4}$ independently denotes hydrogen or a group optionally substituted by one or more identical or different $R^{f4}$ and/or $R^{g4}$ selected from among $C_{1\text{-}6}$alkyl, $C_{2\text{-}6}$alkenyl, $C_{2\text{-}6}$alkynyl, $C_{3\text{-}10}$cycloalkyl, $C_{4\text{-}10}$cycloalkenyl, $C_{6\text{-}10}$aryl, 5-12 membered heteroaryl and 3- to 14-membered heterocyclyl;

each $R^{f4}$ is independently selected from among —$OR^{g4}$, —$SR^{g4}$, —$NR^{g4}R^{g4}$, halogen, —CN, —$NO_2$, —C(O)$R^{g4}$, —C(O)$OR^{g4}$, —C(O)$NR^{g4}R^{g4}$, —C($NR^{h4}$)$NR^{g4}R^{g4}$, —OC(O)$R^{g4}$, —OC(O)$OR^{g4}$, —$S(O)_2R^{g4}$, —$S(O)_2NR^{g4}R^{g4}$, —$NR^{h4}$C(O)$R^{g4}$, —$NR^{h4}$C(O)$OR^{g4}$, —$NR^{h4}$C(O)$NR^{g4}R^{g4}$, —$NR^{h4}$C($NR^{h4}$)$NR^{g4}R^{g4}$ and —$NR^{h4}S(O)_2R^{g4}$, as well as the bivalent substituent =O, while the latter may only be a substituent in non-aromatic ring systems;

each $R^{g4}$ is independently selected from among hydrogen, $C_{1\text{-}6}$alkyl, $C_{2\text{-}6}$alkenyl, $C_{2\text{-}6}$alkynyl, $C_{1\text{-}6}$haloalkyl, $C_{3\text{-}10}$cycloalkyl, $C_{4\text{-}10}$cycloalkylalkyl, $C_{4\text{-}10}$cycloalkenyl, $C_{6\text{-}10}$aryl, 5-12 membered heteroaryl and 3- to 14-membered heterocyclyl and each $R^{h4}$ is independently selected from among hydrogen and $C_{1\text{-}4}$alkyl.

25. A compound according to claim 1, wherein $R^3$ denotes a group

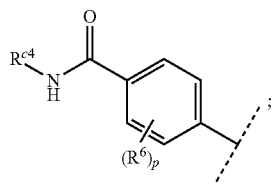

each $R^6$ is independently selected from among $C_{1\text{-}4}$alkyl, —O—$C_{1\text{-}4}$alkyl and halogen;

p denotes 0, 1 or 2;

$R^{c4}$ denotes hydrogen or a group optionally substituted by one or more identical or different $R^{d4}$ and/or $R^{e4}$ selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^{d4}$ is independently selected from among —$OR^{e4}$, —$SR^{e4}$, —$NR^{e4}R^{e4}$, halogen, —CN, —$NO_2$, —C(O)$R^{e4}$, —C(O)$OR^{e4}$, —C(O)$NR^{e4}R^{e4}$, —C($NR^{h4}$)$NR^{e4}R^{e4}$, —OC(O)$R^{e4}$, —OC(O)$OR^{e4}$, —S(O)$_2R^{e4}$, —S(O)$_2NR^{e4}R^{e4}$, —$NR^{h4}$C(O)$R^{e4}$, —$NR^{h4}$C(O)$OR^{e4}$, —$NR^{h4}$C(O)$NR^{e4}R^{e4}$, —$NR^{h4}$C($NR^{h4}$)$NR^{e4}R^{e4}$ and —$NR^{h4}$S(O)$_2R^{e4}$, as well as the bivalent substituent =O, while the latter may only be a substituent in non-aromatic ring systems;

each $R^{e4}$ independently denotes hydrogen or a group optionally substituted by one or more identical or different $R^{f4}$ and/or $R^{g4}$ selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^{f4}$ is independently selected from among —$OR^{g4}$, —$SR^{g4}$, —$NR^{g4}R^{g4}$, halogen, —CN, —$NO_2$, —C(O)$R^{g4}$, —C(O)$OR^{g4}$, —C(O)$NR^{g4}R^{g4}$, —C($NR^{h4}$)$NR^{g4}R^{g4}$, —OC(O)$R^{g4}$, —OC(O)$OR^{g4}$, —S(O)$_2R^{g4}$, —S(O)$_2NR^{g4}R^{g4}$, —$NR^{h4}$C(O)$R^{g4}$, —$NR^{h4}$C(O)$OR^{g4}$, —$NR^{h4}$C(O)$NR^{g4}R^{g4}$, —$NR^{h4}$C($NR^{g4}$)$NR^{g4}R^{g4}$ and —$NR^{h4}$S(O)$_2R^{g4}$, as well as the bivalent substituent =O, while the latter may only be a substituent in non-aromatic ring systems;

each $R^{g4}$ is independently selected from among hydrogen, $C_{1-6}$alkyl, $C_{2-6}$alkenyl, $C_{2-6}$alkynyl, $C_{1-6}$haloalkyl, $C_{3-10}$cycloalkyl, $C_{4-10}$cycloalkylalkyl, $C_{4-10}$cycloalkenyl, $C_{6-10}$aryl, 5-12 membered heteroaryl and 3- to 14-membered heterocyclyl and each $R^{h4}$ is independently selected from among hydrogen and $C_{1-4}$alkyl.

26. A compound according to claim 1, wherein
$R^3$ denotes a group

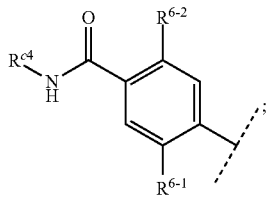

$R^{6-1}$ and $R^{6-2}$ is independently selected from among hydrogen, $C_{1-4}$alkyl, —O—$C_{1-4}$alkyl and halogen and $R^{c4}$ denotes hydrogen or a group optionally substituted by one or more identical or different $R^{d4}$ and/or $R^{e4}$ selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^{d4}$ is independently selected from among —$OR^{e4}$, —$SR^{e4}$, —$NR^{e4}R^{e4}$, halogen, —CN, —$NO_2$, —C(O)$R^{e4}$, —C(O)$OR^{e4}$, —C(O)$NR^{e4}R^{e4}$, —C($NR^{h4}$)$NR^{e4}R^{e4}$, —OC(O)$R^{e4}$, —OC(O)$OR^{e4}$, —S(O)$_2R^{e4}$, —S(O)$_2NR^{e4}R^{e4}$, $NR^{h4}$C(O)$R^{e4}$, —$NR^{h4}$C(O)$OR^{e4}$, —$NR^{h4}$C(O)$NR^{e4}R^{e4}$, —$NR^{h4}$C($NR^{h4}$)$NR^{e4}R^{e4}$ and —$NR^{h4}$S(O)$_2R^{e4}$, as well as the bivalent substituent =O, while the latter may only be a substituent in non-aromatic ring systems;

each $R^{e4}$ independently denotes hydrogen or a group optionally substituted by one or more identical or different $R^{f4}$ and/or $R^{g4}$ selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^{f4}$ is independently selected from among —$OR^{g4}$, —$SR^{g4}$, —$NR^{g4}R^{g4}$, halogen, —CN, —$NO_2$, —C(O)$R^{g4}$, —C(O)$OR^{g4}$, —C(O)$NR^{g4}R^{g4}$, —C($NR^{h4}$)$NR^{g4}R^{g4}$, —OC(O)$R^{g4}$, —OC(O)$OR^{g4}$, —S(O)$_2R^{g4}$, —S(O)$_2NR^{g4}R^{g4}$, —$NR^{h4}$C(O)$R^{g4}$, —$NR^{h4}$C(O)$OR^{g4}$, —$NR^{h4}$C(O)$NR^{g4}R^{g4}$, —$NR^{h4}$C($NR^{g4}$)$NR^{g4}R^{g4}$ and —$NR^{h4}$S(O)$_2R^{g4}$, as well as the bivalent substituent =O, while the latter may only be a substituent in non-aromatic ring systems;

each $R^{g4}$ is independently selected from among hydrogen, $C_{1-6}$alkyl, $C_{2-6}$alkenyl, $C_{2-6}$alkynyl, $C_{1-6}$haloalkyl, $C_{3-10}$cycloalkyl, $C_{4-10}$cycloalkylalkyl, $C_{4-10}$cycloalkenyl, $C_{6-10}$aryl, 5-12 membered heteroaryl and 3- to 14-membered heterocyclyl and each $R^{h4}$ is independently selected from among hydrogen and $C_{1-4}$alkyl.

27. A compound according to claim 23, wherein $R^{c4}$ denotes hydrogen or a group optionally substituted by one or more identical or different $R^{d4}$ and/or $R^{e4}$ selected from among $C_{1-6}$alkyl, $C_{3-10}$cycloalkyl and 3- to 14-membered heterocyclyl;

each $R^{d4}$ is independently selected from among —$OR^{e4}$, —$NR^{e4}R^{e4}$, halogen, —C(O)$R^{e4}$ and —C(O)$NR^{e4}R^{e4}$;

each $R^{e4}$ independently denotes hydrogen or a group optionally substituted by one or more identical or different $R^{f4}$ and/or $R^{g4}$ selected from among $C_{1-6}$alkyl, $C_{3-10}$cycloalkyl and 3- to 14-membered heterocyclyl;

each $R^{f4}$ is independently selected from among —$OR^{g4}$, —$NR^{g4}R^{g4}$, halogen, —C(O)$R^{g4}$, —C(O)$NR^{g4}R^{g4}$ and each $R^{g4}$ is independently selected from among hydrogen, $C_{1-6}$alkyl, $C_{1-6}$haloalkyl, $C_{3-10}$cycloalkyl, $C_{4-10}$cycloalkylalkyl, $C_{6-10}$aryl and 5-12 membered heteroaryl.

28. A compound according to claim 23, wherein $R^{c4}$ denotes a group optionally substituted by one or more identical or different $R^{d4}$ and/or $^{e4}$ selected from among $C_{1-6}$alkyl, cyclopropyl, cyclobutyl, cyclopentyl, cyclohexyl, azetidinyl, pyrrolidinyl, tetrahydropyranyl, 1-aza-bicyclo[2.2.2]octyl, 8-methyl-8-aza-bicyclo[3.2.1]octyl, morpholinyl, piperidinyl and piperazinyl;

each $R^{d4}$ is independently selected from among —$OR^{e4}$, —$NR^{e4}R^{e4}$, halogen, —C(O)$R^{e4}$ and —C(O)$NR^{e4}R^{e4}$;

each $R^{e4}$ independently denotes a group optionally substituted by one or more identical or different $R^{f4}$ and/or $R^{g4}$ selected from among $C_{1-6}$alkyl, cyclopropyl, cyclobutyl, cyclopentyl, cyclohexyl, azetidinyl, pyrrolidinyl, tetrahydropyranyl, 1-aza-bicyclo[2.2.2]octyl, 8-methyl-8-aza-bicyclo[3.2.1]octyl, morpholinyl, piperidinyl and piperazinyl;

each $R^{f4}$ is independently selected from among —$OR^{g4}$, —$NR^{g4}R^{g4}$, halogen, —C(O)$R^{g4}$, —C(O)$NR^{g4}R^{g4}$ and each $R^{g4}$ is independently selected from among hydrogen, $C_{1-6}$alkyl, $C_{1-6}$haloalkyl, cyclopropyl, cyclobutyl, cyclopentyl, cyclohexyl, cyclopropylmethyl, phenyl and 5- to 6-membered heteroaryl.

29. A compound according to claim 23, wherein $R^{c4}$ is selected from among methyl, methoxyethyl, N,N-dimethyl-ethyl, N,N-dimethyl-propyl,

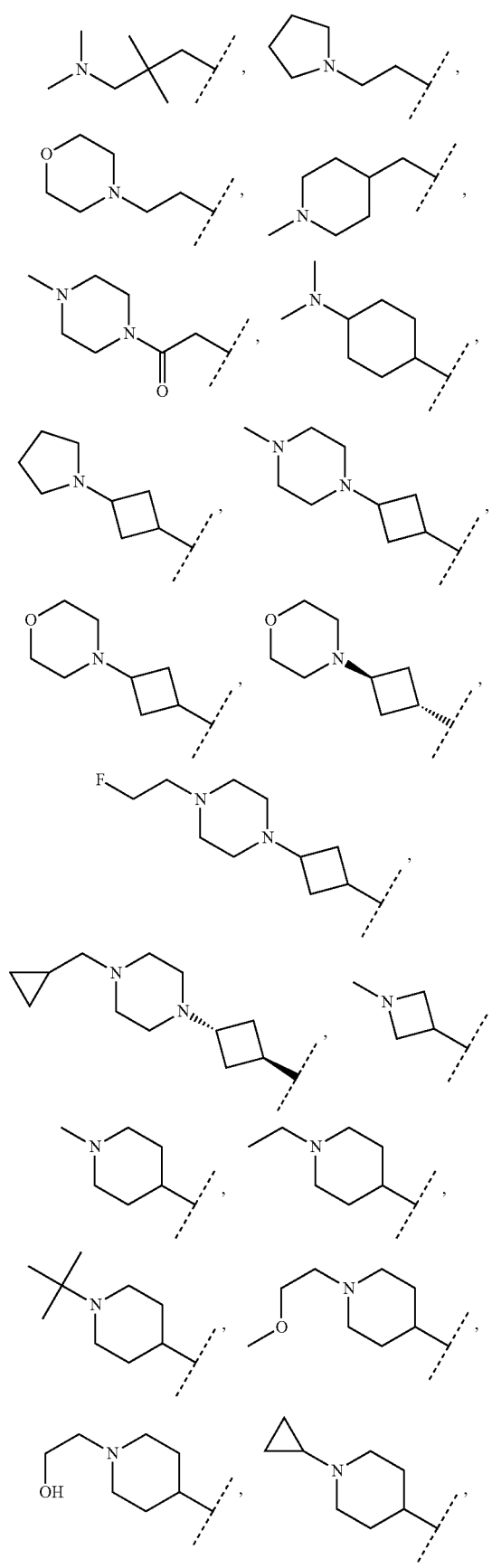
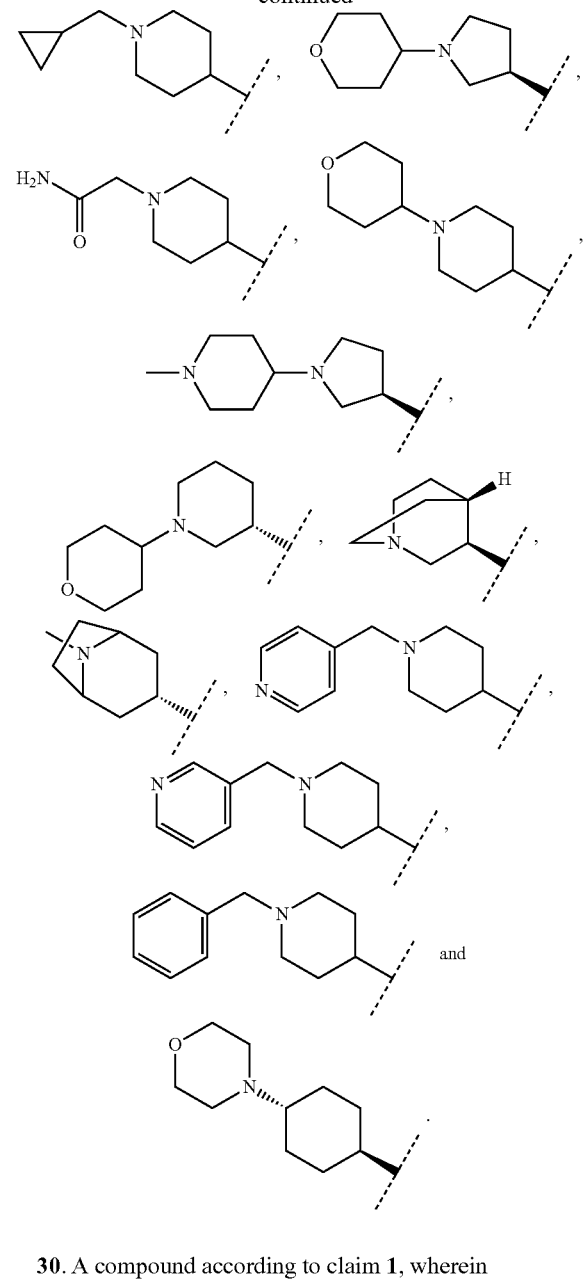

30. A compound according to claim 1, wherein $R^3$ denotes a group

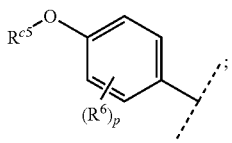

each $R^6$ is independently selected from among $C_{1-4}$alkyl, —O—$C_{1-4}$alkyl and halogen;
p denotes 0, 1 or 2;
$R^{c5}$ denotes hydrogen or a group optionally substituted by one or more identical or different $R^{d5}$ and/or $R^{e5}$ selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^{d5}$ is independently selected from among —$OR^{e5}$, —$SR^{e5}$, —$NR^{e5}R^{e5}$, halogen, —CN, —$NO_2$, —C(O)$R^{e5}$, —C(O)$OR^{e5}$, —C(O)$NR^{e5}R^{e5}$, —C($NR^{h5}$)$NR^{e5}R^{e5}$, —OC(O)$R^{e5}$, —OC(O)$OR^{e5}$, —$S(O)_2R^{e5}$, —$S(O)_2NR^{e5}R^{e5}$, —$NR^{h5}C(O)R^{e5}$, —$NR^{h5}C(O)OR^{e5}$, —$NR^{h5}C(O)NR^{e5}R^{e5}$, —$NR^{h5}C(NR^{h5})NR^{e5}R^{e5}$ and —$NR^{h5}S(O)_2R^{e5}$, as well as the bivalent substituent =O, while the latter may only be a substituent in non-aromatic ring systems;

each $R^{e5}$ independently denotes hydrogen or a group optionally substituted by one or more identical or different $R^{f5}$ and/or $R^{g5}$ selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^{f5}$ is independently selected from among —$OR^{g5}$, —$SR^{g5}$, —$NR^{g5}R^{g5}$, halogen, —CN, —$NO_2$, —C(O)$R^{g5}$, —C(O)$OR^{g5}$, —C(O)$NR^{g5}R^{g5}$, —C($NR^{h5}$)$NR^{g5}R^{g5}$, —OC(O)$R^{g5}$, —OC(O)$OR^{g5}$, —$S(O)_2R^{g5}$, —$S(O)_2NR^{g5}R^{g5}$, —$NR^{h5}C(O)R^{g5}$, —$NR^{h5}C(O)OR^{g5}$, —$NR^{h5}C(O)NR^{g5}R^{g5}$, —$NR^{h5}C(NR^{h5})NR^{g5}R^{g5}$ and —$NR^{h5}S(O)_2R^{g5}$, as well as the bivalent substituent =O, while the latter may only be a substituent in non-aromatic ring systems;

each $R^{g5}$ is independently selected from among hydrogen, $C_{1-6}$alkyl, $C_{2-6}$alkenyl, $C_{2-6}$alkynyl, $C_{1-6}$haloalkyl, $C_{3-10}$cycloalkyl, $C_{4-10}$-cycloalkylalkyl, $C_{4-10}$-cycloalkenyl, $C_{6-10}$aryl, 5-12 membered heteroaryl and 3- to 14-membered heterocyclyl and each $R^{h5}$ is independently selected from among hydrogen and $C_{1-4}$alkyl.

31. A compound according to claim 1, wherein $R^3$ denotes a group

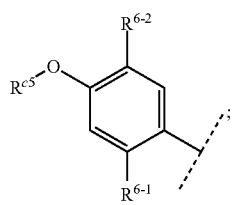

$R^{6-1}$ and $R^{6-2}$ are each independently selected from among hydrogen, $C_{1-4}$alkyl, —O—$C_{1-4}$alkyl and halogen and $R^{c5}$ denotes hydrogen or a group optionally substituted by one or more identical or different $R^{d5}$ and/or $R^{e5}$ selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^{d5}$ is independently selected from among —$OR^{e5}$, —$SR^{e5}$, —$NR^{e5}R^{e5}$, halogen, —CN, —$NO_2$, —C(O)$R^{e5}$, —C(O)$OR^{e5}$, —C(O)$NR^{e5}R^{e5}$, —C($NR^{h5}$)$NR^{e5}R^{e5}$, —OC(O)$R^{e5}$, —OC(O)$OR^{e5}$, —$S(O)_2R^{e5}$, —$S(O)_2NR^{e5}R^{e5}$, —$NR^{h5}C(O)R^{e5}$, —$NR^{h5}C(O)OR^{e5}$, —$NR^{h5}C(O)NR^{e5}R^{e5}$, —$NR^{h5}C(NR^{h5})NR^{e5}R^{e5}$ and —$NR^{h5}S(O)_2R^{e5}$, as well as the bivalent substituent =O, while the latter may only be a substituent in non-aromatic ring systems;

each $R^{e5}$ independently denotes hydrogen or a group optionally substituted by one or more identical or different $R^{f5}$ and/or $R^{g5}$ selected from among $C_{1-6}$alkyl, $C_{2-6}$alkenyl, $C_{2-6}$alkynyl, $C_{3-10}$cycloalkyl, $C_{4-10}$cycloalkenyl, $C_{6-10}$aryl, 5-12 membered heteroaryl and 3- to 14-membered heterocyclyl;

each $R^{f5}$ is independently selected from among —$OR^{g5}$, —$SR^{g5}$, —$NR^{g5}R^{g5}$, halogen, —CN, —$NO_2$, —C(O)$R^{g5}$, —C(O)$OR^{g5}$, —C(O)$NR^{g5}R^{g5}$, —C($NR^{h5}$)$NR^{g5}R^{g5}$, —OC(O)$R^{g5}$, —OC(O)$OR^{g5}$, —$S(O)_2R^{g5}$, —$S(O)_2NR^{g5}R^{g5}$, —$NR^{h5}C(O)R^{g5}$, —$NR^{h5}C(O)OR^{g5}$, —$NR^{h5}C(O)NR^{g5}R^{g5}$, —$NR^{h5}C(NR^{h5})NR^{g5}R^{g5}$ and —$NR^{h5}S(O)_2R^{g5}$, as well as the bivalent substituent =O, while the latter may only be a substituent in non-aromatic ring systems;

each $R^{g5}$ is independently selected from among hydrogen, $C_{1-6}$alkyl, $C_{2-6}$alkenyl, $C_{2-6}$alkynyl, $C_{1-6}$haloalkyl, $C_{3-10}$cycloalkyl, $C_{4-10}$-cycloalkylalkyl, $C_{4-10}$-cycloalkenyl, $C_{6-10}$aryl, 5-12 membered heteroaryl and 3- to 14-membered heterocyclyl and each $R^{h5}$ is independently selected from among hydrogen and $C_{1-4}$alkyl.

32. A compound according to claim 30, wherein $R^{c5}$ denotes hydrogen or a group optionally substituted by one or more identical or different $R^{d5}$ and/or $R^{e5}$ selected from among $C_{1-6}$alkyl, $C_{3-10}$cycloalkyl and 3- to 14-membered heterocyclyl;

each $R^{d5}$ is independently selected from among —$OR^{e5}$, —$NR^{e5}R^{e5}$, halogen, —C(O)$R^{e5}$ and —C(O)$NR^{e5}R^{e5}$ and each $R^{e5}$ is independently selected from among hydrogen, $C_{1-6}$alkyl, $C_{3-10}$cycloalkyl and 3- to 14-membered heterocyclyl.

33. A compound according to claim 30, wherein $R^{c5}$ denotes a group optionally substituted by one or more identical or different $R^{d5}$ and/or $R^{e5}$ selected from among $C_{1-6}$alkyl and 5- to 6-membered, nitrogen-containing heterocyclyl;

each $R^{d5}$ is independently selected from among —$OR^{e5}$, —$NR^{e5}R^{e5}$, halogen, —C(O)$R^{e5}$ and —C(O)$NR^{e5}R^{e5}$ and each $R^{e5}$ is independently selected from among $C_{1-6}$alkyl and 5- to 6-membered, nitrogen-containing heterocyclyl.

34. A compound according to claim 30, wherein $R^{c5}$ is selected from among N,N-dimethylethyl, N,N-dimethyl-propyl,

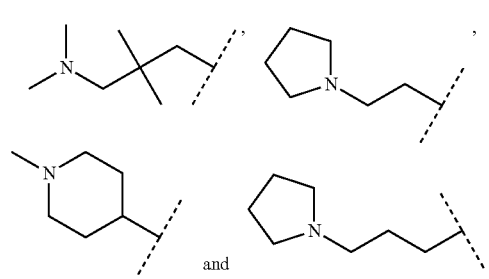

35. A compound according to claim 1, wherein R³ denotes a group

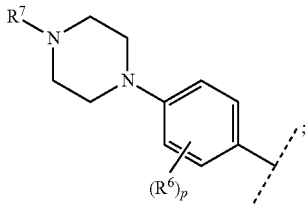

each R⁶ is independently selected from among C₁₋₄alkyl, —O—C₁₋₄alkyl and halogen;
R⁷ is selected from among R^{b6} and R^{c6};
p denotes 0, 1 or 2;
R^{b6} is selected from among —C(O)R^{c6}, —C(O)OR^{c6}, —C(O)NR^{c6}R^{c6}, —S(O)₂R^{c6} and —S(O)₂NR^{c6}R^{c6};
each R^{c6} independently denotes hydrogen or a group optionally substituted by one or more identical or different R^{d6} and/or R^{e6}, selected from among C₁₋₆alkyl, C₂₋₆alkenyl, C₂₋₆alkynyl, C₃₋₁₀cycloalkyl, C₄₋₁₀cycloalkenyl, C₆₋₁₀aryl, 5-12 membered heteroaryl and 3- to 14-membered heterocyclyl;
each R^{d6} is independently selected from among —OR^{e6}, —SR^{e6}, —NR^{e6}R^{e6}, halogen, —CN, —NO₂, —C(O)R^{e6}, —C(O)OR^{e6}, —C(O)NR^{e6}R^{e6}, —C(NR^{h6})NR^{e6}R^{e6}, —OC(O)R^{e6}, —OC(O)OR^{e6}, —S(O)₂R^{e6}, —S(O)₂NR^{e6}R^{e6}, —NR^{h6}C(O)R^{e6}, —NR^{h6}C(O)OR^{e6}, —NR^{h6}C(O)NR^{e6}R^{e6}, —NR^{h6}C(NR^{h6})NR^{e6}R^{e6} and —NR^{h6}S(O)₂R^{e6}, as well as the bivalent substituent =O, while the latter may only be a substituent in non-aromatic ring systems;
each R^{e6} is independently selected from among hydrogen, C₁₋₆alkyl, C₂₋₆alkenyl, C₂₋₆alkynyl, C₃₋₁₀cycloalkyl, C₄₋₁₀cycloalkenyl, C₆₋₁₀aryl, 5-12 membered heteroaryl and 3- to 14-membered heterocyclyl, and
each R^{h6} is independently selected from among hydrogen and C₁₋₄alkyl.

36. A compound according to claim 1, wherein R³ denotes a group

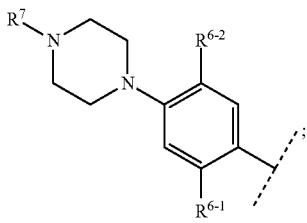

R^{6-1} and R^{6-2} are independently selected from among hydrogen, C₁₋₄alkyl, —O—C₁₋₄alkyl and halogen and R⁷ is selected from among R^{b6} and R^{c6};
R^{b6} is selected from among —C(O)R^{c6}, —C(O)OR^{c6}, —C(O)NR^{c6}R^{c6}, —S(O)₂R^{c6} and —S(O)₂NR^{c6}R^{c6};
each R^{c6} independently denotes hydrogen or a group optionally substituted by one or more identical or different R^{d6} and/or R^{e6}, selected from among C₁₋₆alkyl, C₂₋₆alkenyl, C₂₋₆alkynyl, C₃₋₁₀cycloalkyl, C₄₋₁₀cycloalkenyl, C₆₋₁₀aryl, 5-12 membered heteroaryl and 3- to 14-membered heterocyclyl;
each R^{d6} is independently selected from among —OR^{e6}, —SR^{e6}, —NR^{e6}R^{e6}, halogen, —CN, —NO₂, —C(O) R^{e6}, —C(O)OR^{e6}, —C(O)NR^{e6}R^{e6}, —C(NR^{h6}) NR^{e6}R^{e6}, —OC(O)R^{e6}, —OC(O)OR^{e6}, —S(O)₂R^{e6}, —S(O)₂NR^{e6}R^{e6}, —NR^{h6}C(O)R^{e6}, —NR^{h6}C(O)OR^{e6}, —NR^{h6}C(O)NR^{e6}R^{e6}, —NR^{h6}C(NR^{h6})NR^{e6}R^{e6} and —NR^{h6}S(O)₂R^{e6}, as well as the bivalent substituent =O, while the latter may only be a substituent in non-aromatic ring systems;
each R^{e6} is independently selected from among hydrogen, C₁₋₆alkyl, C₂₋₆alkenyl, C₂₋₆alkynyl, C₃₋₁₀cycloalkyl, C₄₋₁₀cycloalkenyl, C₆₋₁₀aryl, 5-12 membered heteroaryl and 3- to 14-membered heterocyclyl, and
each R^{h6} is independently selected from among hydrogen and C₁₋₄alkyl.

37. A compound according to claim 35, wherein R⁷ is selected from among R^{b6} and R^{c6};
R^{b6} is selected from among —C(O)R^{c6}, —C(O)NR^{c6}R^{c6} and —S(O)₂R^{c6};
each R^{c6} independently denotes hydrogen or a group optionally substituted by one or more identical or different R^{d6} and/or R^{e6}, selected from among C₁₋₆alkyl, C₃₋₆cycloalkyl and 5- to 6-membered heterocyclyl;
each R^{d6} is independently selected from among —OR^{e6}, —NR^{e6}R^{e6}, halogen, —C(O)R^{e6} and —C(O)NR^{e6}R^{e6} and
each R^{e6} is independently selected from among hydrogen, C₁₋₆alkyl, C₃₋₆cycloalkyl and 5- to 6-membered heterocyclyl.

38. A compound according to claim 1, wherein R³ denotes pyrazolyl, which is optionally mono- or disubstituted by C₁₋₄alkyl or C₃₋₅cycloalkyl.

39. A compound according to claim 1, wherein R³ denotes a group

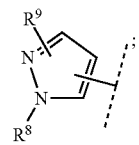

R⁸ denotes a group optionally substituted by one or more identical or different R^{b7} and/or R^{c7}, selected from among C₁₋₆alkyl, C₃₋₆cycloalkyl and 5- to 7-membered heterocyclyl;
each R^{b7} is independently selected from among —OR^{c7}, —NR^{c7}R^{c7}, halogen, —C(O)R^{c7} and —C(O)NR^{c7}R^{c7};
each R^{c7} independently denotes hydrogen or a group optionally substituted by one or more identical or different R^{d7} and/or R^{e7}, selected from among C₁₋₆alkyl, C₃₋₆cycloalkyl, 5- to 6-membered heteroaryl and 5- to 7-membered heterocyclyl;
each R^{d7} is independently selected from among —OR^{e7}, —NR^{e7}R^{e7}, halogen, —C(O)R^{e7} and —C(O)NR^{e7}R^{e7};
each R^{e7} independently denotes hydrogen or a group optionally substituted by one or more identical or different R^{f7} and/or R^{g7}, selected from among C₁₋₆alkyl, C₃₋₆cycloalkyl, 5- to 6-membered heteroaryl and 5- to 7-membered heterocyclyl;
each R^{f7} is independently selected from among —OR^{g7}, —NR^{g7}R^{g7}, halogen, —C(O)R^{g7} and —C(O)NR^{g7}R^{g7};
each R^{g7} independently denotes hydrogen or C₁₋₆alkyl;
R⁹ is selected from among hydrogen, C₁₋₄alkyl and C₃₋₅cycloalkyl.

40. A compound according to claim 1, wherein $R^3$ denotes a group

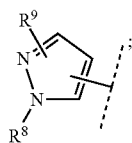

$R^8$ is selected from among $C_{1-4}$alkyl, $C_{3-5}$cycloalkyl, $C_{1-4}$alkoxy-$C_{1-4}$alkyl, $(C_{1-4}$alkyl$)$NH—$C_{1-4}$alkyl and $(C_{1-4}$alkyl$)_2$N—$C_{1-4}$alkyl;

$R^9$ is selected from among hydrogen, $C_{1-4}$alkyl and $C_{3-5}$cycloalkyl.

41. A compound according to claim 1, selected from the group consisting of:

I-168 (5S)-N-[1-(2-methoxyethyl)pyrazol-3-yl]-5,8-dimethyl-9-phenyl-5,6-dihydropyrazolo[3,4-h]quinazolin-2-amine;

I-194 N-[1-(2-dimethylaminoethyl)pyrazol-3-yl]-5,8-dimethyl-9-phenyl-5,6-dihydropyrazolo[3,4-h]quinazolin-2-amine;

I-201 N-[1-(2-dimethylaminoethyl)pyrazol-3-yl]-8-methyl-9-phenyl-5,6-dihydropyrazolo[3,4-h]quinazolin-2-amine;

I-204 N-[1-(2-methoxyethyl)pyrazol-3-yl]-5,8-dimethyl-9-phenyl-5,6-dihydropyrazolo[3,4-h]quinazolin-2-amine;

I-222 9-[4-(difluoromethoxy)phenyl]-N-[1-(2-dimethylaminoethyl)pyrazol-3-yl]-8-methyl-5,6-dihydropyrazolo[3,4-h]quinazolin-2-amine;

I-271 (5S)-N-[1-(2-methoxyethyl)pyrazol-3-yl]-5,8-dimethyl-9-phenyl-5,6-dihydropyrazolo[3,4-h]quinazolin-2-amine;

I-225 N-[1-(2-methoxyethyl)pyrazol-3-yl]-8-methyl-9-[(3-methylphenyl)methyl]-5,6-dihydropyrazolo[3,4-h]quinazolin-2-amine I-205 1-[4-[4-[[9-[4-(difluoromethoxy)phenyl]-8-methyl-5,6-dihydropyrazolo[3,4-h]quinazolin-2-yl]amino]pyrazol-1-yl]piperidin-1-yl]ethanone;

I-198 N-[1-[2-[2-methoxyethyl(methyl)amino]ethyl]pyrazol-3-yl]-8-methyl-9-phenyl-5,6-dihydropyrazolo[3,4-h]quinazolin-2-amine;

I-197 8-methyl-9-phenyl-N-[1-(2-pyrrolidin-1-ylethyl)pyrazol-3-yl]-5,6-dihydropyrazolo[3,4-h]quinazolin-2-amine;

I-195 N-[1-(2-dimethylaminoethyl)pyrazol-3-yl]-8-methyl-9-(naphthalen-1-ylmethyl)-5,6-dihydropyrazolo[3,4-h]quinazolin-2-amine;

I-193 9-[(2-chlorophenyl)methyl]-N-[1-(2-dimethylaminoethyl)pyrazol-3-yl]-8-methyl-5,6-dihydropyrazolo[3,4-h]quinazolin-2-amine;

I-189 N-[1-(2-dimethylaminoethyl)pyrazol-3-yl]-8-methyl-9-(3-methylthiophen-2-yl)-5,6-dihydropyrazolo[3,4-h]quinazolin-2-amine;

I-187 N-[1-(2-methoxyethyl)pyrazol-3-yl]-8-methyl-9-[(2-methylphenyl)methyl]-5,6-dihydropyrazolo[3,4-h]quinazolin-2-amine;

I-186 1-[4-[4-[(5,8-dimethyl-9-phenyl-5,6-dihydropyrazolo[3,4-h]quinazolin-2-yl)amino]pyrazol-1-yl]piperidin-1-yl]ethanone;

I-185 8-methyl-N-[1-[2-(4-methylpiperazin-1-yl)ethyl]pyrazol-3-yl]-9-phenyl-5,6-dihydropyrazolo[3,4-h]quinazolin-2-amine;

I-171 9-(4-chlorophenyl)-N-[1-(2-methoxyethyl)pyrazol-3-yl]-8-methyl-5,6-dihydropyrazolo[3,4-h]quinazolin-2-amine;

I-166 2-[4-[2-[3-[(8-methyl-9-phenyl-5,6-dihydropyrazolo[3,4-h]quinazolin-2-yl)amino]pyrazol-1-yl]ethyl]piperazin-1-yl]ethanol;

I-167 N-[1-[2-[4-(2-methoxyethyl)piperazin-1-yl]ethyl]pyrazol-3-yl]-8-methyl-9-phenyl-5,6-dihydropyrazolo[3,4-h]quinazolin-2-amine;

I-217 9-[(3-methoxyphenyl)methyl]-8-methyl-N-(1-methylpyrazol-3-yl)-5,6-dihydropyrazolo[3,4-h]quinazolin-2-amine;

I-210 9-[4-(difluoromethoxy)phenyl]-N-[1-(2-methoxyethyl)pyrazol-3-yl]-8-methyl-5,6-dihydropyrazolo[3,4-h]quinazolin-2-amine;

I-208 9-benzyl-N-[1-(2-dimethylaminoethyl)pyrazol-3-yl]-8-methyl-5,6-dihydropyrazolo[3,4-h]quinazolin-2-amine;

I-192 9-[(2-chlorophenyl)methyl]-N-[1-(2-methoxyethyl)pyrazol-3-yl]-8-methyl-5,6-dihydropyrazolo[3,4-h]quinazolin-2-amine;

I-182 8-methyl-9-phenyl-N-[1-(2-piperazin-1-ylethyl)pyrazol-3-yl]-5,6-dihydropyrazolo[3,4-h]quinazolin-2-amine;

I-180 9-(3-chlorothiophen-2-yl)-N-[1-(2-methoxyethyl)pyrazol-3-yl]-8-methyl-5,6-dihydropyrazolo[3,4-h]quinazolin-2-amine;

I-176 1-[4-[4-[[9-(4-methoxyphenyl)-8-methyl-5,6-dihydropyrazolo[3,4-h]quinazolin-2-yl]amino]pyrazol-1-yl]piperidin-1-yl]ethanone;

I-175 N-[1-[2-[4-(dimethylamino)piperidin-1-yl]ethyl]pyrazol-3-yl]-8-methyl-9-phenyl-5,6-dihydropyrazolo[3,4-h]quinazolin-2-amine;

I-181 9-(3-chlorothiophen-2-yl)-N-(1-ethylpyrazol-3-yl)-8-methyl-5,6-dihydropyrazolo[3,4-h]quinazolin-2-amine;

I-202 9-[(2-chlorophenyl)methyl]-N-(1-ethylpyrazol-3-yl)-8-methyl-5,6-dihydropyrazolo[3,4-h]quinazolin-2-amine;

I-224 N-(1-ethylpyrazol-3-yl)-8-methyl-9-[(3-methylphenyl)methyl]-5,6-dihydropyrazolo[3,4-h]quinazolin-2-amine;

I-237 9-[4-(difluoromethoxy)phenyl]-N-(1-ethylpyrazol-3-yl)-8-methyl-5,6-dihydropyrazolo[3,4-h]quinazolin-2-amine;

I-236 9-[4-(difluoromethoxy)phenyl]-N-[1-(2-dimethylaminoethyl)pyrazol-4-yl]-8-methyl-5,6-dihydropyrazolo[3,4-h]quinazolin-2-amine;

I-30 9-(2-chlorophenyl)-N-(1-ethylpyrazol-3-yl)-8-methyl-5,6-dihydropyrazolo[3,4-h]quinazolin-2-amine;

I-112 4-[[9-(2-chlorophenyl)-8-methyl-5,6-dihydropyrazolo[3,4-h]quinazolin-2-yl]amino]-3-methoxy-N-(1-methylpiperidin-4-yl)benzamide;

I-40 9-(2-chlorophenyl)-5,8-dimethyl-N-(1-propane-2-ylpyrazol-3-yl)-5,6-dihydropyrazolo[3,4-h]quinazolin-2-amine;

I-42 9-(2-chlorophenyl)-5,8-dimethyl-N-(1-methylpyrazol-3-yl)-5,6-dihydropyrazolo[3,4-h]quinazolin-2-amine;

I-97 9-(2-chlorophenyl)-N-[2-methoxy-4-(4-methylpiperazin-1-yl)phenyl]-5,8-dimethyl-5,6-dihydropyrazolo[3,4-h]quinazolin-2-amine;

I-157 4-[[9-(2-chlorophenyl)-5,8-dimethyl-5,6-dihydropyrazolo[3,4-h]quinazolin-2-yl]amino]-3-methoxy-N-(1-methylpiperidin-4-yl)benzamide; and II-8 4-[[9-(2-chlorophenyl)-5,8-dimethyl-5,6-dihydropyrazolo[3,4-h]quinazolin-2-yl]amino]-3-methoxybenzoic acid;
or a salt thereof.

42. A pharmaceutical composition comprising a compound of formula (I), according to claim 1, or a pharmaceutically acceptable salt thereof, and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,735,386 B2 | Page 1 of 1 |
| APPLICATION NO. | : 13/187100 | |
| DATED | : May 27, 2014 | |
| INVENTOR(S) | : Treu | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 90 days.

Signed and Sealed this
Eighteenth Day of November, 2014

Michelle K. Lee
*Deputy Director of the United States Patent and Trademark Office*